US006586368B1

(12) United States Patent
Takano et al.

(10) Patent No.: US 6,586,368 B1
(45) Date of Patent: Jul. 1, 2003

(54) CONDENSED HETEROCYLIC COMPOUNDS AND HERBICIDES CONTAINING THEM

(75) Inventors: Minoru Takano, Kameoka (JP); Shinichi Kawamura, Osaka (JP); Takashi Komori, Toyonaka (JP)

(73) Assignee: Sumitomo Chemical Company, Limited, Osaka-fu (JP)

( * ) Notice: Subject to any disclaimer, the term of this patent is extended or adjusted under 35 U.S.C. 154(b) by 0 days.

(21) Appl. No.: 09/762,479

(22) PCT Filed: Sep. 2, 1999

(86) PCT No.: PCT/JP99/04758

§ 371 (c)(1), (2), (4) Date: Feb. 7, 2001

(87) PCT Pub. No.: WO00/15633

PCT Pub. Date: Mar. 23, 2000

(30) Foreign Application Priority Data

Sep. 10, 1998 (JP) .......................................... 10-257237
Jan. 11, 1999 (JP) .......................................... 11-004373
May 24, 1999 (JP) .......................................... 11-143300

(51) Int. Cl.$^7$ ........................ A01N 43/72; C07D 403/02
(52) U.S. Cl. ........................................ 504/222; 544/238
(58) Field of Search ........................... 504/222; 544/238

(56) References Cited

FOREIGN PATENT DOCUMENTS

| | | |
|---|---|---|
| EP | A188259 | 7/1986 |
| EP | 0476679 A1 * | 3/1992 |
| EP | A476697 | 3/1992 |
| EP | A563916 | 10/1993 |
| WO | A9712884 | 4/1997 |
| WO | A9712886 | 4/1997 |
| WO | A9838188 | 8/1998 |
| WO | WO 2002000653 * | 2/2002 |

OTHER PUBLICATIONS

Gilchrist, et al, J. Chem. Soc. Perkin I, 1973 (7), 555–61.*
Gilchrist et al., Journal of the Chemical Society, vol. 6, pp. 555–561 (1973).

Buckle et al., Tetrahedron Letter, vol. 33, No. 8, pp. 1109–1112 (1992).

Gilchrist et al., JCS Chemical Communications, pp. 1519–1520 (1971).

Daidone et al., Heterocycles, vol. 43, No. 11, pp. 2385–2396 (1996).

* cited by examiner

*Primary Examiner*—Joseph K. McKane
*Assistant Examiner*—Andrea D. Small
(74) *Attorney, Agent, or Firm*—Birch, Stewart, Kolasch & Birch, LLP

(57) ABSTRACT

Condensed heterocyclic compounds of general formula (I) wherein T is carbon or nitrogen; when T is carbon, then the bond between T and A is a double bond, the bond between A and Y is a single bond, and Y is oxygen, sulfur, or optionally substituted NH; or when T is nitrogen, then the bond between T and A is a single bond, the bond between A and Y is a double bond, and Y is nitrogen or optionally substituted CH; A is nitrogen or optionally substituted CH; $R^1$ is hydrogen, halogen, alkyl, haloalkyl, hydroxymethyl, nitro, or cyano; $R^2$ is hydrogen, halogen, alkyl, haloalkyl, hydroxymethyl, nitro, cyano, or the like; $R^3$ is hydrogen, halogen, alkyl, haloalkyl, hydroxymethyl, nitro, cyano, or the like; $R^4$ is hydrogen, halogen, alkyl, halo-alkyl, hydroxymethyl, nitro, or cyano; and Q is a saturated or unsaturated 5- or 6- membered heterocyclic ring containing one to four nitrogen atoms, or a saturated or unsaturated cyclopentylideneamino group containing one or two nitrogen heteroatoms and one oxygen or sulfur heteroatom.

(I)

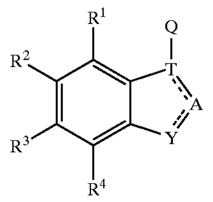

17 Claims, No Drawings

CONDENSED HETEROCYLIC COMPOUNDS AND HERBICIDES CONTAINING THEM

This application is the national phase under 35 U.S.C. § 371 of PCT International Application No. PCT/JP99/04758, which has an International filing date of Sep. 2, 1999, which designated the, United States of America.

TECHNICAL FIELD

The present invention relates to condensed heterocyclic compounds and their use.

DISCLOSURE OF THE INVENTION

The present inventors have extensively studied to find compounds having excellent herbicidal activity. As a result, they have found that the condensed heterocyclic compounds of general formula I as depicted below have excellent herbicidal activity, thereby completing the present invention.

The present invention provides condensed heterocyclic compounds of general formula I:

[I]

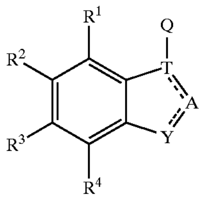

(hereinafter referred to as the present compounds)

wherein T is carbon or nitrogen; when T is carbon, then the bond between T and A is a double bond, the bond between A and Y is a single bond, and Y is oxygen, sulfur, or N—$R^{142}$; or when T is nitrogen, then the bond between T and A is a single bond, the bond between A and Y is a double bond, and Y is nitrogen or C—$R^{152}$;

wherein $R^{142}$ is hydrogen, $C_1$–$C_5$ alkyl, $C_1$–$C_5$ haloalkyl, $C_3$–$C_6$ alkenyl, $C_3$–$C_6$ alkynyl, cyano, —$COR^{143}$, —$N(R^{145})R^{146}$, or —N=$C(R^{147})R^{148}$; $R^{152}$ is hydrogen, halogen, $C_1$–$C_3$ alkyl, nitro, amino, cyano, or —$COR^{153}$;

wherein $R^{143}$ is hydrogen, $C_1$–$C_3$ alkyl, $C_1$–$C_3$ haloalkyl, hydroxyl, $C_1$–$C_5$ alkoxy, or —$N(R^{156})N^{157}$; $R^{145}$ and $R^{146}$ are independently hydrogen, $C_1$–$C_5$ alkyl, $C_1$–$C_5$ haloalkyl, formyl, ($C_1$–$C_5$ alkyl)carbonyl, ($C_1$–$C_5$ haloalkyl)carbonyl, or ($C_1$–$C_6$ alkoxy) carbonyl; $R^{147}$ and $R^{148}$ are independently hydrogen or $C_1$–$C_5$ alkyl; $R^{153}$ is hydrogen, $C_1$–$C_3$ alkyl, $C_1$–$C_3$ haloalkyl, hydroxyl, $C_1$–$C_5$ alkoxy, or —$N(R^{154})R^{155}$;

wherein $R^{156}$ and $R^{157}$ are independently hydrogen, $C_1$–$C_5$ alkyl, $C_1$–$C_5$ haloalkyl, formyl, ($C_1$–$C_5$ alkyl) carbonyl, ($C_1$–$C_5$ haloalkyl)carbonyl, or ($C_1$–$C_5$ alkoxy)carbonyl; $R^{154}$ and $R^{155}$ are independently hydrogen, $C_1$–$C_5$ alkyl, $C_1$–$C_5$ haloalkyl, ($C_1$–$C_5$ alkoxy)carbonyl, formyl, ($C_1$–$C_5$ alkyl)carbonyl, or ($C_1$–$C_5$ haloalkyl)carbonyl;

A is nitrogen or C—$R^{141}$ wherein $R^{141}$ is hydrogen, halogen, or $C_1$–$C_3$ alkyl;

$R^1$ is hydrogen, halogen, $C_1$–$C_3$ alkyl, $C_1$–$C_3$ haloalkyl, hydroxymethyl, nitro, or cyano;

$R^2$ is hydrogen, halogen, $C_1$–$C_{11}$ alkyl, $C_1$–$C_{11}$ haloalkyl, hydroxymethyl, nitro, cyano, —$N(R^9)R^{10}$, —$OR^{11}$, —$SR^{12}$, —$SO_2R^{13}$, —COX, —$COOR^{14}$, —$CON(R^{15})R^{16}$, —$COR^{17}$, —$C(R^{26})$=$NOR^{19}$, —$C(R^{27})$=$C(R^{21})R^{22}$, or —$CH(R^{23})$—$CH(R^{24})R^{25}$;

$R^3$ is hydrogen, halogen, $C_1$–$C_{11}$ alkyl, $C_1$–$C_{11}$ haloalkyl, hydroxymethyl, nitro, cyano, —$N(R^{59})R^{60}$, —$OR^{61}$, —$SR^{62}$, —$SO_2R^{63}$, —COX, —$COOR^{64}$, —$CON(R^{65})R^{66}$, —$COR^{67}$, —$C(R^{76})$=$NOR^{69}$, —$C(R^{77})$=$C(R^{71})R^{72}$, or —$CH(R^{73})$—$CH(R^{74})R^{75}$;

$R^4$ is hydrogen, halogen, $C_1$–$C_3$ alkyl, $C_1$–$C_3$ haloalkyl, hydroxymethyl, nitro, or cyano;

wherein X is chlorine or bromine;

$R^9$ and $R^{59}$ are independently hydrogen, $C_1$–$C_5$ alkyl, ($C_1$–$C_5$ alkyl)carbonyl, or ($C_1$–$C_5$ alkoxy)carbonyl;

$R^{10}$, $R^{11}$, and $R^{12}$ are independently hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl, $C_3$–$C_{10}$ cycloalkyl $C_1$–$C_3$ alkyl, $C_3$–$C_{10}$ alkenyl, $C_3$–$C_{10}$ haloalkenyl, $C_3$–$C_{10}$ alkynyl, $C_3$–$C_{10}$ haloalkynyl, cyano $C_1$–$C_6$ alkyl, ($C_1$–$C_5$ alkyl) carbonyl, ($C_1$–$C_5$ haloalkyl)carbonyl, ($C_3$–$C_{10}$ cycloalkyl)carbonyl, ($C_1$–$C_5$ alkyl)carbonyl, $C_1$–$C_5$ alkyl, ($C_1$–$C_5$ haloalkyl)carbonyl $C_1$–$C_5$ alkyl, hydroxy $C_1$–$C_5$ alkyl, $C_1$–$C_5$ alkoxy $C_1$–$C_5$ alkyl, $C_1$–$C_5$ alkylthio $C_1$–$C_5$ alkyl, ($C_1$–$C_5$ alkoxy)carbonyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, —$C(R^{43})(R^{44})$—C(=O)$ON(R^{45})R^{46}$, —$C(R^{47})(R^{48})$ —$CON(R^{49})R^{50}$, —$CH_2$—$C(R^{56})$=$NOR^{55}$, —CHMe—$C(R^{58})$=$NOR^{57}$, ($C_3$–$C_{10}$ alkenoxy)carbonyl $C_1$–$C_5$ alkyl, ($C_3$–$C_{10}$ alkynoxy)carbonyl $C_1$–$C_5$ alkyl, phenoxycarbonyl, benzyloxycarbonyl, carboxy ($C_1$–$C_5$ alkoxy)carbonyl $C_1$–$C_5$ alkyl, ($C_1$–$C_{10}$ alkoxy) carbonyl ($C_1$–$C_5$ alkoxy)carbonyl $C_1$–$C_5$ alkyl, ($C_1$–$C_{10}$ haloalkoxy)carbonyl($C_1$–$C_5$ alkoxy)carbonyl $C_1$–$C_5$ alkyl, ($C_3$–$C_{10}$ cycloalkoxy)carbonyl($C_1$–$C_5$ alkoxy)carbonyl $C_1$–$C_5$ alkyl, ($C_3$–$C_{10}$ alkenoxy) carbonyl($C_1$–$C_5$ alkoxy)carbonyl $C_1$–$C_5$ alkyl, ($C_3$–$C_{10}$ alkynoxy)carbonyl($C_1$–$C_5$ alkoxy)carbonyl $C_1$–$C_5$ alkyl, carboxy($C_1$–$C_5$ alkyl)carbonyl, ($C_1$–$C_{10}$ alkoxy) carbonyl($C_1$–$C_5$ alkyl)carbonyl, ($C_1$–$C_{10}$ haloalkoxy) carbonyl($C_1$–$C_5$ alkyl)carbonyl, $C_1$–$C_5$ alkylsulfonyl, $C_1$–$C_5$ haloalkylsulfonyl, —$SO_2N(R^{51})R^{52}$, —$CON(R^{53})R^{54}$, optionally substituted benzyl, or optionally substituted phenyl;

$R^{60}$, $R^{61}$, and $R^{62}$ are independently hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl, $C_3$–$C_{10}$ cycloalkyl $C_1$–$C_3$ alkyl, $C_3$–$C_{10}$ alkenyl, $C_3$–$C_{10}$ haloalkenyl, $C_3$–$C_{10}$ alkynyl, $C_3$–$C_{10}$ haloalkynyl, cyano $C_1$–$C_6$ alkyl, ($C_1$–$C_5$ alkyl) carbonyl, ($C_1$–$C_5$ haloalkyl)carbonyl, ($C_3$–$C_{10}$ cycloalkyl)carbonyl, ($C_1$–$C_5$ alkyl)carbonyl $C_1$–$C_5$ alkyl, ($C_1$–$C_5$ haloalkyl)carbonyl $C_1$–$C_5$ alkyl, hydroxy $C_1$–$C_5$ alkyl, $C_1$–$C_5$ alkoxy $C_1$–$C_5$ alkyl, $C_1$–$C_5$ alkylthio $C_1$–$C_5$ alkyl, ($C_1$–$C_5$ alkoxy)carbonyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_{10}$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, —$C(R^{163})(R^{164})$—C(=O)$ON(R^{165})R^{166}$, —$C(R^{167})R^{168}$)—$CON(R^{169})R^{170}$, —$CH_2$—C(=$NOR^{175})R^{176}$, —CHMe—C(=$NOR^{177})R^{178}$, ($C_3$–$C_{10}$ alkenoxy) carbonyl $C_1$–$C_5$ alkyl, ($C_3$–$C_{10}$ alkynoxy)carbonyl $C_1$–$C_5$ alkyl, phenoxycarbonyl, benzyloxycarbonyl, carboxy($C_1$–$C_5$ alkoxy)carbonyl $C_1$–$C_5$ alkyl, ($C_1$–$C_{10}$ alkoxy)carbonyl ($C_1$–$C_5$ alkoxy)carbonyl $C_1$–$C_5$ alkyl, ($C_1$–$C_{10}$ haloalkoxy)carbonyl ($C_1$–$C_5$ alkoxy)carbonyl $C_1$–$C_5$ alkyl, ($C_3$–$C_{10}$ cycloalkoxy)carbonyl($C_1$–$C_5$ alkoxy)carbonyl $C_1$–$C_5$ alkyl, ($C_3$–$C_{10}$ alkenoxy) carbonyl($C_1$–$C_5$ alkoxy)carbonyl $C_1$–$C_5$ alkyl, ($C_3$–$C_{10}$ alkynoxy)carbonyl($C_1$–$C_5$ alkoxy)carbonyl $C_1$–$C_5$ alkyl, carboxy($C_1$–$C_5$ alkyl)carbonyl, ($C_1$–$C_{110}$ alkoxy)carbonyl($C_1$–$C_5$ alkyl)carbonyl, ($C_1$–$C_{10}$ haloalkoxy)carbonyl($C_1$–$C_5$ alkyl)carbonyl, $C_1$–$C_5$ alkylsulfonyl, $C_1$–$C_5$ haloalkylsulfonyl, —$SO_2N(R^{171})R^{172}$, —$CON(R^{173})R^{174}$, optionally substituted benzyl, or optionally substituted phenyl;

wherein $R^{43}$, $R^{44}$, $R^{163}$, and $R^{164}$ are independently hydrogen, halogen, $C_1$–$C_5$ alkyl, or $C_1$–$C_5$ haloalkyl;

$R^{45}$, $R^{46}$, $R^{165}$, and $R^{166}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{45}$ and $R^{46}$ may be combined at their ends to form, together with the adjacent nitrogen atom, a 3- to 7-membered saturated ring, or $R^{165}$ and $R^{166}$ may be combined at their ends to form, together with the adjacent nitrogen atom, a 3- to 7-membered saturated ring;

$R^{47}$, $R^{48}$, $R^{167}$, and $R^{168}$ are independently hydrogen, halogen, $C_1$–$C_5$ alkyl, or $C_1$–$C_5$ haloalkyl;

$R^{49}$, $R^{50}$, $R^{169}$, and $R^{170}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{49}$ and $R^{50}$ may be combined at their ends to form, together with the adjacent nitrogen atom, a 3- to 7-membered saturated ring containing zero to one oxygen atom or NH group in the ring, or $R^{169}$ and $R^{170}$ may be combined at their ends to form, together with the adjacent nitrogen atom, a 3- to 7-membered saturated ring containing zero to one oxygen atom or NH group in the ring;

$R^{51}$, $R^{52}$, $R^{171}$, and $R^{172}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{51}$ and $R^{52}$ may be combined at their ends to form, together with the adjacent nitrogen atom, a 3- to 7-membered saturated ring containing zero to one oxygen atom or NH group in the ring, or $R^{171}$ and $R^{172}$ may be combined at their ends to form, together with the adjacent nitrogen atom, a 3- to 7-membered saturated ring containing zero to one oxygen atom or NH group in the ring;

$R^{53}$, $R^{54}$, $R^{173}$, and $R^{174}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{53}$ and $R^{54}$ may be combined at their ends to form, together with the adjacent nitrogen atom, a 3- to 7-membered saturated ring containing zero to one oxygen atom or NH group in the ring, or $R^{173}$ and $R^{174}$ may be combined at their ends to form, together with the adjacent nitrogen atom, a 3- to 7-membered saturated, ring containing zero to one oxygen atom or NH group in the ring;

$R^{55}$, $R^{57}$, $R^{175}$, and $R^{177}$ are independently hydrogen or $C_1$–$C_3$ alkyl;

$R^{56}$, $R^{58}$, $R^{176}$, and $R^{178}$ are independently hydrogen, $C_1$–$C_5$ alkyl, ($C_1$–$C_5$ alkoxy)carbonyl, ($C_1$–$C_5$ haloalkoxy)carbonyl, ($C_3$–$C_5$ cycloalkoxy)carbonyl, ($C_3$–$C_5$ alkenoxy)carbonyl, or ($C_3$–$C_5$ alkynoxy) carbonyl;

$R^{13}$ is hydroxy, chlorine, $C_1$–$C_{10}$ alkyl, $C_1$–$C_{10}$ haloalkyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, —$N(R^{79})R^{80}$, or —$OR^{81}$;

$R^{63}$ hydroxy, chlorine, $C_1$–$C_{10}$ alkyl, $C_1$–$C_{10}$ haloalkyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, —$N(R^{179})R^{180}$, or —$OR^{181}$;

wherein $R^{79}$ and $R^{179}$ are independently hydrogen, $C_1$–$C_5$ alkyl, $C_1$–$C_5$ haloalkyl, $C_3$–$C_8$ cycloalkyl, $C_3$–$C_6$ alkenyl, $C_3$–$C_6$ alkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl; $R^{80}$ and $R^{180}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{79}$ and $R^{80}$ may be combined at their ends to form, together with the adjacent nitrogen atom, a 3- or 7-membered saturated ring containing zero to one oxygen atom or NH group in the ring; or $R^{179}$ and $R^{180}$ may be combined at their ends to form, together with the adjacent nitrogen atom, a 3- or 7-membered saturated ring containing zero to one oxygen atom or NH group in the ring; and $R^{81}$ and $R^{181}$ are independently $C_1$–$C_5$ alkyl, $C_1$–$C_5$ haloalkyl, $C_3$–$C_8$ cycloalkyl, $C_3$–$C_6$ alkenyl, $C_3$–$C_6$ alkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl;

$R^{14}$ is hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl, $C_3$–$C_{10}$ cycloalkyl $C_1$–$C_3$ alkyl, $C_3$–$C_{10}$ alkenyl, $C_3$–$C_{10}$ haloalkenyl, $C_3$–$C_{10}$ alkynyl, $C_3$–$C_{10}$ haloalkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, ($C_3$–$C_{10}$ alkenoxy)carbonyl $C_1$–$C_5$ alkyl, ($C_3$–$C_{10}$ alkynoxy) carbonyl $C_1$–$C_5$ alkyl, —$N(R^{82})R^{83}$, optionally substituted benzyl, or optionally substituted phenyl;

$R^{64}$ is hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl, $C_3$–$C_{10}$ cycloalkyl $C_1$–$C_3$ alkyl, $C_3$–$C_{10}$ alkenyl, $C_3$–$C_{10}$ haloalkenyl, $C_3$–$C_{10}$ alkynyl, $C_3$–$C_{10}$ haloalkynyl, carboxy $C_1$–$C_5$ alkyl, ($C_1$–$C_{10}$ alkoxy)carbonyl $C_1$–$C_5$ alkyl, ($C_3$–$C_{10}$ haloalkoxy)carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, ($C_3$–$C_{10}$ alkenoxy)carbonyl $C_1$–$C_5$ alkyl, ($C_3$–$C_{10}$ alkynoxy) carbonyl $C_1$–$C_5$ alkyl, —$N(R^{182})R^{183}$, optionally substituted benzyl, or optionally substituted phenyl;

wherein $R^{82}$ and $R^{182}$ are independently hydrogen, $C_1$–$C_5$ alkyl, $C_1$–$C_5$ haloalkyl, $C_3$–$C_8$ cycloalkyl, $C_3$–$C_6$ alkenyl, $C_3$–$C_6$ alkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl; $R^{83}$ and $R^{183}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{82}$ and $R^{83}$ may be combined at their ends to form, together with the adjacent nitrogen atom, a 3- to 7-membered saturated ring containing zero to one oxygen atom or NH group in the ring; or $R^{182}$ and $R^{183}$ may be combined at their ends to form, together with the adjacent nitrogen atom, a 3- to 7-membered saturated ring containing zero to one oxygen atom or NH group in the ring;

$R^{15}$ and $R^{65}$ are independently hydrogen, $C_1$–$C_{10}$ alkyl, $C_1$–$C_{10}$ haloalkyl, $C_3$–$C_{10}$ cycloalkyl, $C_3$–$C_{10}$ cycloalkyl $C_1$–$C_3$ alkyl, $C_3$–$C_{10}$ alkenyl, $C_3$–$C_{10}$ alkynyl, cyano $C_1$–$C_6$ alkyl, carboxy $C_1$–$C_5$ alkyl, ($C_1$–$C_{10}$ alkoxy)carbonyl $C_1$–$C_5$ alkyl, optionally substituted benzyl, or optionally substituted phenyl; $R^{16}$ and $R^{66}$ are independently hydrogen, $C_1$–$C_{10}$ alkyl, or $C_1$–$C_{10}$ haloalkyl; or $R^{15}$ and $R^{16}$ may be combined at their ends to form, together with the adjacent nitrogen atom, a 3- to 7-membered saturated ring containing zero to one oxygen atom or NH group in the ring; or $R^{65}$ and $R^{66}$ may be combined at their ends to form, together with the adjacent nitrogen atom, a 3- to 7-membered saturated ring containing zero to one oxygen atom or NH group in the ring;

$R^{17}$, $R^{26}$, $R^{27}$, $R^{67}$, $R^{76}$, and $R^{77}$ are independently hydrogen, cyano, $C_1$–$C_{10}$ alkyl, $C_1$–$C_{10}$ haloalkyl, $C_3$–$C_{10}$ cycloalkyl, $C_3$–$C_{10}$ cycloalkyl $C_1$–$C_3$ alkyl, ($C_1$–$C_6$ alkoxy)carbonyl, or ($C_1$–$C_6$ alkoxy) carbonylmethyl;

$R^{19}$ and $R^{69}$ are independently hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl, $C_3$–$C_{10}$ cycloalkyl $C_1$–$C_3$ alkyl, $C_3$–$C_{10}$ alkenyl, $C_3$–$C_{10}$ haloalkenyl, $C_3$–$C_{10}$ alkynyl, $C_3$–$C_{10}$ haloalkynyl, cyano $C_1$–$C_6$ alkyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl;

$R^{21}$ and $R^{71}$ are independently hydrogen, halogen, $C_1$–$C_3$ alkyl, or $C_1$–$C_3$ haloalkyl;

$R^{22}$ and $R^{25}$ are independently carboxy, ($C_1$–$C_{10}$ alkoxy) carbonyl, ($C_1$–$C_{10}$ haloalkoxy)carbonyl, ($C_3$–$C_{10}$ cycloalkoxy)carbonyl, ($C_3$–$C_{10}$ halocycloalkoxy) carbonyl, carboxy($C_1$–$C_5$ alkoxy)carbonyl, ($C_1$–$C_{10}$ alkoxy)carbonyl ($C_1$–$C_5$ alkoxy)carbonyl, ($C_1$–$C_{10}$ haloalkoxy)carbonyl ($C_1$–$C_5$ alkoxy)carbonyl, ($C_3$–$C_{10}$ cycloalkoxy)carbonyl ($C_1$–$C_5$ alkoxy)carbonyl, ($C_3$–$C_{10}$ alkenoxy)carbonyl ($C_1$–$C_5$ alkoxy)carbonyl, ($C_3$–$C_{10}$ alkynoxy)carbonyl ($C_1$–$C_5$ alkoxy)carbonyl, —CON($R^{84}$)$R^{85}$, or —C(=O)ON($R^{86}$)$R^{87}$;

$R^{72}$ and $R^{75}$ are independently carboxy, ($C_1$–$C_{10}$ alkoxy) carbonyl, ($C_1$–$C_{10}$ haloalkoxy)carbonyl, ($C_3$–$C_{10}$ cycloalkoxy)carbonyl, ($C_3$–$C_{10}$ halocycloalkoxy) carbonyl, carboxy($C_1$–$C_5$ alkoxy)carbonyl, ($C_1$–$C_{10}$ alkoxy)carbonyl ($C_1$–$C_5$ alkoxy)carbonyl, ($C_1$–$C_{10}$ haloalkoxy)carbonyl ($C_1$–$C_5$ alkoxy)carbonyl, ($C_3$–$C_{10}$ cycloalkoxy)carbonyl ($C_1$–$C_5$ alkoxy)carbonyl, ($C_3$–$C_{10}$ alkenoxy)carbonyl ($C_1$–$C_5$ alkoxy)carbonyl, ($C_3$–$C_{10}$ alkynoxy)carbonyl ($C_1$–$C_5$ alkoxy)carbonyl, —CON($R^{184}$$R^{185}$, or —C(=O)ON($R^{186}$)$R^{187}$;

wherein $R^{84}$ and $R^{184}$ are independently hydrogen, $C_1$–$C_5$ alkyl, $C_1$–$C_5$ haloalkyl, $C_3$–$C_8$ cycloalkyl, $C_3$–$C_6$ alkenyl, $C_3$–$C_6$ alkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl; $R^{85}$ and $R^{185}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{84}$ and $R^{85}$ may be combined at their ends to form, together with the adjacent nitrogen atom, a 3- to 7-membered saturated ring containing zero to one oxygen atom or NH group in the ring; or $R^{184}$ and $R^{185}$ may be combined at their ends to form, together with the adjacent nitrogen atom, a 3- to 7-membered saturated ring containing zero to one oxygen atom or NH group in the ring;

$R^{86}$ and $R^{186}$ are independently hydrogen, $C_1$–$C_5$ alkyl, $C_1$–$C_5$ haloalkyl, $C_3$–$C_8$ cycloalkyl, $C_3$–$C_6$ alkenyl, $C_3$–$C_6$ alkynyl, carboxy $C_1$–$C_5$ alkyl, ($C_1$–$C_{10}$ alkoxy) carbonyl $C_1$–$C_5$ alkyl ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl; $R^{87}$ and $R^{187}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{86}$ and $R^{87}$ may be combined at their ends to form, together with the adjacent nitrogen atom, a 3- to 7-membered saturated ring; or $R^{186}$ and $R^{187}$ may be combined at their ends to form, together with the adjacent nitrogen atom, a 3- to 7-membered saturated ring;

$R^{23}$, $R^{24}$, $R^{73}$, and $R^{74}$ are independently hydrogen, halogen, $C_1$–$C_3$ alkyl, or $C_1$–$C_3$ haloalkyl; and Q is any one group of Q1 to Q23 of the general formula:

Q1

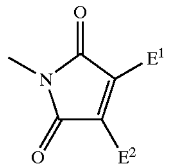

Q2

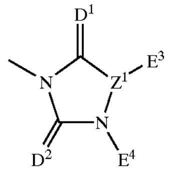

Q3

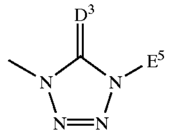

Q4

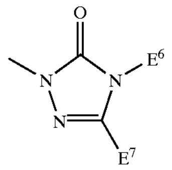

Q5

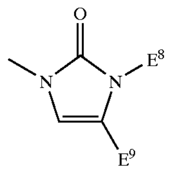

Q6

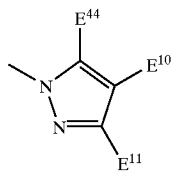

-continued
Q7
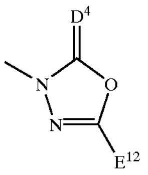
Q8
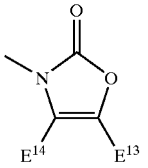
Q9
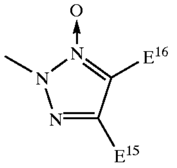
Q10
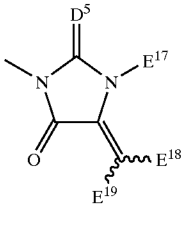
Q11
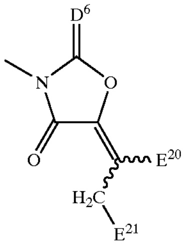
Q12
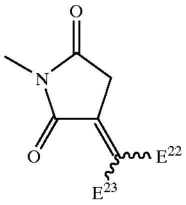
Q13
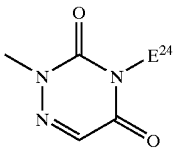
Q14
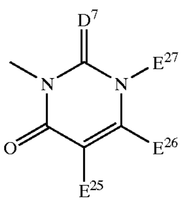
-continued
Q15
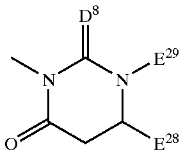
Q16
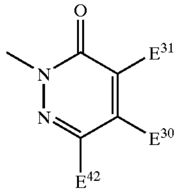
Q17
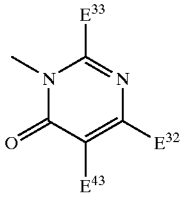
Q18
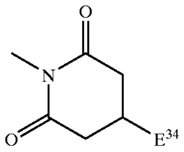
Q19
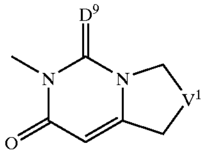
Q20
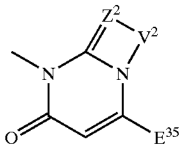
Q21
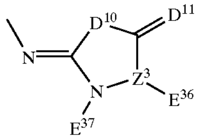
Q22
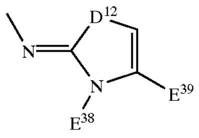
Q23
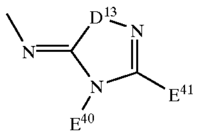
wherein:
in Q1, $E^1$ and $E^2$ are independently $C_1$–$C_6$ alkyl optionally substituted with halogen, or $C_3$–$C_6$ cycloalkyl optionally substituted with halogen; or $E^1$ and $E^2$ may be combined at their ends to form, together with the atoms attached thereto, a 4- to 7-membered unsaturated ring containing zero to two O, S, SO, $SO_2$, or NH groups in the ring (which unsaturated ring includes no aromatic rings), and the ring may optionally be substituted with methyl or halogen;

in Q2, $E^3$ and $E^4$ are independently $C_1$–$C_6$ alkyl optionally substituted with halogen, or $C_3$–$C_6$ cycloalkyl optionally substituted with halogen; or $E^3$ and $E^4$ may be combined at their ends to form, together with the atoms attached thereto, a 4- to 7-membered saturated or unsaturated ring containing zero to two O, S, SO, $SO_2$, or NH groups in the ring, and the ring may optionally be substituted with methyl or halogen; $D^1$ and $D^2$ are independently oxygen or sulfur; and $Z^1$ is nitrogen or CH;

in Q3, $E^5$ is hydrogen or $C_1$–$C_6$ alkyl optionally substituted with halogen; and $D^3$ is oxygen or sulfur;

in Q4, $E^6$ and $E^7$ are independently hydrogen, $C_1$–$C_6$ alkyl optionally substituted with halogen, or $C_3$–$C_6$ cycloalkyl optionally substituted with halogen; or $E^6$ and $E^7$ may be combined at their ends to form, together with the atoms attached thereto, a 4- to 7-membered saturated or unsaturated ring containing zero to two O, S, SO, $SO_2$, or NH groups in the ring, and the ring may optionally be substituted with methyl or halogen;

in Q5, $E^8$ and $E^9$ are independently hydrogen, $C_1$–$C_6$ alkyl optionally substituted with halogen, or $C_3$–$C_6$ cycloalkyl optionally substituted with halogen; or $E^8$ and $E^9$ may be combined at their ends to form, together with the atoms attached thereto, a 4- to 7-membered saturated or unsaturated ring containing zero to two O, S, SO, $SO_2$, or NH groups in the ring, and the ring may optionally be substituted with methyl or halogen;

in Q6, $E^{10}$ is hydrogen, $C_1$–$C_6$ alkyl optionally substituted with halogen, or $C_1$–$C_3$ alkoxy optionally substituted with halogen; $E^{11}$ is hydrogen or $C_1$–$C_6$ alkyl optionally substituted with halogen; or $E^{10}$ and $E^{11}$ may be combined at their ends to form, together with the atoms attached thereto, a 4- to 7-membered saturated or unsaturated ring containing zero to two O, S, SO, $SO_2$, or NH groups in the ring (which unsaturated ring includes no aromatic rings), and the ring may optionally be substituted with methyl or halogen; and $E^{44}$ is halogen or $C_1$–$C_3$ alkyl;

in Q7, $E^{12}$ is $C_1$–$C_6$ alkyl optionally substituted with halogen; and $D^4$ is oxygen or sulfur;

in Q8, $E^{13}$ is $C_1$–$C_6$ alkyl optionally substituted with halogen; and $E^{14}$ is hydrogen or halogen;

in Q9, $E^{15}$ is hydrogen or $C_1$–$C_6$ alkyl; $E^{16}$ is $C_1$–$C_6$ alkyl optionally substituted with halogen; or $E^{15}$ and $E^{16}$ may be combined at their ends to form, together with the atoms attached thereto, a 4- to 7-membered saturated or unsaturated ring containing zero to two O, S, SO, $SO_2$, or NH groups in the ring (which unsaturated ring includes no aromatic rings), and the ring may optionally be substituted with methyl or halogen;

in Q10, $E^{17}$, $E^{18}$, and $E^{19}$ are independently hydrogen or $C_1$–$C_6$ alkyl; and $D^5$ is oxygen or sulfur;

in Q11, $E^{20}$ and $E^{21}$ are independently hydrogen or $C_1$–$C_6$ alkyl; and $D^6$ is oxygen or sulfur;

in Q12, $E^{22}$ and $E^{23}$ are independently hydrogen or $C_1$–$C_6$ alkyl;

in Q13, $E^{24}$ is hydrogen or $C_1$–$C_3$ alkyl;

in Q14, $E^{25}$ is hydrogen, $C_1$–$C_3$ alkyl, or halogen; $E^{26}$ is $C_1$–$C_3$ alkyl optionally substituted with halogen; $E^{27}$ is hydrogen, amino, $C_1$–$_6$ alkyl, $C_3$–$C_6$ alkenyl, $C_3$–$C_6$ alkynyl, or optionally substituted benzyl; and $D^7$ is oxygen or sulfur;

in Q15, $E^{28}$ is $C_1$–$C_3$ alkyl optionally substituted with halogen; $E^{29}$ is hydrogen, amino, $C_1$–$C_6$ alkyl, $C_1$–$C_6$ alkenyl, $C_3$–$C_6$ alkynyl, or optionally substituted benzyl; and $D^8$ is oxygen or sulfur;

in Q16, $E^{30}$ is $C_1$–$C_3$ alkyl optionally substituted with halogen, $E^{31}$ is hydrogen or $C_1$–$C_3$ alkyl optionally substituted with halogen; or $E^{30}$ and $E^{31}$ may be combined at their ends to form, together with the atoms attached thereto, a 4- to 7-membered saturated or unsaturated ring containing zero to two O, S, SO, $SO_2$, or NH groups in the ring (which unsaturated ring includes no aromatic rings), and the ring may optionally be substituted with methyl or halogen; and $E^{42}$ is hydrogen or $C_1$–$C_3$ alkyl optionally substituted with halogen;

in Q17, $E^{32}$ is $C_1$–$C_3$ alkyl optionally substituted with halogen; $E^{33}$ is hydrogen, halogen, amino, $C_1$–$C_3$ alkyl optionally substituted with halogen, $C_1$–$C_3$ alkoxy optionally substituted with halogen, or $C_1$–$C_3$ alkylthio optionally substituted with halogen; and $E^{43}$ is hydrogen or $C_1$–$C_3$ alkyl optionally substituted with halogen;

in Q18, $E^{34}$ is $C_1$–$C_3$ alkyl optionally substituted with halogen;

in Q19, $D^9$ is oxygen or sulfur; and $V^1$ is $—CH_2—$, $—CH_2—CH_2—$, or $—CH_2—CH_2—CH_2—$;

in Q20, $E^{35}$ is $C_1$–$C_3$ alkyl optionally substituted with halogen; $Z^2$ is nitrogen or CH; and $V^2$ is $—CH_2—CH_2—$, —CH=CH—, —N=CH—, —CH=N—, or —N=N—;

in Q21, $E^{36}$ and $E^{37}$ are independently $C_1$–$C_6$ alkyl; or $E^{36}$ and $E^{37}$ may be combined at their ends to form, together with the atoms attached thereto, a 4- to 7-membered saturated or unsaturated ring containing zero to two O, S, SO, $SO_2$, or NH groups in the ring, and the ring may optionally be substituted with methyl or halogen; $D^{10}$ and $D^{11}$ are independently oxygen or sulfur; and $Z^3$ is nitrogen or CH;

in Q22, $E^{38}$ is hydrogen or $C_1$–$C_6$ alkyl; $E^{39}$ is $C_1$–$C_3$ alkyl optionally substituted with halogen; or $E^{38}$ and $E^{39}$ may be combined at their ends to form, together with the atoms attached thereto, a 4- to 7-membered saturated or unsaturated ring containing zero to two O, S, SO, $SO_2$, or NH groups in the ring, and the ring may optionally be substituted with methyl or halogen; and $D^{12}$ is oxygen or sulfur; and in Q23, $E^{40}$ is hydrogen or $C_1$–$C_6$ alkyl; $E^{41}$ is $C_1$–$C_3$ alkyl, or $C_3$–$C_6$ cycloalkyl; or $E^{40}$ and $E^{41}$ may be combined at their ends to form, together with the atoms attached thereto, a 4- to 7-membered saturated or unsaturated ring containing zero to two O, S, SO, $SO_2$, or NH groups in the ring, and the ring may optionally be substituted with methyl or halogen; and $D^{13}$ is oxygen or sulfur.

The present invention further provides herbicides containing them as active ingredients, and condensed heterocyclic compounds of general formula II:

[II]

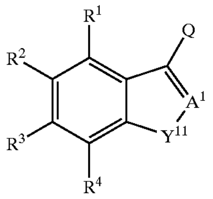

wherein $A^1$ is C—$R^{31}$ and $Y^{11}$ is oxygen, sulfur, or N—$R^{32}$; wherein $R^{31}$ is nitro, amino, cyano, carboxyl, or ($C_1$–$C_3$ alkoxy)carbonyl, and $R^{32}$ is hydrogen, $C_1$–$C_5$ alkyl, $C_3$–$C_6$ alkenyl, or $C_3$–$C_6$ alkynyl; and Q, $R^1$, $R^2$, $R^3$, and $R^4$ are as defined above, which heterocyclic compounds are useful as intermediates for the production of the present compounds.

Mode for Carrying Out the Invention

For the groups represented by $R^{142}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_6$ alkenyl may include allyl and 1-methylpropenyl; and $C_3$–$C_6$ alkynyl may include propargyl and 1-methylpropynyl.

For the groups-represented by $R^{143}$, $C_1$–$C_3$ alkyl may include methyl, ethyl, propyl, and isopropyl; $C_1$–$C_3$ haloalkyl may include trifluoromethyl and difluoromethyl; and $C_1$–$C_5$ alkoxy may include methoxy, ethoxy, propoxy, and isopropoxy.

For the groups represented by $R^{145}$ or $R^{146}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; ($C_1$–$C_5$ alkyl)carbonyl may include acetyl, ethylcarbonyl, propylcarbonyl, isopropylcarbonyl, and butylcarbonyl; ($C_1$–$C_5$ haloalkyl) carbonyl may include trifluoroacetyl, difluoroacetyl, chlorodifluoroacetyl, and dichloroacetyl; and ($C_1$–$C_5$ alkoxy)carbonyl may include methoxycarbonyl, ethoxycarbonyl, and isopropoxycarbonyl.

For the groups represented by $R^{147}$ or $R^{148}$, $C_1$–$C_5$ alkyl may include methyl, ethyl, propyl, isopropyl, butyl, isobutyl, and amyl.

For the elements or groups represented by $R^{152}$, halogen may include fluorine, chlorine, bromine, and iodine; and $C_1$–$C_3$ alkyl may include methyl, ethyl, propyl, and isopropyl.

For the groups represented by $R^{153}$, $C_1$–$C_3$ alkyl may include methyl, ethyl, propyl, and isopropyl; $C_1$–$C_3$ haloalkyl may include trifluoromethyl and difluoromethyl; and $C_1$–$C_5$ alkoxy may include methoxy, ethoxy, propoxy, and isopropoxy.

For the groups represented by $R^{156}$ or $R^{157}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; ($C_1$–$C_5$ alkyl)carbonyl may include acetyl, ethylcarbonyl, propylcarbonyl, isopropylcarbonyl, and butylcarbonyl; ($C_1$–$C_5$ haloalkyl) carbonyl may include trifluoroacetyl, difluoroacetyl, chlorodifluoroacetyl, and dichloroacetyl; and ($C_1$–$C_5$ alkoxy)carbonyl may include methoxycarbonyl, ethoxycarbonyl, and isopropoxycarbonyl.

For the groups represented by $R^{154}$ or $R^{155}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; ($C_1$–$C_5$ alkyl)carbonyl may include acetyl, ethylcarbonyl, propylcarbonyl, isopropylcarbonyl, and butylcarbonyl; ($C_1$–$C_5$ haloalkyl) carbonyl may include trifluoroacetyl, difluoroacetyl, chlorodifluoroacetyl, and dichloroacetyl; and ($C_1$–$C_5$ alkoxy)carbonyl may include methoxycarbonyl, ethoxycarbonyl, and isopropoxycarbonyl.

For the groups or elements represented by $R^{141}$, $C_1$–$C_3$ alkyl may include methyl, ethyl, and isopropyl; and halogen may include fluorine, chlorine, bromine, and iodine.

For groups represented by $R^{31}$, ($C_1$–$C_3$ alkoxy)carbonyl may include methoxycarbonyl, ethoxycarbonyl, propoxycarbonyl, and isopropoxycarbonyl.

For the groups represented by $R^{32}$, $C_1$–$C_5$ alkyl may include methyl, ethyl, propyl, isopropyl, butyl, isobutyl, and amyl; $C_3$–$C_6$ alkenyl may include allyl and 1-methylpropenyl; and $C_3$–$C_6$ alkynyl may include propargyl and 1-methylpropynyl.

For the elements or groups represented by $R^1$, halogen may include fluorine, chlorine, bromine, and iodine; $C_1$–$C_3$ alkyl may include methyl and ethyl; and $C_1$–$C_3$ haloalkyl may include trifluoromethyl and difluoromethyl.

For the elements or groups represented by $R^2$ or $R^3$, halogen may include fluorine, chlorine, bromine, and iodine; $C_1$–$C_{11}$ alkyl may include methyl, ethyl, and isopropyl; and $C_1$–$C_{11}$ haloalkyl may include trichloromethyl, trifluoromethyl, chlorodifluoromethyl, difluoromethyl, pentafluoroethyl, and 1,1-difluoroethyl.

For the elements or groups represented by $R^4$, halogen may include fluorine, chlorine, bromine, and iodine; $C_1$–$C_3$ alkyl may include methyl and ethyl; and $C_1$–$C_3$ haloalkyl may include trifluoromethyl and difluoromethyl.

For the groups represented by $R^9$ or $R^{59}$, $C_1$–$C_5$ alkyl may include methyl, ethyl, propyl, isopropyl, isobutyl, butyl, t-butyl (wherein "t" means "tertiary"; this also holds below), and isoamyl; ($C_1$–$C_5$ alkyl)carbonyl may include acetyl, ethylcarbonyl, propylcarbonyl, isopropylcarbonyl, and butylcarbonyl; and ($C_1$–$C_5$ alkoxy)carbonyl may include methoxycarbonyl, ethoxycarbonyl, isopropoxycarbonyl, butoxycarbonyl, and t-butoxycarbonyl.

For the groups represented by $R^{10}$, $R^{11}$, $R^{12}$, $R^{60}$, $R^{61}$, or $R^{62}$, $C_1$–$C_{10}$ alkyl may include methyl, ethyl, propyl, isopropyl, isobutyl, butyl, t-butyl, isoamyl, pentyl, hexyl, heptyl, and octyl; $C_1$–$C_{10}$ haloalkyl may include 2-fluoroethyl, 2-chloroethyl, 2-bromoethyl, 3-chlorobutyl, 3-bromobutyl, difluoromethyl, and 2,2,2-trifluoroethyl; $C_3$–$C_{10}$ cycloalkyl may include cyclopentyl and cyclohexyl; $C_1$–$C_{10}$ halocycloalkyl may include 4,4,-difluorocyclopentyl and 3-chlorocyclohexyl; $C_3$–$C_{10}$ cycloalkyl $C_1$–$C_3$ alkyl may include cyclopropylmethyl, cyclopentylmethyl, and cyclohexylmethyl; $C_3$–$C_{10}$ alkenyl may include allyl, 1-methyl-2-propenyl, 3-butenyl, 2-butenyl, 3-methyl-2-butenyl, and 2-methyl-3-butenyl; $C_3$–$C_{10}$ haloalkenyl may include 2-chloro-2-propenyl and 3,3-dichloro-2-propenyl; $C_3$–$C_{10}$ alkynyl may include propargyl, 1-methyl-2-propynyl, 2-butynyl, 3-butynyl, and 1,1-dimethyl-2-propynyl; $C_3$–$C_{10}$ haloalkynyl may include 3-iodo-2-propynyl and 3-bromo-2-propynyl; cyano $C_1$–$C_6$ alkyl may include cyanomethyl and cyanoethyl; ($C_1$–$C_5$ alkyl)carbonyl may include acetyl, ethylcarbonyl, propylcarbonyl, isopropylcarbonyl, and butylcarbonyl; ($C_1$–$C_5$ haloalkyl)carbonyl may include trifluoroacetyl, difluoroacetyl, chlorodifluoroacetyl, and dichloroacetyl; ($C_3$–$C_{10}$ cycloalkyl)carbonyl may include cyclopropylcarbonyl and cyclopentylcarbonyl; ($C_1$–$C_5$ alkyl)carbonyl $C_1$–$C_5$ alkyl may include 2-oxopropyl, 3-methyl-2-oxobutyl, and 3-oxopentyl; ($C_1$–$C_5$ haloalkyl)carbonyl $C_1$–$C_5$ alkyl may include 3,3,3-trifluoro-2-oxopropyl; hydroxy $C_1$–$C_5$ alkyl may include 2-hydroxyethyl and 4-hydroxybutyl; $C_1$–$C_5$ alkoxy $C_1$–$C_5$ alkyl may include methoxymethyl, 1-methoxyethyl, and ethoxymethyl; $C_1$–$C_5$ alkylthio $C_1$–$C_5$ alkyl may include methylthiomethyl and methylthioethyl; ($C_1$–$C_5$ alkoxy)carbonyl may include methoxycarbonyl, ethoxycarbonyl, isopropoxycarbonyl, butoxycarbonyl, and t-butoxycarbonyl; carboxy $C_1$–$C_5$ alkyl may include carboxymethyl, 1-carboxyethyl, and 2-carboxyethyl; ($C_1$–$C_{10}$ alkoxy)carbonyl $C_1$–$C_5$ alkyl may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-butoxycarbonylethyl; ($C_1$–$C_{10}$ haloalkoxy)carbonyl $C_1$–$C_5$ alkyl may include 2-chloroethoxycarbonylmethyl, 2,2,2-trifluoroethoxycarbonylmethyl, 3-bromopropoxycarbonylmethyl, 1-(2-chloroethoxy)carbonylethyl, and 1-(2,2,2-trifluoroethoxy)carbonyl; ($C_3$–$C_{10}$ cycloalkoxy)carbonyl $C_1$–$C_5$ alkyl may include cyclopentyloxycarbonylmethyl, cyclohexyloxycarbonylmethyl, 1-cyclopentyloxycarbonylethyl, and 1-cyclohexyloxycarbonylethyl; ($C_3$–$C_{10}$ halocycloalkoxy)carbonyl $C_1$–$C_5$ alkyl may include 4-fluorocyclohexyloxycarbonylmethyl; ($C_3$–$C_{10}$ alkenoxy)carbonyl $C_1$–$C_5$ alkyl may include allyoxycarbonylmethyl, 1-methyl-2-propenyloxycarbonylmethyl, 1-allyloxycarbonylethyl, and 1-(1-methyl-2-propenyloxy)carbonylethyl; ($C_3$–$C_{10}$ alkynoxy)carbonyl $C_1$–$C_5$ alkyl may include propargyloxycarbonylmethyl, 1-methyl-2-propynyloxycarbonylmethyl, 1-propargyloxycarbonylethyl, 1-(1-methyl-2-propynyloxy)carbonylethyl; carboxy($C_1$–$C_5$ alkoxy)carbonyl $C_1$–$C_5$ alkyl may include carboxymethoxycarbonylmethyl, 1-carboxyethoxycarbonylmethyl, 1-carboxy-1-methylethoxycarbonylmethyl, 1-(carboxymethoxycarbonyl)ethyl, 1-(1-carboxyethoxycarbonyl)ethyl, and 1-(1-carboxy-1-methylethoxycarbonyl)ethyl; ($C_1$–$C_{10}$ alkoxy)carbonyl($C_1$–$C_5$ alkoxy)carbonyl $C_1$–$C_5$ alkyl may include methoxycarbonylmethoxycarbonylmethyl, 1-methoxycarbonylethoxycarbonylmethyl, 1-methoxycarbonyl-1-methylethoxycarbonylmethyl, 1-(methoxycarbonylmethoxycarbonyl)ethyl, 1-(1-methoxycarbonylethoxycarbonyl)ethyl, 1-(1-methoxycarbonyl-1-methylethoxycarbonyl)ethyl, ethoxycarbonylmethoxycarbonylmethyl, 1-ethoxycarbonylethoxycarbonylmethyl, 1-ethoxycarbonyl-1-methylethoxycarbonylmethyl, 1-(ethoxycarbonylmethoxycarbonyl)ethyl, 1-(1-ethoxycarbonylethoxycarbonyl)ethyl, 1-(1-ethoxycarbonyl-1-methylethoxycarbonyl)ethyl, isopropoxycarbonylmethoxycarbonylmethyl, 1-isopropoxycarbonylethoxycarbonylmethyl, 1-isopropoxycarbonyl-1-methylethoxycarbonylmethyl, 1-(isopropoxycarbonylmethoxycarbonyl)ethyl, 1-(1-isopropoxycarbonylethoxycarbonyl)ethyl, and 1-(1-isopropoxycarbonyl-1-methylethoxycarbonyl)ethyl; ($C_1$–$C_{10}$ haloalkoxy)carbonyl($C_1$–$C_5$ alkoxy)carbonyl $C_1$–$C_5$ alkyl may include 2-chloroethoxycarbonylmethoxycarbonylmethyl, 1-(2-chloroethoxycarbonyl)ethoxycarbonylmethyl, 1-(2-chloroethoxycarbonyl)-1-methylethoxycarbonylmethyl, 1-(2-chloroethoxycarbonylmethoxycarbonyl)ethyl, 1-{1-(2-chloroethoxycarbonyl)ethoxycarbonyl}ethyl, and 1-{1-(2-chloroethoxycarbonyl)-1-methylethoxycarbonyl}-ethyl; ($C_3$–$C_{10}$ cycloalkoxy)carbonyl($C_1$–$C_5$ alkoxy)carbonyl $C_1$–$C_5$ alkyl may include cyclopentyloxycarbonylmethoxycarbonylmethyl, 1-cyclopentyloxycarbonylethoxycarbonylmethyl, 1-cyclopentyloxycarbonyl-1-methylethoxycarbonylmethyl, 1-(cyclopentyloxycarbonylmethoxycarbonyl)ethyl, 1-(1-cyclopentyloxycarbonylethoxycarbonyl)ethyl, 1-(1-cyclopentyloxycarbonyl-1-methylethoxycarbonyl)ethyl, cyclohexyloxycarbonylmethoxycarbonylmethyl, 1-cyclohexyloxycarbonylethoxycarbonylmethyl, 1-cyclohexyloxycarbonyl-1-ethylethoxycarbonylmethyl, 1-(cyclohexyloxycarbonylmethoxycarbonyl)ethyl, 1-(1-cyclohexyloxycarbonylethoxycarbonyl)ethyl, and 1-(1-cyclohexyloxycarbonyl-1-methylethoxycarbonyl)ethyl; ($C_3$–$C_{10}$ alkenoxy)carbonyl($C_1$–$C_5$ alkoxy)carbonyl $C_1$–$C_5$ alkyl may include allyloxycarbonylmethoxycarbonylmethyl, 1-allyloxycarbonylethoxycarbonylmethyl, 1-allyloxycarbonyl-1-methylethoxycarbonylmethyl, 1-(allyloxycarbonylmethoxycarbonyl)ethyl, 1-(1-allyloxycarbonylethoxycarbonyl)ethyl, and 1-(1-allyloxycarbonyl-1-methylethoxycarbonyl)ethyl; ($C_3$–$C_{10}$ alkynoxy)carbonyl($C_1$–$C_5$ alkoxy)carbonyl $C_1$–$C_5$ alkyl may include propargyloxycarbonylmethoxycarbonylmethyl, 1-propargyloxycarbonylethoxycarbonylmethyl, 1-propargyloxycarbonyl-1-methylethoxycarbonylmethyl, 1-(propargyloxycarbonylmethoxycarbonyl)ethyl, 1-(1-propargyloxycarbonylethoxycarbonyl)ethyl, and 1-(1-propargyloxycarbonyl-1-methylethoxycarbonyl)ethyl; carboxy($C_1$–$C_5$ alkyl)carbonyl may include carboxymethylcarbonyl, carboxyethylcarbonyl, 1-carboxy-1-methylethylcarbonyl, 2-carboxyethylcarbonyl, 3-carboxypropylcarbonyl, and 3-carboxy-1-methylpropylcarbonyl; ($C_1$–$C_{10}$ alkoxy)carbonyl($C_1$–$C_5$ alkyl)carbonyl may include methoxycarbonylmethylcarbonyl, 1-methoxycarbonylethylcarbonyl, 1-methoxycarbonyl-1-methylethylcarbonyl, 2-methoxycarbonylethylcarbonyl, 3-methoxycarbonylpropylcarbonyl, 3-methoxycarbonyl-1-methylpropylcarbonyl, ethoxycarbonylmethylcarbonyl, 1-ethoxycarbonylethylcarbonyl, 1-ethoxycarbonyl-1-methylethylcarbonyl, 2-ethoxycarbonylethylcarbonyl, 3-ethoxycarbonylpropylcarbonyl, and 3-ethoxycarbonyl-1-methylpropylcarbonyl; ($C_1$–$C_{10}$ haloalkoxy)carbonyl($C_1$–$C_5$ alkyl)carbonyl may include 2-chloroethoxycarbonylmethylcarbonyl, 2,2,2-trifluoroethoxycarbonylmethylcarbonyl, 3-bromopropoxycarbonylmethylcarbonyl, 1-(2-chloroethoxy)carbonylethylcarbonyl, and 1-(2,2,2-trifluoroethoxy)carbonylethylcarbonyl; $C_1$–$C_5$ alkylsulfonyl may include methylsulfonyl, ethylsulfonyl, propylsulfonyl, isopropylsulfonyl, and butylsulfonyl; $C_1$–$C_5$ haloalkylsulfonyl may include chloromethylsulfonyl, and trifluoromethylsulfonyl; optionally substituted benzyl may include benzyl; and optionally substituted phenyl may include phenyl.

For the groups represented by $R^{13}$ or $R^{63}$, $C_1$–$C_{10}$ alkyl may include methyl, ethyl, propyl, isopropyl, butyl, and isoamyl; $C_1$–$C_{10}$ haloalkyl may include trifluoromethyl; carboxy $C_1$–$C_5$ alkyl may include carboxymethyl, carboxyethyl, 1-carboxyethyl, and 2-carboxypropyl; ($C_1$–$C_{10}$ alkoxy)carbonyl $C_1$–$C_5$ alkyl may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxyvcarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-butoxycarbonylethyl; ($C_1$–$C_{10}$ haloalkoxy)carbonyl $C_1$–$C_5$ alkyl may include 2-chloroethoxycarbonylmethyl, 2,2,2-trifluoroethoxycarbonylmethyl, 3-bromopropoxycarbonylmethyl, 1-(2-chloroethoxy) carbonylethyl, and 1-(2,2,2-trifluoroethoxy)carbonylethyl; ($C_3$–$C_{10}$ cycloalkoxy)carbonyl $C_1$–$C_5$ alkyl may include cyclopentyloxycarbonylmethyl, cyclohexyloxycarbonylmethyl, 1-cyclopentyloxycarbonylethyl, and 1-cyclohexyloxycarbonylethyl; and ($C_3$–$C_{10}$ halocycloalkoxy)carbonyl $C_1$–$C_5$ alkyl may include 4-fluorocyclo hexyloxycarbonylmethyl.

For the groups represented by $R^{14}$ or $R^{64}$, $C_1$–$C_{10}$ alkyl may include methyl, ethyl, propyl, isopropyl, isobutyl, butyl, t-butyl, isoamyl, pentyl, hexyl, heptyl, and octyl; $C_1$–$C_{10}$ haloalkyl may include 2-fluoroethyl, 2-chloroethyl, 2-bromoethyl, 3-chlorobutyl, 3-bromobutyl, difluoromethyl, and 2,2,2-trifluoroethyl; $C_3$–$C_{10}$ cycloalkyl may include cyclopentyl and cyclohexyl; $C_3$–$C_{10}$ halocycloalkyl may include 4,4,-difluorocyclopentyl and 3-chlorocyclohexyl; $C_3$–$C_{10}$ cycloalkyl $C_1$–$C_3$ alkyl may include cyclopropylmethyl, cyclopentylmethyl, and cyclohexylm-ethyl; $C_3$–$C_{10}$ alkenyl may include allyl, 1-methyl-2-propenyl, 3-butenyl, 2-butenyl, 3-methyl-2-butenyl, and 2-methyl-3-butenyl; $C_3$–$C_{10}$ haloalkenyl may include 2-chloro-2-propenyl, and 3,3-dichloro-2-propenyl; $C_3$–$C_{10}$ alkynyl may include propargyl, 1-methyl-2-propynyl, 2-butynyl, 3-butynyl, and 1,1-dimethyl-2-propynyl; $C_3$–$C_{10}$ haloalkynyl may include 3-iodo-2-propynyl, and 3-bromo-2-propynyl; carboxy $C_1$–$C_5$ alkyl may include carboxymethyl, 1-carboxyethyl, 2-carboxyethyl, and 1-carboxy-1-methylethyl; ($C_1$–$C_{10}$ alkoxy)carbonyl $C_1$–$C_5$ alkyl may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonyl methyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, 1-t-butoxycarbonylethyl, 1-methoxycarbonyl-1-methylethyl, 1-ethoxycarbonyl-1-methylethyl, 1-propoxycarbonyl-1-methylethyl, 1-isopropoxycarbonyl-1-methylethyl, 1-butoxycarbonyl-1-methylethyl, 1-isobutoxycarbonyl-1-methylethyl, 1-t-butoxycarbonyl-1-methylethyl, 1-amyloxycarbonyl-1-methylethyl, 1-isoamyloxycarbonyl-1-methylethyl, and 1-t-butoxycarbonyl-1-methylethyl; ($C_1$–$C_{10}$ haloalkoxy)carbonyl $C_1$–$C_5$ alkyl may include 2-chloroethoxycarbonylmethyl, 2,2,2-trifluoroethoxycarbonylmethyl, 3-bromopropoxycarbonylmethyl, 1-(2-chloroethoxy) carbonylethyl, 1-(2,2,2-trifluoroethoxy)carbonylethyl, 1-(2-chloroethoxy)carbonyl-1-methylethyl, and 1-(2,2,2-trifluoroethoxy)carbonyl-1-methylethyl; ($C_3$–$C_{10}$ cycloalkoxy)carbonyl $C_1$–$C_5$ alkyl may include cyclopentyloxycarbonylmethyl, cyclohexyloxycarbonylmethyl, 1-cyclopentyloxycarbonylethyl, 1-cyclohexyloxycarbonylethyl, 1-cyclopentyloxycarbonyl-1-methylethyl, and 1-cyclohexyloxycarbonyl-1-methylethyl; ($C_3$–$C_{10}$ halocycloalkoxy)carbonyl $C_1$–$C_5$ alkyl may include 4-fluorocyclohexyloxycarbonylmethyl, and 1-(4-fluorocyclohexyloxycarbonyl)-1-methylethyl; ($C_3$–$C_{10}$ alkenoxy)carbonyl $C_1$–$C_5$ alkyl may include allyloxycarbonylmethyl, 1-methyl-2-propenyloxycarbonylmethyl, 1-allyloxycarbonylethyl, 1-(1-methyl-2-propenyloxy)carbonylethyl, 1-allyloxycarbonyl-1-methylethyl, and 1-(1-methyl-2-propenyloxy)carbonyl-1-methylethyl; ($C_3$–$C_{10}$ alkynoxy)carbonyl $C_1$–$C_5$ alkyl may include propargyloxycarbonylmethyl, 1-methyl-2-propynyloxycarbonylmethyl, 1-propargyloxycarbonylethyl, 1-(1-methyl-2-propynyloxy)carbonylethyl, 1-propargyloxycarbonyl-1-methylethyl, and 1-(1-methyl-2-propynyloxy)carbonyl-1-methylethyl; optionally substituted benzyl may include benzyl; and optionally substituted phenyl may include phenyl.

For the groups represented by $R^{15}$ or $R^{65}$, $C_1$–$C_{10}$ alkyl may include methyl, ethyl, propyl, isopropyl, isobutyl, butyl, t-butyl, isoamyl, pentyl, hexyl, heptyl, and octyl; $C_1$–$C_{10}$ haloalkyl may include 2-fluoroethyl, 2-chloroethyl, 2-bromoethyl, 3-chlorobutyl, 3-bromobutyl, difluoromethyl, and 2,2,2-trifluoroethyl; $C_3$–$C_{10}$ cycloalkyl may include cyclopentyl, and cyclohexyl; $C_3$–$C_{10}$ cycloalkyl $C_1$–$C_3$ alkyl may include cyclopropylmethyl, cyclopentylmethyl, and cyclohexylmethyl; $C_3$–$C_{10}$ alkenyl may include allyl, 1-methyl-2-propenyl, 3-butenyl, 2-butenyl, 3-methyl-2-butenyl, and 2-methyl-3-butenyl; $C_3$–$C_{10}$ alkynyl may include propargyl, 1-methyl-2-propynyl, 2-butynyl, 3-butynyl, and 1,1-dimethyl-2-propynyl; cyano $C_1$–$C_6$ alkyl may include cyanomethyl, and cyanoethyl; carboxy$C_1$–$C_5$ alkyl may include carboxymethyl, 1-carboxyethyl, and 2-carboxyethyl; ($C_1$–$C_{10}$ alkoxy)carbonyl $C_1$–$C_5$ alkyl may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-butoxycarbonylethyl; optionally substituted benzyl may include benzyl; and optionally substituted phenyl may include phenyl.

For the groups represented by $R^{16}$ or $R^{66}$, $C_1$–$C_{10}$ alkyl may include methyl, ethyl, propyl, isopropyl, isobutyl, butyl, t-butyl, isoamyl, pentyl, hexyl, heptyl, and octyl; and $C_1$–$C_{10}$ haloalkyl may include 2-fluoroethyl, 2-chloroethyl, 2-bromoethyl, 3-chlorobutyl, 3-bromobutyl, difluoromethyl, and 2,2,2-trifluoroethyl.

The 3- to 7-membered saturated ring, which is formed by combining $R^{15}$ and $R^{16}$ or $R^{65}$ and $R^{66}$ at their ends, together with the adjacent nitrogen atom, and which contains zero to one oxygen atom or NH group in the ring, may include aziridine ring, azetidine ring, pyrrolidine ring, piperidine ring, morpholine ring, and piperazine ring.

For the groups represented by $R^{17}$, $R^{26}$, $R^{27}$, $R^{67}$, $R^{76}$, or $R^{77}$, $C_1$–$C_{10}$ alkyl may include methyl, ethyl, propyl, isopropyl, isobutyl, butyl, t-butyl, isoamyl, pentyl, hexyl, heptyl, and octyl; $C_1$–$C_{10}$ haloalkyl may include 2-fluoroethyl, 2-chloroethyl, 2-bromoethyl, 3-chlorobutyl, 3-bromobutyl, difluoromethyl, and 2,2,2-trifuoroethyl; $C_3$–$C_{10}$ cycloalkyl may include cyclopentyl, and cyclohexyl; $C_3$–$C_{10}$ cycloalkyl $C_1$–$C_3$ alkyl may include cyclopropylmethyl, cyclopentylmethyl, and cyclohexylmethyl; ($C_1$–$C_6$ alkoxy)carbonyl may include methoxycarbonyl, ethoxycarbonyl, propoxycarbonyl, and isopro-poxycarbonyl; and ($C_1$–$C_6$ alkoxy)carbonylmethyl may include methoxy carbonylmethyl, ethoxycarbonylmethyl, and isopropoxycarbonylmethyl.

For the groups represented by $R^{19}$ or $R^{69}$, $C_1$–$C_{10}$ alkyl may include methyl, ethyl, propyl, isopropyl, isobutyl, butyl, t-butyl, isoamyl, pentyl, hexyl, heptyl, and octyl; $C_1$–$C_{10}$ haloalkyl may include 2-fluoroethyl, 2-chloro-ethyl, 2-bromoethyl, 3-chlorobutyl, 3-bromobutyl, difluoromethyl, and 2,2,2-trifluoroethyl; $C_3$–$C_{10}$ cycloalkyl may include cyclopentyl and cyclohexyl; $C_3$–$C_{10}$ halocycloalkyl may include 4,4,-difluorocyclopentyl and 3-chlorocyclohexyl; $C_3$–$C_{10}$ cycloalkyl $C_1$–$C_3$ alkyl may include cyclopropylmethyl, cyclopentylmethyl, and cyclohexylmethyl; $C_3$–$C_{10}$ alkenyl may include allyl, 1-methyl-2-propenyl, 3-butenyl, 2-butenyl, 3-methyl-2-butenyl, and 2-methyl-3-butenyl; $C_3$–$C_{10}$ haloalkenyl may include 2-chloro-2-propenyl, and 3,3-dichloro-2-propenyl; $C_3$–$C_{10}$ alkynyl may include propargyl, 1-methyl-2-propynyl, 2-butynyl, 3-butynyl, and 1,1-dimethyl-2-propynyl; $C_3$–$C_{10}$ haloalkynyl may include 3-iodo-2-propynyl, and 3-bromo-2-propynyl; cyano $C_1$–$C_6$ alkyl may include cyanomethyl and cyanoethyl; carboxy $C_1$–$C_5$ alkyl may include carboxymethyl, 1-carboxyethyl, and 2-carboxyethyl; ($C_1$–$C_{10}$ alkoxy)carbonyl $C_1$–$C_5$ alkyl may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-butoxycarbonylethyl; ($C_1$–$C_{10}$ haloalkoxy)carbonyl $C_1$–$C_5$ alkyl may include 2-chloroethoxycarbonylmethyl, 2,2,2-trifluoroethoxycarbonylmethyl, 3-bromopropoxycarbonylmethyl, 1-(2-chloroethoxy) carbonylethyl, and 1-(2,2,2-trifluoroethoxy)carbonylethyl; ($C_3$–$C_{10}$ cycloalkoxy)carbonyl $C_1$–$C_5$ alkyl may include cyclopentyloxycarbonylmethyl, cyclohexyloxycarbonylmethyl, 1-cyclopentyloxycarbonylethyl, and 1-cyclohexyloxycarbonylethyl; and ($C_3$–$C_{10}$ halocycloalkoxy)carbonyl $C_1$–$C_5$ alkyl may include 4-fluorocyclohexyloxycarbonylmethyl.

For the elements or groups represented by $R^{21}$ or $R^{71}$, halogen may include fluorine, chlorine, bromine, and iodine; $C_1$–$C_3$ alkyl may include methyl and ethyl; and $C_1$–$C_3$ haloalkyl may include trifluoromethyl.

For the groups represented by $R^{22}$, $R^{25}$, $R^{72}$, or $R^{75}$, ($C_1$–$C_{10}$ alkoxy) carbonyl may include methoxycarbonyl, ethoxycarbonyl, propoxycarbonyl, isopropoxycarbonyl, butoxycarbonyl, t-butoxycarbonyl, amyloxycarbonyl, and isoamyloxycarbonyl; ($C_1$–$C_{10}$ haloalkoxy)carbonyl may include 2-chloroethoxycarbonyl, 2-fluoroethoxycarbonyl, 3-bromopropoxycarbonyl, 3-chlorobutoxycarbonyl, and 5,5-dichloroamyloxycarbonyl; ($C_3$–$C_{10}$ cycloalkoxy) carbonyl may include cyclopentyloxycarbonyl and cyclohexylcarbonyl; ($C_3$–$C_{10}$ halocycloalkoxy)carbonyl may include 4,4-difluorocyclohexyloxycarbonyl; carboxy($C_1$–$C_5$ alkoxy)carbonyl may include carboxymethoxycarbonyl, 1-carboxyethoxycarbonyl, and 1-carboxy-1-methylethoxycarbonyl; ($C_1$–$C_{10}$ alkoxy)carbonyl($C_1$–$C_5$ alkoxy)carbonyl may include methoxycarbonylmethoxycarbonyl, 1-methoxycarbonylethoxycarbonyl, 1-methoxycarbonyl-1-methylethoxycarbonyl, ethoxycarbonylmethoxycarbonyl, 1-ethoxycarbonylethoxycarbonyl, 1-ethoxycarbonyl-1-methylethoxycarbonyl, isopropoxycarbonylmethoxycarbonyl, 1-isopropoxycarbonylethoxycarbonyl, and 1-isopropoxycarbonyl-1-methylethoxycarbonyl; ($C_1$–$C_{10}$ haloalkoxy)carbonyl($C_1$–$C_5$ alkoxy)carbonyl may include 2-chloroethoxycarbonylmethoxycarbonyl, 1-(2-chloroethoxycarbonyl)ethoxycarbonyl, and 1-(2-chloroethoxycarbonyl)-1-methylethoxycarbonyl; ($C_3$–$C_{10}$ cycloalkoxy)carbonyl($C_1$–$C_5$ alkoxy)carbonyl may include cyclopentyloxycarbonylmethoxycarbonyl, 1-cyclopentyloxycarbonylethoxycarbonyl, 1-cyclopentyloxycarbonyl-1-methylethoxycarbonyl, cyclohexyloxycarbonylmethoxycarbonyl, 1-cyclohexyloxycarbonylethoxycarbonyl, and 1-cyclohexyloxycarbonyl-1-methylethoxycarbonyl; ($C_3$–$C_{10}$ alkenoxy)carbonyl($C_1$–$C_5$ alkoxy)carbonyl may include allyloxycarbonylmethoxycarbonyl, 1-allyloxycarbonylethoxycarbonyl, and 1-allyloxycarbonyl-1-methylethoxycarbonyl; and ($C_3$–$C_{10}$ alkynoxy)carbonyl ($C_1$–$C_5$ alkoxy)carbonyl may include propargyloxycarbonylmethoxycarbonyl, 1-propargyloxycarbonylethoxycarbonyl, and 1-propargyloxycarbonyl-1-methylethoxycarbonyl For the elements or groups represented by $R^{23}$, $R^{24}$, $R^{73}$, or $R^{74}$, halogen may include fluorine, chlorine, bromine, and iodine; $C_1$–$C_3$ alkyl may include methyl, and ethyl; and $C_1$–$C_3$ haloalkyl may include trifluoromethyl.

For the elements or groups represented by $R^{43}$, $R^{44}$, $R^{163}$, or $R^{164}$, halogen may include fluorine, chlorine, bromine, and iodine; $C_1$–$C_5$ alkyl may include methyl, ethyl, propyl, isopropyl, butyl, isobutyl, and amyl; and $C_1$–$C_5$ haloalkyl may include trifluoromethyl.

For the groups represented by $R^{45}$, $R^{46}$, $R^{165}$, or $R^{166}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; and $C_3$–$C_6$ alkynyl may include propargyl and 1-methylpropynyl.

The 3- to 7-membered saturated ring, which is formed by combining $R^{45}$, and $R^{46}$ or $R^{165}$ and $R^{166}$ at their ends, together with the adjacent nitrogen atom, may include aziridine ring, azetidine ring, pyrrolidine ring, and piperidine ring.

For the elements and groups represented by $R^{47}$, $R^{48}$, $R^{167}$, or $R^{168}$, halogen may include fluorine, chlorine, bromine, and iodine; $C_1$–$C_5$ alkyl may include methyl, ethyl, propyl, isopropyl, butyl, isobutyl, and amyl; and $C_1$–$C_5$ haloalkyl may include trifluoromethyl.

For the groups represented by $R^{49}$, $R^{50}$, $R^{169}$, or $R^{170}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl, and 1-methylpropenyl; and $C_3$–$C_6$ alkynyl may include propargyl and 1-methylpropynyl.

The 3- to 7-membered ring, which is formed by combining $R^{49}$ and $R^{50}$ or $R^{169}$ and $R^{170}$ at their ends, together with the adjacent nitrogen atom, and which contains zero to one oxygen atom or NH group in the ring, may include aziridine ring, azetidine ring, pyrrolidine ring, piperidine ring, morpholine ring, and piperazine ring.

For the groups represented by $R^{51}$, $R^{52}$, $R^{171}$, or $R^{172}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; and $C_3$–$C_6$ alkynyl may include propargyl and 1-methylpropynyl.

The 3- to 7-membered ring, which is formed by combining $R^{51}$ and $R^{52}$ or $R^{171}$ and $R^{172}$ at their ends, together with the adjacent nitrogen atom, and which contains zero to one oxygen atom or NH group in the ring, may include aziridine ring, azetidine ring, pyrrolidine ring, piperidine ring, morpholine ring, and piperazine ring.

For the groups represented by $R^{53}$, $R^{54}$, $R^{173}$, or $R^{174}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; and $C_3$–$C_6$ alkynyl may include propargyl and 1-methylpropynyl.

The 3- to 7-membered ring, which is formed by combining $R^{53}$ and $R^{54}$ or $R^{173}$ and $R^{174}$ at their ends, together with the adjacent nitrogen atom, and which contains zero to one oxygen atom or NH group in the ring, may include aziridine ring, azetidine ring, pyrrolidine ring, piperidine ring, morpholine ring, and piperazine ring.

For the groups represented by $R^{55}$, $R^{57}$, $R^{175}$, or $R^{177}$, $C_1$–$C_3$ alkyl may include methyl, ethyl, and propyl.

For the groups represented by $R^{55}$, $R^{57}$, $R^{175}$, or $R^{177}$, $C_1$–$C_5$ alkyl may include methyl, ethyl, propyl, isopropyl, butyl, isobutyl, and amyl; ($C_1$–$C_5$ alkoxy)carbonyl may include methoxycarbonyl, ethoxycarbonyl, and propyloxycarbonyl; ($C_1$–$C_5$ haloalkoxy)carbonyl may include trifluoromethoxycarbonyl and 2,2,2-trifluoroethoxycarbonyl; ($C_3$–$C_5$ cycloalkoxy)carbonyl may include cyclopropyloxycarbonyl; ($C_3$–$C_5$ alkenoxy)carbonyl may include allyloxycarbonyl; and ($C_3$–$C_5$ alkynoxy)carbonyl may include propargyloxycarbonyl.

For the groups represented by $R^{79}$ or $R^{179}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; $C_3$–$C_6$ alkynyl may include propargyl and 1-methylpropynyl; carboxy $C_1$–$C_5$ alkyl may include carboxymethyl, 1-carboxyethyl, and 2-carboxyethyl; ($C_1$–$C_{10}$ alkoxy) carbonyl $C_1$–$C_5$ alkyl may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-butoxycarbonylethyl; ($C_1$–$C_{10}$ haloalkoxy)carbonyl $C_1$–$C_5$ alkyl may include 2-chloroethoxycarbonylmethyl, 2,2,2-trifluoroethoxycarbonylmethyl, 3-bromopropoxycarbonylmethyl, 1-(2-chloroethoxy) carbonylethyl, and 1-(2,2,2-trifluoroethoxy)carbonylethyl; ($C_3$–$C^{10}$ cycloalkoxy)carbonyl $C_1$–$C_5$ alkyl may include cyclopentyloxycarbonylmethyl, cyclohexyloxycarbonylmethyl, 1-cyclopentyloxycarbonylethyl, and 1-cyclohexyloxycarbonylethyl; and ($C_3$–$C_{10}$ halocycloalkoxy) carbonyl $C_1$–$C_5$ alkyl may include 4-fluorocyclohexyloxycarbonylmethyl.

For the groups represented by $R^{80}$ or $R^{180}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; and $C_3$–$C_6$ alkynyl may include propargyl and 1-methylpropynyl.

The 3- to 7-membered ring, which is formed by combining $R^{79}$ and $R^{80}$ or $R^{179}$ and $R^{180}$ at their ends, together with the adjacent nitrogen atom, and which contains zero to one oxygen atom or NH group in the ring, may include aziridine ring, azetidine ring, pyrrolidine ring, piperidine ring, morpholine ring, and piperazine ring.

For the groups represented by $R^{81}$ or $R^{181}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; $C_3$–$C_6$ alkynyl may include propargyl and 1-methylpropynyl; carboxy $C_1$–$C_5$ alkyl may include carboxymethyl, 1-carboxyethyl, and 2-carboxyethyl; ($C_1$–$C_{10}$ alkoxy) carbonyl $C_1$–$C_5$ alkyl may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-butoxycarbonylethyl; ($C_1$–$C_{10}$ haloalkoxy)carbonyl $C_1$–$C_5$ alkyl may include 2-chloroethoxycarbonylmethyl, 2,2,2-trifluoroethoxycarbonylmethyl, 3-bromopropoxycarbonylmethyl, 1-(2-chloroethoxy) carbonylethyl, and 1(2,2,2-trifluoroethoxy)carbonylethyl; ($C_3$–$C_{10}$ cycloalkoxy)carbonyl $C_1$–$C_5$ alkyl may include cyclopentyloxycarbonylmethyl, cyclohexyloxycarbonylmethyl, 1-cyclopentyloxycarbonylethyl, and 1-cyclohexyloxycarbonylethyl; and ($C_3$–$C_{10}$ halocycloalkoxy)carbonyl $C_1$–$C_5$ alkyl may include 4-fluorocyclohexyloxycarbonylmethyl.

For the groups represented by $R^{82}$ or $R^{182}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; $C_3$–$C_6$ alkynyl may include propargyl and 1-methylpropynyl; carboxy $C_1$–$C_5$ alkyl may include carboxymethyl, 1-carboxyethyl, and 2-carboxyethyl; ($C_1$–$C_{10}$ alkoxy) carbonyl $C_1$–$C_5$ alkyl may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-butoxycarbonylethyl; ($C_1$–$C_{10}$ haloalkoxy)carbonyl $C_1$–$C_5$ alkyl may include 2-chloroethoxycarbonylmethyl, 2,2,2-trifluoroethoxycarbonylmethyl, 3-bromopropoxycarbonylmethyl, 1-(2-chloroethoxy) carbonylethyl, and 1-(2,2,2-trifluoroethoxy)carbonylethyl; ($C_3$–$C_{10}$ cycloalkoxy)carbonyl $C_1$–$C_5$ alkyl may include cyclopentyloxycarbonylmethyl, cyclohexyloxycarbonylmethyl, 1-cyclopentyloxycarbonylethyl, and 1-cyclohexyloxycarbonylethyl; and ($C_3$–$C_{10}$ halocycloalkoxy)carbonyl $C_1$–$C_5$ alkyl may include 4-fluorocyclohexyloxycarbonylmethyl.

For the groups represented by $R^{83}$ or $R^{183}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include; allyl and 1-methylpropenyl; and $C_3$–$C_6$ alkynyl may include propargyl and 1methylpropynyl.

The 3- to 7-membered ring, which is formed by combining $R^{82}$ and $R^{83}$ or $R^{182}$ and $R^{183}$ at their ends, together with the adjacent nitrogen, and which contains zero to one oxygen atom or NH group in the ring, may include aziridine ring, azetidine ring, pyrrolidine ring, piperidine ring, morpholine ring, and piperazine ring.

For the groups represented by $R^{84}$ or $R^{184}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; $C_3$–$C_6$ alkynyl may include propargyl and 1-methylpropynyl; carboxy $C_1$–$C_5$ alkyl may include carboxymethyl, 1-carboxyethyl, and 2-carboxyethyl; ($C_1$–$C_{10}$ alkoxy) carbonyl $C_1$–$C_5$ alkyl may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-butoxycarbonylethyl; ($C_1$–$C_{10}$ haloalkoxy)carbonyl $C_1$–$C_5$ alkyl may include 2-chloroethoxycarbonylmethyl, 2,2,2-trifluoroethoxycarbonylmethyl, 3-bromopropoxycarbonylmethyl, 1-(2-chloroethoxy) carbonylethyl, and 1-(2,2,2-trifluoroethoxy)carbonylethyl; ($C_3$–$C_{10}$ cycloalkoxy)carbonyl $C_1$–$C_5$ alkyl may include cyclopentyloxycarbonylmethyl, cyclohexyloxy-carbonylmethyl, 1-cyclopentyloxycarbonylethyl, and 1-cyclohexyloxycarbonylethyl; and ($C_3$–$C_{10}$ halocycloalkoxy)carbonyl $C_1$–$C_5$ alkyl may include 4-fluorocyclohexyloxycarbonylmethyl.

For the groups represented by $R^{85}$ or $R^{185}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; and $C_3$–$C_6$ alkynyl may include propargyl and 1-methylpropynyl.

The 3- to 7-membered ring, which is formed by combining $R^{84}$ and $R^{85}$ or $R^{184}$ and $R^{185}$ at their ends, together with the adjacent nitrogen atom, and which contains zero to one oxygen atom or NH group in the ring, may include aziridine ring, azetidine ring, pyrrolidine ring, piperidine ring, morpholine ring, and piperazine ring.

For the groups represented by $R^{86}$ or $R^{186}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; $C_3$–$C_6$ alkynyl may include propargyl and 1-methylpropynyl; carboxy $C_1$–$C_5$ alkyl may include carboxymethyl, 1-carboxyethyl, and 2-carboxyethyl; ($C_1$–$C_{10}$ alkoxy) carbonyl $C_1$–$C_5$ alkyl may include methoxycarbonylmethyl. ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-butoxycarbonylethyl; ($C_1$–$C_{10}$ haloalkoxy)carbonyl $C_1$–$C_5$ alkyl may include 2-chloroethoxycarbonylmethyl, 2,2,2-trifluoroethoxycarbonylmethyl, 3-bromopropoxycarbonylmethyl, 1-(2-chloroethoxy) carbonylethyl, and 1-(2,2,2-trifluoroethoxy)carbonylethyl; ($C_3$–$C_{10}$ cycloalkoxy)carbonyl $C_1$–$C_5$ alkyl may include cyclopentyloxycarbonylmethyl, cyclohexyloxycarbonylmethyl, 1-cyclopentyloxycarbonylethyl, and 1-cyclohexyloxycarbonylethyl; and ($C_3$–$C_{10}$ halocycloalkoxy)carbonyl $C_1$–$C_5$ alkyl may include 4-fluorocyclohexyloxycarbonylmethyl.

For the groups represented by $R^{87}$ or $R^{187}$, $C_1$–$C_5$ alkyl may include methyl, ethyl, propyl, isopropyl, butyl, isobutyl, and amyl; $C_1$–$C_5$ haloalkyl may include 2-chloroethyl, 2-fluoroethyl, 2,2,2-trifluoroethyl, 2,2,2-trichloroethyl, and 3-bromopropyl; $C_3$–$C_8$ cycloalkyl may include cyclopentyl, cyclohexyl, and cycloheptyl; $C_3$–$C_6$ alkenyl may include allyl and 1-methylpropenyl; and $C_3$–$C_6$ alkynyl may include propargyl and 1-methylpropynyl.

The 3- to 7-membered ring, which is formed by combining $R^{86}$ and $R^{87}$ or $R^{186}$ and $R^{187}$ at their ends, together with the adjacent nitrogen atom, may include aziridine ring, azetidine ring, pyrrolidine ring, and piperidine ring.

For the groups represented by $E^1$ or $E^2$, $C_1$–$C_6$ alkyl optionally substituted with halogen may include methyl, ethyl, propyl, isopropyl, butyl, isobutyl, amyl, trifluoromethyl, difluoromethyl, and chlorodifluoromethyl; and $C_3$–$C_6$ cycloalkyl optionally substituted with halogen may include cyclopropyl cyclobutyl, and cyclopentyl.

The 4- to 7-membered unsaturated rig, which is formed by combining $E^1$ and $E^2$ at their ends and which contains, together with the atoms attached thereto on Q1, zero to two O, S, SO, $SO_2$ or NH groups (which ring may optionally be substituted with methyl or halogen), may include those in which tetramethylene, trimethylene, or 2,2-dimethyltrimethylene is formed by $E^1$ and $E^2$ For the groups represented by $E^3$ or $E^4$, $C_1$–$C_6$ alkyl optionally substituted with halogen may include methyl, ethyl, propyl, isopropyl, butyl, isobutyl, amyl, trifluoromethyl, difluoromethyl, chlorodifluoromethyl, and 3-fluoropropyl; and $C_3$–$C_6$ cycloalkyl optionally substituted with halogen may include cyclopropyl, cyclobutyl, and cyclopentyl.

The 4- or 7-membered saturated or unsaturated ring, which is formed by combining $E^3$ and $E^4$ at their ends and which contains, together with the atoms attached thereto on Q2, zero to two O, S, SO, $SO_2$ or NH groups (which ring may optionally be substituted with methyl or halogen), may include those in which tetramethylene, trimethylene, or 2,2-dimethyltrimethylene is formed by $E^3$ and $E^4$.

For the groups represented by $E^5$, $C_1$–$C_6$ alkyl optionally substituted with halogen may include methyl, ethyl, propyl, isopropyl, butyl, isobutyl, amyl, trifluoromethyl, difluoromethyl, chlorodifluoromethyl, 2-fluoroethyl, 3-fluoropropyl, and 4-fluorobutyl.

For the groups or elements represented by $E^6$ or $E^7$, $C_1$–$C_6$ alkyl optionally substituted with halogen may include methyl, ethyl, propyl, isopropyl, butyl, isobutyl, amyl, trifluoromethyl, difluoromethyl, chlorodifluoromethyl, and 3-fluoropropyl; and $C_3$–$C_6$ cycloalkyl optionally substituted with halogen may include cyclopropyl, cyclobutyl, and cyclopentyl.

The 4- to 7-membered saturated or unsaturated ring, which is formed by combining $E^6$ and $E^7$ at their ends and which contains, together with the atoms attached thereto on Q4, zero to two O, S, SO, $SO_2$ or NH groups (which ring may optionally be substituted with methyl or halogen), may include those in which tetramethylene, trimethylene, or 2,2-dimethyltrimethylene is formed by $E^6$ and $E^7$.

For the groups represented by $E^8$ or $E^9$, $C_1$–$C_6$ alkyl optionally substituted with halogen may include methyl, ethyl, propyl, isopropyl, butyl, isobutyl, amyl, trifluoromethyl, difluoromethyl, chlorodifluoromethyl, and 3-fluoropropyl; and $C_3$–$C_6$ cycloalkyl optionally substituted with halogen may include cyclopropyl, cyclobutyl, and cyclopentyl.

The 4- to 7-membered saturated or unsaturated ring, which is formed by combining $E^8$ and $E^9$ at their ends and which contains, together with the atoms attached thereto on Q5, zero to two O, S, SO, $SO_2$ or NH groups (which ring may optionally be substituted with methyl or halogen), may include those in which tetramethylene, trimethylene, or 2,2-dimethyltrimethylene is formed by $E^8$ and $E^9$.

For the groups represented by $E^{10}$, $C_1$–$C_6$ alkyl optionally substituted with halogen may include methyl, ethyl, propyl, isopropyl, butyl, isobutyl, amyl, trifluoromethyl, difluoromethyl, chlorodifluoromethyl, and 3-fluoropropyl; and $C_1$–$C_3$ alkoxy optionally substituted with halogen may include methoxy, ethoxy, propoxy, isopropoxy, trifluoromethoxy, and difluoromethoxy.

For the groups represented by $E^{11}$, $C_1$–$C_6$ alkyl optionally substituted with halogen may include methyl, ethyl, propyl, isopropyl, butyl, isobutyl, amyl, trifluoromethyl, difluoromethyl, chlorodifluoromethyl, pentafluoroethyl, and 3-fluoropropyl.

The 4- to 7-membered saturated or unsaturated ring, which is formed by combining $E^{10}$ and $E^{11}$ at their ends and which contains, together with the atoms attached thereto on Q6, zero to two O, S, SO, $SO_2$ or NH groups (which ring may optionally be substituted with methyl or halogen), may include those in which tetramethylene, trimethylene, or 2,2-dimethyltrimethylene is formed by $E^{10}$ and $E^{11}$.

For the elements or groups represented by $E^{44}$, halogen may include fluorine, chlorine, bromine, or iodine; and $C_1$–$C_3$ alkyl may include methyl, ethyl, propyl, and isopropyl For the groups represented by $E^{12}$, $C_1$–$C_6$ alkyl optionally substituted with halogen may include methyl, ethyl, propyl, isopropyl, butyl, isobutyl, t-butyl, amyl, trifluoromethyl, difluoromethyl, chlorodifluoromethyl, and pentafluoroethyl.

For the groups represented by $E^{13}$, $C_1$–$C_6$ alkyl optionally substituted with halogen may include methyl, ethyl, propyl, isopropyl, butyl, isobutyl, t-butyl, amyl, trifluoromethyl, difluoromethyl, chlorodifluoromethyl, and pentafluoroethyl.

For the elements represented by $E^{14}$, halogen may include chlorine, bromine, and iodine.

For the groups represented by $E^{15}$, $C_1$–$C_6$ alkyl may include methyl, ethyl, propyl, isopropyl, butyl, isobutyl, t-butyl, and amyl.

For the groups represented by $E^{16}$, $C_1$–$C_6$ alkyl optionally substituted with halogen may include methyl, ethyl, propyl, isopropyl, butyl, isobutyl, t-butyl, amyl, trifluoromethyl, difluoromethyl, chlorodifluoromethyl, and pentafluoroethyl.

The 4- to 7-membered saturated or unsaturated ring, which is formed by combining $E^{15}$ and $E^{16}$ at their ends and which contains, together with the atoms attached thereto on Q9, zero to two O, S, SO, $SO_2$ or NH groups (which ring may optionally be substituted with methyl or halogen), may include those in which tetramethylene, trimethylene, or 2,2-dimethyltrimethylene is formed by $E^{15}$ and $E^{16}$.

For the groups represented by $E^{17}$, $E^{18}$, or $E^{19}$, $C_1$–$C_6$ alkyl may include methyl, ethyl, propyl, isopropyl, butyl, isobutyl, and amyl.

For the groups represented by $E^{20}$ or $E^{21}$, $C_1$–$C_6$ alkyl may include methyl, ethyl, propyl, isopropyl, butyl, isobutyl, and amyl.

For the groups represented by $E^{22}$ or $E^{23}$, $C_1$–$C_6$ alkyl may include methyl, ethyl, propyl, isopropyl, butyl, isobutyl, and amyl.

For the groups represented by $E^{24}$, $C_1$–$C_3$ alkyl may include methyl, ethyl, propyl, and isopropyl.

For the groups or elements represented by $E^{25}$, $C_1$–$C_3$ alkyl may include methyl, ethyl, propyl, and isopropyl; and halogen may include fluorine, chlorine, bromine, and iodine.

For the groups represented by $E^{26}$, $C_1$–$C_3$ alkyl optionally substituted with halogen may include methyl, ethyl, propyl, isopropyl, trifluoromethyl, difluoromethyl, chlorodifluoromethyl, and pentafluoroethyl.

For the groups represented by $E^{27}$, $C_1$–$C_6$ alkyl may include methyl, ethyl, propyl, isopropyl, isobutyl, butyl, isoamyl, pentyl, and hexyl; $C_3$–$C_6$ alkenyl may include allyl, 1-methyl-2-propenyl, 3-butenyl, 2-butenyl, 3-methyl-2-butenyl, and 2-methyl-3-butenyl; $C_3$–$C_6$ alkynyl may include propargyl, 1-methyl-2-propynyl, 2-butynyl, 3-butynyl, and 1,1-dimethyl-2-propynyl; and optionally substituted benzyl may include benzyl.

For the groups represented by $E^{28}$, $C_1$–$C_3$ alkyl optionally substituted with halogen may include methyl, ethyl, propyl, isopropyl, trifluoromethyl, difluoromethyl, chlorodifluoromethyl, and pentafluoroethyl For the groups represented by $E^{29}$, $C_1$–$C_6$ alkyl may include methyl, ethyl, propyl, isopropyl, isobutyl, butyl, isoamyl, pentyl, and hexyl; $C_3$–$C_6$ alkenyl may include allyl, 1-methyl-2-propenyl, 3-butenyl, 2-butenyl, 3-methyl-2-butenyl, and 2-methyl-3-butenyl; $C_3$–$C_6$ alkynyl may include propargyl, 1-methyl-3-propynyl, 2-butynyl, 3-butynl, and 1,1-dimethyl-2-propynyl; and optionally substituted benzyl may include benzyl.

For the groups represented by $E^{30}$ or $E^{31}$, $C_1$–$C_3$ alkyl optionally substituted with halogen may include methyl, ethyl, propyl, isopropyl, trifluoromethyl, difluoromethyl, chlorodifluoromethyl, and pentafluoroethyl.

The 4- to 7-membered unsaturated ring, which is formed by combining $E^{30}$ and $E^{31}$ at their ends and which contains zero to two O, S, SO, $SO_2$ or NH groups (which ring may optionally be substituted with methyl or halogen), may include the cases where tetramethylene or trimethylene is formed by $E^{30}$ and $E^{31}$.

For the groups represented by $E^{42}$, $C_1$–$C_3$ alkyl optionally substituted with halogen may include methyl, ethyl, propyl, isopropyl, trifluoromethyl, difluoromethyl, chlorodifluoromethyl, and pentafluoroethyl.

For the groups represented by $E^{32}$, $C_1$–$C_3$ alkyl optionally substituted with halogen may include methyl, ethyl, propyl, isopropyl, trifluoromethyl, difluoromethyl, chlorodifluoromethyl, and pentafluoroethyl.

For the elements or groups represented by $E^{33}$, halogen may include chlorine, bromine, and iodine; $C_1$–$C_3$ alkyl optionally substituted with halogen may include methyl, ethyl, propyl, isopropyl, trifluoromethyl, difluoromethyl, chlorodifluoromethyl and pentafluoroethyl; $C_1$–$C_3$ alkoxy optionally substituted with halogen may include methoxy and ethoxy; and $C_1$–$C_3$ alkylthio optionally substituted with halogen may include methylthio and ethylthio.

For the groups represented by $E^{43}$, $C_1$–$C_3$ alkyl optionally substituted with halogen may include methyl, ethyl, propyl, isopropyl, trifluoromethyl, difluoromethyl, chlorodifluoromethyl, and pentafluoroethyl.

For the groups represented by $E^{34}$, $C_1$–$C_3$ alkyl optionally substituted with halogen may include methyl, ethyl, propyl, isopropyl, trifluoromethyl, difluoromethyl, chlorodifluoromethyl, and pentafluoroethyl.

For the groups represented by $E^{35}$, $C_1$–$C_3$ alkyl optionally substituted with halogen may include methyl, ethyl, propyl, isopropyl, trifluoromethyl, difluoromethyl, chlorodifluoromethyl, and pentafluoroethyl.

For the groups represented by $E^{36}$ or $E^{37}$, $C_1$–$C_6$ alkyl may include methyl, ethyl, propyl, isopropyl, isobutyl, butyl, isoamyl, pentyl, and hexyl.

The 4- to 7-membered saturated or unsaturated ring, which is formed by combining $E^{36}$ and $E^{37}$ at their ends and which contains, together with the atoms attached thereto on Q21, zero to two O, S, SO, $SO_2$ or NH groups (which ring may optionally be substituted with methyl or halogen), may include the cases where tetramethylene, trimethylene, or 2,2-dimethyltrimethylene is formed by $E^{36}$ and $E^{37}$.

For the groups represented by $E^{38}$, $C_1$–$C_6$ alkyl may include methyl, ethyl, propyl, isopropyl, isobutyl, butyl, isoamyl, pentyl, and hexyl.

For the groups represented by $E^{39}$, $C_1$–$C_3$ alkyl optionally substituted with halogen may include methyl, ethyl, propyl, isopropyl, trifluoromethyl, difluoromethyl, chlorodifluoromethyl, and pentafluoroethyl.

The 4- to 7-membered saturated or unsaturated ring, which is formed by combining $E^{38}$ and $E^{39}$ at their ends and which contains, together with the atoms attached thereto on Q22, zero to two O, S, SO, $SO_2$ or NH groups (which ring may optionally be substituted with methyl or halogen), may include the cases where tetramethylene, trimethylene, or 2,2-dimethyltrimethylene is formed by $E^{38}$ and $E^{39}$.

For the groups represented by $E^{40}$, $C_1$–$C_6$ alkyl may include methyl, ethyl, propyl, isopropyl, isobutyl, butyl, isoamyl, pentyl, and hexyl.

For the groups represented by $E^{41}$, $C_1$–$C_3$ alkyl may include methyl, ethyl, propyl, and isopropyl; and $C_3$–$C_6$ cycloalkyl may include cyclopropyl, cyclopentyl, and cyclohexyl.

The 4- to 7-membered saturated or unsaturated ring, which is formed by combining $E^{40}$ and $E^{41}$ at their ends and which contains, together with the atoms attached thereto on Q23 (which ring may optionally be substituted with methyl or halogen), may include the cases where tetramethylene, trimethylene, or 2,2-dimethyltrimethylene is formed by $E^{40}$ and $E^{41}$.

For the present compounds, there may exist geometrical isomers based on the presence of a double bond, or optical isomers and diastereomers based on the presence of at least one asymmetric carbon atom, and all of these isomers and their mixtures are also included within the scope of the present invention.

The preferred substituents from the viewpoint of herbicidal activity may include CH, $CCH_3$, CCl, CBr and N, more preferably CH and N, for A, and Q1, Q2, Q4, Q6, Q14, Q16, Q18, Q19 and Q20 for Q.

When Q is Q1, compounds in which $E^1$ and $E^2$ are combined at their ends to form, together with the atoms attached thereto, a 5- to 7-membered unsaturated ring are preferred, and in particular; compounds in which the unsaturated ring is a 6-membered ring are more preferred.

When Q is Q2, compounds in which $E^3$ and $E^4$ are combined at their ends to form, together with the atoms attached thereto, a 5- to 7-membered saturated or unsaturated ring are preferred, and in particular, compounds in which the saturated or unsaturated ring is a 6-membered ring and $D^1$ and $D^2$ are oxygen are more preferred.

When Q is Q4, compounds in which $E^6$ is $C_1$–$C_6$ alkyl optionally substituted with halogen and $E^7$ is C–$C_6$ alkyl optionally substituted with halogen are preferred, and in particular, compounds in which $E^6$ is methyl substituted with fluorine (e.g., trifluoromethyl, chlorodifluoromethyl, difluoromethyl) or ethyl substituted with fluorine (e.g., pentafluoroethyl, 1,1-difluoroethyl) and $E^7$ is methyl or ethyl are more preferred. In addition, compounds in which $E^6$ and $E^7$ are combined at their ends to form, together with the atoms attached thereto, a 5- or 7-membered saturated or unsaturated ring are preferred, and in particular, compounds in which the saturated or unsaturated ring is a 6-membered ring are more preferred.

When Q is Q6, compounds in which $E^{10}$ is $C_1$–$C_6$ alkyl optionally substituted with halogen, $E^{11}$ is $C_1$–$C_6$ alkyl optionally substituted with halogen, and $E^{44}$ is chlorine or bromine are preferred, and in particular, compounds in which $E^{10}$ is methyl substituted with fluorine (e.g., trifluoromethyl, chlorodifluoromethyl, difluoromethyl) or ethyl substituted with fluorine (e.g., pentafluoroethyl, 1,1-difluoroethyl) and $E^{11}$ is methyl or ethyl are more preferred. In addition, compounds in which $E^{10}$ and $E^{11}$ are combined at their ends to form, together with the atoms attached thereto, a 5- to 7-membered saturated or unsaturated ring are preferred, and in particular, compounds in which the saturated or unsaturated ring is a 6-membered ring are more preferred.

When Q is Q14, compounds in which $D^7$ is oxygen, $E^{25}$ is hydrogen, $E^{26}$ is $C_1$–$C_3$ alkyl optionally with halogen, and $E^{27}$ is $C_1$–$C_3$ alkyl are preferred, and in particular, compounds in which $E^{26}$ is methyl substituted with fluorine (e.g., trifluoromethyl, chlorodifluoromethyl, difluoromethyl) or ethyl substituted with fluorine (e.g., pentafluoroethyl, 1,1-difluoroethyl) and $E^{27}$ is methyl or ethyl are more preferred.

When Q is Q16, compounds in which $E^{30}$ is $C_1$–$C_3$ alkyl optionally substituted with halogen, $E^{31}$ is hydrogen or $C_1$–$C_3$ alkyl, and $E^{42}$ is hydrogen or $C_1$–$C_3$ alkyl are preferred, and in particular, compounds in which $E^{30}$ is methyl, methyl substituted with fluorine (e.g., trifluoromethyl, chlorodifluoromethyl, difluoromethyl), or ethyl substituted with fluorine (e.g., pentafluoroethyl, 1,1-difluoroethyl), $E^{31}$ is hydrogen or methyl, and $E^{42}$ is hydrogen or methyl are more preferred. In addition, compounds in which $E^{30}$ and $E^{31}$ are combined at their ends to form, together with the atoms attached thereto, a 5- or 7-membered saturated or unsaturated ring are preferred, and in particular, compounds in which the saturated or unsaturated ring is a 5- or 6-membered ring are more preferred.

When Q is Q18, compounds in which $E^{34}$ is $C_1$–$C_3$ alkyl optionally substituted with halogen are preferred, and in particular, compounds in which $E^{34}$ is methyl substituted with fluorine (e.g., trifluoromethyl, chlorodifluoromethyl, difluoromethyl) or ethyl substituted with fluorine (e.g., pentafluoroethyl, 1,1-difluoroethyl) are more preferred.

When Q is Q19, compounds in which $V^1$ is $—CH_2—$ or $—CH_2—CH_2—$ are preferred.

When Q is Q20, compounds in which $E^{35}$ is $C_1$–$C_3$ alkyl optionally substituted with halogen, $Z^2$ is nitrogen, and $V^2$ is $—CH_2—CH_2—$ or $—CH{=}CH—$ are preferred, and in particular, compounds in which $E^{35}$ is methyl substituted with fluorine (e.g., trifluoromethyl, chlorodifluoromethyl, difluoromethyl) or ethyl substituted with fluorine (e.g., pentafluoroethyl, 1,1-difluoroethyl) are more preferred.

Specific examples of the preferred compounds are recited below:

Methyl 3-[3-methyl-2,6-dioxo-4-(trifluoromethyl)-1,2,3,6-tetrahydropyrimidin-1-yl]benzo[b]furan-5-carboxylate;

Ethyl 3-[3-methyl-2,6-dioxo-4-(trifluoromethyl)-1,2,3,6-tetrahydropyrimidin-1-yl]benzo[b]furan-5-carboxylate;

Isopropyl 3-[3-methyl-2,6-dioxo-4-(trifluoromethyl)-1,2,3,6-tetraydropyrimidin-1-yl]benzo[b]furan-5-carboxylate;

Methyl 3-[3-methyl-2,6-dioxo-4-(trifluoromethyl)-1,2 3,6-tetrahydropyrimidin-1-yl]-6-nitrobenzo[b]furan-5-carboxylate;

Ethyl 3-[3-methyl-2,6-dioxo-4-(trifluoromethyl)-1,2,3,6-tetrahydropyrimidin-1-yl]-6-nitrobenzo[b]furan-5-carboxylate;

Methyl 6-chloro-3-[3-methyl-2,6-dioxo-4-(trifluoromethyl)-1,2,3,6-tetrahydropyrimidin-1-yl]benzo[b]furan-5-carboxylate;

Ethyl 6-chloro-3-[3-methyl-2,6-dioxo-4-(trifluoromethyl)-1,2,3,6-tetrahydropyrimidin-1-yl]benzo[b]furan-5-carboxylate;

Methyl 7-chloro-3-[3-methyl-2,6-dioxo-4-(trifluoromethyl)-1,2,3,6-tetrahydropyrimidin-1-yl]benzo[b]furan-5-carboxylate;

Ethyl 7-chloro-3-[3-methyl-2,6-dioxo-4-(trifluoromethyl)-1,2,3,6-tetrahydropyrimidin-1-yl]benzo[b]furan-5-carboxylate;

3-(5-Methoxybenzo[b]furan-3-yl)-1-methyl-6-(trifluoromethyl)-1,2,3,4-tetrahydropyrimidine-2,4-dione;

3-(5-Methoxy-6-nitrobenzo[b]furan-3-yl)-1-methyl-6-(trifluoromethyl)-1,2,3,4-tetrahydropyrimidine-2,4-dione;

3-(6-Chloro-5-methoxybenzo[b]furan-3-yl)-1-methyl-6-(trifluoromethyl)-1,2,3,4-tetrahydropyrimidine-2,4-dione;

3-(7-Chloro-5-methoxybenzo[b]furan-3-yl)-1-methyl-6-(trifluoromethyl)-1,2,3,4-tetrahydropyrimidine-2,4-dione;

3-[5-(Allyloxy)benzo[b]furan-3-yl]-1-methyl-6-(trifluoromethyl)-1,2,3,4-tetrahydropyrimidine-2,4-dione;

3-[5-(Allyloxy)-6-nitrobenzo[b]furan-3-yl]-1-methyl-6-(trifluoromethyl)-1,2,3,4-tetrahydropyrimidine-2,4-dione;

3-[5-(Allyloxy)-6-chlorobenzo[b]furan-3-yl]-1-methyl-6-(trifluoromethyl)-1,2,3,4-tetrahydropyrimidine-2,4-dione;

3-[5-(Allyloxy)-7-chlorobenzo[b]furan-3-yl]-1-methyl-6-(trifluoromethyl)-1,2,3,4-tetrahydropyrimidine-2,4-dione;

1-Methyl-3-[5-(prop-2-ynyloxy)benzo[b]furan-3-yl]-6-(trifluoroethyl)-1,2,3,4-tetrahydropyrimidine-2,4-dione;

1-Methyl-3-[6-nitro-5-(prop-2-ynyloxy)benzo[b]furan-3-yl]-6-(trifluoromethyl)-1,2,3,4-tetrahydropyrimidine-2,4-dione;

3-[6-Chloro-5-(prop-2-ynyloxy)benzo[b]furan-3-yl]-1-methyl-6-(trifluoromethyl)-1,2,3,4-tetrahydropyrimidine-2,4-dione;

3-[7-Chloro-5-(prop-2-ynyloxy)benzo[b]furan-3-yl]-1-methyl-6-(trifluoromethyl)-1,2,3,4-tetrahydropyrimidine-2,4-dione;

Ethyl 2-({3-[3-methyl-2,6-dioxo-4-(trifluoromethyl)-1,2,3,6-tetrahydropyrimidin-1-yl]benzo[b]furan-5-yl}oxy)propanoate;

Ethyl 2-({6-chloro-3-[3-methyl-2,6-dioxo-4-(trifluoromethyl)-1,2,3,6-tetrahydropyrimidin-1-yl]benzo[b]furan-5-yl}oxy)propanoate;

Ethyl 2-({7-chloro-3-[3-methyl-2,6-dioxo-4-(trifuoromethyl)-1,2,3,6-tetrahydropyrimidin-1-yl]benzo[b]furan-5-yl}oxy)propanoate;

1-Methyl-3-[5-(methylthio)benzo[b]furan-3-yl]-6-(trifluoromethyl)-1,2,3,4-tetrahydropyrimidine-2,4-dione;

1-Methyl-3-[5-(methylthio)-6-nitrobenzo[b]furan-3-yl]-6-(trifluoromethyl)-1,2,3,4-tetrahydropyrimidine-2,4-dione;

3-[6-Chloro-5-(methylthio)benzo[b]furan-3-yl]-1-methyl-6-(trifluoromethyl)-1,2,3,4-tetrahydropyrimidine-2,4-dione;

3-[7-Chloro-5-(methylthio)benzo[b]furan-3-yl]-1-methyl-6-(trifluoromethyl)-1,2,3,4-tetrahydropyrimidine-2,4-dione;

Ethyl 2-({3-[3-methyl-2,6-dioxo-4-(trifluoromethyl)-1,2,3,6-tetrahydropyrimidin-1-yl]-6-nitrobenzo[b]furan-5-yl}thio)propanoate;

Ethyl 2-({6-chloro-3-[3-methyl-2,6-dioxo-4-(trifluoromethyl)-1,2,3,6-tetrahydropyrimidim-1-yl]benzo[b]furan-5-yl}thio)propanoate;

Ethyl 2-({7-chloro-3-[3-methyl-2,6-dioxo-4-(trifluoromethyl)-1,2,3,6-tetrahydropyrimidin-1-yl] benzo[b]furan-5-yl}thio)propanoate;

3-(5,7-Dichlorobenzo[b]furan-3-yl)-1-methyl-6-(trifluoromethyl)-1,2,3,4-tetrahydropyrimidine-2,4-dione;

3-(5-Bromo-7-chlorobenzo[b]furan-3-yl)-1-methyl-6-(trifluoromethyl)-1,2,3,4-tetrahydropyrimidine-2,4-dione; and 3-(7-Chloro-5-methylbenzo[b]furan-3-yl)-1-methyl-6-(trifluoromethyl)-1,2,3,4-tetrahydropyrimidine-2,4-dione.

The present compounds can be produced, for example, by Producing Processes 1 to 27 as described below.

PRODUCING PROCESS 1

In the process, compound a-1 of the general formula:

a-1

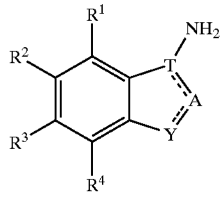

wherein T, A, Y, $R^1$, $R^2$, $R^3$, and $R^4$ are as defined above, is reacted with acid anhydride a-5 of the general formula:

a-5

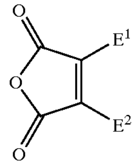

wherein $E^1$ and $E^2$ are as defined above.

The reaction is carried out without solvent or in a solvent. The reaction temperature is usually in the range of 50° C. to 200° C. The reaction time is usually in the range of 1 to 100 hours. The amounts of reagents to be used in the reaction are 1 mole of acid anhydride a-5 relative to 1 mole of compound a-1, which is the stoichiometric ratio but can be freely changed depending upon the reaction conditions.

The solvent which can be used may include aliphatic hydrocarbons such as hexane, heptane, octane, and ligroin; aromatic hydrocarbons such as benzene, toluene, ethylbenzene, xylene, and mesitylene; halogenated hydrocarbons such as chlorobenzene, dichlorobenzene, and trichlorobenzene; ethers such as 1,4-dioxane, tetrahydrofuran, ethylene glycol dimethyl ether, and methyl t-butyl ether; nitro compounds such as nitromethane and nitrobenzene; organic acids such as acetic acid and propionic acid; acid amides such as N,N-dimethylformamide; sulfur compounds such as dimethylsulfoxide and sulforane; and mixtures thereof. In addition, acids such as p-toluenesulfonic acid can also be used as a reaction catalyst.

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography. (see JP-A 55-139359.)

PRODUCING PROCESS 2

This is the producing process according to the following scheme:

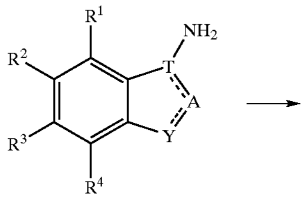

a-1

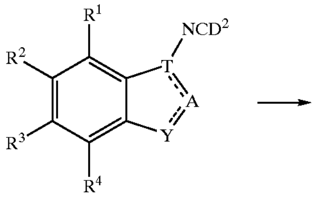

a-2

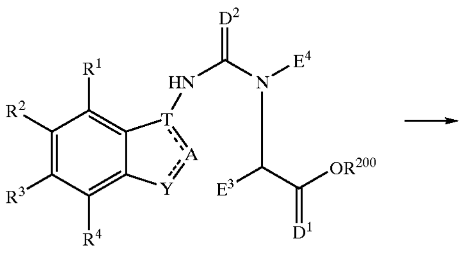

a-3

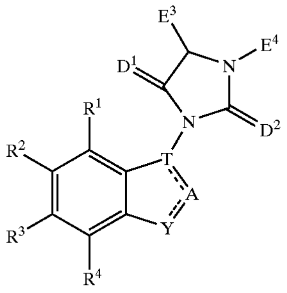

a-4 wherein $R^1$, $R^2$, $R^3$, $R^4$, $D^1$, $D^2$, $E^3$, $E^4$, T, A, and Y are as defined above, $R^{200}$ is $C_1$–$C_5$ alkyl (e.g., methyl, ethyl) or hydrogen.

The reactions in the respective steps can be carried out, for example, according to the processes as described in JP-A 61-27985, or for example, by the following processes.

1). Process of Producing Compound a-2 from Compound a-1

Compound a-2 can be produced by converting compound a-1 into an isocyanate or isothiocyanate derivative in a solvent or without solvent.

Agent for conversion into isocyanate or isothiocyanate derivatives: phosgene, trichloromethyl chloroformate, oxalyl chloride, thiophosgene, etc.

Amount of agent for conversion into isocyanate or isothiocyanate derivatives: 1 equivalent to an excess amount relative to 1 mole of compound a-1

Solvent: aromatic hydrocarbons such as benzene and toluene; halogenated aromatic hydrocarbons such as chlorobenzene; etc.

Reaction temperature: room temperature to the reflux temperature of the agent for conversion into isocyanate or isothiocyanate derivatives Reaction time: a moment to 48 hours.

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound a-3 from Compound a-2

Compound a-3 can be produced by reacting compound a-2 with compound a-6 of the general formula:

a-6

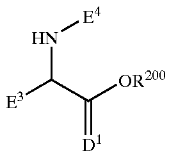

wherein $D^1$, $E^3$, $E^4$, and $R^{200}$ are as defined above, in a solvent in the presence of a base.

Amount of compound a-6: 1 to 5 moles relative to 1 mole of compound a-2

Kind of base: inorganic bases such as sodium hydride and potassium carbonate; organic bases such as triethylamine; metal alcoholates such as sodium methylate; etc.

Amount of base: 0.1 to 10 moles relative to 1 mole of compound a-2

Solvents: ethers such as tetrahydrofuran and 1,4-dioxane; amides such as N,N-dimethylformamide; aromatic hydrocarbons such as benzene and toluene; halogenated aromatic hydrocarbons such as chlorobenzene; alcohols such as ethanol; and mixtures thereof; etc.

Reaction temperature: −15° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound a-4 may be directly obtained depending upon the reaction conditions of this process.

3) Process of Producing Compound a-4 from Compound a-3

Compound a-4 can be produced by reacting compound a-3 in a solvent in the presence of a base.

Kind of base: inorganic bases such as sodium hydride; metal alcoholates such as sodium methylate; etc.

Amount of base: 1 to 5 moles relative to 1 mole of compound a-3

Solvent: ethers such as tetrahydrofuran and 1,4-dioxane; amides such as N,N-dimethylformamide; aromatic hydrocarbons such as benzene and toluene; halogenated aromatic hydrocarbons such as chlorobenzene; alcohols such as methanol and ethanol; and mixtures thereof; etc.

Reaction temperature: −10° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 3

This is the producing process according to the following scheme:

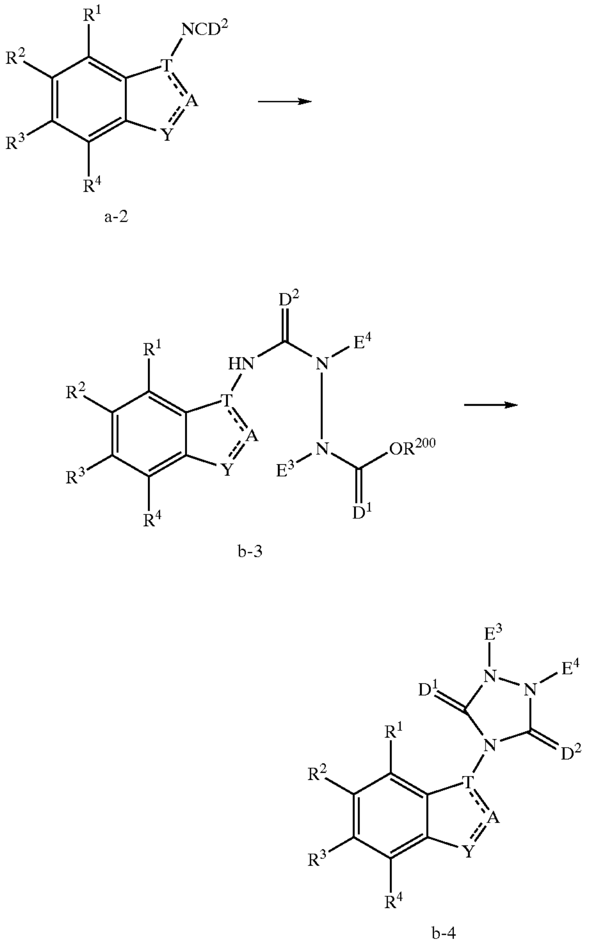

a-2 b-3 b-4 wherein $R^1$, $R^2$, $R^3$, $R^4$, $R^{200}$, $D^1$, $D^2$, $E^3$, $E^4$, T, A, and Y are as defined above.

The reactions in the respective steps can be carried out, for example, according to the processes as described in JP-A 61-27985, or for example, by the following processes.

1) Process of Producing Compound b-3 from Compound a-2

Compound b-3 can be produced by reacting compound a-2 with compound b-5 of the general formula:

b-5

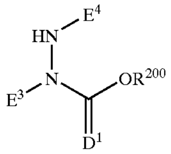

wherein $D^1$, $E^3$, $E^4$, and $R^{200}$ are as defined above, in a solvent in the presence of a base.

Amount of compound b-5: 1 to 5 moles relative to 1 mole of compound a-2

Kind of base: inorganic bases such as sodium hydride and potassium carbonate; organic bases such as triethylamine; metal alcoholates such as sodium methylate; etc.

Amount of base: 0.1 to 10 moles relative to 1 mole of compound a-2

Solvent: ethers such as tetrahydrofuran and 1,4-dioxane; amides such as N,N-dimethylformamide; aromatic hydrocarbons such as benzene and toluene; halogenated aromatic hydrocarbons such as chlorobenzene; alcohols such as ethanol; and mixtures thereof; etc.

Reaction temperature: −15° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound b-4 may be directly obtained depending upon the reaction conditions of this process.

2) Process of Producing Compound b-4 from Compound b-3

Compound b-4 can be produced by reacting compound b-3 in a solvent in the presence of a base.

Kind of base: inorganic bases such as sodium hydride; metal alcoholates such as sodium methylate; etc.

Amount of base: 1 to 5 moles relative to 1 mole of compound b-3

Solvent: ethers such as tetrahydrofuran and 1,4-dioxane; amides such as N,N-dimethylformamide; aromatic hydrocarbons such as benzene and toluene; halogenated aromatic hydrocarbons such as chlorobenzene; alcohols such as methanol and ethanol; and mixtures thereof; etc.

Reaction temperature: −10° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 4

This is the producing process according to the following scheme:

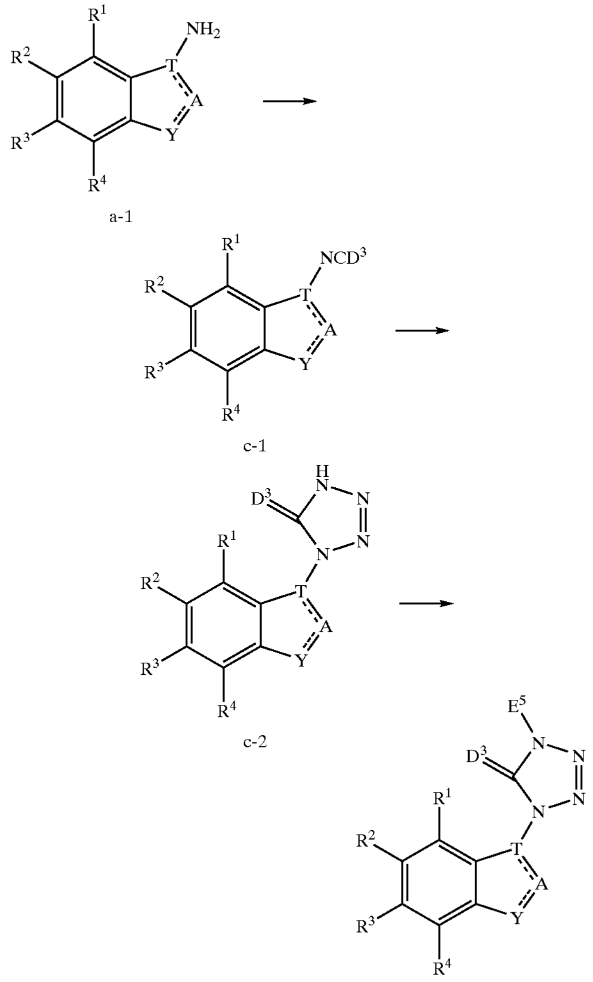

a-1 c-1 c-2 c-3 wherein $R^1$, $R^2$, $R^3$, $R^4$, $D^3$, $E^5$, T, A, and Y are as defined above.

The reactions in the respective steps can be carried out, for example, according to the processes as described in WO87/03873, or for example, by the following processes.

1) Process of Producing Compound c-1 from Compound a-1

Compound c-1 can be produced from compound a-1 according to the process as described above in Producing Process 2, Step 1).

2) Process of Producing Compound c-2 from Compound c-1

Compound c-2 can be produced by reacting compound c-1 and trimethylsilyl azide in a solvent or without solvent.

Amount of trimethylsilyl azide: 1 to 3 moles relative to 1 mole of compound c-1

Solvent: benzene, toluene, chlorobenzene, etc.

Reaction temperature: room temperature to the reflux temperature

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

3) Process of Producing Compound c-3 from Compound c-2

Compound c-3 can be produced by reacting compound c-2 and compound c-4 of the general formula:

$M^1$—$E^5$    c-4 wherein $E^5$ is as defined above and $M^1$ is chlorine, bromine, iodine, or methanesulfonyloxy, in a solvent in the presence of a base.

Amount of compound c-4: 1 to 3 moles relative to 1 mole of compound c-2

Kind of base: sodium hydride, potassium carbonate, etc.

Amount of base: 1 to 10 moles relative to 1 mole of compound c-2

Solvent: N,N-dimethylformamide, tetrahydrofuran, etc.

Reaction temperature: room temperature to 150° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 5

This is the producing process according to the following scheme:

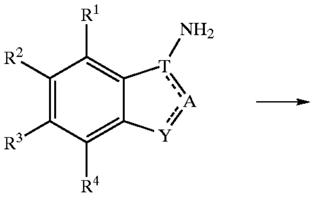

a-1

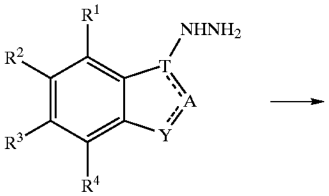

d-1

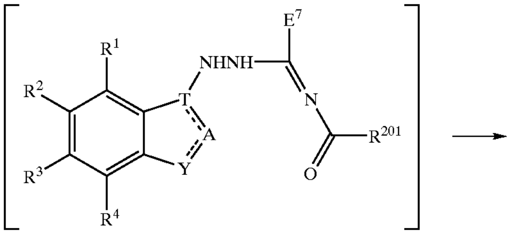

d-2

-continued

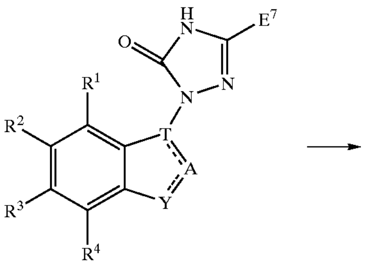

d-3

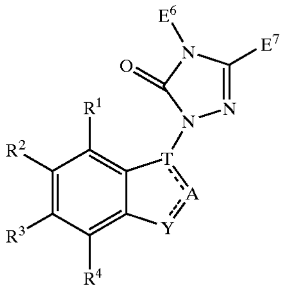

d-4 wherein $R^{201}$ is methoxy, ethoxy or dimethylamino; and $R^1$, $R^2$, $R^3$, $R^4$, $E^6$, $E^7$, T, A, and Y are as defined above.

The reactions in the respective steps can be carried out, for example, according to the processes as described in JP-A 60-149571, or for example, by the following processes.

1) Process of Producing Compound d-1 from Compound a-1

Compound d-1 can be produced by converting compound a-1 into a diazonium salt with sodium nitrite in the presence of an acid and then reacting the diazonium salt with a reducing agent such as tin (II) chloride. (see Organic Synthesis Collective Volume 1, p. 442.)

(Diazonium Salt Formation)

Amount of sodium nitrite: 1 to 2 moles relative to 1 mole of compound a-1

Kind of acid: hydrochloric acid etc.

Amount of acid: 1 mole to an excess amount relative to 1 mole of compound a-1

Solvent: water, ethanol, hydrochloric acid, etc.

Reaction temperature: −15° C. to room temperature

Reaction time: a moment to 24 hours (Reduction Reaction)

Kind of reducing agent: tin (II) chloride etc.

Amount of reducing agent: 3 to 10 moles relative to 1 mole of compound a-1

Solvent: hydrochloric acid etc.

Reaction temperature: −15° C. to room temperature

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound d-3 from Compound d-1

Compound d-3 can be produced by reacting compound d-1 and compound d-5 of the general formula:

d-5

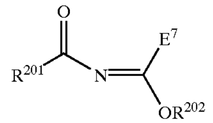

wherein $E^7$ and $R^{201}$ are as defined above and $R^{202}$ is methyl or ethyl, in a solvent, if necessary, in the presence of a base, to give intermediate d-2 and then reacting the intermediate d-2 in the presence of a base.

Intermediate d-2 may be isolated.

(Reaction of Compound d-1 into Compound d-2)

Amount of compound d-5: 1 to 3 moles relative to 1 mole of compound d-1.

Kind of base: organic bases such as triethylamine and pyridine; metal alcoholates such as sodium methylate and sodium ethylate; inorganic bases such as sodium hydroxide and potassium carbonate; etc.

Solvent: aromatic hydrocarbons such as benzene, toluene, and xylene; halogenated aromatic hydrocarbons such as chlorobenzene; alcohols such as ethanol and isopropanol; amides such as N,N-dimethylformamide; ethers such as tetrahydrofuran and 1,4-dioxane; etc.

Reaction temperature: 0° C. to the reflux temperature of the solvent

Reaction time: a moment to 48 hours (Reaction of Compound d-2 into Compound d-3)

Kind of base: organic bases such as triethylamine and pyridine; metal alcoholates such as sodium methylate and sodium ethylate; inorganic bases such as sodium hydroxide and potassium carbonate; etc.

Amount of base: 0.1 to 10 moles relative to 1 mole of compound a-1

Solvent: aromatic hydrocarbons such as benzene, toluene, and xylene; halogenated aromatic hydrocarbons such as chlorobenzene; alcohols such as ethanol and isopropanol; amides such as N,N-dimethylformamide; ethers such as tetrahydrofuran and 1,4-dioxane; etc.

Reaction temperature: 0° C. to the reflux temperature of the solvent

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

3) Process of Producing Compound d-4 from Compound d-3

Compound d-4 can be produced by reacting compound d-3 with compound d-6 of the general formula:

$M^1—E^6$ d-6 wherein $E^6$ and $M^1$ are as defined above, in a solvent in the presence of a base.

Amount of compound d-6: 1 to 3 moles relative to 1 mole of compound d-3

Kind of base: sodium hydride, potassium carbonate, etc.

Amount of base: 1 to 10 moles relative to 1 mole of compound d-3

Solvent: N,N-dimethylformamide, tetrahydrofuran, etc.

Reaction temperature: 0° C. to the reflux temperature of the solvent

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound d-3 can also be produced according to the following scheme. (see JP-A 7-503253.)

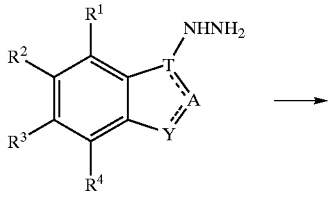

d-1

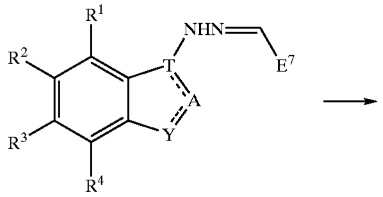

e-1

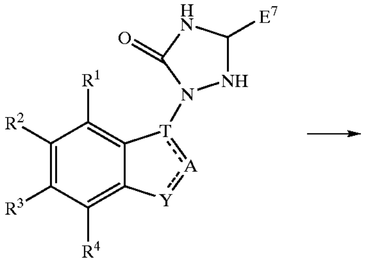

e-2

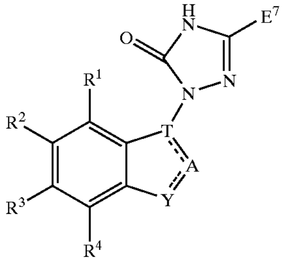

d-3 wherein $R^1$, $R^2$, $R^3$, $R^4$, $E^7$, T, A, and Y are as defined above.

1) Process of Producing Compound e-1 from Compound d-1

Compound e-1 can be produced by reacting compound d-1 with compound e-3 of the general formula:

e-3

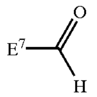

wherein $E^7$ is as defined above, in a solvent.

Amount of compound e-3: 1 to 10 moles relative to 1 mole of compound d-3

Solvent: water; alcohols such as ethanol and t-butanol; and mixtures thereof; etc.

Reaction temperature: −15° C. to 70° C.

Reaction time: a moment to 24 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound e-1 can also be used as such for the reaction in the next step without isolation.

2) Process of Producing Compound e-2 from Compound e-1

Compound e-2 can be produced by reacting compound e-1 with an alkali metal cyanate, in a solvent, if necessary, in the presence of an acid.

Kind of alkali metal cyanate: NaOCN, KOCN, etc.

Amount of alkali metal cyanate: 1 to 3 moles relative to 1 mole of compound e-1

Kind of acid: organic acids such as acetic acid

Amount of acid: 0.01 to 1 mole relative to 1 mole of compound e-1

Solvent: water; alcohols such as ethanol and t-butanol; and mixtures thereof; etc.

Reaction temperature: −15° C. to 80° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallzation or column chromatography.

Compound e-2 can also be used as such in the next step without isolation.

3) Process of Producing Compound d-3 from Compound e-2

Compound d-3 can be produced by oxidizing compound e-2 with an oxidizing agent such as halogen, hypohalous acid, or hypohalite in a solvent.

Kind of oxidizing agent: chlorine, hypochlorous acid, sodium hypochlorite, etc.

Amount of oxidizing agent: 1 to 3 moles relative to 1 mole of compound e-2

Solvent: water; alcohols such as ethanol and t-butanol; and mixtures thereof; etc.

Reaction temperature: −15° C. to 60° C.

Reaction time: a moment to 48 hours

After completion of the reaction, the reaction mixture is subjected to post-treatments, for example; the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 6

This is the producing process according to the following scheme:

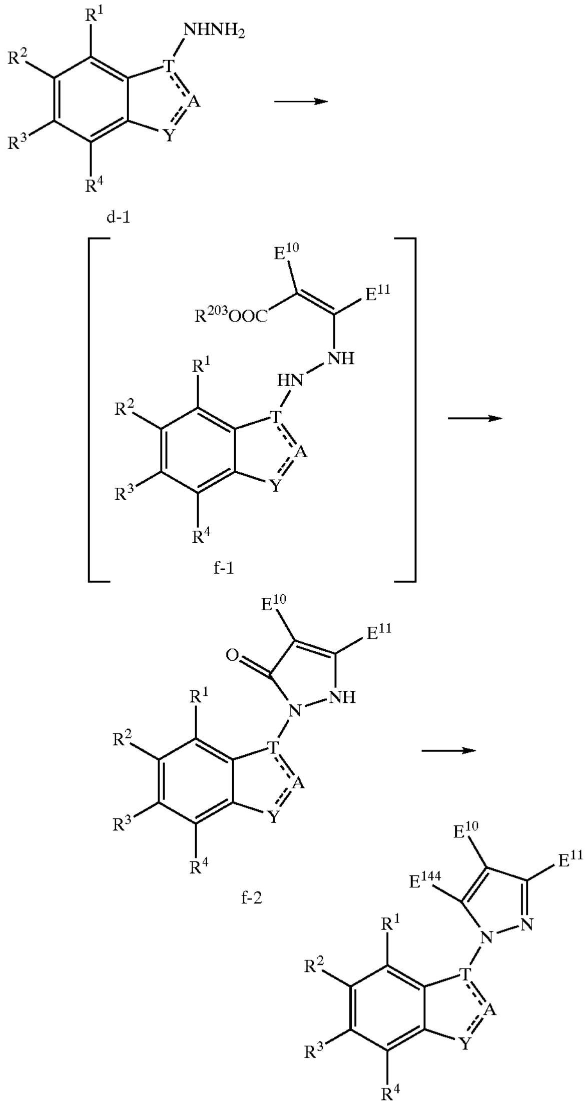

d-1 f-1 f-2 f-3 wherein $R^1$, $R^1$, $R^3$, $R^4$, $E^{10}$, $E^{11}$, T, A, and Y are as defined above; $E^{144}$ is halogen; and $R^{203}$ is methyl or ethyl.

The reactions in the respective steps can be carried out, for example, according to the processes as described in JP-A 60-233061, or for example, by the following processes.

1) Process of Producing Compound f-2 from Compound d-1

Compound f-2 can be produced by reacting compound d-1 with compound f-4 of the general formula:

f-4

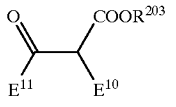

wherein $E^{10}$, $E^{11}$, and $R^{203}$ are as defined above, in a solvent, if necessary, in the presence of an acid.

Amount of compound f-4: 1 to 10 moles relative to 1 mole of compound d-1

Solvent: water; alcohols such as ethanol, isopropanol and butanol; aromatic hydrocarbons such as benzene and toluene; organic acids such as acetic acid and propionic acid; and mixtures thereof; etc.

Kind of acid: p-toluenesulfonic acid, hydrochloric acid, acetic acid, etc.

Amount of acid: 0.0001 mole to an excess amount relative to 1 mole of compound d-1

Reaction temperature: room temperature to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound f-3 from Compound f-2

Compound f-3 can be produced by reacting compound f-2 with a halogenating agent in a solvent or without solvent under normal pressure or increased pressure.

Kind of halogenating agent: phosphorous oxychloride, phosphorous pentachloride, oxalyl chloride, phosgene, trichloromethyl chloroformate, etc.

Amount of halogenating agent: 1 mole to an excess amount relative to 1 mole of compound f-2

Solvent: aromatic hydrocarbons such as benzene and toluene; halogenated aromatic hydrocarbons such as chlorobenzene; etc.

Reaction temperature: 50° C. to 250° C.

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

The compounds wherein $E^{10}$ is $CF_2H$ can also be produced according to the following scheme:

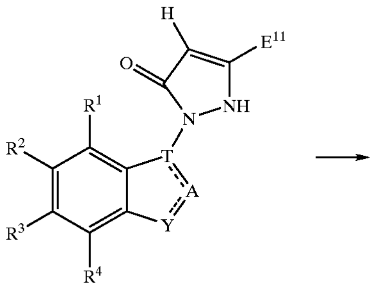

g-1

-continued

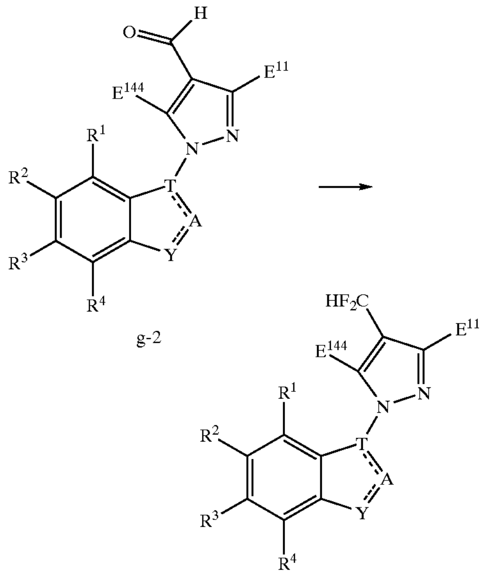

g-2 g-3 wherein $R^1$, $R^2$, $R^3$, $R^4$, $E^{11}$, $E^{144}$, T, A, and Y are defined above.

1) Process of Producing Compound g-2 from Compound g-1

Compound g-2 can be produced by reacting compound g-1 with a Vilsmeier reagent (prepared from dimethylformamide and a halide such as phosphorus oxychloride, phosphorus pentachloride, oxalyl chloride, phosgene or trichloromethyl chloroformate; see Jikken Kagaku Koza, 4th Edition, 21, p. 110) in a solvent or without solvent.

Amount of Vilsmeier reagent: 1 to 20 moles relative to 1 mole of compound g-1

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; etc.

Reaction temperature: −10° C. to 150° C.

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaing the desired compound. The compound can be purified by a technique such as recrystallization or column chromatography.

2) Process of Producing Compound g-3 from Compound g-2

Compound g-3 can be produced by reacting compound g-2 with a fluorinating agent in a solvent.

Kind of fluorinating agent: dimethylaminosulfur trifluoride etc.

Amount of fluorinating agent: 1 to 10 moles relative to 1 mole of compound g-2

Solvent: halogenated aromatic hydrocarbons such as chlorobenzene; halogenated aliphatic hydrocarbons such as chloroform; etc.

Reaction temperature: −10° C. to room temperature

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 7

This is the producing process according to the following scheme:

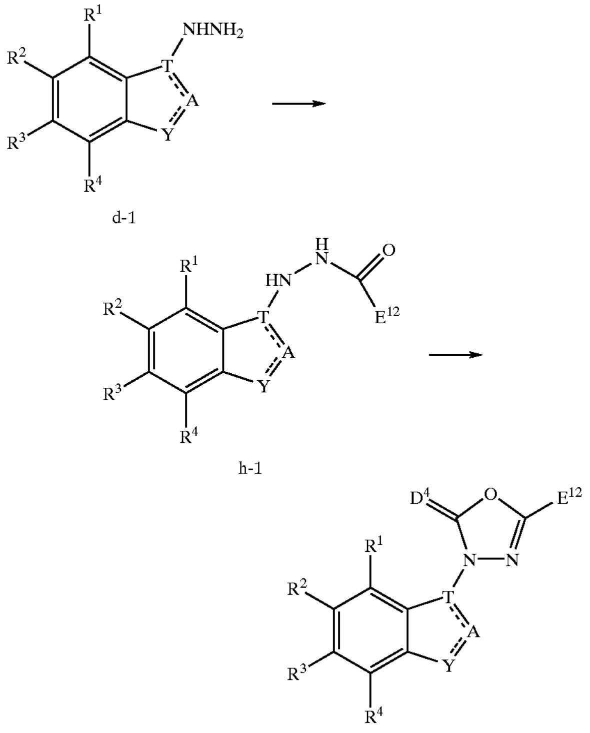

d-1 h-1 h-2 wherein $R^1$, $R^2$, $R^3$, $R^4$, $E^{12}$, $D^4$, T, A, and Y are as defined above.

The reactions in the respective steps can be carried out, for example, according to the processes as described in JP-A 60-109578, or for example, by the following processes.

1) Process of Producing Compound h-1 from Compound d-1

Compound h-1 can be produced by reacting compound d-1 with an acylating agent selected from compound h-3 of the general formula:

h-3

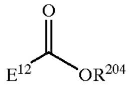

wherein $E^{12}$ is as defined above and $R^{204}$ is hydrogen, methyl, or ethyl, compound h-4 of the general formula:

h-4

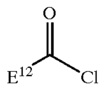

wherein $E^{12}$ is as defined above, and compound h-5 of the general formula:

h-5

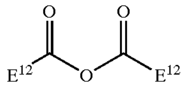

wherein $E^{12}$ is as defined above, in a solvent or without solvent.

Amount of acylating agent: 1 to 5 moles relative to 1 mole of compound d-1

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; etc.

Reaction temperature: −10° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound h-2 from Compound h-1

Compound h-2 can be produced by reacting compound h-1 with compound h-6 of the general formula:

h-6

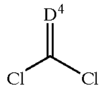

wherein $D^4$ is as defined above, in a solvent in the presence of a base.

Amount of compound h-6: 1 to 5 moles of compound h-1

Kind of base: organic bases such as ti4triethylamine and pyridine; inorganic bases such as potassium carbonate; etc.

Amount of base: 1 to 5 moles relative to 1 mole of compound h-1

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; etc.

Reaction temperature: −10° C. to room temperature

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 8

This is the producing process according to the following scheme:

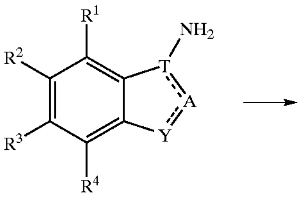

a-1

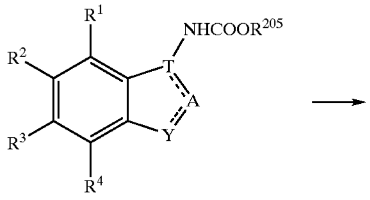

i-1

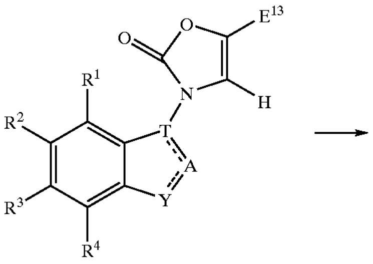

i-2

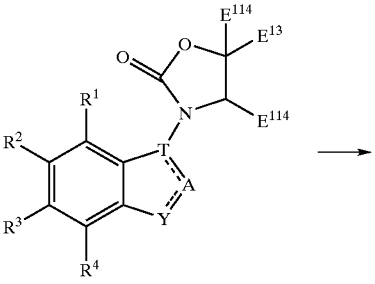

i-3

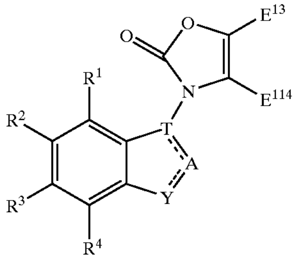

i-4 wherein $R^1$, $R^2$, $R^3$, $R^4$, $E^{13}$, T, A, and Y are as defined above; $E^{114}$ is halogen; and $R^{205}$ is methyl or ethyl.

The reactions in the respective steps can be carried out, for example, according to the processes as described in JP-A 6-145011, or for example, by the following processes.

1) Process of Producing Compound i-1 from Compound a-1

Compound i-1 can be produced by reacting compound a-1 with a chloroformate i-5 of the general formula:

$ClCOOR^{205}$ i-5 wherein $R^{205}$ is as defined above, in a solvent in the presence of a base.

Amount of chloroformate i-5: 1 to 10 moles relative to 1 mole of compound a-1

Kind of base: N,N-dimethylaniline, N,N-diethylaniline, etc.

Amount of base: 1 to 10 moles relative to 1 mole of compound a-1

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; etc.

Reaction temperature: room temperature to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound i-2 from Compound i-1

Compound i-2 can be produced by reacting compound i-1 with compound i-6 of the general formula:

i-6

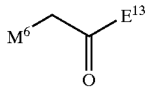

wherein $E^{13}$ is as defined above and $M^6$ is chlorine or bromine, in a solvent in the presence of lithium bis(trimethylsilyl)amide.

Amount of compound i-6: 1 to 10 moles relative to 1 mole of compound i-1

Amount of lithium bis(trimethylsilyl)amide: 1 to 10 moles relative to 1 mole of compound i-1

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; etc.

Reaction temperature: room temperature to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

3) Process of Producing Compound i-3 from Compound i-2

Compound i-3 can be produced by reacting compound i-2 with a halogenating agent in a solvent.

Kind of halogenating agent: chlorine, bromine, etc.

Amount of halogenating agent: 1 mole to large excess relative to 1 mole of compound i-2

Solvent: halogenated aromatic hydrocarbons such as chlorobenzene; halogenated aliphatic hydrocarbons such as chloroform; etc.

Reaction temperature: 10° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

4) Process of Producing Compound i-4 from Compound i-3

Compound i-4 can be produced by reacting compound i-3 with a base in a solvent.

Kind of base: organic bases such as triethyl amine and 1,8-diazabicylo[5.4.0]undec-7-ene; etc.

Amount of base: 1 mole to large excess relative to 1 mole of compound i-3

Solvent: dimethylsulfoxide etc.

Reaction temperature: 10° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 9

This is the producing process according to the following scheme:

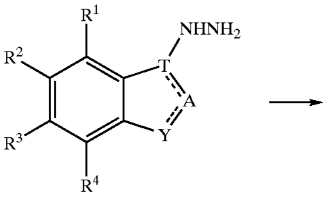

d-1

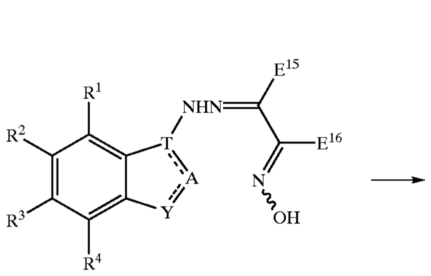

j-1

-continued

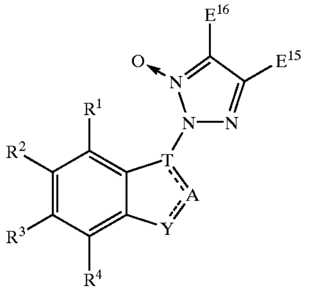

j-2 wherein $R^1$, $R^2$, $R^3$, $R^4$, $E^{15}$, $E^{16}$, T, A, and Y are as defined above.

The reactions in the respective steps can be carried out, for example, according to the processes as described in JP-A 60-104073, or for example, by the following processes.

1) Process of Producing Compound j-1 from Compound d-1

Compound j-1 can be produced by reacting compound d-1 with compound j-3 of the general formula:

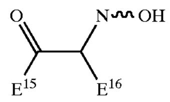

j-3 wherein $E^{15}$ and $E^{16}$ are as defined above, in a solvent, if necessary, in the presence of an acid.

Amount of compound j-3: 1 to 5 moles relative to 1 mole of compound d-1

Solvent: toluene, ethanol, acetic acid, tetrahydrofuran, etc.

Acid: p-toluenesulfonic acid etc.

Reaction temperature: −10° C. to 100° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound j-2 from Compound j-1

Compound j-2 can be produced by reacting compound j-1 with an oxidizing agent in a solvent in the presence of a pyridine.

Amount of pyridine: 1 to 2 moles relative to 1 mole of compound j-1

Kind of oxidizing agent: copper (II) sulfate etc.

Amount of oxidizing agent: 1 to 5 moles relative to 1 mole of compound j-1

Solvent: toluene, ethanol, acetic acid, tetrahydrofuran, etc.

Reaction temperature: −10° C. to 100° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 10

This is the producing process according to the following scheme:

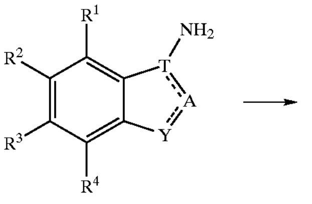

a-1

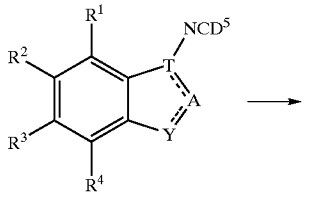

k-1

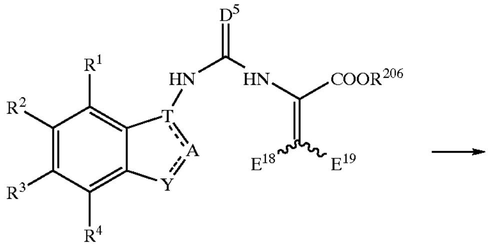

k-2

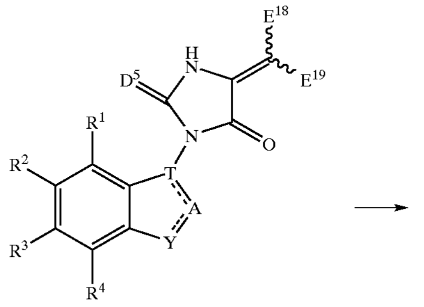

k-3

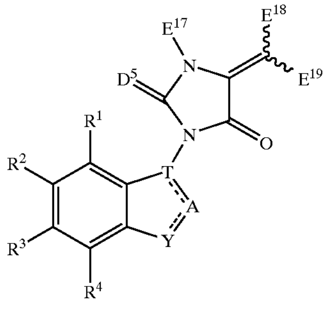

k-4 wherein $R^1$, $R^2$, $R^3$, $R^4$, $E^{17}$, $E^{18}$, $E^{19}$, $D^5$, T, A, and Y are as defined above and $R^{206}$ is methyl or ethyl.

The reactions in the respective steps can be carried out, for example, according to the processes as described in JP-A 63-183567, or for example, by the following processes.

1) Process of Producing Compound k-1 from Compound a-1

Compound k-1 can be produced from compound a-1 according to the process as described above in Producing Process 2, Step 1).

2) Process of Producing Compound k-2 from Compound k-1

Compound k-2 can be produced by reacting compound k-1 with compound k-5 of the general formula:

k-5

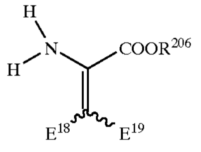

wherein $E^{18}$, $E^{19}$, and $R^{206}$ are as defined above, in a solvent in the presence of a base.

Amount of compound k-5: 1 to 2 moles relative to 1 mole of compound k-1

Kind of base: triethylamine, potassium carbonate, sodium hydride, sodium methylate, etc.

Amount of base: 1 to 5 moles relative to 1 mole of compound k-1

Solvent: toluene, ethanol, tetrahydrofuran, N,N-dimethylformamide, etc.

Reaction temperature: −10° C. to 100° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound k-3 may be obtained directly depending upon the reaction conditions of this process.

3) Process of Producing Compound k-3 from Compound k-2

Compound k-3 can be produced by reacting compound k-2 in a solvent in the presence of a base.

Kind of base: potassium carbonate, sodium hydride, sodium methylate, etc.

Amount of base: 1 to 5 moles relative to 1 mole of compound k-2

Solvent: toluene, ethanol, tetrahydrofuran, N,N-dimethylformamide, etc.

Reaction temperature: −10° C. to 100° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

4) Process of Producing Compound k-4 from Compound k-3

Compound k-4 can be produced by reacting compound k-3 with compound k-6 of the general formula:

$M^7—E^{17}$ k-6 wherein $E^7$ is as defined above and $M^7$ is iodine, bromine, or chlorine, in a solvent in the presence of a base.

Amount of compound k-6: 1 to 2 molesrelative to 1 mole of compound k-3

Kind of base: triethylamine, potassium carbonate, sodium hydride, sodium methylate, etc.

Amount of base: 1 to 5 moles relative to 1 mole of compound k-3

Solvent: toluene, ethanol, tetrahydrofuran, N,N-diinethylformamide, etc.

Reaction temperature: −10° C. to 100° C.

Reaction time: a moment to 48 hours

After completion of the reaction, the reaction mixture is subjected to ost-treatments, for example, the reaction mixture is poured into water, and he deposited crystals are collected by filtration and dried; or the reaction mixture is extracted with an organic solvent, and the organic layer was dried and concentrated; or the reaction mixture is concentrated, thereby obtaiing the desired compound. The compound can be purified by a technique such as recrystallization or column chromatography.

PRODUCING PROCESS 11

This is the producing process according to the following scheme:

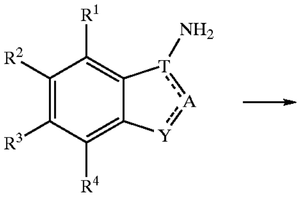

a-1

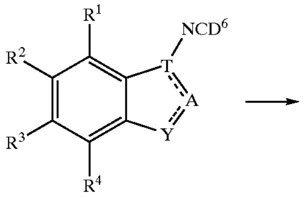

1-1

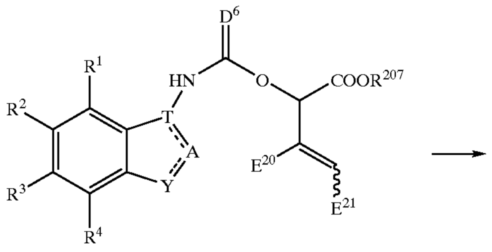

1-2

-continued

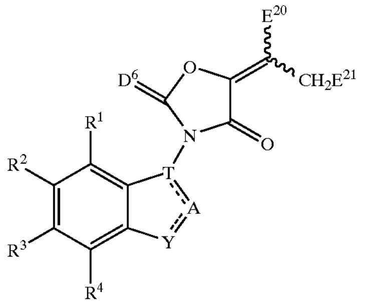

1-3 wherein $R^1$, $R^2$, $R^3$, $R^4$, $E^{20}$, $E^{21}$, $D^6$, T, A, and Y are as defined above and $R^{207}$ is methyl or ethyl.

The reactions in the respective steps can be carried out, for example, according to the processes as described in WO87/62357, or for example, by the following processes.

1) Process of Producing Compound 1-1 from Compound a-1

Compound 1-1 can be produced from compound a-1 according to the process as described above in Producing Process 2, Step 1).

2) Process of Producing Compound 1-2 from Compound 1-1

Compound 1-2 can be produced by reacting compound 1-1 with compound 1-4 of the general formula.

1-4

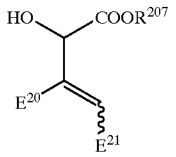

wherein $E^{20}$, $E^{21}$, and $R^{207}$ are as defined above, in a solvent in the presence of a base.

Amount of compound 1-4: 1 to 2 moles relative to 1 mole of compound 1-1

Kind of base: triethylamine, potassium carbonate, sodium hydride, sodium methylate, etc.

Amount of base: 1 to 5 moles relative to 1 mole of compound 1-1

Solvent: toluene, ethanol, tetrahydrofuran, N,N-dimethylformamide, etc.

Reaction temperature: −10° C. to 100° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound 1-3 may be obtained directly depending upon the reaction conditions of this process.

3) Process of Producing Compound 1-3 from Compound 1-2

Compound 1-3 can be produced by reacting compound 1-2 in a solvent in the presence of a base.

Kind of base: potassium carbonate, sodium hydride, sodium methylate, etc.

Amount of base: 1 to 5 moles relative to 1 mole of compound 1-2

Solvent: toluene, ethanol, tetrahydrofuran, N,N-dimethylformamide, etc.

Reaction temperature: −10° C. to 100° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 12

This is the producing process according to the following scheme:

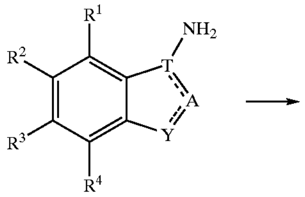

a-1

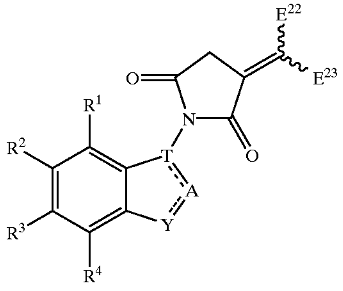

m-1 wherein $R^1$, $R^2$, $R^3$, $R^4$, $E^{22}$, $E^{23}$, T, A, and Y are as defined above.

The reactions in the respective steps can be carried out, for example, according to the processes as described in JP-A 61-103801, or for example, by the following processes.

1) Process of Producing Compound m-1 from Compound a-1

Compound m-1 can be produced by reacting compound a-1 with acid anhydride m-2 of the general formula:

m-2

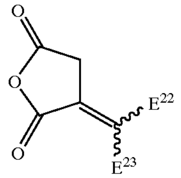

wherein $E^{22}$ and $E^{23}$ are as defined above, usually without solvent, or in a solvent, if necessary, in the presence of an acid.

The reaction temperature is usually in the range of 50° C. to 200° C. The reaction time is usually in the range of 1 to 100 hours. The amounts of agents to be used in the reaction are 1 mole of acid anhydride m-2 relative to 1 mole of compound a-1, which; is the stoichiometric ratio but can be freely changed depending upon the reaction conditions.

The solvent which can be used may include aliphatic hydrocarbons such as hexane, heptane, octane, and ligroin; aromatic hydrocarbons such as benzene, toluene, ethylbenzene, xylene, and mesitylene; halogenated hydrocarbons such as chlorobenzene, dichlorobenzene, and trichlorobenzene; ethers such as 1,4-dioxane, tetrahydrofuran, ethylene glycol dimethyl ether, and methyl t-butyl ether; nitro compounds such as nitromethane and nitrobenzene; organic acids such as acetic acid and propionic acid; acid amides such as N,N-dimethylformamide; sulfur compounds such as dimethylsulfoxide and sulforane; and mixtures thereof As the acid, p-toluenesulfonic acid can be used.

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 13

This is the producing process according to the following scheme:

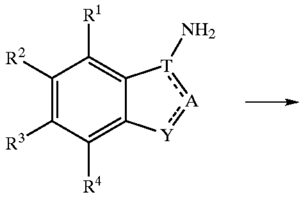

a-1

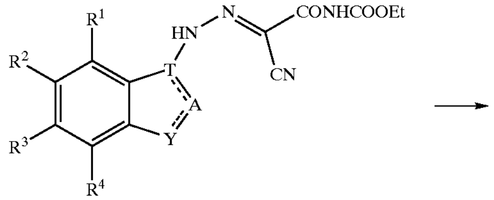

n-1

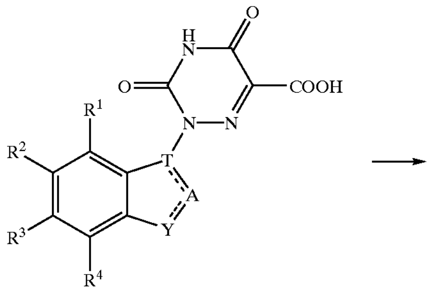

n-2

-continued

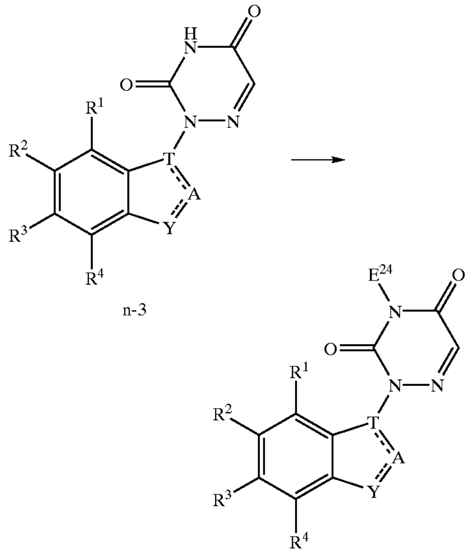

n-3 n-4 wherein $R^1$, $R^2$, $R^3$, $R^4$, $E^{24}$, T, A, and Y are as defined above.

The reactions in the respective steps can be carried out, for example, according to the processes as described in WO86/00072, or for example, by the following processes.

1) Process of Producing Compound n-1 from Compound a-1

Compound n-1 can be produced by converting compound a-1 into a diazonium salt with sodium nitrite in a solvent in the presence of an acid and then reacting the diazonium salt with compound n-5 of the formula:

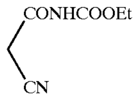

n-5 in a solvent in the presence of a base.

(Diazonium salt formation)

Amount of sodium nitrite: 1 to 2 moles relative to 1 mole of compound a-1

Kind of acid: hydrochloric acid etc.

Amount of acid: 1 mole to an excess amount relative to 1 mole of compound a-1

Solvent: water, ethanol, hydrochloric acid, etc.

Reaction temperature: −15° C. to room temperature

Reaction time: a moment to 24 hours (Reaction with compound n-5)

Amount of compound n-5: 1 to 5 moles relative to 1 mole of compound a-1

Kind of base: sodium acetate etc.

Amount of base: 0.8 to 3 moles relative to 1 mole of acid used in the forgoing step Solvent: ethanol, water, etc.

Reaction temperature: 0°C. to 60° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound n-2 from Compound n-1

Compound n-2 can be produced by reacting compound n-1 in a solvent in the presence of a base.

Kind of base: sodium hydroxide, potassium hydroxide, etc.

Amount of base: 1 to 10 moles relative to 1 mole of compound n-1

Solvent: ethanol, N,N-dimethylformamide, water, and mixtures thereof; etc.

Reaction temperature: 0° C. to 110° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

3) Process of Producing Compound n-3 from Compound n-2

Compound n-3 can be produced by reacting compound n-2 in a solvent in the presence of thioacetic acid.

Amount of thioacetic acid: 0.1 to 10 moles relative to 1 mole of compound n-2

Solvent: xylene etc.

Reaction temperature: reflux temperature

Reaction time: a moment to 72 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

4) Process of Producing Compound n-4 from Compound n-3

Compound n-4 can be produced by reacting compound n-3 with compound n-6 of the general formula:

$M^8—E^{24}$ n-6 wherein $E^{24}$ is as defined above and $M^8$ is iodine, bromine, or chlorine, in a solvent in the presence of a base.

Amount of compound n-6: 1 to 10 moles relative to 1 mole of compound n-3

Kind of base: potassium carbonate, sodium hydride, etc.

Amount of base: 1 to 10 moles relative to 1 mole of compound n-3

Solvent: acetone, tetrahydrofuran, N,N-dimethylformamide, etc.

Reaction temperature: 0° C. to 100° C.

Reaction time: a moment to 72 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 14

This is the producing process according to the following scheme:

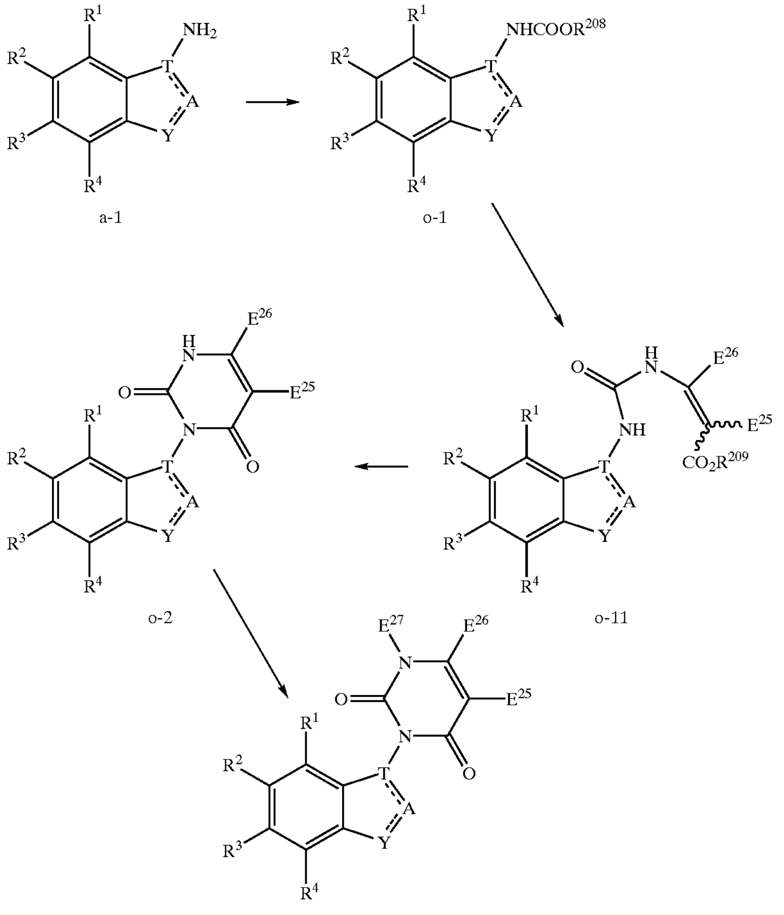

a-1 o-1 o-2 o-11 o-3 wherein $R^1$, $R^2$, $R^3$, $R^4$, $E^{25}$, $E^{26}$, $E^{27}$, T, A, and Y are as defined above, and $R^{208}$ and $R^{209}$ are independently $C_1$–$C_5$ alkyl (e.g., methyl, ethyl, propyl).

The reactions in the respective steps can be carried out, for example, according to the processes as described in JP-A 5-4959 and JP-A 63-41466, or for example, by the following processes.

1) Process of Producing Compound o-1 from Compound a-1

Compound o-1 can be produced from compound a-1 and chloroformate o-4 of the general formula:

$ClCOOR^{208}$ o-4 wherein $R^{208}$ is as defined above, according to the process as described above in Producing Process 8, Step 1).

2) Process of Producing Compound o-11from Compound o-1

Compound o-11 can be produced by reacting compound o-1 with compound o-5 of the general formula:

o-5

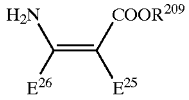

wherein $E^{25}$, $E^{26}$, and $R^{209}$are as defined above, in a solvent in the presence of a base.

Amount of compound o-5: 0.9 to 10 moles relative to 1 mole of compound o-1

Kind of base: inorganic bases such as sodium hydride; metal alcoholates such as sodium methylate and sodium ethylate; etc.

Amount of base: 0.1 to 10 moles relative to 1 mole of compound o-1

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; and mixtures thereof; etc.

Reaction temperature: room temperature to the reflux temperature of the solvent

Reaction time: a moment to 120 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound o-11can also be used as such for the reaction in the next step without isolation.

3) Process of Producing Compound o-2 from Compound o-11

Compound o-2 can be produced by reacting compound o-11 in a solvent in the presence of a base.

Kind of base: inorganic bases such as sodium hydride and potassium carbonate; metal alcoholates such as sodium methylate and sodium ethylate; etc.

Amount of base: 0.1 to 10moles relative to 1 mole of compound o-11

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; sulfur compound such as dimethylsulfoxide; and mixtures thereof Reaction temperature: room temperature to the reflux temperature of the solvent Reaction time: a moment to 120 hours After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound o-2 can also be used as such for the reaction in the next step without isolation.

4) Process of Producing Compound o-3 from Compound o-2

Compound o-3 can be produced by reacting compound o-2 with compound o-6 of the general formula:

$M^9$—$E^{27}$ o-6 wherein $E^{27}$ is as defined above and $M^9$ is iodine, bromine, chlorine, methanesulfonyloxy, or 2,4-dinitrophenoxy, in a solvent in the presence of a base.

Amount of compound o-6: 0.9 to 10 moles relative to 1 mole of compound o-2

Kind of base: inorganic bases such as sodium hydride, potassium carbonate, and sodium hydroxide; metal alcoholates such as sodium methylate and sodium ethylate; etc.

Amount of base: 0.1 to 10 moles relative to 1 mole of compound o-2

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; etc.

Reaction temperature: 0° C. to the reflux temperature of the solvent

Reaction time: a moment to 120 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 15

This is the producing process according to the following scheme:

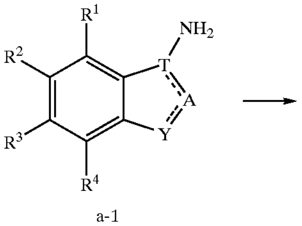

a-1

-continued

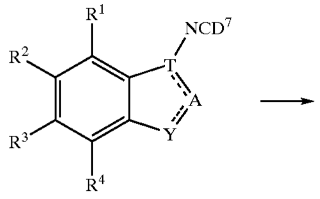

p-1

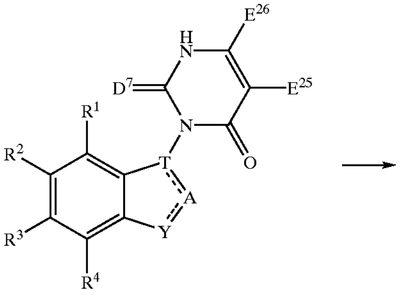

p-2

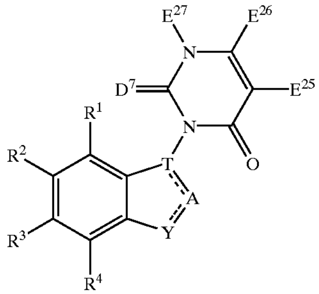

p-3 wherein $R^1$, $R^2$, $R^3$, $R^4$, $D^7$, $E^{25}$, $E^{26}$, $E^{27}$, T, A, and Y are as defined above.

The reactions in the respective steps can be carried out, for example, according to the processes as described in JP-A 63-41466, or for example, by the following processes.

1) Process of Producing Compound p-1 from Compound a-1

Compound p-1 can be produced from compound a-1 according to the process as described above in Producing Process 2, Step 1).

2) Process of Producing Compound p-2 from Compound p-1

Compound p-2 can be produced by reacting compound p-1 with compound p-7 of the general formula:

p-7

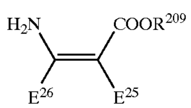

wherein $E^{25}$, $E^{26}$, and $R^{209}$ are as defined above, in a solvent in the presence of a base.

Amount of compound p7: 0.9 to 10 moles relative to 1 mole of compound p-1

Kind of base: inorganic bases such as sodium hydride, potassium hydroxide, and sodium hydroxide; metal alcoholates such as sodium methylate and sodium ethylate; etc.

Amount of base: 0.1 to 10 moles relative to 1 mole of compound p-1

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; and mixtures thereof; etc.

Reaction temperature: −40° C. to the reflux temperature of the solvent

Reaction time: a moment to 72 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound p-2 can also be used as such for the reaction in the next step without isolation.

3) Process of Producing Compound p-3 from Compound p-2

Compound p-3 can be produced by reacting compound p-2 with compound o-6 of the general formula:

$$M^9—E^{27} \qquad \text{o-6}$$

wherein $E^{27}$ and $M^9$ are as defined above, in a solvent in the presence of a base.

Amount of compound o-6: 0.9 to 10 moles relative to 1 mole of compound p-2

Kind of base: inorganic bases such as sodium hydride, potassium hydroxide, and sodium hydroxide; metal alcoholates such as sodium methylate and sodium ethylate; etc.

Amount of base: 0.1 to 10 moles relative to 1 mole of compound p-2

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; etc.

Reaction temperature: −10° C. to the reflux temperature of the solvent

Reaction time: a moment to 72 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 16

This is the producing process according to the following scheme:

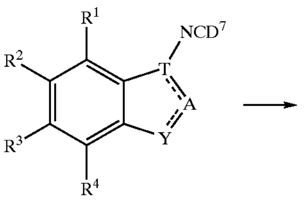

p-1

-continued

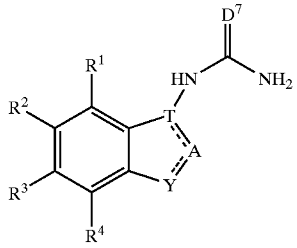

p-4

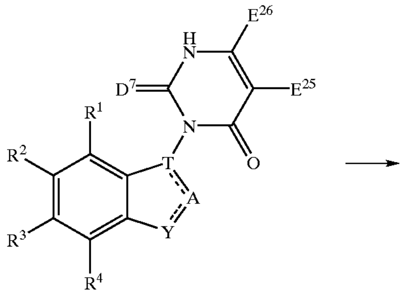

p-2

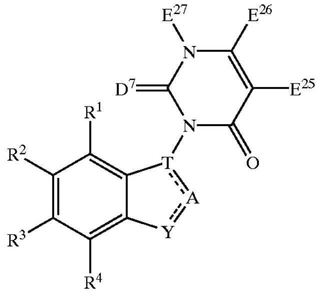

p-3 wherein $R^1$, $R^2$, $R^3$, $R^4$, $D^7$, $E^{25}$, $E^{26}$, $E^{27}$, T, A, and Y as defined above.

The reactions in the respective steps can be carried out, for example, according to the processes as described in JP-A 63-41466, or for example, by the following processes.

1) Process of Producing Compound p-4 from Compound p-1

Compound p-4 can be produced by reacting compound p-1 with ammonia in a solvent.

Amount of ammonia: 1 mole to large excess relative to 1 mole of compound p-1

Solvent: water, methanol, ethanol, tetrahydrofuran, 1,4-dioxane, etc.

Reaction temperature: −20° C. to 100° C.

Reaction time: a moment to 24 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound p-2 from Compound p-4

Compound p-2 can be produced by reacting compound p-4 with compound p-9 of the general formula:

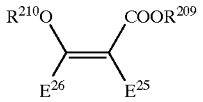

p-9 wherein $E^{25}$, $E^{26}$, and $R^{209}$ are as defined above and $R^{210}$ is methyl, in a solvent in the presence of a base.

Amount of compound p-9: 0.9 to 10 moles relative to 1 mole of compound p-4

Kind of base: inorganic bases such as sodium hydride, potassium hydroxide, and sodium hydroxide; metal alcoholates such as sodium methylate and sodium ethylate; etc.

Amount of base: 0.1 to 10 moles relative to 1 mole of compound p-4

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; etc.

Reaction temperature: room temperature to the reflux temperature of the solvent

Reaction time: a moment to 120 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound p-2 can also be used as such for the reaction in the next step without isolation.

3) Process of Producing Compound p-3 from Compound p-2

Compound p-3 can be produced by reacting compound p-2 with compound o-6 of the general formula:

$M^9—E^{27}$ o-6 wherein $E^{27}$ and $M^9$ are as defined above, in a solvent in the presence of a base.

Amount of compound o-6: 0.9 to 10 moles relative to 1 mole of compound p-2

Kind of base: inorganic bases such as sodium hydride, potassium hydroxide, and sodium hydroxide; metal alcoholates such as sodium methylate and sodium ethylate; etc.

Amount of base: 0.1 to 10 moles relative to 1 mole of compound p-2

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; etc.

Reaction temperature: −10° C. to the reflux temperature of the solvent

Reaction time: a moment to 72 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 17

This is the producing process according to the following scheme:

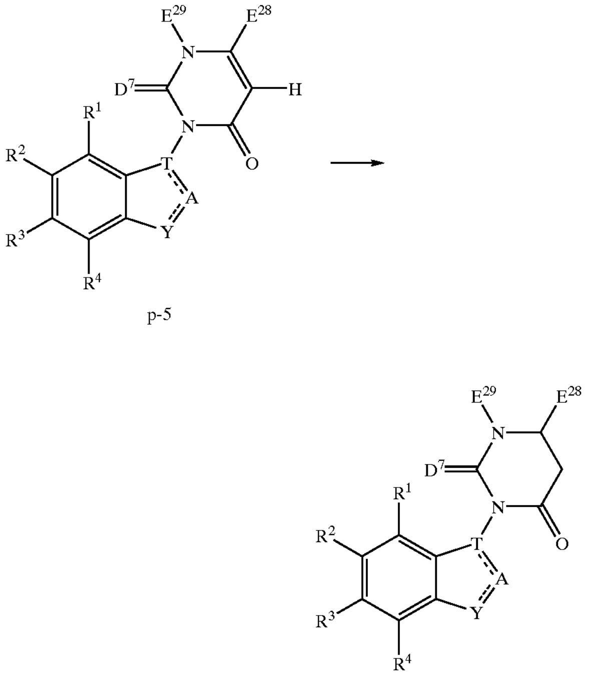

p-5 p-6 wherein $R^1$, $R^2$, $R^3$, $R^4$, $D^7$, $E^{28}$, $E^{29}$, A, T, and Y are as defined above.

The reactions in the respective steps can be carried out, for example, according to the processes as described in JP-A 6-92943, or for example, by the following processes.

1) Process of Producing Compound p-6 from Compound p-5

Compound p-6 can be produced by reducing compound p-5 in a solvent.

Kind of reducing agent: $NaBH_4$ etc.

Amount of reducing agent: 1 to 10 moles relative to 1 mole of compound p-5

Solvent: water, methanol, ethanol, acetic acid, etc.

Reaction temperature: −10° C. to the reflux temperature of the solvent

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 18

This is the producing process according to the following scheme:

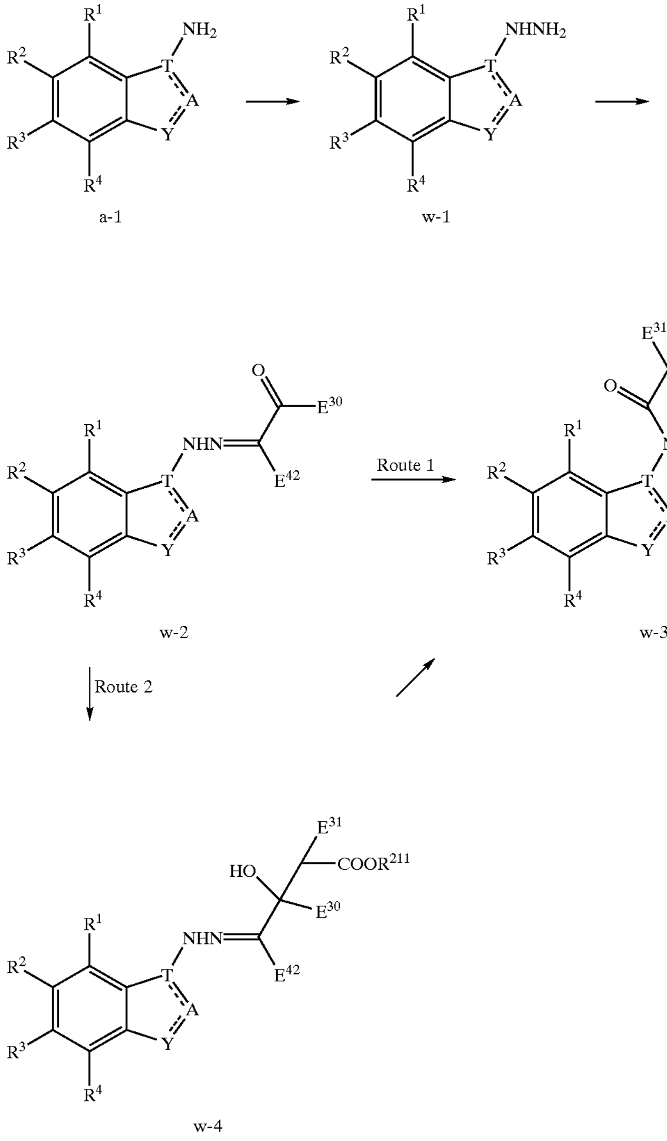

a-1 w-1 w-2 w-3 w-4 wherein $R^1$, $R^2$, $R^3$, $R^4$, $E^{30}$, $E^{31}$, $E^{42}$, T, A, and Y are as defined above, and $R^{211}$ is hydrogen, methyl, or ethyl.

The reactions in the respective steps can be carried out, for example, according to the processes as described in JP-A 9-323977 and WO98/17632, or for example, by the following processes.

1) Process of Producing Compound w-1 from Compound a-1

Compound w-1 can be produced from compound a-1 according to the process as described above in Producing Process 5, Step 1).

2) Process of Producing Compound w-2 from Compound w-1

Compound w-2 can be produced by reacting compound w-8 of the general formula:

w-8

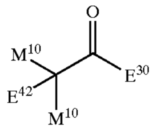

wherein $E^{30}$ and $E^{42}$ are as defined above and $M^{10}$ is iodine, bromine, or chlorine, with water in the presence of a base to form compound w-9 of the general formula:

w-9

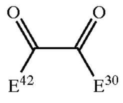

wherein $E^{30}$ and $E^{42}$ are as defined above (reaction 1), and then reacting the carbonyl derivative with compound w-1 (reaction 2).

(Reaction 1)

Reaction 1 is usually carried out in a solvent. The reaction temperature is usually in the range of 20° C. to 100° C. The reaction time is usually in the range of a moment to 72 hours. The amounts of agents to be used in the reaction are 2 moles of each of the water and base relative to 1 mole compound w-8, which is ideal but can be freely changed depending upon the reaction conditions.

As the base to be used, both organic bases and inorganic bases can be used, examples of which are sodium acetate and potassium acetate.

The solvent which can be used may include aromatic hydrocarbons such as benzene, toluene, and xylene; halogenated hydrocarbons such as chlorobenzene; ethers such as tetrahydrofuran and 1,4-dioxane; esters such as ethyl acetate and butyl acetate; nitro compounds such as nitromethane and nitrobenzene; nitrites such as acetonitrile; amides such as N,N-di-methylformamide; alcohols such as methanol, ethanol, and isopropanol; water; and mixtures thereof (Reaction 2)

Reaction 2 is usually carried out in a solvent. The reaction temperature is usually in the range of −20° C. to 200° C. The reaction time is usually in the range of a moment to 72 hours. The amounts of agents to be used in the reaction are 1 mole of compound w-1 relative to 1 mole of compound w-8, which is ideal but can be freely changed depending upon the reaction conditions. Depending upon the conditions, salts of compound w-1, such as hydrochloride salt and sulfate salt, can also be used.

The solvent which can be used may include aromatic hydrocarbons such as benzene, toluene, and xylene; halogenated hydrocarbons such as chlorobenzene; ethers such as tetrahydrofuran and 1,4-dioxane; esters such as ethyl acetate and butyl acetate; nitro compounds such as nitromethane and nitrobenzene; nitrites such as acetonitrile; amides such as N,N-di-methylformamide; alcohols such as methanol, ethanol, and isopropanol; water; and mixtures thereof.

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

3) Process of Producing Compound w-3 from Compound w-2 (Route 1)

Compound w-3 can be produced by reacting compound w-2 with phosphorane compound w-10 of the general formula:

w-10

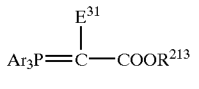

wherein $E^{31}$ is as defined above; $R^{213}$ is methyl or ethyl; and Ar is optionally substituted phenyl (e.g., phenyl), in a solvent.

This reaction is usually carried out in a solvent. The reaction temperature is usually in the range of −20° C. to 150° C, preferably 0° C. to 100° C. The reaction time is usually in the range of a moment to 72 hours. The amounts of agents to be used in the reaction are 1 mole of compound w-10 relative to 1 mole of compound w-2, which is ideal but can be freely changed depending upon the reaction conditions.

The solvent which can be used may include aromatic hydrocarbons such as benzene, toluene, and xylene; halogenated hydrocarbons such as chlorobenzene; ethers such as tetrahydrofuran and 1,4-dioxane; esters such as ethyl acetate and butyl acetate; nitro compounds such as nitromethane and nitrobenzene; nitrites such as acetonitrile; amides such as N,N-di-methylformamide; alcohols such as methanol, ethanol, and isopropanol; water; and mixtures thereof.

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

4) Process of Producing Compound w-4 from Compound w-2 (Route 2)

Compound w-4 can be produced by reacting compound w-2 with compound w-11 of the general formula:

w-11

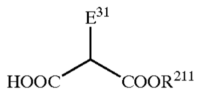

wherein $E^{31}$ and $R^{211}$ are as defined above, in the presence of a base.

This reaction is usually carried out in a solvent. The reaction temperature is usually in the range of 20° C. to 200° C., preferably 40° C. to 150° C. The reaction time is usually in the range of a moment to 72 hours. The amounts of agents to be used in the reaction are usually 1 to 10 moles of compound w-11, preferably 1 to 2 moles of compound w-11, which is ideal, relative to 1 mole of compound w-2. The amount of base is usually 1 mole to large excess, preferably 1 to 10 moles, relative to 1 mole of compound w-11

The base which can be used may include organic bases such as triethylamine and tributylamine.

The solvent which can be used may include aromatic hydrocarbons such as benzene, toluene, and xylene; halogenated hydrocarbons such as chlorobenzene; ethers such as tetrahydrofuran and 1,4-dioxane; esters such as ethyl acetate and butyl acetate; nitro compounds such as nitromethane and nitrobenzene; nitrites such as acetonitrile; amides such as N,N-di-methylformamide; alcohols such as methanol, ethanol, and isopropanol; water; and mixtures thereof.

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining he desired compound. The compound can be purified by a technique such as recrystallization or column chromatography.

5) Process of Producing Compound w-3 from Compound w-4

Compound w-3 can be produced by reacting compound w-4, if necessary, in the presence of a base or acid, or in an acid-base mixed system.

This reaction is usually carried out in a solvent. The reaction temperature is usually in the range of 20° C. to 200° C., preferably 40° C. to 150° C. The reaction time is usually in the range of a moment to 96 hours.

The kind of base used, if necessary, may include organic bases such as pyridine; and metal alcoholates such as sodium methylate. The amount of base is usually 1 mole to large excess, preferably 1 to 10 moles, which is ideal, relative to 1 mole of compound w-4.

The kind of add used, if necessary, may include organic acids such as acetic acid and benzoic acid; and p-toluenesulfonic acid. The amount of acid is usually 1 mole to large excess, preferably 1 to 10 moles, which is ideal, relative to 1 mole of compound w-4.

The solvent which can be used may include aromatic hydrocarbons such as benzene, toluene, and xylene; halogenated hydrocarbons such as chlorobenzene; ethers such as tetrahydrofuran and 1,4-dioxane; esters such as ethyl acetate and butyl acetate; nitro compounds such as nitromethane and nitrobenzene; nitrites such as acetonitrile; amides such as N,N-di-methylformamide; alcohols such as methanol, ethanol, and isopropanol; and mixtures thereof.

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound w-7 (i.e., compound w-2 wherein $E^{42}$ is H) can also be produced according to the following scheme:

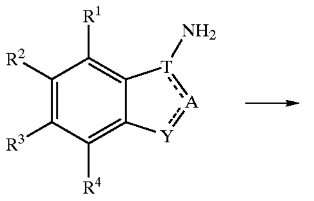

a-1

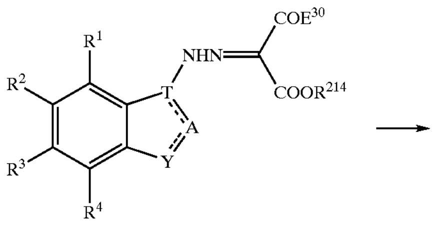

w-5

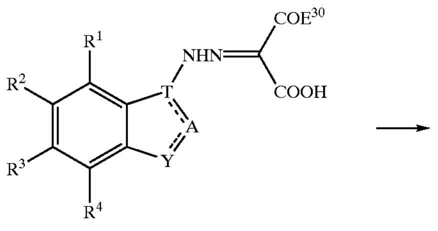

w-6

-continued

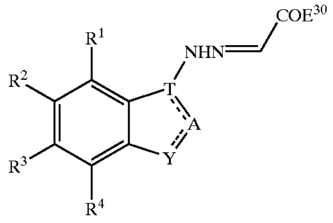

w-7 wherein $R^1$, $R^2$, $R^3$, $R^4$, $E^{30}$, T, A, and Y are as defined above, and $R^{214}$ is methyl or ethyl.

The reactions in the respective steps can be carried out, for example, according to the processes as described in JP-A 9-323977, or for example, by the following processes.

6) Process of Producing Compound w-5 from Compound a-1 (see Tetrahedron, vol. 35, p. 2013 (1979))

Compound w-5 can be produced by converting compound a-1 into a diazonium salt with sodium nitrite in a solvent in the presence of an acid, and then reacting the diazonium salt with compound w-12 of the general formula:

w-12

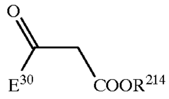

wherein $E^{30}$ and $R^{214}$ are as defined above, in a solvent in the presence of a base.

(Diazonium salt formation)

Amount of sodium nitrite: 1 to 2 moles relative to 1 mole of compound a-1

Kind of acid: hydrochloric acid etc.

Amount of acid: 1 to 100 moles relative to 1 mole of compound a-1

Solvent: water, ethanol, hydrochloric acid, etc.

Reaction temperature: −15° C. to room temperature

Reaction time: a moment to 24 hours (Reaction with compound w-12)

Amount of compound w-12: 1 to 5 moles relative to 1 mole of compound a-1

Kind of base: sodium acetate etc.

Amount of base: 0.8 to 3 moles relative to 1 mole of acid used in the forgoing step Solvent: ethanol, water, etc.

Reaction temperature: 0° C. to 60° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

6) Process of Producing Compound w-6 from Compound w-5

Compound w-6 can be produced by reacting compound w-5 in a solvent in the presence of a base.

The reaction temperature is usually in the range of 0° C. to 150° C.

The reaction time is usually in the range of a moment to 72 hours. The amounts of agents to be used in the reaction are 1 mole of base relative to 1 mole of compound w-5, which is ideal but can be freely changed, if necessary. The base may include inorganic bases such as sodium hydroxide, lithium hydroxide, lithium hydroxide monohydrate, barium hydroxide, and potassium hydroxide.

The solvent which can be used may include aromatic hydrocarbons such as benzene, toluene, and xylene; halogenated hydrocarbons such as chlorobenzene; ethers such as tetrahydrofuran and 1,4-dioxane; nitrites such as acetonitrile; amides such as N,N-dimethylformamide; alcohols such as methanol, ethanol, and isopropanol; water; and mixtures thereof.

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

7) Process of Producing Compound w-7 from Compound w-6

Compound w-7 can be produced by heating compound w-6 in a solvent.

The reaction temperature is usually in the range of 50° C. to 200° C. The reaction time is usually in the range of a moment to 72 hours.

The solvent which can be used may include aromatic hydrocarbons such as benzene, toluene, and xylene; halogenated hydrocarbons such as chlorobenzene; ethers such as tetrahydrofuran and 1,4-dioxane; nitrites such as acetonitrile; amides such as N,N-dimethylformamride; alcohols such as methanol, ethanol and isopropanol; nitrogen-containing aromatic compounds such as pyridine and picoline; sulfur compounds such as dimethylsulfoxide; tertiary amines such as N,N-dimethylailine; water; and mixtures thereof.

In this reaction, metals such as copper powder may be used as a catalyst, if necessary.

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 19

This is the producing process according to the following scheme:

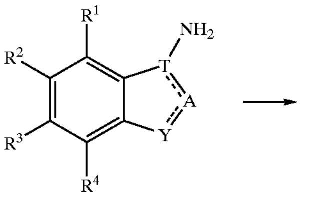

a-1

-continued

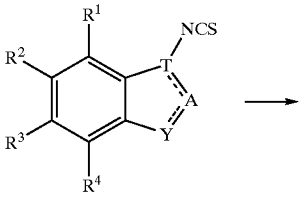

r-1

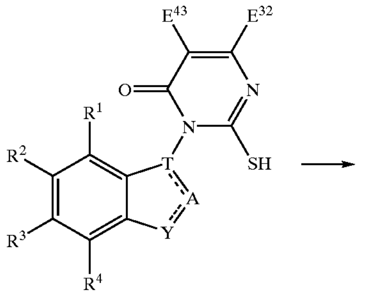

r-2

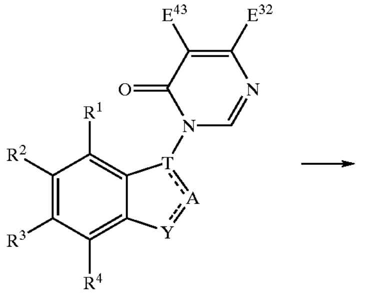

r-3

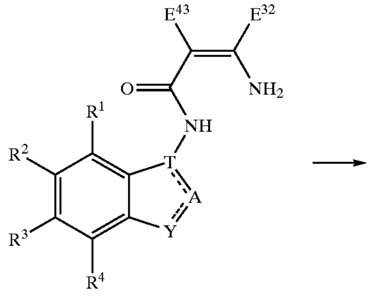

r-4

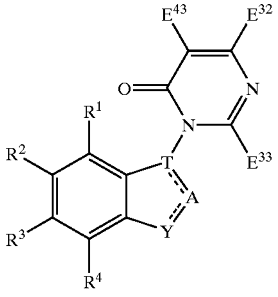

r-5 wherein $R^1$, $R^2$, $R^3$, $R^4$, $E^{32}$, $E^{33}$, $E^{43}$, T, A, and Y are as described above.

The reactions in the respective steps can be carried out, for example, according to the processes as described in JP-A 6-25186, or for example, by the following processes.

1) Process of Producing Compound r-1 from Compound a-1

Compound r-1 can be produced by converting compound a-1 into an isothiocyanate derivative in a solvent or without solvent.

Agent for conversion into isothiocyanate derivatives: thiophosgene etc.

Amount of agent for conversion into isothiocyanate derivatives: 1 equivalent to an excess amount relative to 1 mole of compound a-1

Solvent: aromatic hydrocarbons such as benzene and toluene; halogenated aromatic hydrocarbons such as chlorobenzene; etc.

Reaction temperature: room temperature to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound r-2 from Compound r-1

Compound r-2 can be produced by reacting compound r-1 with compound r-6 of the general formula:

r-6

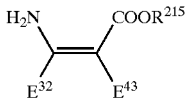

wherein $E^{32}$ and $E^{43}$ are as defined above and $R^{215}$ is methyl, ethyl, or propyl in a solvent in the presence of a base.

Amount of compound r-6: 0.9 to 10 moles relative to 1 mole of compound r-1

Kind of base: inorganic bases such as sodium hydride, potassium hydroxide, and sodium hydroxide; metal alcoholates such as sodium methylate and sodium ethylate; etc.

Amount of base: 0.1 to 10 moles relative to 1 mole of compound r-1

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; etc.

Reaction temperature: −10° C. to the reflux temperature of the solvent

Reaction time: a moment to 72 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chrormatography.

3) Process of Producing Compound r-3 from Compound r-2

Compound r-3 can be produced by reacting compound r-2 with Raney nickel in a solvent in the presence of a base.

Amount of Raney nickel: 1 to 20 moles relative to 1 mole of compound r-2

Kind of base: nitrogen-containing compounds such as pyridine; organic bases such as triethylamine; ammonia; etc.

Amount of base: 0. 1 to 20 moles relative to compound r-2

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; alcohols such as methanol and ethanol; water; and mixtures thereof; etc.

Reaction temperature: −10° C. to the reflux temperature of the solvent

Reaction time: a moment to 72 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

4) Process of Producing Compound r-4 from Compound r-3

Compound r-4 can be produced by reacting compound r-3 in a solvent in the presence of a base.

Kind of base: metal alcoholates such as sodium methylate and sodium ethylate; etc.

Amount of base: 1 to 20 moles relative to compound r-3

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; alcohols such as methanol and ethanol; water; and mixtures thereof; etc.

Reaction temperature: 20° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

5) Process of Producing Compound r-5 from Compound r-4

Compound r-5 can be produced by reacting compound r-4 with an acylating agent selected from compound r-7 of the general formula:

r-7

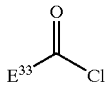

wherein $E^{33}$ is as defined above, or compound r-8 of the general formula:

r-8

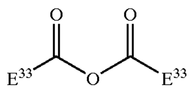

wherein $E^{33}$ is as defined above, in a solvent.

Amount of acylating agent: 1 to 5 moles relative to 1 mole of compound r-4

Solvent: organic acids such as acetic acid and propionic acid; etc.

Reaction temperature: the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 20

This is the producing process according to the following scheme:

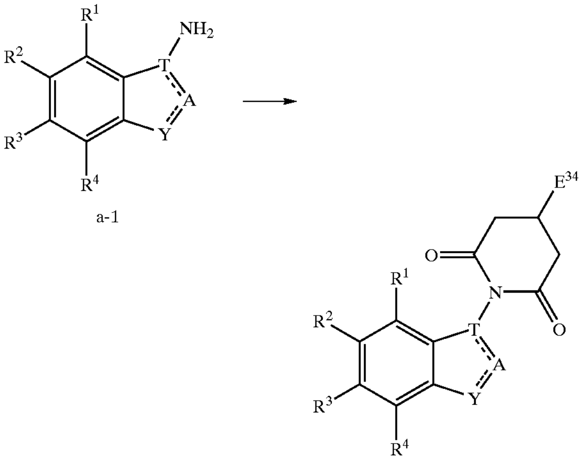

a-1 s-1 wherein $R^1$, $R^2$, $R^3$, $R^4$, $E^{34}$, T, A, and Y are as defined above.

The reaction can be carried out, for example, according to the process as described in JP-A 4-356463, or for example, by the following process.

1) Process of Producing Compound s-1 from Compound a-1

Compound s-1 can be produced by reacting compound a-1 with acid anhydride s-2 of the general formula:

s-2

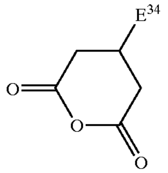

wherein $E^{34}$ is as defined above, in a solvent, if necessary, in the presence of an acid.

Amount of acid anhydride s-2: 1 to 5 moles relative to 1 mole of compound a-1

Solvent: organic acids such as acetic acid and propionic acid; aromatic hydrocarbons such as benzene and toluene; etc.

Kind of acid: p-toluenesulfonic acid etc.

Reaction temperature: room temperature to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 21

This is the producing process according to the following scheme:

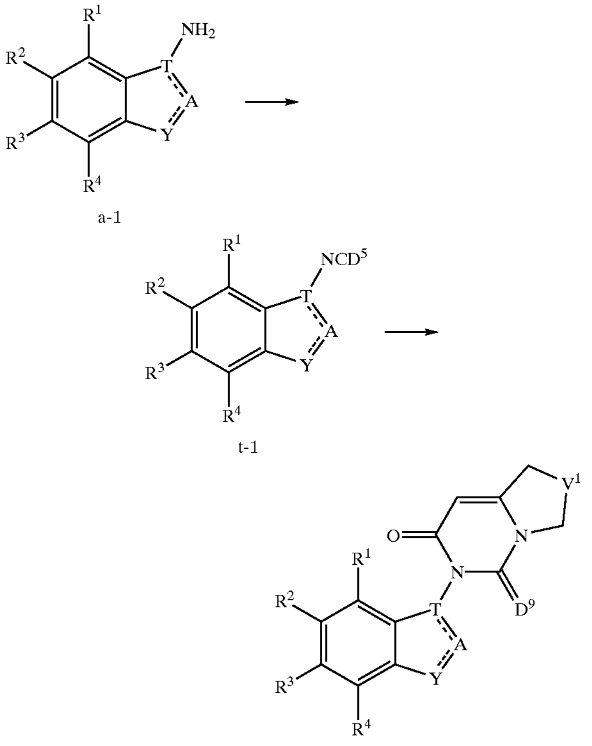

a-1 t-1 t-2 wherein $R^1$, $R^2$, $R^3$, $R^4$, $D^9$, $V^1$, T, A, and Y are as defined above.

The reactions in the respective steps can be carried out, for example, according to the processes as described in JP-A 5-25173, or for example, by the following processes.

1) Process of Producing Compound t-1 from Compound a-1

Compound t-1 can be produced from compound a-1 according to the process as described above in Producing Process 2, Step 1).

2) Process of Producing Compound t-2 from Compound t-1

Compound t-2 can be produced by reacting compound t-1 with compound t-3 of the general formula:

t-3

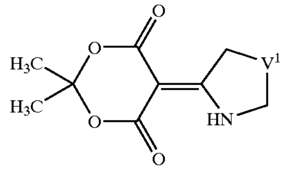

wherein $V^1$ is as defined above, in a solvent in the presence of a base.

Amount of compound t-3: 0.9 to 10 moles relative to 1 mole of compound t-1

Kind of base: inorganic bases such as sodium hydride, potassium hydroxide, and sodium hydroxide; metal alcoholates such as sodium methylate and sodium ethylate; etc.

Amount of base: 0.1 to 10 moles relative to 1 mole of compound t-1

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; and mixtures thereof; etc.

Reaction temperature: −40° C. to the reflux temperature of the solvent

Reaction time: a moment to 72 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 22

This is the producing process according to the following schemes:

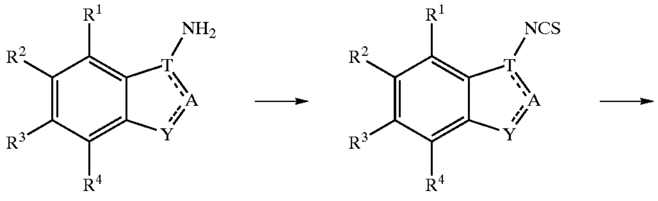

a-1 u-1

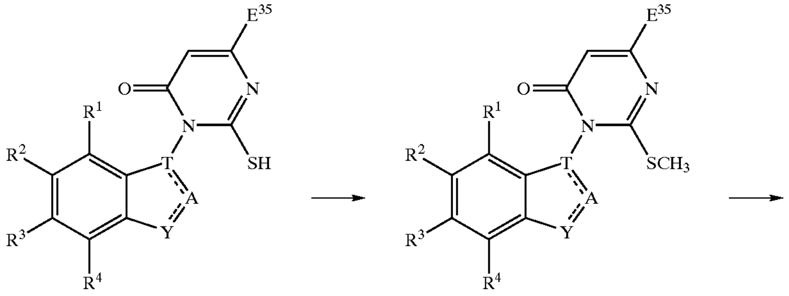

u-2 u-3

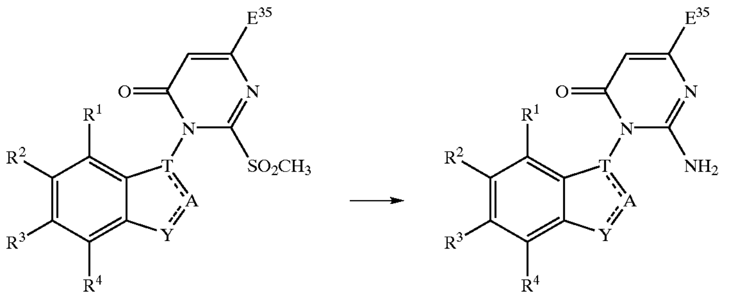

u-4 u-5

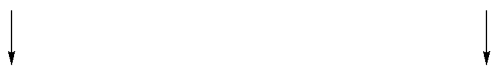

-continued

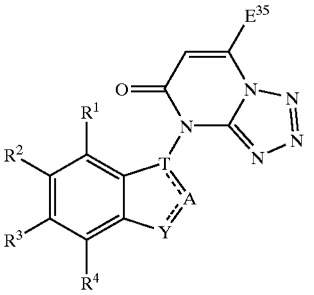

u-6

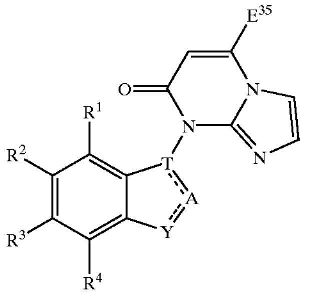

u-7

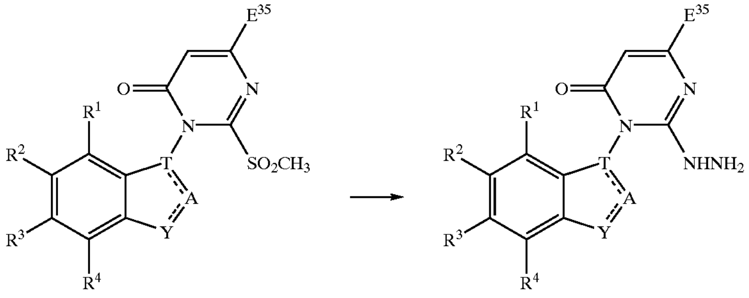

u-4 u-8

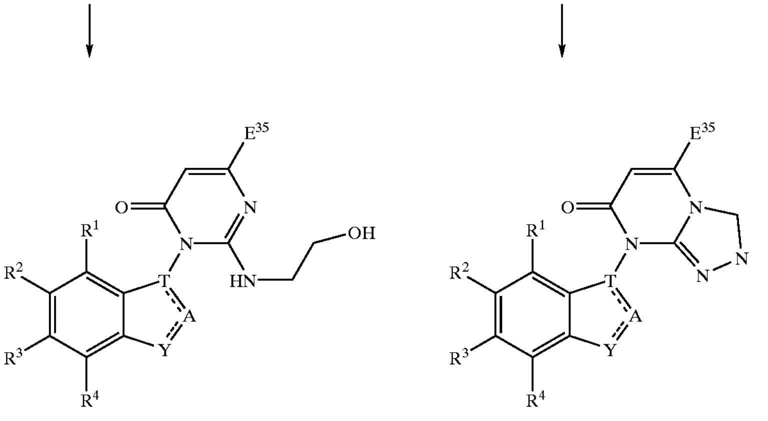

u-9 u-10

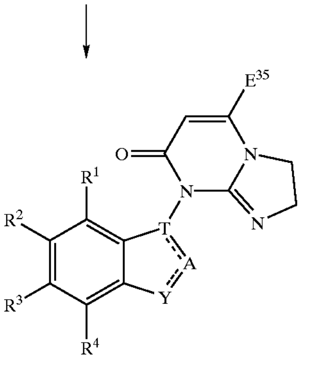

u-11 wherein $R^1$, $R^2$, $R^3$, $R^4$, $E^{35}$, A, T, and Y are as defined above.

The reactions in the respective steps can be carried out, for example, according to the processes as described in WO98/14452, or for example, by the following processes.

1) Process of Producing Compound u-1 from Compound a-1

Compound u-1 can be produced from compound a-1 according to the process as described above in Producing Process 19, Step 1).

2) Process of producing compound u-2 from Compound u-1

Compound u-2 can be produced by reacting compound u-1 with compound u-12 of the general formula:

u-12

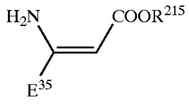

wherein $E^{35}$ and $R^{215}$ are as defined above, in a solvent in the presence of a base.

Amount of compound u-12: 0.9 to 10 moles relative to 1 mole of compound u-1

Kind of base: inorganic bases such as sodium hydride, potassium hydroxide, and sodium hydroxide; metal alcoholates such as sodium methylate and sodium ethylate; etc.

Amount of base: 0.1 to 10 moles relative to 1 mole of compound u-1

Solvent: aromatic hydrocarbons such as benzene and toluene; halogenated aromatic hydrocarbons such as chlorobenzene; amides such as N,N-dimethylformamide; ethers such as tetrahydrofuran; halogenated aliphatic hydrocarbons such as chloroform; and mixtures thereof; etc.

Reaction temperature: −10° C. to the reflux temperature of the solvent

Reaction time: a moment to 72 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated,. thereby obtaining the desired compound. The compound can be purified by a technique such as recrystallization or column chromatography.

3) Process of Producing Compound u-3 from Compound u-2

Compound u-3 can be produced by reacting compound u-2 with a methylating agent such as methyl iodide or dimethyl sulfate in a solvent in the presence of a base.

Kind of base: organic bases such as triethylamine; nitrogen-containing compounds such as pyridine; inorganic bases such as sodium hydride, potassium carbonate, and potassium hydroxide; etc.

Amount of base: 1 to 20 moles relative to 1 mole of compound u-2

Amount of methylating agent: 1 to 20 moles relative to 1 mole of compound u-2

Solvent: aromatic hydrocarbons such as benzene and toluene; halogenated aromatic hydrocarbons such as chlorobenzene; ethers such as tetrahydrofuran; amides such as N,N-dimethylformamide; water; and mixtures thereof; etc.

Reaction temperature: −10° C. to room temperature

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

4) Process of Producing Compound u-4 from Compound u-3

Compound u-4 can be produced by reacting compound u-3 with an oxidizing agent in a solvent.

Kind of oxidizing agent: m-chloroperbenzoic acid, aqueous hydrogen peroxide, etc.

Amount of oxidizing agent: 2 to 20 moles relative to 1 mole of compound u-3

Solvent: aromatic hydrocarbons such as benzene and toluene; halogenated aromatic hydrocarbons such as chlorobenzene; halogenated aliphatic hydrocarbons such as chloroform; water; and mixtures thereof; etc.

Reaction temperature: −20° C. to room temperature

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

5) Process of Producing Compound u-5 from Compound u-4

Compound u-5 can be produced by reacting compound u-4 with ammonia in a solvent.

Amount of ammonia: 1 mole to large excess relative to 1 mole of compound u-4

Solvent: t-butanol, isopropanol, etc.

Reaction temperature: −20° C. to 40° C.

Reaction time: a moment to 10 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

6) Process of Producing Compound u-6 from Compound u-4

Compound u-6 can be produced by reacting compound u-4 with an azidizing agent such as sodium azide or trimethylsilyl azide in a solvent such as methanol, ethanol, and water.

Amount of azidizing agent: 1 equivalent to an excess amount relative to 1 mole of compound u-4

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

7) Process of Producing Compound u-7 from Compound u-5

Compound u-7 can be produced by reacting compound u-5 with a haloacetaldehyde such as chloroacetaldehyde (40% aqueous solution) in a solvent.

The amount of haloacetaldehyde is 1 equivalent to an excess amount relative to 1 mole of compound u-5. The solvent may include ethers such as 1,4-dioxane and tetrahydrofuran; water; and mixtures thereof; etc. The reaction temperature is in the range of 40° C. to the reflux temperature of the solvent. The reaction time is in the range of a moment to 20 hours.

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining he desired compound. The compound can be purified by a technique such as recrystallization or column chromatography.

8) Process of Producing Compound u-8 from Compound u-4

Compound u-8 can be produced by reacting compound u-4 with hydrazine (hydrate) in a solvent or without solvent.

Amount of hydrazine: 1 mole to a large excess amount relative to 1 mole of compound u-4

Solvent: t-butanol, isopropanol, etc.

Reaction temperature: −20° C. to 40° C.

Reaction time: a moment to 10 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

9) Process of Producing Compound u-9 from Compound u-4

Compound u-9 can be produced by reacting compound u-4 with 2-ethanolamine in a solvent or without solvent.

Amount of 2-ethanolamine: 1 mole to a large excess amount relative to 1 mole of compound u-4

Solvent: t-butanol, isopropanol, etc.

Reaction temperature: −20° C. to 40° C.

Reaction time: a moment to 10 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

10) Process of Producing Compound u-10 from Compound-u-8

Compound u-10 can be produced by reacting compound u-8 with formic acid in a solvent or without solvent, if necessary, in the presence of another acid.

Kind of acid: p-toluenesulfonic acid, hydrochloric acid, etc.

Amount of acid: 0.001 mole to a large excess amount relative to 1 mole of compound u-8

Amount of formic acid: 1 mole to a large excess amount to 1 mole of compound u-8

Solvent: aromatic hydrocarbons such as benzene and toluene; halogenated aromatic hydrocarbons such as chlorobenzene; amides such as N-N-dimethylformamide; ethers such as tetrahydrofuran; halogenated aliphatic hydrocarbons such as chloroform; alcohols such as methanol and ethanol; water; and mixtures thereof, etc.

Reaction temperature: 40° C. to the reflux temperature of the solvent

Reaction time: a moment to 10 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

11) Process of Producing Compound u-11 from Compound u-9

Compound u-11 can be produced by reacting compound u-9 in a solvent or without solvent in the presence of an acid.

Kind of acid: p-toluenesulfonic acid, hydrochloric acid, sulfuric acid, polyphosphoric acid, etc.

Amount of acid: 0.001 mole to a large excess amount relative to 1 mole of compound u-9

Solvent: aromatic hydrocarbons such as benzene and toluene; halogenated aromatic hydrocarbons such as chlorobenzene; amides such as N-N-dimethylformamide; ethers such as tetrahydrofuran; halogenated aliphatic hydrocarbons such as chloroform; alcohols such as methanol and ethanol; water; and mixtures thereof; etc.

Reaction temperature: 40° C. to the reflux temperature of the solvent

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 23

This is the producing process according to the following scheme:

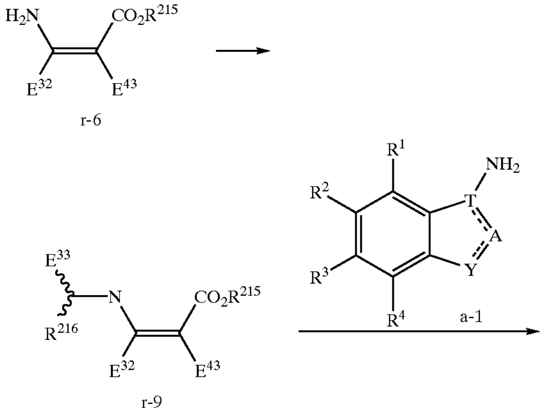

r-6 r-9 a-1

-continued

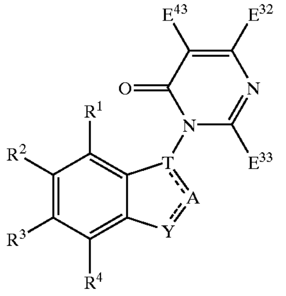

r-5 wherein $R^1$, $R^2$, $R^3$, $R^4$, $R^{25}$, $E^{32}$, $E^{33}$, $E^{43}$, T, A, and Y are as defined above; and $R^{216}$is $C_1$–$C_6$ alkoxy (e.g., methoxy, ethoxy) or $NR^{217}(R^{218}$ (e.g., dimethylamino, dimethylamino) wherein $R^{217}$ and $R^{218}$ are independently $C_1$–$C_5$ alkyl.

The reactions in the respective steps can be carried out, for example, according to the processes as described in Bull. Soc. Chim. Fr. (134, pp. 47–57, 1997), or for example, by the following processes.

1) Process of Producing Compound r-9 from Compound r-6

Compound r-9 can be produced by reacting compound r-6 with compound r-10 of the general formula:

r-10

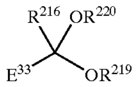

wherein $E^{33}$ and $R^{216}$ are as defined above; $R^{219}$ and $R^{220}$ are independently $C_1$–$C_6$ alkyl (e.g., methyl, ethyl), in a solvent, if necessary, in the presence of an acid.

Amount of compound r-10: 1 mole to an excess amount relative to 1 mole of compound r-6

Kind of acid: organic acids such as acetic acid and p-toluenesulfonic acid

Amount of acid: a catalytic amount to large excess relative to 1 mole of compound r-6

Solvent: aromatic hydrocarbons such as benzene and toluene; halogenated aromatic hydrocarbons such as chlorobenzene; ethers such as tetrahydrofuran and 1,4-dioxane; amides such as N,N-dimethylformamide; alcohols such as methanol, ethanol, and isopropanol; water; and mixtures thereof; etc.

Reaction temperature: 10° C. to the reflux temperature of the solvent

Reaction time: a moment to 96 hours,

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound r-5 from Compound r-9

Compound r-5 can be produced by reacting compound r-9 with compound a-1 in a solvent, if necessary, in the presence of an acid.

Amount of compound a-1: 0.9 to 1.1 moles relative to 1 mole of compound r-9

Kind of acid: organic acids such as acetic acid and p-toluenesulfonic acid

Amount of acid: a catalytic amount to large excess relative to 1 mole of compound r-9

Solvent: aromatic hydrocarbons such as benzene and toluene; halogenated aromatic hydrocarbons such as chlorobenzene; ethers such as tetrahydrofuran and 1,4-dioxane; amides such as N,N-dimethylformamide; alcohols such as methanol, ethanol, and isopropanol; water; and mixtures thereof; etc.

Reaction temperature: 10° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Depending upon the kinds of $R^1$, $R^2$, $R^3$, $R^4$, Y, T, and A, the formation of Q may be followed by the introduction or formation of $R^1$, $R^2$, $R^3$, $R^4$, Y, T, and A. In these producing processes, protective groups may be used, if necessary, for the protection, of functional groups from the reactions. (see "Protective Groups in Organic Synthesis" written by T. W. Greene.) The following are examples of these producing processes.

PRODUCING PROCESS 24

This is the producing process according to the following scheme:

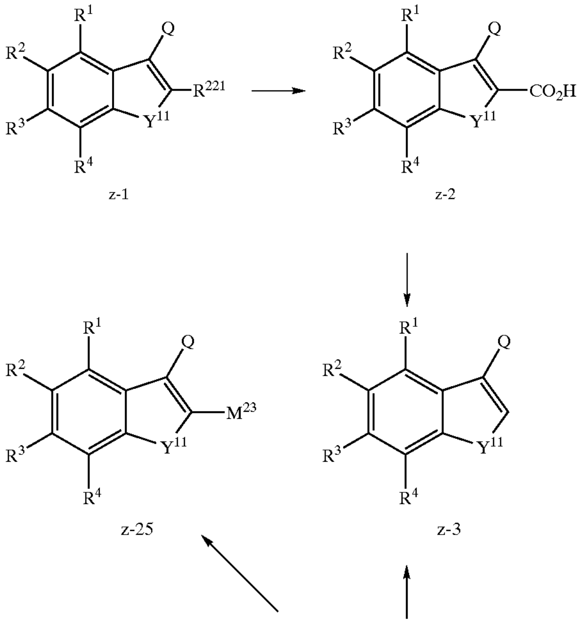

-continued

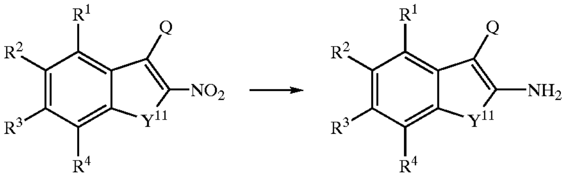

z-23 z-24 wherein $R^1$, $R^2$, $R^3$, $R^4$, $Y^{11}$, and Q are as defined above; $R^{221}$ is methoxycarbonyl, ethoxycarbonyl, propoxycarbonyl, isopropoxycarbonyl, aminocarbonyl, or nitrile; and $M^{23}$ is fluorine, chlorine, or bromine.

The reactions in the respective steps can be carried out, for example, by the following processes.

1) Process of Producing Compound z-2 from Compound z-1

Compound z-2 can be produced by reacting with compound z-1 in a solvent in the presence of a base or acid, and, if necessary, in the presence of a phase transfer catalyst.

Kind of base: inorganic bases such as sodium hydroxide, potassium hydroxide, and lithium hydroxide; etc.

Amount of base: 0.9 to 10 moles relative to 1 mole of compound z-1

Kind of acid: hydrochloric acid, sulfuric acid, etc.

Amount of acid: 1 mole to an excess amount relative to 1 mole of compound z-1

Kind of phase transfer catalyst: tetrabutylammonium bromide etc.

Solvent: aromatic hydrocarbons such as benzene and toluene; halogenated aromatic hydrocarbons such as chlorobenzene; ethers such as tetrahydrofuran and 1,4-dioxane; amides such as N,N-dimethylformamide; alcohols such as methanol, ethanol, and isopropanol; water; and mixtures thereof; etc.

Reaction temperature: 10° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound z-3 from Compound z-2

Compound z-3 can be produced by heating compound z-2 in a solvent, if necessary, in the presence of an acid or base.

Kind of base: nitrogen-containing compounds such as quinoline and pyridine; amides such as N,N-dimethylformamide; sulfur compounds such as sulforane; aromatic hydrocarbons such as xylene and mesitylene; and mixtures thereof; etc.

Amount of base: 0.9 mole to an excess amount relative to 1 mole of compound z-2

Kind of acid: hydrochloric acid, sulfuric acid, etc.

Amount of acid: 1 mole to an excess amount relative to 1 mole of compound z-2

Kind of phase transfer catalyst: tetrabutylammonium bromide etc.

Solvent: amides such as N,N-dimethylformamide; sulfur compounds such as sulforane; aromatic hydrocarbons such as xylene and mesitylene; halogenated aromatic hydrocarbons such as chlorobenzene; ethers such as tetrahydrofuran and 1,4-dioxane; and mixtures thereof; etc.

Reaction temperature: 50° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

In this process, metal catalysts such as copper may be used in their catalytic amounts.

3) Process of Producing Compound z-24 from Compound z-23

Compound z-24 can be produced by reducing compound z-23 with iron powder in a solvent.

Amount of iron powder: 2 to 10 moles relative to 1 mole of compound z-23

Solvent: acetic acid, water, and mixtures thereof, etc.

Reaction temperature: 15° C. to 110° C.

Reaction time: a moment to 100 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

4) Process of Producing Compound z-25 from Compound z-24

Compound z-25 can be produced by converting compound z-24 into a diazonium salt with sodium nitrite in the presence of an acid and then reacting the diazonium salt with copper halide such as copper (I) chloride or copper (I) bromide.

(Diazonium salt formation)

Amount of sodium nitrite: 1 to 2 moles relative to 1 mole of compound z-24

Kind of acid: sulfuric acid, hydrochloric acid, etc.

Amount of acid: 1 mole to 100 moles relative to 1 mole of compound z-24

Solvent: water, ethanol, hydrochloric acid, etc.

Reaction temperature: −15° C. to room temperature

Reaction time: a moment to 24 hours (Reaction with copper halide)

Kind of copper halide: copper (C) chloride, copper (I) bromide, etc.

Amount of copper halide: 1 to 10 moles relative to 1 mole of compound z-24

Solvent: hydrochloric acid, hydrobromic acid, etc.

Reaction temperature: −10° C. to 80° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

5) Process of Producing Compound z-3 from Compound z-24

Compound z-3 can be produced by converting compound z-24 into a diazonium salt with sodium nitrite in the presence of an acid and then reacting the diazonium salt in a solvent.

(Diazonium salt formation)

Amount of sodium nitrite: 1 to 2 moles relative to 1 mole of compound z-24

Kind of acid: sulfuric acid, hydrochloric acid, etc.

Amount of acid: 1 mole to 100 moles relative to 1 mole of compound z-24

Solvent: water, ethanol, hydrochloric acid, etc.

Reaction temperature: −15° C. to room temperature

Reaction time: a moment to 24 hours (Thermal decomposition).

Solvent: sulfuric acid, water, etc.

Reaction temperature: room temperature to 200° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 25

This is the producing process according to the following scheme:

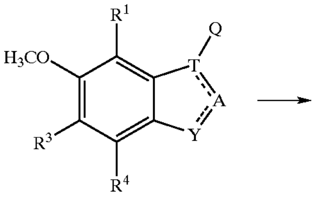

z-4

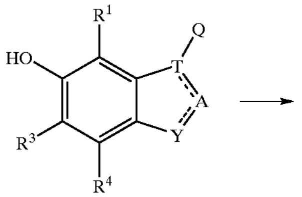

z-5

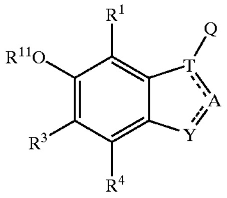

z-6 wherein $R^1$, $R^3$, $R^4$, $R^{11}$, Q, T, A, and Y are as defined above.

The reactions in the respective steps can be carried out, for example, by the following processes.

1) Process of Producing Compound z-5 from Compound z-4

Compound z-5 can be produced by demethylating compound z-4 in a solvent in the presence of an acid or trimethylsilane iodide.

Kind of acid: inorganic acids such as hydrochloric acid and sulfuric acid; Lewis acids such as boron tribromide and aluminum chloride; etc.

Amount of acid: 1 mole to an excess amount relative to 1 mole of compound z-4

Amount of trimethylsilane iodide: 1 mole to an excess amount relative to 1 mole of compound z-4

Solvent: aromatic hydrocarbons such as benzene and toluene; halogenated aromatic hydrocarbons such as chlorobenzene; halogenated hydrocarbons such as chloroform; ethers such as tetrahydrofuran and 1,4-dioxane; amides such as N,N-dimethylformamide; alcohols such as methanol, ethanol, and isopropanol; water; and mixtures thereof; etc.

Reaction temperature: 0° C. to the reflux temperature of the solvent

Reaction time: a moment to 168 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound z-6 from Compound z-5

Compound z-6 can be produced by reacting compound z-5 with compound z-18 of the general formula:

$M^9—R^{11}$ z-18 wherein $M^9$ and $R^{11}$ are as defined above, in a solvent in the presence of a base.

Amount of compound z-18: 1 to 2 moles relative to 1 mole of compound z-5

Kind of base: potassium carbonate, sodium hydride, etc.

Amount of base: 1 to 5 moles relative to 1 mole of compound z-5

Solvent: aromatic hydrocarbons such as benzene and toluene; halogenated aromatic hydrocarbons such as chlorobenzene; halogenated hydrocarbons such as chloroform; ethers such as tetrahydrofuran and 1,4-dioxane; amides such as N,N-dimethylformamide; alcohols such as methanol, ethanol, and isopropanol; water; and mixtures thereof; etc.

Reaction temperature: −10° C. to 100° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 26

This is the producing process according to the following scheme:

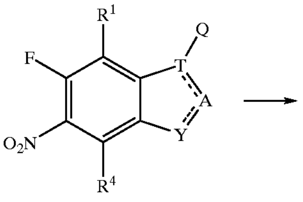

z-7

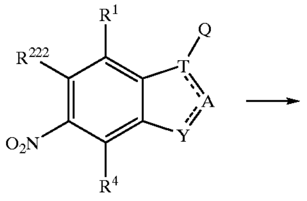

z-8

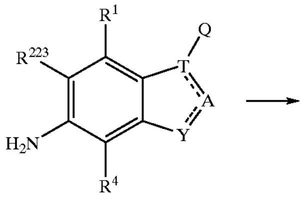

z-9

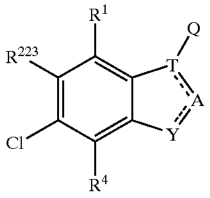

z-10 wherein $R^1$, $R^4$, Q, T, A, and Y are as defined above; $R^{222}$ is —$OR^{11}$ or —$SR^{12}$ wherein $R^{11}$ and $R^{12}$ are as defined above; and $R^{223}$ is —$OR^{224}$ or —$SR^{225}$ wherein $R^{224}$ and $R^{225}$ are the same or different and independently hydrogen, $C_1$–$C_{10}$ alkyl, $C_3$–$C_{10}$ cycloalkyl, $C_3$–$C_{10}$ cycloalkyl $C_1$–$C_3$ alkyl, $C_3$–$C_{10}$ alkenyl; $C_3$–$C_{10}$ alkynyl, $C_1$–$C_5$ alkoxy $C_1$–$C_5$ allkyl, $C_1$–$C_5$ alkylthio $C_1$–$C_5$ alkyl, or optionally substituted phenyl.

The reactions in the respective steps can be carried out, for example, by the following processes.

1) Process of Producing Compound z-8 from Compound z-7

Compound z-8 can be produced by reacting compound z-19 of the general formula:

$$H—R^{222} \qquad z\text{-}19$$

wherein $R^{222}$ is as defined above, in a solvent in the presence of a base.

Amount of compound z-19: 1 to 5 moles relative to 1 mole of compound z-7

Kind of base: organic bases such as triethylamine, inorganic bases such as potassium carbonate and sodium hydride; alkoxides such as sodium methoxide and sodium thiomethoxide; etc.

Amount of base: 1 to 5 moles relative to 1 mole of compound z-7

Solvent: aromatic hydrocarbons such as benzene and toluene; halogenated aromatic hydrocarbons such as chlorobenzene; halogenated hydrocarbons such as chloroform; ethers such as tetrahydrofuran and 1,4-dioxane; amides such as N,N-dimethylformamide; alcohols such as methanol, ethanol, and isopropanol; water; and mixtures thereof, etc.

Reaction temperature: −10° C. to the reflux temperature of the solvent

Reaction time: a moment to 72 hours;

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound z-8 wherein $R^{222}$ is —$OR^{224}$ or —$SR^{225}$; and $R^{224}$ and $R^{224}$ are as defined above (hereinafter referred to as compound z-8') can be used to produce compound z-9 or compound z-10 as shown in the following processes.

2) Process of Producing Compound z-9 from Compound z-8'

Compound z-9 can be produced by reducing compound z-8' with iron powder in a solvent.

Amount of iron powder: 2 to 10 moles relative to 1 mole of compound z-8'

Solvent: acetic acid, water, and mixtures thereof; etc.

Reaction temperature: 15° C. to 110° C.

Reaction time: a moment to 100 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

3) Process of Producing Compound z-10 from Compound z-9

Compound z-10 can be produced by converting compound z-9 into a diazonium salt with sodium nitrite in the presence of an acid and then reacting the diazonium salt with a chloride such as copper (I) chloride.

(Diazonium salt formation)

Amount of sodium nitrite: 1 to 2 moles relative to 1 mole of compound z-9

Kind of acid: hydrochloric acid, etc.

Amount of acid: 1 mole to 100 moles relative to 1 mole of compound z-9

Solvent: water, ethanol, hydrochloric acid, etc.

Reaction temperature: −15° C. to room temperature

Reaction time: a moment to 24 hours (Reaction with chloride)

Kind of chloride: copper (a) chloride etc.

Amount of chloride: 1 to 10 moles relative to 1 mole of compound z-9

Solvent: hydrochloric acid etc.

Reaction temperature: −10° C. to 80° C.

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

PRODUCING PROCESS 27

This is the producing process according to the following process:

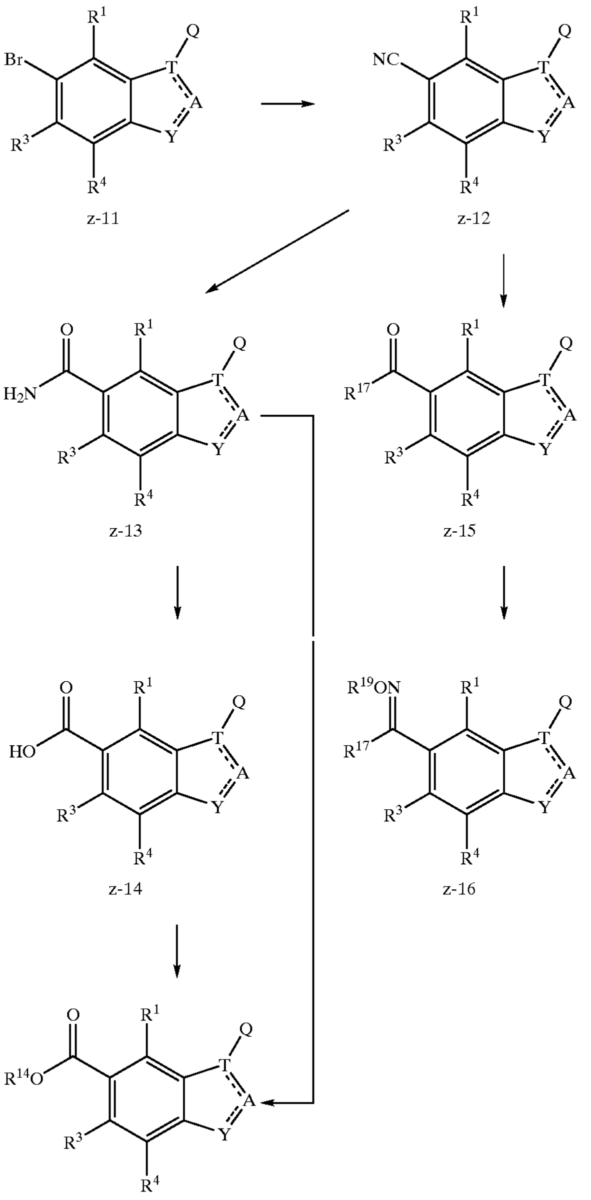

z-11 z-12 z-13 z-15 z-14 z-16 z-17 wherein $R^1$, $R^3$, $R^4$, $R^{14}$, $R^{17}$, $R^{19}$, Q, T, A, and Y are as defined above.

The reactions in the respective steps can be carried out, for example, by the following processes.

1) Process of Producing Compound z-12 from Compound z-11

Compound z-12 can be produced by reacting compound z-11 with copper (I) cyanide in a solvent.

Amount of copper (I) cyanide: 1 to 4 moles relative to 1 mole of compound z-11

Kind of solvent: amides such as N,N-dimethylformamide and N-methylpyrrolidone; sulfur compound such as dimethylsulfoxide; etc.

Reaction temperature: 40° C. to the reflux temperature of the solvent

Reaction time: a moment to 120 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound z-13 from Compound z-12

Compound z-13 can be produced by reacting compound z-12 with water in the presence of an acid.

Amount of water: 1 mole to an excess amount relative to 1 mole of compound z-12

Kind of acid: hydrochloric acid, sulfuric acid, etc.

Amount of acid: 1 mole to an excess amount relative to 1 mole of compound z-12

Reaction temperature: 10° C. to 50° C.

Reaction time: a moment to 24 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

3) Process of Producing Compound z-14 from Compound z-13

Compound z-14 can be produced by reacting compound z-13 with water in the presence of an acid or base.

Amount of water: 1 equivalent to an excess amount relative to 1 mole of compound z-13

Kind of acid: hydrochloric acid, sulfuric acid, etc.

Amount of acid: 1 equivalent to an excess amount relative to 1 mole of compound z-13

Kind of base: sodium hydroxide, potassium hydroxide, etc.

Amount of base: 1 to 3 equivalents relative to 1 mole of compound z-13

Reaction temperature: room temperature to 150° C.

Reaction time: a moment to 120 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

4) Process of Producing Compound z-17 from Compound z-14

Compound z-17 can be produced by reacting compound z-14 with thionyl chloride to form an acid chloride compound (reaction 1) and then reacting the acid chloride compound with compound z-20 of the general formula:

$HO—R^{14}$ z-20 wherein $R^{14}$ is as defined above, in a solvent in the presence of a base (reaction 2).

(Reaction 1)

Amount of thionyl chloride: 1 mole to an excess amount relative to compound z-14

Reaction temperature: 40° C. to the reflux temperature of thionyl chloride

Reaction time: a moment to 10 hours

After completion of the reaction, the reaction mixture was concentrated and used as the starting material for reaction 2.

(Reaction 2)

Amount of compound z-20: 1 mole to an excess amount relative to 1 mole of compound z-14

Kind of base: pyridine, triethylamine, potassium carbonate, etc.

Amount of base: 1 to 5 moles relative to 1 mole of compound z-14

Solvent: aromatic hydrocarbons such as benzene and toluene; halogenated aromatic hydrocarbons such as chlorobenzene; halogenated hydrocarbons such as chloroform; ethers such as tetrahydrofuran and 1,4-dioxane; amides such as N,N-dimethylformamide; alcohols such as methanol, ethanol, and isopropanol; water; and mixtures thereof; etc.

Reaction temperature: −10° C. to the reflux temperature of the solvent

Reaction time: a moment to 120 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

5) Process of Producing Compound z-17 from Compound z-13

Compound z-17 can be produced by reacting compound z-13 with compound z-20 of the general formula:

$HO—R^{14}$ z-20 wherein $R^{14}$ is as defined above, in a solvent in the presence of a boron trihalide compound.

Amount of compound z-20: 1 mole to an excess amount relative to 1 mole of compound z-13

Kind of boron trihaihde compound: boron trifluoride, boron trichloride, boron tribromide, etc.

Amount of boron trihalide compound: 1 mole to an excess amount relative to 1 mole of compound z-13

Solvent: aromatic hydrocarbons such as benzene and toluene; halogenated aromatic hydrocarbons such as chlorobenzene; ethers such as tetrahydrofuran and 1,4-dioxane; amides such as N,N-dimethylformamide; alcohols such as methanol, ethanol, and isopropanol; water; and mixtures thereof; etc.

Reaction temperature: 50° C. to the reflux temperature of the solvent

Reaction time: a moment to 120 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

6) Process of Producing Compound z-15 from Compound z-12

Compound z-15 can be produced by reacting compound z-12 with compound z-2 1 of the general formula:

$M^{11}—Mg—R^{17}$ z-21 wherein $R^{17}$ is as defined above and $M^{11}$ is chlorine or bromine, in a solvent.

Amount of compound z-21: 1 to 1.3 moles relative to 1 mole of compound z-12

Solvent: aromatic hydrocarbons such as benzene and toluene; halogenated aromatic hydrocarbons such as chlorobenzene; halogenated hydrocarbons such as chloroform; ethers such as tetrahydrofuran and 1,4-dioxane; amides such as N,N-dimethylformamide; alcohols such as methanol, ethanol, and isopropanol; water; and mixtures thereof; etc.

Reaction temperature: 0° C. to the reflux temperature of the solvent

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

7) Process of Producing Compound z-16 from Compound z-15

Compound z-16 can be produced by reacting compound z-15 with compound z-22 of the general formula:

$R^{19}ONH_2$ z-22 wherein $R^{19}$ is as defined above, in a solvent, if necessary, in the presence of a base.

Amount of compound z-22: 1 to 3 moles relative to 1 mole of compound z-15

Kind of base: triethylamine, pyridine, potassium carbonate, etc.

Amount of base: 1 to 5 moles relative to 1 mole of compound z-15

Solvent: aromatic hydrocarbons such as benzene and toluene; halogenated aromatic hydrocarbons such as chlorobenzene; ethers such as tetrahydrofuran and 1,4-dioxane; alcohols such as methanol, ethanol, and isopropanol; water; and mixtures thereof; etc.

Reaction temperature: 0° C. to the reflux temperature of the solvent

Reaction time: a moment to 120 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

In addition to the above processes, the present compounds can also be produced by making reference to, for example, JP-A 5-213970, EP 683160-A1, and JP-A 61-161288.

The processes of producing some of the starting materials used in the production of the present compounds are explained below.

REFERENCE PRODUCING PROCESS 1

This is the producing process according to the following scheme:

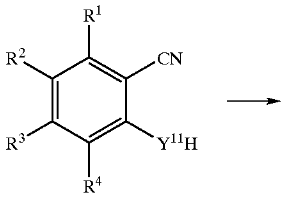

v-1

-continued

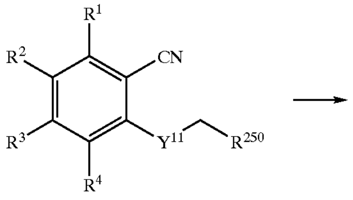

v-2

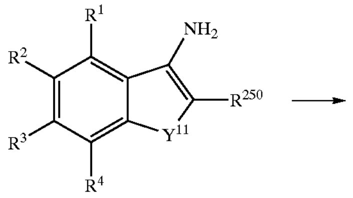

v-3

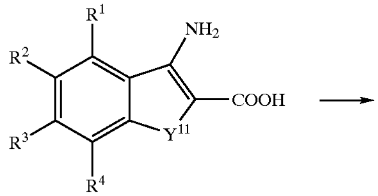

v-4

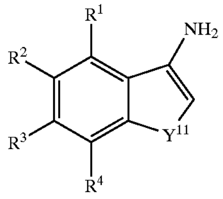

v-5 wherein $R^1$, $R^2$, $R^3$, $R^4$, and $Y^{11}$ are as defined above; and $R^{250}$ is carboxy, methoxycarbonyl, ethoxycarbonyl, aminocarbonyl, or nitrile.

The reactions in the respective steps can be carried out, for example, according to the processes as described in Indian Journal of Chemistry. (vol. 20B, pp. 391–393, 1981), Indian Journal of Chemistry (vol. 14B, pp. 6886–6891, 1981), Organic Syntheses (vol. 33, p. 43, 1953), or for example, by the following processes.

1) Process of Producing Compound v-2 from Compound v-1

Compound v-2 can be produced by reacting compound v-1 with compound v-19 of the general formula:

v-19

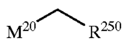

wherein $R^{250}$ is as defined above and $M^{20}$ is chlorine, bromine, or iodine, in a solvent in the presence of a base.

Kind of base: inorganic bases such as potassium carbonate, sodium hydride, and sodium hydroxide; organic bases such as triethylamine; nitrogen-containing compounds such as pyridine; metal alcoholates such as sodium methylate and sodium ethylate; etc.

Amount of base: 1 to 5 moles relative to 1 mole of compound v-1

Amount of compound v-19: 0.9 to 3 moles relative to 1 mole of compound v-1

Solvent: aromatic hydrocarbons such as benzene and toluene; halogenated aromatic hydrocarbons such as chlorobenzene; ketones such as acetone; ethers such as tetrahydrofuran; amides such as N,N-dimethylformamide; alcohols such as methanol, ethanol, and isopropanol; water; and mixtures thereof, etc.

Reaction temperature: 0° C. to the reflux temperature of the solvent

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound v-3 from Compound v-2

Compound v-3 can be produced by reacting compound v-2 in a solvent in the presence of a base.

Kind of base: inorganic bases such as potassium carbonate, sodium hydride, and sodium hydroxide; metal alcoholates such as sodium methylate and sodium ethylate; etc.

Amount of base: 1 to 10 moles relative to 1 mole of compound v-2

Solvent: aromatic hydrocarbons such as benzene and toluene; halogenated aromatic hydrocarbons such as chlorobenzene; ethers such as tetrahydrofuran; amides such as N,N-dimethylformamide; alcohols such as methanol, ethanol, and isopropanol; water; and mixtures thereof; etc.

Reaction temperature: 10° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

3) Process of Producing Compound v-4 from Compound v-3

Compound v-4 can be produced by reacting compound v-3 in a solvent in the presence of a base or acid and, if necessary, in the presence of a phase transfer catalyst.

Kind of base: inorganic bases such as sodium hydroxide and potassium hydroxide; etc.

Amount of base: 0.9 to 10 moles relative to 1 mole of compound v-3

Kind of acid: hydrochloric acid, sulfuric acid, etc.

Amount of acid: 1 mole to an excess amount relative to 1 mole of compound v-3

Kind of phase transfer catalyst: tetrabutylammonium bromide etc.

Solvent: aromatic hydrocarbons such as benzene and toluene; halogenated aromatic hydrocarbons such as chlorobenzene; ethers such as tetrahydrofuran and 1,4-dioxane; amides such as N,N-dimethylformamide; alcohols such as methanol, ethanol, and isopropanol; water; and mixtures thereof; etc.

Reaction temperature: 10° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

4) Process of Producing Compound v-5 from Compound v-4

Compound v-5 can be produced by heating compound v-4 in a solvent, if necessary, in the presence of a base or acid.

Kind of base: nitrogen-containing compounds such as quinoline and pyridine; amides such as N,N-dimethylformamide; sulfur compounds such as sulforane; aromatic hydrocarbons such as xylene and mesitylene; and mixtures thereof; etc.

Amount of base: 0.9 mole to an excess amount relative to 1 mole of compound v-4

Kind of acid: hydrochloric acid, sulfuric acid, etc.

Amount of acid: 1 mole to an excess amount relative to 1 mole of compound v-4

Solvent: amides such as N,N-dimethylformamide; sulfur compounds such as sulforane; aromatic hydrocarbons such as xylene and mesitylene; halogenated aromatic hydrocarbons such as chlorobenzene; ethers such as tetrahydrofuran and 1,4-dioxane; and mixtures thereof, etc.

Reaction temperature: 50° C. to the reflux temperature of the solvent

Reaction time: a moment to 96 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

In this process, metal catalysts such as copper may be used.

Compound v-1 as the starting material in this producing process can also be produced from the corresponding benzaldehyde derivative by making reference to, for example, Shin Jikken Kagaku Koza (published by Maruzen Kabushiki Kaisha) vol. 14, pp. 1466–1470. The benzaldehyde derivative to be used as the starting material at that time can also be produced by making reference to, for example, EP 0312338-A1, Synthetic Communication, 24(12), pp. 1757–1760 (1994), and J. Chem. Soc. Perkin I, pp. 318–321 (1978).

Compound v-2 as the intermediate can also be produced according to the following scheme 1 or 2.

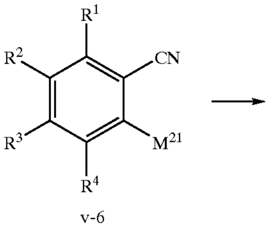

v-6

-continued

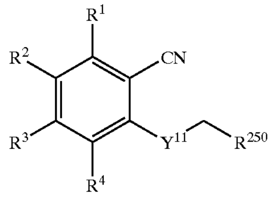

v-2 wherein $R^1$, $R^2$, $R^3$, $R^4$, $R^{250}$, and $Y^{11}$ are as defined above; and $M^{21}$ is fluorine, chlorine, or bromine.

5) Process of Producing Compound v-2 from Compound v-6

Compound v-2 can be produced by reacting compound v-6 with compound v-17 of the formula:

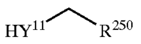

v-17 wherein $Y^{11}$ and $R^{250}$ are as defined above, in a solvent in the presence of a base.

Kind of base: inorganic bases such as potassium carbonate, sodium hydride, sodium hydroxide, and potassium fluoride; organic bases such as triethylamine; nitrogen-containing compounds such as pyridine; etc.

Amount of base: 1 to 10 moles relative to 1 mole of compound v-6

Amount of compound v-17: 0.9 to 10 moles relative to 1 mole of compound v-6

Solvent: aromatic hydrocarbons such as benzene and toluene; halo-genated aromatic hydrocarbons such as chlorobenzene; ketones such as acetone; ethers such as tetrahydrofuran and 1,4-dioxane; amides such as N,N-dimethylformamide; and mixtures thereof; etc.

Reaction temperature: 0° C. to the reflux temperature of the solvent

Reaction time: a moment to 72 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

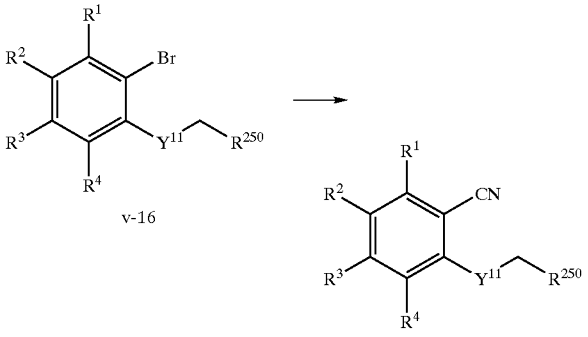

v-16 v-2 wherein $R^1$, $R^2$, $R^3$, $R^4$, $R^{250}$, and $Y^{11}$ are as defined above.

1) Process of Producing Compound v-2 from Compound v-16

Compound v-2 can be produced by reacting compound v-16 with copper (I) cyanide in a solvent.

Amount of copper (I) cyanide: 1 to 4 moles relative to 1 mole of compound v-16

Kind of solvent: amides such as N,N-dimethylformamide and N-methylpyrrolidone; sulfur compound such as dimethylsulfoxide; etc.

Reaction temperature: 40° C. to the reflux temperature of the solvent

Reaction time: a moment to 120 hours

After completion of the reaction, ammonia water is added, if necessary, to the reaction mixture, which is then extracted with an organic solvent, and the organic layer is dried and concentrated, thereby obtaining the desired compound. The compound can be purified by a technique such as recrystallization or column chromatography.

REFERENCE PRODUCING PROCESS 2

This is the producing process according to the following scheme:

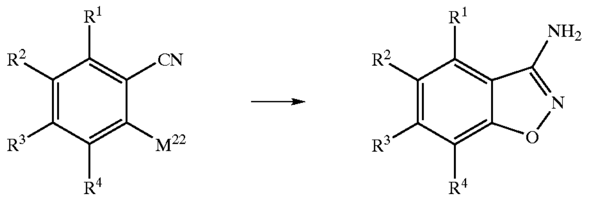

v-7 v-8 wherein $R^1$, $^2$, $R^3$, and $R^4$ are as defined above; and $M^{22}$ is fluorine or chlorine.

The reactions in the respective steps can be carried out, for example, according to the processes as described in Tetrahedron Letters (vol. 37, No. 17, pp. 2885–2886, 1996), or for example, by the following processes.

1) Process of Producing Compound v-8 from Compound v-7

Compound v-8 can be produced by reacting compound v-7 with aceto-hydroxamic acid in a solvent in the presence of a base.

Amount of hydroxamic acid: 1 to 3 moles relative to 1 mole of compound v-7

Kind of base: potassium t-butoxide, sodium hydride, etc.

Amount of base: 1 to 3 moles relative to 1 mole of compound v-7

Solvent: N,N-dimethylformamide, dimethylsulfoxide, tetrahydrofuran, etc.

Reaction temperature: room temperature to 100° C.

Reaction time a moment to 100 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

REFERENCE PRODUCING PROCESS 3

This is the producing process according to the following scheme:

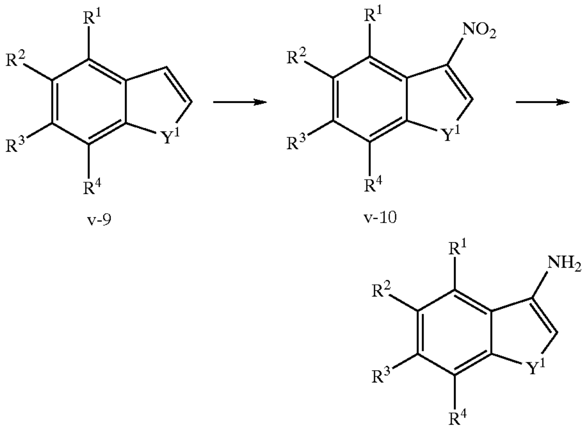

v-9 v-10 v-11 wherein $R^1$, $R^2$, $R^3$, and $R^4$ are as defined above; $Y^1$ is oxygen, sulfur, or N-$R^{142}$; and $R^{142}$ is as defined above.

The reactions in the respective steps can be carried out, for example, by the following processes.

1) Process of Producing Compound v-10 from Compound v-9

Compound v-10 can be produced by reacting compound v-9 with a nitrating agent in a solvent or without solvent.

Kind of nitrating agent: nitric acid etc.

Amount of nitrating agent: 1 to 1.5 moles relative to 1 mole of compound v-9

Solvent: acetic anhydride etc.

Reaction temperature: −10° C. to 50° C.

Reaction time: a moment to 100 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound v-11 from Compound v-10

Compound v-11 can be produced by reducing compound v-10 with iron powder in a solvent.

Amount of iron powder: 1 to 10 moles relative to 1 mole of compound v-10

Solvent: acetic acid, water, and mixtures thereof, etc.

Reaction temperature: 15° C. to 110° C.

Reaction time: a moment to 100 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

REFERENCE PRODUCING PROCESS 4

This is the producing process according to the following scheme:

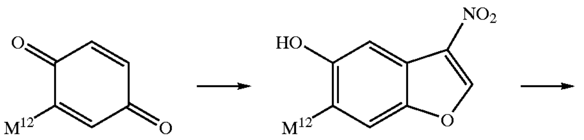

v-12 v-13

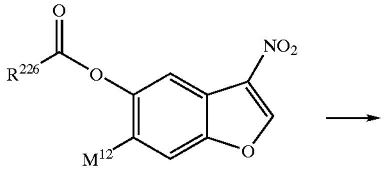

v-14

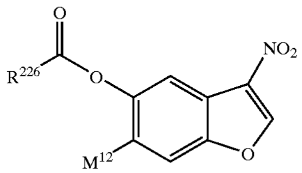

v-15 wherein $R^{226}$ is $C_1$–$C_{10}$ alkyl and $M^{12}$ is fluorine or chlorine.

The reactions in the respective steps can be carried out, for example, according to the processes as described in Khim. Geterotsikl. Soedin (1990, Issue 5, pp. 597–600), Khim. Geterotsikl. Soedin (1989, Issue 5, pp. 704), or for example, by the following processes.

1) Process of Producing Compound v-13 from Compound v-12

Compound v-13 can be produced by reacting compound v-12 with nitroenamine compound v-18 of the formula:

v-18

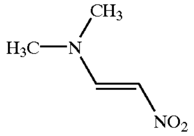

in a solvent and, if necessary, in the presence of an acid.

Amount of compound v-18: 1 to 3.0 moles relative to 1 mole of compound v-12

Kind of acid: acetic acid, p-toluenesulfonic acid, sulfuric acid, etc.

Amount of acid: a catalytic amount to a large excess amount relative to 1 mole of compound v-12

Solvent: aromatic hydrocarbons such as toluene and xylene; ethers such as tetrahydrofuran; organic acids such as acetic acid and propionic acid; amides such as N,N-dimethylformamide; and mixtures thereof; etc.

Reaction temperature: –10° C. to the reflux temperature of the solvent

Reaction time: a moment to 100 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

2) Process of Producing Compound v-14 from Compound v-13

Compound v-14 can be produced by reacting compound v-13 with an alkylcarbonylating agent in a solvent and, if necessary, in the presence of an acid and a base.

Kind of alkylcarbonylating agent: acetic anhydride, acetyl chloride, etc.

Amount of alkylcarbonylating agent: 1 to 2.0 moles relative to 1 mole of compound v-13

Kind of acid: acetic acid, p-toluenesulfonic acid, sulfuric acid, etc.

Amount of acid: a catalytic amount to a large excess amount relative to 1 mole of compound v-13

Kind of base: sodium hydroxide, potassium carbonate, triethylamine, etc.

Amount of base: a catalytic amount to a large excess amount relative to 1 mole of compound v-13

Solvent: aromatic hydrocarbons such as toluene and xylene; ethers such as tetrahydrofuran; organic acids such as acetic acid and propionic add; inorganic acids such as sulfuric acid; amides such as N,N-dimethylformamide; and mixtures thereof; etc.

Reaction temperature: –10° C. to the reflux temperature of the solvent

Reaction time: a moment to 100 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

3) Process of Producing Compound v-15 from Compound v-14

Compound v-15 can be produced by reducing compound v-14 with iron powder in a solvent.

Amount of iron powder: 1 to 10 moles relative to 1 mole of compound v-14

Solvent: acetic acid, water, and mixtures thereof, etc.

Reaction temperature: 15° C. to 110° C.

Reaction time: a moment to 100 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

REFERENCE PRODUCING PROCESS 5

This is the producing process according to the following scheme:

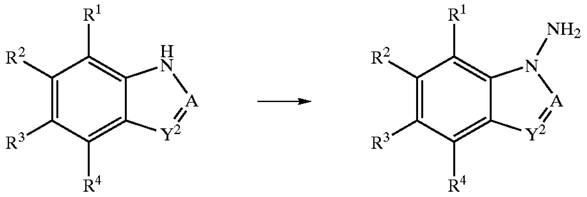

x-5 x-3 wherein $R^1$, $R^2$, $R^3$, $R^4$, and A are as defined above; $Y^2$ is nitrogen or C—$R^{152}$; and $R^{152}$ is as defined above.

The reaction can be carried out, for example, according to the processes as described in Synthesis (Issue 1, pp. 1–17, 1977), J. Med. Chem. (Vol. 39, pp. 570–581, 1996), or for example, by the following process.

1) Process of Producing Compound x-3 from Compound x-5

Compound x-3 can be produced by reacting compound x-5 with an aminating agent in a solvent in the presence of a base.

Kind of base: inorganic bases such as potassium carbonate, sodium hydride, sodium hydroxide, and potassium hydroxide; etc.

Amount of base: 1 to 20 moles relative to 1 mole to compound x-5

Kind of aminating agent: hydroxylamine=O-sulfonic acid, chloramine, O-(2,4-dinitrophenyl)hydroxylamine, etc.

Amount of aminating agent: 0.9 to 5 moles relative to 1 mole of compound x-5

Solvent: aromatic hydrocarbons such as benzene and toluene; halogenated aromatic hydrocarbons such as chlorobenzene; ethers such as tetrahydrofuran; amides such as N,N-dimethylformamide; alcohols such as methanol, ethanol, and isopropanol; and mixtures thereof; etc.

Reaction temperature: −10° C. to the reflux temperature of the solvent

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

Compound x-5 used as the intermediate in the above reaction can be produced, for example, according to the processes as described in JP-A 7-508259, JP-A 7-508500, WO93/18008, and WO94/25446.

REFERENCE PRODUCING PROCESS 6

This is the producing process according to the following scheme:

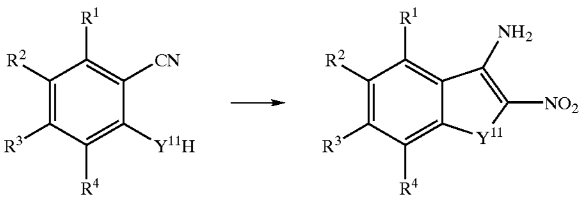

v-1 v-20 wherein $R^1$, $R^2$, $R^3$, $R^4$, and $Y^{11}$ are as defined above.

The reaction can be carried out, for example, according to the process as described in Chem. Pharm. Bull. 32(11), pp. 4260–4270 (1984), or for example, by the following scheme:

1) Process of Producing Compound v-20 from Compound v-1

Compound v-20 can be produced by reacting compound v-1 with bromonitromethane in a solvent in the presence of a base.

Kind of base: inorganic bases such as potassium carbonate, sodium hydride, and sodium hydroxide; organic bases such as triethylamine; nitrogen-containing compounds such as pyridine; metal alcoholates such as sodium methylate and sodium ethylate; etc.

Amount of base: 1 to 5 moles relative to 1 mole of compound v-1

Amount of bromonitromethane: 0.9 to 3 moles realtive to 1 mole of compound v-1

Solvent: aromatic hydrocarbons such as benzene and toluene;

halogenated aromatic hydrocarbons such as chlorobenzene; ketones such as acetone; ethers such as tetrahydrofuran; amides such as N,N-dimethylformamide; alcohols such as methanol, ethanol, and isopropanol; and mixtures thereof, etc.

Reaction temperature: 0° C. to the reflux temperature of the solvent

Reaction time: a moment to 48 hours

After completion of the reaction, the reaction mixture is subjected to post-treatments, for example, the reaction mixture is poured into water, and the deposited crystals are collected by filtration and dried; or the reaction mixture is extracted with an organic solvent, and the organic layer was dried and concentrated; or the reaction mixture is concentrated, thereby obtaining the desired compound. The compound can be purified by a technique such as recrystallization or column chromatography.

REFERENCE PRODUCING PROCESS 7

This is the producing process according to the following scheme:

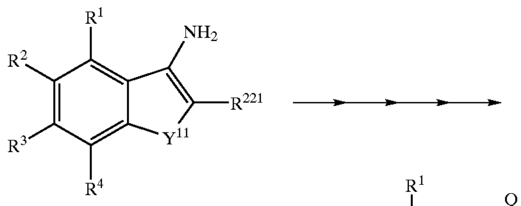

V-23

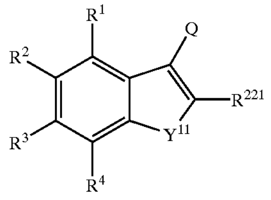

z-1

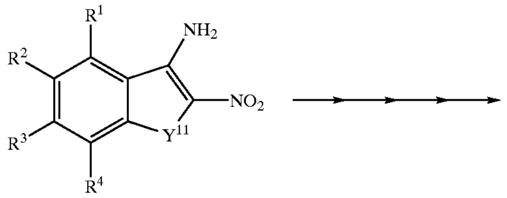

V-22

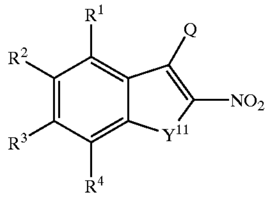

z-23 wherein $R^1$, $R^2$, $R^3$, $R^4$, $R^{221}$, $Y^{11}$, and Q are as defined above.

The reactions in the respective steps can be carried out according to the processes as described in Producing Processes 1 to 23.

The benzonitrile derivatives used in Reference Producing Processes 1 and 2 can be produced from the corresponding benzaldehyde derivatives or benzamide derivatives. (see Shin Jikken Kagaku Koza, edited by Nihon Kagaku Kai, Maruzen Kabushiki Kaisha, 14, pp. 1466–1474)

Examples of the present compounds which can be prepared according to the above producing process are illustrated below; however, the present invention is not limited to these examples.

In the examples, Me indicates methyl; Et, ethyl; Pr, propyl; Bu, butyl; Pen, pentyl; Hex, hexyl; Hep, heptyl; Oct, octyl; i-, iso-; s-, sec-; c-, cyclo-; and groups not particularly indicated are in normal form.

Compounds of the general formulas:

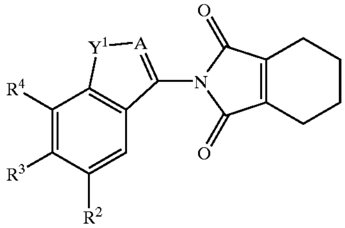

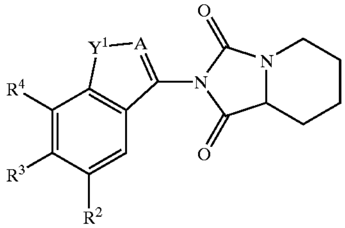

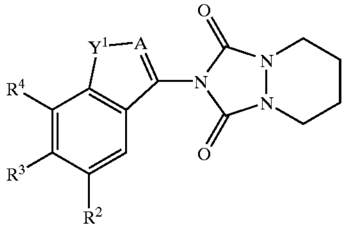

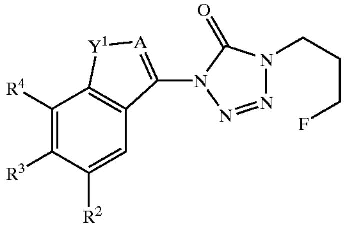

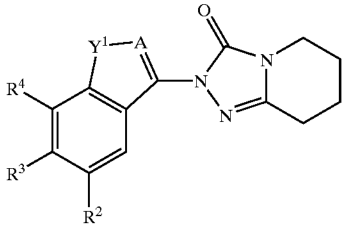

-continued

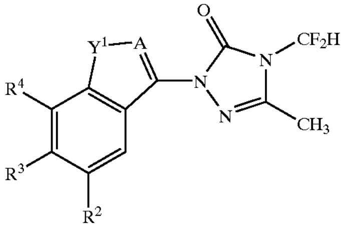

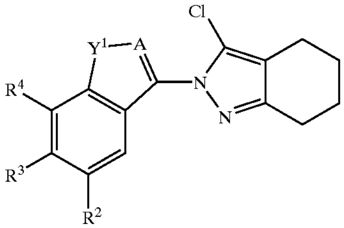

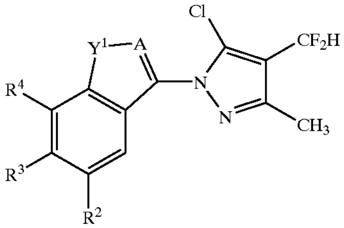

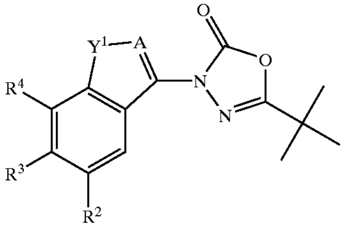

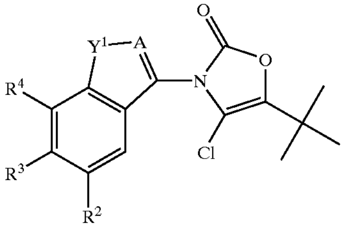

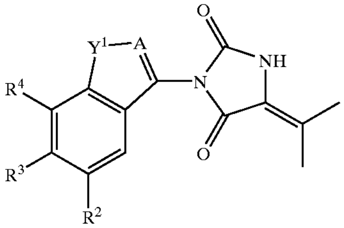

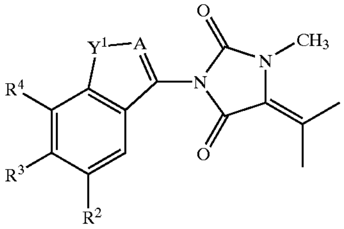

-continued
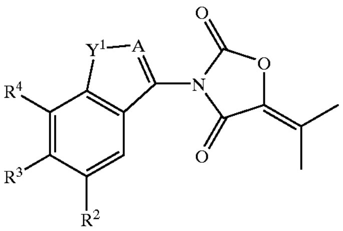
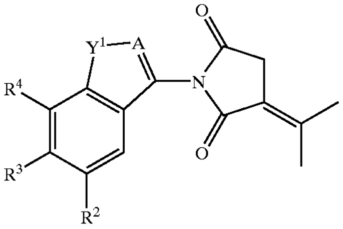
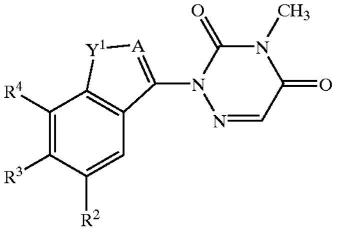
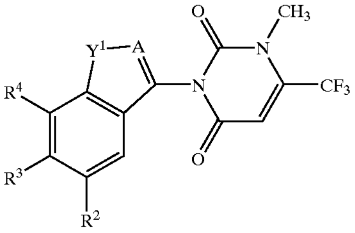
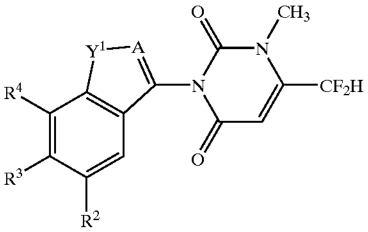
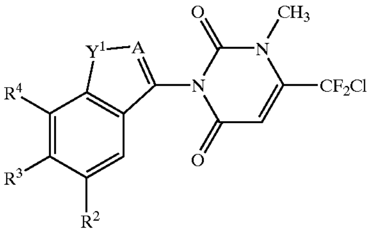
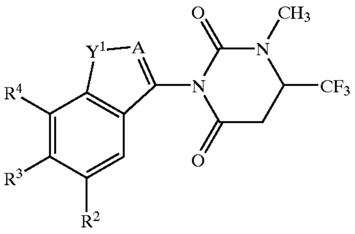
-continued
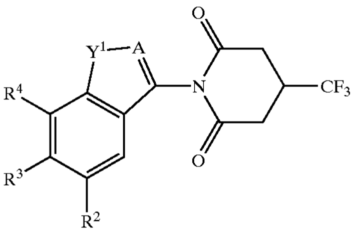
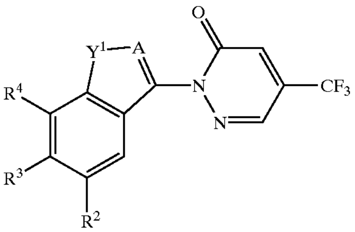
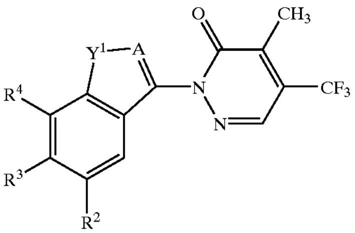
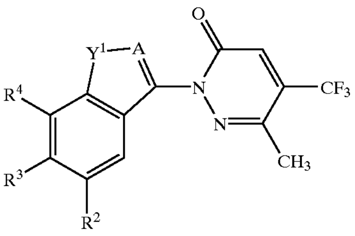
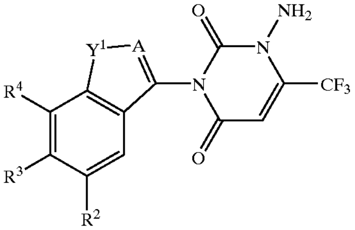
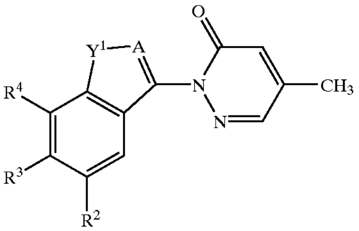
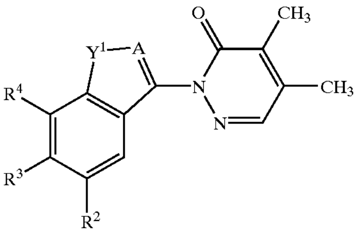

-continued
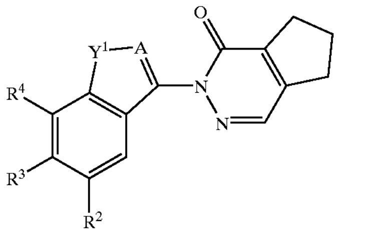
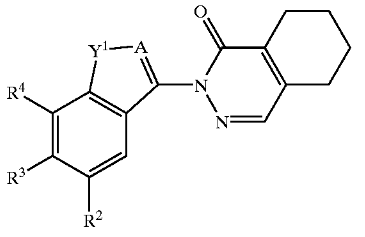
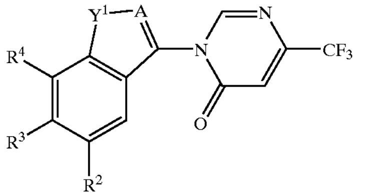
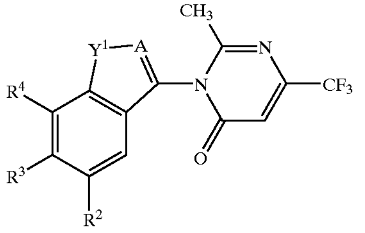
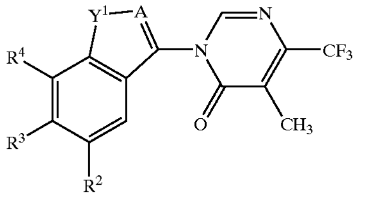
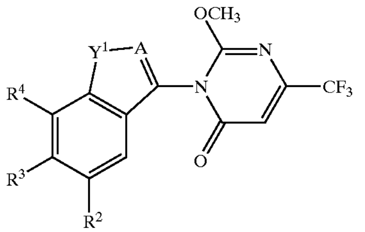
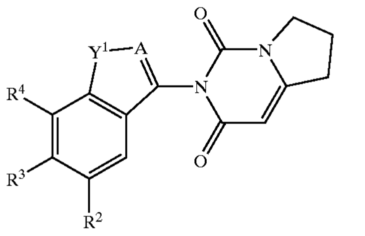
-continued
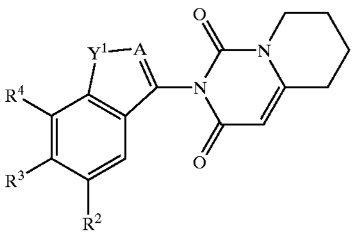
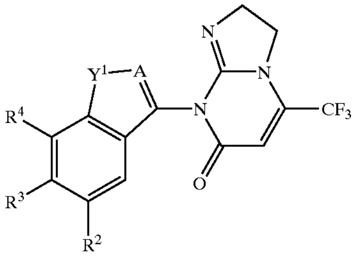
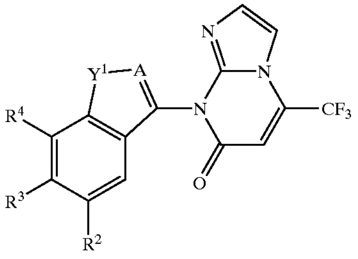
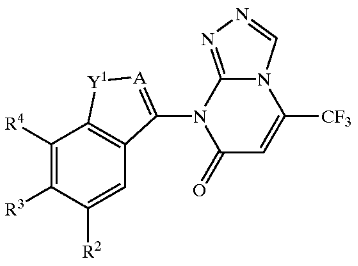
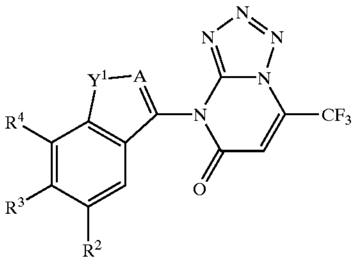
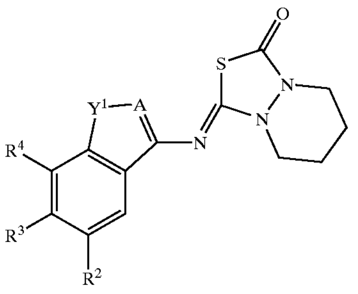

-continued
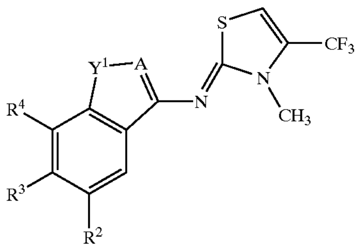
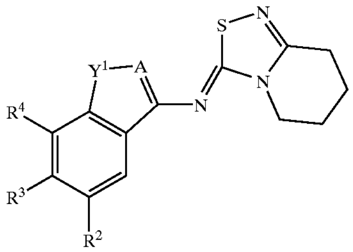
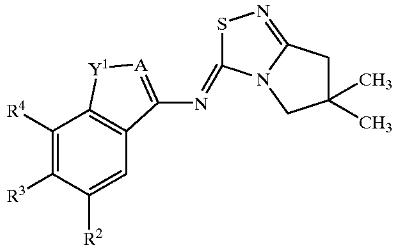
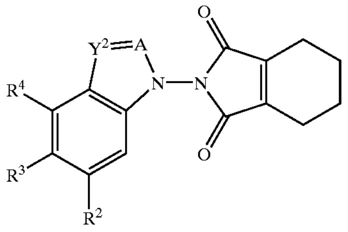
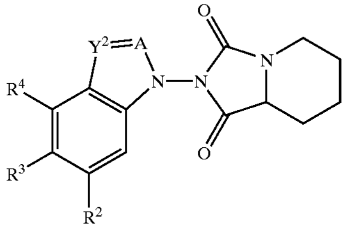
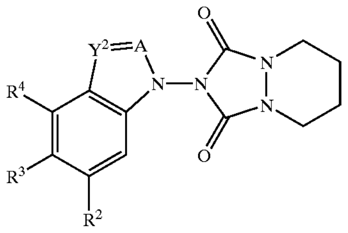
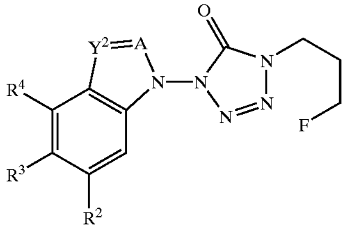
-continued
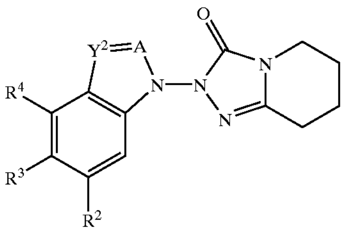
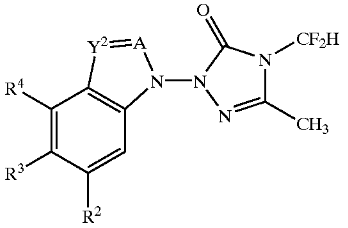
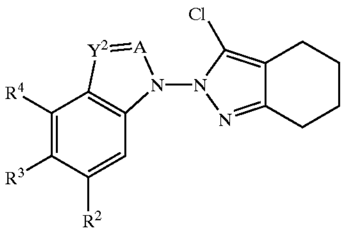
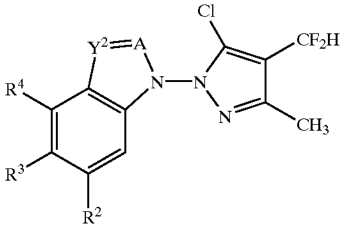
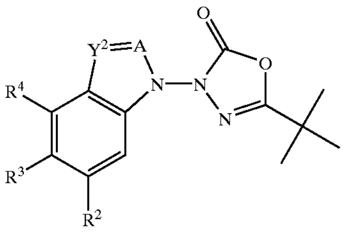
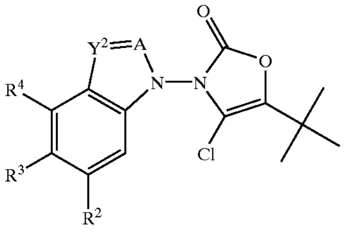
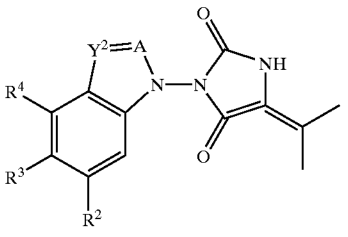

-continued
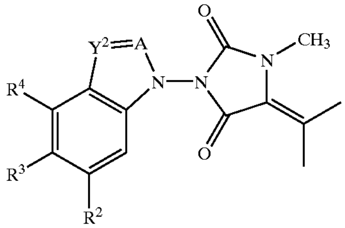
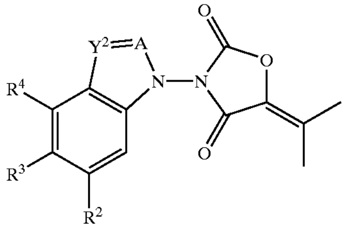
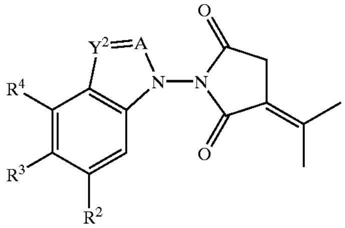
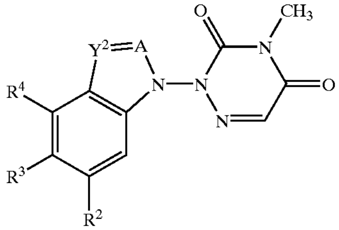
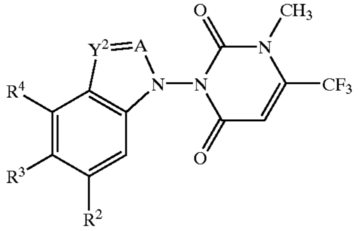
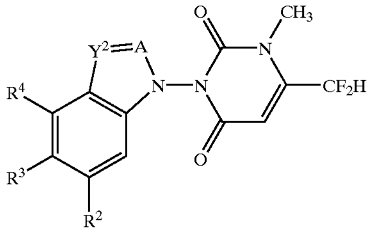
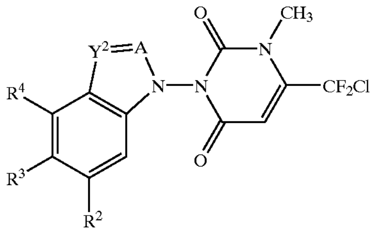
-continued
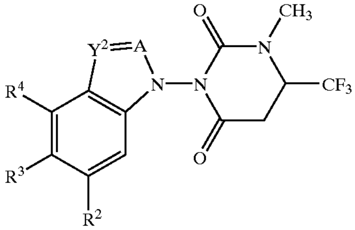
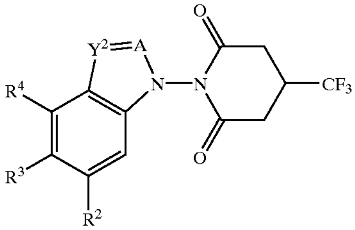
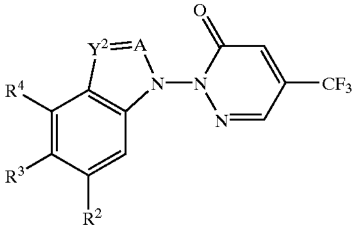
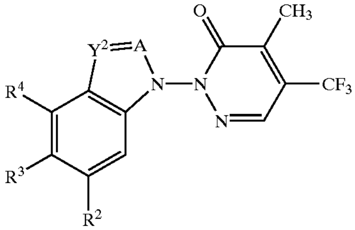
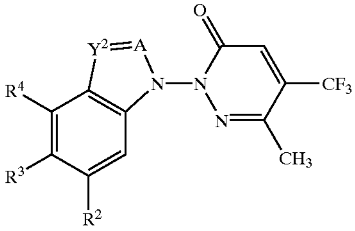
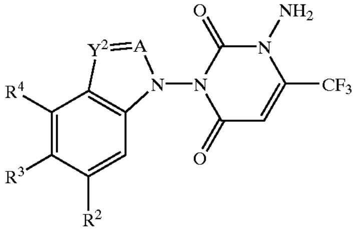
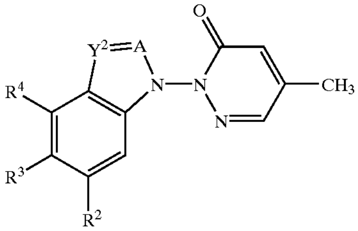

-continued
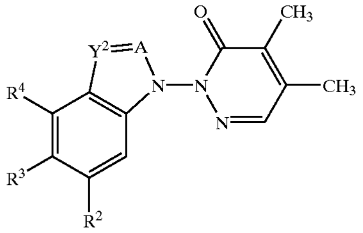
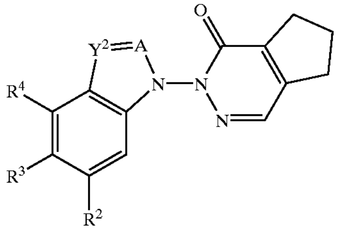
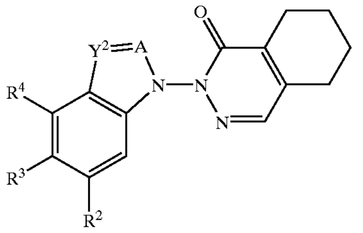
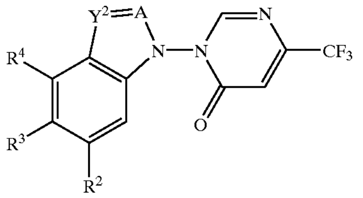
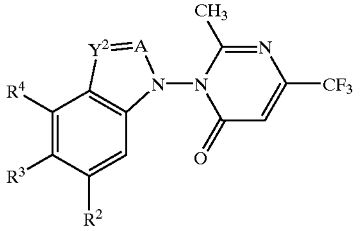
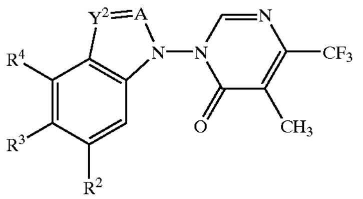
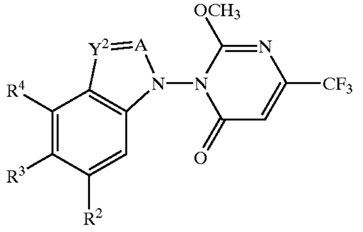
-continued
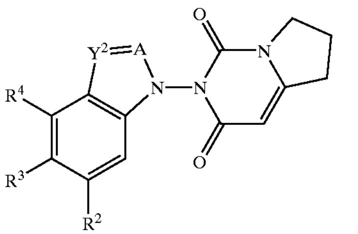
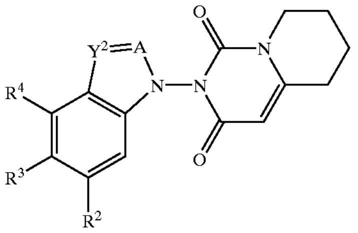
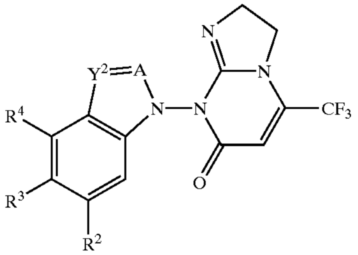
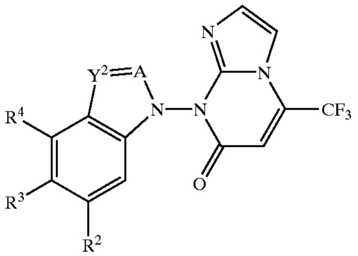
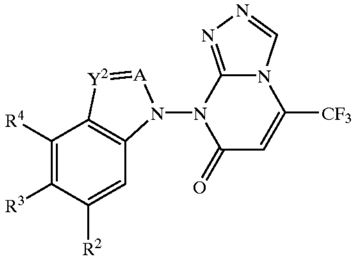
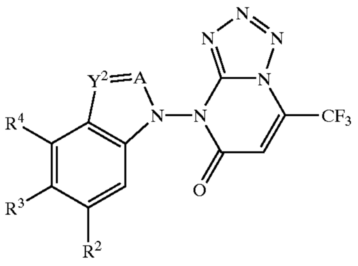

-continued

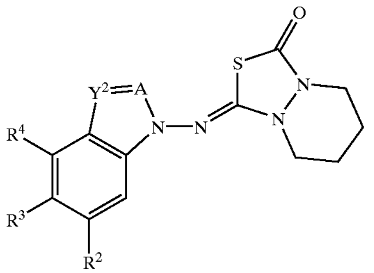

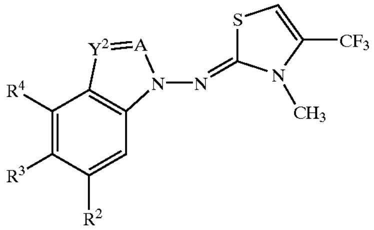

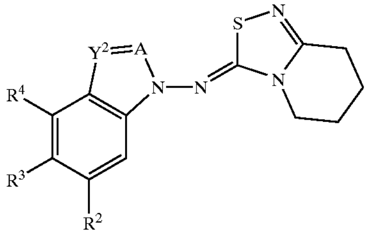

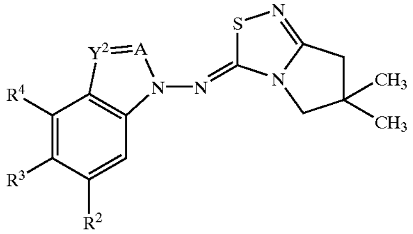

wherein

A's are selected from nitrogen or CH;

$Y^1$'s are selected from oxygen or sulfur;

$Y^2$'s are selected from nitrogen or CH, $R^2$'s are selected from hydrogen, fluorine, chlorine, bromine, iodine, $CH_2OH$, CHO, COOH, $CONH_2$, COCl, $SO_2Cl$, $COGH_3$; SH, OH, $NH_2$, $NO_2$, CN, $CH_3$, $CH_2Br$, $CHB_2$, $CBr_3$, $CH_2F$, $CHF_2$, $CF_3$, O-Me, O-Et, O-Pr, O-i-Pr, O-Bu, O-i-Bu, O-s-Bu, O-Pen, O-c-Pen, O-Hex, O-c-Hex, O-Hep, O-Oct, $OCH_2CH_2F$, $OCH_2CH_2Cl$, $OCH_2CH_2Br$, $OCH_2CF_3$, $OCH_2OCH_3$, $OCH_2CH_2OCH_3$, $OCH_2CH_2OCH_2CH_3$, $OCH_2SCH_3$, $OCH_2CH_2SCH_3$, $OCH_2CH_2SCH_2CH_3$, $OCH_2CH{=}CH_2$, $OCH(CH_3)CH{=}CH_2$, $OC(CH_3)_2CH{=}CH_2$, $OCH_2C(Cl){=}CH_2$, $OCH(CH_3)C(Cl){=}CH_2$, $OCH_2C(CH_3){=}CH_2$, $OCH_2C{\equiv}CH$, $OCH(CH_3)C{\equiv}CH$, $OC(CH_3)_2C{\equiv}CH$, $OCH_2$-c-Pr, $OCH_2$-c-Pen, $OCH_2$-c-Hex, $OCH_2CN$, $OCH(CH_3)CN$, OCOMe, OCOEt, OCOPr, OCO-i-Pr, $OCOCF_3$, $OCOCF_2H$, $OCH_2COOH$, $OCH_2COOMe$, $OCH_2COOEt$, $OCH_2GOOPr$, $OCH_2COO$-i-Pr, $OCH_2COOBu$, $OCH_2COO$-s-Bu, $OCH_2COOPen$, $OCH_2COOHex$, $OCH_2COOHep$, $OCH_2COO$-c-Pen, $OCH_2COO$-c-Hex, $OCH_2COOCH_2CH{=}CH_2$, $OCH_2COOCH_2C{\equiv}OCH$, $OCH_2COOPh$, $OCH_2COOCH_2Ph$, $OCH_2C({=}NOMe)COOMe$, $OCH_2C({=}NOMe)COOEt$, $OCH_2C({=}NOMe)COOPr$, $OCH_2COOCH_2COOH$, $OCH_2COOCH_2COOMe$, $OCH_2COOCH_2COOEt$, $OCH_2COOCH_2COOPr$, $OCH_2COOCH_2COO$-i-Pr, $OCH_2COOCH_2COOBu$, $OCH_2COOCH_2COO$-c-Pen, $OCH_2COOCH_2COO$-c-Hex, $OCH_2COOCH_2COOCH_2CH{=}CH_2$, $OCH_2COOCH_2COOCH_2C{\equiv}CH$, $OCH_2COOCH(CH_3)COOH$, $OCH_2COOCH(CH_3)COOMe$, $OCH_2COOCH(CH_3)COOEt$, $OCH_2COOCH(CH_3)COOPr$, $OCH_2COOCH(CH_3)COO$-i-Pr, $OCH_2COOCH(CH_3)COOBu$, $OCH_2COOCH(CH_3)COO$-c-Pen, $OCH_2COOCH(CH_3)COO$-c-Hex, $OCH_2COOCH(CH_3)COOCH_2CH{=}CH_2$, $OCH_2COOCH(CH_3)COOCH_2C{\equiv}CH$, $OCH_2COOC(CH_3)_2COOH$, $OCH_2COOC(CH_3)_2COOMe$, $OCH_2COOC(CH_3)_2COOEt$, $OCH_2COOC(CH_3)_2COOPr$, $OCH_2COOC(CH_3)_2COO$-i-Pr, $OCH_2COOC(CH_3)_2COOBu$, $OOH_2COOC(CH_3)_2COO$-c-Pen, $OCH_2COOC(CH_3)_2COO$-c-Hex, $OCH_2COOC(CH_3)_2COOCH_2CH{=}CH_2$, $OCH_2COOC(CH_3)_2COOCH_2C{\equiv}CH$, $OCH(CH_3)COOH$, $OCH(CH_3)COOMe$, $OCH(CH_3)COOEt$, $OCH(CH_3)COOPr$, $OCH(CH_3)COO$-i-Pr, $OCH(CH_3)COOBu$, $OCH(CH_3)COO$-s-Bu, $OCH(CH_3)COOPen$, $OCH(CH_3)COOHex$, $OCH(CH_3)COOHep$, $OCH(CH_3)COO$-c-Pen, $OCH(CH_3)COO$-c-Hex, $OCH(CH_3)COOCH_2CH{=}CH_2$, $OCH(CH_3)COOCH_2C{\equiv}CH$, $OCH(CH_3)COOPh$, $OCH(CH_3)COOCH_2Ph$, $OCH(CH_3)C({=}NOMe)COOMe$, $OCH(CH_3)C({=}NOMe)COOEt$, $OCH(CH_3)C({=}NOMe)COOPr$, $OCH(CH_3)COOCH_2COOH$, $OCH(CH_3)COOCH_2COOMe$, $OCH(CH_3)COOCH_2COOEt$, $OCH(CH_3)COOCH_2COOPr$, $OCH(CH_3)COOCH_2COO$-i-Pr, $OCH(CH_3)COOCH_2COOBu$, $OCH(CH_3)COOCH_2COO$-c-Pen, $OCH(CH_3)COOCH_2COO$-c-Hex, $OCH(CH_3)COOCH_2COOCH_2CH{=}CH_2$, $OCH(CH_3)COOH_2COOCH_2C{\equiv}CH$, $OCH(CH_3)COOCH(CH_3)COOH$, $OCH(CH_3)COOH(CH_3)COOMe$, $OCH(CH_3)COOCH(CH_3)COOEt$, $OCH(CH_3)COOCH(CH_3)COOPr$, $OCH(CH_3)COOCH(CH_3)COO$-i-Pr, $OCH(CH_3)COOCH(CH_3)COOBu$, $OCH(CH_3)COOCH(CH_3)COO$-c-Pen, $OCH(CH_3)COOCH(CH_3)COO$-c-Hex, $OCH(CH_3)COOCH(CH_3)COOCH_2CH{=}CH_2$, $OCH(CH_3)COOCH(CH_3)COOCH_2C{\equiv}CH$, $OCH(CH_3)COOC(CH_3)_2COOH$, $OCH(CH_3)COOC(CH_3)_2COOMe$, $OCH(CH_3)COOC(CH_3)_2COOEt$, $OCH(CH_3)COOC(CH_3)_2COOPr$, $OCH(CH_3)COOC(CH_3)_2COO$-i-Pr, $OCH(CH_3)COOC(CH_3)_2COOBu$, $OCH(CH_3)COOC(CH_3)_2COO$-c-Pen, $OCH(CH_3)COOC(CH_3)_2COO$-c-Hex, $OCH(CH_3)COOC(CH_3)_2COOCH_2CH{=}CH_2$, $OCH(CH_3)COOC(CH_3)_2COOCH_2C{\equiv}CH$, $OCH_2CON(Me)_2$, $OCH_2CON(Et)_2$, $OCH(CH_3)CON(Me)_2$, $OCH(CH_3)CON(Et)_2$, S-Me, S-Et, S-Pr, S-i-Pr, S-Bu, S-i-Bu, S-s-Bu, S-Pen, S-c-Pen, S-Hex, S-c-Hex, S-Hep, S-Oct, $SCH_2CH_2F$, $SCH_2CH_2Cl$, $SCH_2CH_2Br$, $SCH_2CF_3$, $SCH_2OCH_3$, $SCH_2CH_2OCH_3$, $SCH_2CH_2OCH_2CH_3$, $SCH_2SCH_3$, $SCH_2CH_2SCH_3$, $SCH_2CH_2SCH_2CH_3$, $SCH_2CH{=}CH_2$, $SCH(CH_3)CH{=}CH_2$, $SC(CH_3)_2CH{=}CH_2$, $SCH_2C(Cl)CH_2$, $SCH(CH_3)C(Cl){=}CH_2$, $SCH_2C(CH_3){=}CH_2$, $SCH_2C{\equiv}CH$, $SCH(CH_3)C{\equiv}CH$, $SC(CH_3)_2C{\equiv}CH$, $SCH_2$-c-Pr, $SCH_2$-c-Pen, $SCH_2$-c-Hex, $SCH_2CN$, $SCH(CH_3)CN$, SCOMe, SCOEt, SCOPr, SCO-i-Pr, $SCOCF_3$, $SCOCF_2H$, $SCH_2COOH$, $SCH_2COOMe$, $SCH_2COOEt$, $SCH_2COOPr$, $SCH_2COO$-i-Pr, $SCH_2COOBu$, $SCH_2COO$-s-Bu, $SCH_2COOPen$, $SCH_2COOHex$, $SCH_2COOHep$, $SCH_2COO$-c-Pen, $SCH_2COO$-c-Hex, $SCH_2COOCH_2CH{=}CH_2$, $SCH_2COOCH_2C{\equiv}CH$, $SCH_2COOPh$, $SCH_2COOCH_2Ph$, $SCH_2COOCH_2COOH$, $SCH_2COOCH_2COOMe$, $SCH_2COOCH_2COOEt$, $SCH_2COOCH_2COOPr$, $SCH_2COOCH_2COO$-i-Pr, $SCH_2COOCH_2COOBu$, $SCH_2COOCH_2COO$-c-Pen, $SCH_2COOCH_2COO$-c-Hex, $SCH_2COOCH_2COOCH_2CH{=}CH_2$, $SCH_2COOCH_2COOCH_2C{\equiv}CH$, $SCH_2COOCH(CH_3)COOH$, $SCH_2COOCH(CH_3)COOMe$, $SCH_2COOCH$ (CHOCOOEt, $SCH_2COOCH(CH_3)COOPr$, $SCH_2COOCH(CH_3)COO$-i-Pr, $SCH_2COOCH(CH_3)COOBu$, $SCH_2COOCH(CH_3)COO$-c-Pen, $SCH_2COOH(CH_3)COO$-c-Hex, $SCH_2COOCH(CH_3)COOCH_2CH{=}CH_2$, $SCH_2COOH(CH_3)COOCH_2C{\equiv}CH$, $SCH_2COOC(CH_3)_2COOH$, $SCH_2COOC(CH_3)_2COOMe$, $SCH_2COOC(CH_3)_2COOEt$, $SCH_2COOC(CH_3)_2COOPr$, $SCH_2COOC(CH_3)_2COO$-i-Pr, $SCH_2COOC(CH_3)_2COOBu$, $SCH_2COOC(CH_3)_2COO$-c-Pen, $SCH_2COOC(CH_3)_2COO$-c-Hex, $SCH_2COOC(CH_3)_2COOCH_2CH{=}CH_2$, $SCH_2COOC(CH_3)_2COOCH_2C{\equiv}CH$, $SCH(CH_3)COOH$, $SCH(CH_3)COOMe$, $SCH(CH_3)COOEt$, $SCH(CH_3)COOPr$, $SCH(CH_3)COO$-i-Pr, $SCH(CH_3)COOBu$, $SCH(CH_3)COO$-s-Bu, $SCH(CH_3)COOPen$, $SCH(CH_3)COOHex$, $SCH(CH_3)COOHep$, $SCH(CH_3)COO$-c-Pen, $SCH(CH_3)COO$-c-Hex, $SCH(CH_3)COOCH_2CH{=}CH_2$, $SCH(CH_3)COOCH_2C{\equiv}CH$, $SCH(CH_3)COOPh$, $SCH(CH_3)COOCH_2Ph$, $SCH(CH_3)COOCH_2COOH$, $SCH(CH_3)COOCH_2COOMe$, $SCH(CH_3)COOCH_2COOEt$, $SCH(CH_3)COOCH_2COOPr$, $SCH(CH_3)COOCH_2COO$-i-Pr, $SCH(CH_3)COOCH_2COOBu$, $SCH(CH_3)COOCH_2COO$-c-Pen, $SCH(CH_3)COOCH_2COO$-c-Hex, $SCH(CH_3)COOCH_2COOCH_2CH{=}CH_2$, $SCH(CH_3)COOCH_2COOCH_2C{\equiv}CH$, $SCH(CH_3)COOCH(CH_3)COOH$, $SCH(CH_3)COOCH(CH_3)COOMe$, $SCH(CH_3)COOCH(CH_3)COOEt$, $SCH(CH_3)COOCH(CH_3)COOPr$, $SCH(CH_3)COOCH(CH_3)COO$-i-Pr, $SCH(CH_3)COOCH(CH_3)COOBu$, $SCH(CH_3)COOCH(CH_3)COO$-c-Pen, $SCH(CH_3)COOCH(CH_3)COO$-c-Hex, $SCH(CH_3)COOCH(CH_3)COOCH_2CH{=}CH_2$, $SCH(CH_3)COOCH(CH_3)COOCH_2C{\equiv}CH$, $SCH(CH_3)COOC(CH_3)_2COOH$, $SCH(CH_3)COOC(CH_3)_2COOMe$, $SCH(CH_3)COOC(CH_3)_2COOEt$, $SCH(CH_3)COOC(CH_3)_2COOPr$, $SCH(CH_3)COOC(CH_3)_2COO$-i-Pr, $SCH(CH_3)COOC(CH_3)_2COOBu$, $SCH(CH_3)COOC(CH_3)_2COO$-c-Pen, $SCH(CH_3)COOC(CH_3)_2COO$-c-Hex, $SCH(CH_3)COOC(CH_3)_2COOCH_2CH{=}CH_2$, $SCH(CH_3)COOC(CH_3)_2COOCH_2C{\equiv}CH$, $SCH_2CON(Me)_2$, $SCH_2CON(Et)_2$, $SCH(CH_3)CON(Me)_2$, $SCH(CH_3)CON(Et)_2$, NH-Me, NH-Et, NH-Pr, NH-i-Pr, NH-Bu, NH-i-Bu, NH-s-Bu, NH-Pen, NH-c-Pen, NH-Hex, NH-c-Hex, NH-Hep, NH-Oct, $NHCH_2CH{=}CH_2$, $NHCH(CH_3)CH{=}CH_2$, $NHC(CH_3)_2CH{=}CH_2$, $NHCH_2C(Cl){=}CH_2$, $NHCH(CH_3)C(Cl){=}CH_2$, $NHCH_2C(CH_3){=}CH_2$, $NHCH_2C{\equiv}CH$, $NHCH(CH_3)C{\equiv}CH$, $NHC(CH_3)_2C{\equiv}CH$, $NHCH_2$-c-Pr, $NHCH_2$-c-Pen, $NHCH_2$-c-Hex, $NHCH_2CN$, $NHCH(CH_3)CN$, NHCOMe, NHCOEt, NHCOPr, NHCO-i-Pr, $NHCOCF_3$, $NHCOCF_2H$, NHCOOMe, NHCOOEt, NHCOOPr, NHCOO-i-Pr, $NHSO_2Me$, $NHSO_2Et$, $NHSO_2Pr$, $NHSO_2$-i-Pr, $NHSO_2CH_2Cl$, $NHSO_2CF_3$, $NHCH_2COOH$, $NHCH_2COOMe$, $NHCH_2COOEt$, $NHCH_2COOPr$, $NHCH_2COO$-i-Pr, $NHCH_2COOBu$, $NHCH_2COO$-s-Bu, $NHCH_2COOPen$, $NHCH_2COOHex$, $NHCH_2COOHep$, $NHCH_2COO$-c-Pen, $NHCH_2COO$-c-Hex, $NHCH_2COOCH_2CH{=}CH_2$, $NHCH_2COOCH_2C{\equiv}CH$, $NHCH_2COOPh$, $NHCH_2COOCH_2Ph$, $NHCH_2COOCH_2COOH$, $NHCH_2COOCH_2COOMe$, $NHCH_2COOCH_2COOEt$, $NHCH_2COOCH_2COOPr$, $NHCH_2COOCH_2COO$-i-Pr, $NHCH_2COOCH_2COOBu$, $NHCH_2COOCH_2COO$-c-Pen, $NHCH_2COOCH_2COO$-c-Hex, $NHCH_2COOCH_2COOCH_2CH{=}CH_2$, $NHCH_2COOCH_2COOCH_2C{\equiv}CH$, $NHCH_2COOCH(CH_3)COOH$, $NHCH_2COOCH(CH_3)COOMe$, $NHCH_2COOCH(CH_3)COOEt$, $NHCH_2COOCH(CH_3)COOPr$, $NHCH_2COOCH(CH_3)COO$-i-Pr, $NHCH_2COOCH(CH_3)COOBu$, $NHCH_2COOCH(CH_3)COO$-c-Pen, $NHCH_2COOCH(CH_3)COO$-c-Hex, $NHCH_2COOCH(CH_3)COOCH_2CH{=}CH_2$, $NHCH_2COOCH(CH_3)COOCH_2C{\equiv}CH$, $NHCH_2COOC(CH_3)_2COOH$, $NHCH_2COOC(CH_3)_2COOMe$, $NHCH_2COOC(CH_3)_2COOEt$, $NHCH_2COOC(CH_3)_2COOPr$, $NHCH_2COOC(CH_3)_2COO$-i-Pr, $NHCH_2COOC(CH_3)_2COOBu$, $NHCH_2COOC(CH_3)_2COO$-c-Pen, $NHCH_2COOC(CH_3)_2COO$-c-Hex, $NHCH_2COOC(CH_3)_2COOCH_2CH{=}CH_2$, $NHCH_2COOC(CH_3)_2COOCH_2C{\equiv}CH$, $NHCH(CH_3)COOH$, $NHCH(CH_3)COOMe$, $NHCH(CH_3)COOEt$, $NHCH(CH_3)COOPr$, $NHCH(CH_3)COO$-i-Pr, $NHCH(CH_3)COOBu$, $NHCH(CH_3)COO$-s-Bu, $NHCH(CH_3)COOPen$, $NHCH(CH_3)COOHex$, $NHCH(CH_3)COOHep$, $NHCH(CH_3)COO$-c-Pen, $NHCH(CH_3)COO$-c-Hex, $NHCH(CH_3)COOCH_2CH{=}CH_2$, $NHCH(CH_3)COOCH_2C{\equiv}CH$, $NHCH(CH_3)COOPh$, $NHCH(CH_3)COOCH_2Ph$, $NHCH(CH_3)COOCH_2COOH$, $NHCH(CH_3)COOCH_2COOMe$, $NHCH(CH_3)COOCH_2COOEt$, $NHCH(CH_3)COOCH_2COOPr$, $NHCH(CH_3)COOCH_2COO$-i-Pr, $NHCH(CH_3)COOCH_2COOBu$, $NHCH(CH_3)COOCH_2COO$-c-Pen, $NHCH(CH_3)COOCH_2COO$-c-Hex, $NHCH(CH_3)COOCH_2COOCH_2CH{=}CH_2$, $NHCH(CH_3)COOCH_2COOCH_2C{\equiv}CH$, $NHCH(CH_3)COOCH(CH_3)COOH$, $NHCH(CH_3)COOCH(CH_3)COOMe$, $NHCH(CH_3)COOCH(CH_3)COOEt$, $NHCH(CH_3)COOCH(CH_3)COOPr$, $NHCH(CH_3)COOCH(CH_3)COO$-i-Pr, $NHCH(CH_3)COOCH(CH_3)COOBu$, $NHCH(CH_3)COOCH(CH_3)COO$-c-Pen, $NHCH(CH_3)COOCH(CH_3)COO$-c-Hex, $NHCH(CH_3)COOCH(CH_3)COOCH_2CH{=}CH_2$, $NHCH(CH_3)COOCH(CH_3)COOCH_2C{\equiv}CH$, $NHCH(CH_3)COOC(CH_3)_2COOH$, $NHCH(CH_3)COOC(CH_3)_2COOMe$, $NHCH(CH_3)COOC(CH_3)_2COOEt$, $NHCH(CH_3)COOC(CH_3)_2COOPr$, $NHCH(CH_3)COOC(CH_3)_2COO$-i-Pr, $NHCH(CH_3)COOC(CH_3)_2COOBu$, $NHCH(CH_3)COOC(CH_3)_2COO$-c-Pen, $NHCH(CH_3)COOC(CH_3)_2COO$-c-Hex, $NHCH(CH_3)COOC(CH_3)_2COOCH_2CH{=}CH_2$, $NHCH(CH_3)COOC(CH_3)_2COOCH_2C{\equiv}CH$, $NHCH_2CON(Me)_2$, $NHCH_2CON(Et)_2$, $NHCH(CH_3)CON(Me)_2$, $NHCH(CH_3)CON(Et)_2$, COOH, COOMe, COOEt, COOPr, COO-i-Pr, COOBu, COO-s-Bu, COOPen, COOHex, $COOCH_2Ph$, COO-c-Pen, COO-c-Hex, $COOCH_2COOH$, $COOCH_2COOMe$, $COOCH_2COOEt$, $COOCH_2COOPr$, $COOCH_2COO$-i-Pr, $COOCH_2COOBu$, $COOCH_2COO$-c-Pen, $COOCH_2COO$-c-Hex, $COOCH_2COOCH_2CH{=}CH_2$, $COOCH_2COOCH_2C{\equiv}CH$, $COOCH(CH_3)COOH$, $COOCH(CH_3)COOMe$, $COOCH(CH_3)COOEt$, $COOCH(CH_3)COOPr$, $COOCH(CH_3)COO$-i-Pr, $COOCH(CH_3)COOBu$, $COOCH(CH_3)COO$-c-Pen, $COOCH(CH_3)COO$-c-Hex, $COOCH(CH_3)COOCH_2CH{=}CH_2$, $COOCH(CH_3)COOCH_2C{\equiv}CH$, $COOC(CH_3)_2COOH$, $COOC(CH_3)_2COOMe$, $COOC(CH_3)_2COOEt$, $COOC(CH_3)_2COOPr$, $COOC(CH_3)_2COO$-i-Pr, $COOC(CH_3)_2COOBu$, $COOC(CH_3)_2COO$-c-Pen, $COOC(CH_3)_2COO$-c-Hex, $COOC(CH_3)_2COOCH_2CH{=}CH_2$, $COOC(CH_3)_2COOCH_2C{\equiv}CH$, $CON(Et)_2$, $CON(Me)_2$, $CON(Et)_2$, $CH_2CH_2COOH$, $CH_2CH_2COOMe$, $CH_2CH_2COOEt$, $CH_2CH_2COOPr$, $CH_2CH_2COO$-i-Pr, $CH_2CH_2COOBu$, $CH_2CH(Cl)COOH$, $CH_2CH(Cl)COOMe$, $CH_2CH(Cl)COOEt$, $CH_2CH(Cl)COOPr$, $CH_2CH(Cl)COO$-i-Pr, $CH_2CH(Cl)COOBu$, CH=CHCOOH, CH=CHCOOMe, CH=CHCOOEt, CH=CHCOOPr, CH=CHCOO-i-Pr, CH=CHCOOBu, CH=C(Cl)COOH, CH=C(Cl)COOMe, CH=C(Cl)COOEt, CH=C(Cl)COOPr, CH=C(Cl)COO-i-Pr, CH=C(Cl)COOBu, C(Me)=CHCOOH, C(Me)=CHCOOMe, C(Me)=CHCOOEt, C(Me)=CHCOOPr, C(Me)=CHCOO-i-Pr, C(Me)=CHCOOBu, CH=C(Me)COOH, CH=C(Me)COOMe, CH=C(Me)COOEt, CH=C(Me)COOPr, CH=C(Me)COO-i-Pr, CH=C(Me)COOBu, CH=NOH, CH=NOMe, CH=NOEt, CH=NOPr, CH=NO-i-Pr, CH=NOBu, C(Me)=NOH, C(Me)=NOMe, C(Me)=NEt, C(Me)=NOPr, C(Me)=NO-i-Pr, C(Me)=NOBu, $CH{=}NOCH_2COOMe$, $CH{=}NOCH_2COOEt$, $CH{=}NOCH_2COOPr$, $CH{=}NOCH_2COO$-i-Pr, $CH{=}NOCH_2COOBu$, $C(Me){=}NOCH_2COOMe$, $C(Me){=}NOCH_2COOEt$, $C(Me){=}NOCH_2COOPr$, $C(Me){=}NOCH_2COO$-i-Pr, or $(Me){=}NOCH_2COOBu$;

$R^3$'s are selected from hydrogen, fluorine, chlorine, bromine, iodine, $NO_2$, CN, O-Me, O-Et, O-Pr, O-i-Pr, O-Bu, O-i-Bu, O-s-Bu, O-Pen, O-c-Pen, O-Hex, O-c-Hex, O-Hep, O-Oct, $OCH_2COOMe$, $OCH_2COOEt$, $OCH_2COOPr$, $OCH_2COO$-i-Pr, $OCH_2COOBu$, $OCH_2COO$-s-Bu, $OCH_2COOPen$, $OCH_2COOHex$, $OCH_2COOHep$, $OCH_2C({=}NOMe)COOMe$, $OCH_2C({=}NOMe)COOEt$, $OCH_2C({=}NOMe)COOPr$, $OCH(CH_3)COOMe$, $OCH(CH_3)COOEt$, $OCH(CH_3)COOPr$, $OCH(CH_3)COO$-i-Pr, $OCH(CH_3)COOBu$, $OCH(CH_3)COO$-s-Bu, $OCH(CH_3)COOPen$, $OCH(CH_3)COOHex$, $OCH(CH_3)COOHep$, $OCH(CH_3)C({=}NOMe)COOMe$, $OCH(CH_3)C({=}NOMe)COOEt$, or $OCH(CH_3)C({=}NOMe)COOPr$; and $R^4$'s are selected from hydrogen, fluorine, chlorine, bromine, iodine, $NO_2$, or CN.

EXAMPLES

The present invention will be further illustrated by the following Production Examples, Formulation Examples, and lest Examples; however, the present invention is not limited to these Examples. The numbers of the present compounds are those as shown in Tables 1 to 54.

Production Example 1

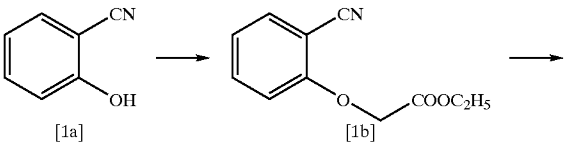

[1a] [1b]

-continued

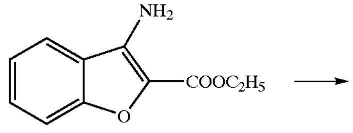

[1c]

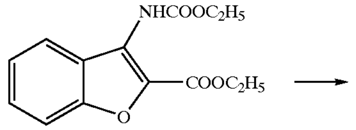

[1d]

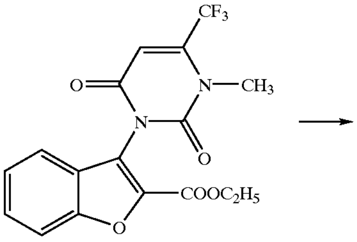

[1e]

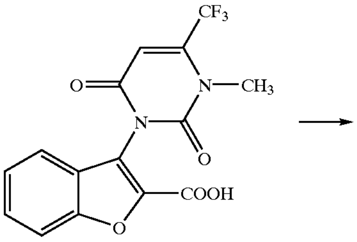

[1f]

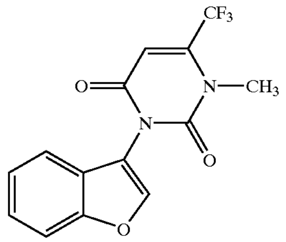

[1g]

To a suspension of 60.0 g of potassium carbonate in 300 ml of acetone was added 25 g of compound 1a and then added 35.7 g of ethyl bromoacetate, and the mixture was heated and stirred at the reflux-temperature of acetone for 1 hour. The reaction mixture was then cooled to room temperature and filtered to remove insoluble matter. The filtrate was concentrated to give 45.8 g of compound 1b as a crude product.

To a solution of 45.8 g of this crude product of compound 1b in 300 ml of N,N-dimethylformamide was added 30.0 g of potassium carbonate, and the mixture was heated and stirred at a temperature of 100° C. to 110° C. for 5 hours. The reaction mixture was then cooled to room temperature and poured into water, which was extracted with t-butyl methyl ether. The organic layer was washed with water and then with diluted hydrochloric acid, dried over anhydrous magnesium sulfate, and then concentrated to give 36.5 g of compound 1c as crystals.

$^1$H-NMR (300 MHz, $CDCl_3$, TMS, δ (ppm)): 1.44 (3H, t, J=7.09 Hz), 4.44 (2H, q, J=7.07 Hz), 4.65–5.38 (2H, br), 7.21–7.27 (1H, m), 7.44–7.57 (3H, m).

To a solution of 10.2 g of compound 1c in 50 ml of tetrahydrofaran was added 6.5 g of ethyl chloroformate and 7.3 g of N,N-diethylaniline, and the mixture was heated and stirred at the reflux temperature of tetrahydrofuran for 3 hours. The reaction mixture was then cooled to room temperature and poured into water, which was extracted with ethyl acetate. The organic layer was washed with water and then with diluted hydrochloric acid, dried over anhydrous magnesium sulfate, and then concentrated to give 13.05 g of compound 1d.

m.p.: 90.6° C.

To a suspension of 2.4 g of sodium hydride in 50 ml of N,N-dimethylformamide was added 11.0 g of ethyl 4,4,4-trifluoro-3-aminochrotonate below 10° C., and the mixture was stirred for 30 minutes. The reaction mixture was then warmed to room temperature, to which a solution of 13.0 g of compound 1d in 20 ml of N,N-dimethylformamide was added, and the reaction mixture was then warmed to 100° C. to 110° C., at which temperature the mixture was kept and stirred for 2.5 hours. The reaction mixture was then cooled to room temperature, to which 10.0 g of methyl iodide was added, and the mixture was stirred at room temperature overnight. The reaction mixture was then poured into water, which was extracted with t-butyl methyl ether. The organic layer was washed with water and then with diluted hydrochloric acid, dried over anhydrous magnesium sulfate, and then concentrated. The residue was subjected to silica gel chromatography (eluent, hexane:ethyl acetate=4:1) to give 4.56 g of compound 1e.

m.p.: 107.2° C.

First, 1.0 g of compound 1e was added to 5 ml of 85% sulfuric acid, and the mixture was warmed to 110° C., heated and stirred for 5 minutes. The reaction mixture was then poured into water, and the deposited crystals were collected by filtration and dried to give 0.81 g of compound 1f.

$^1$H-NMR (250 MHz, $CDCl_3$, TMS, δ (ppm)): 3.59–3.60 (3H, m), 6.41 (1H, s), 7.26–7.67 (4H, m).

First, 0.7 g of compound 1f and 0.05 g of copper powder were added to 3 ml of quinoline, and the mixture was warmed to 150° C., at which temperature the mixture was kept and stirred for 1 hour. The reaction mixture was then poured into water, which was extracted with ethyl acetate. The organic layer was washed with water and then with diluted hydrochloric acid, dried over anhydrous magnesium sulfate, and then concentrated. The residue was subjected to silica gel chromatography (eluent, hexane:ethyl acetate 5:1) to give 0.43 g of compound 1g (the present compound 1-1).

$^1$H-NMR (250 MHz, $CDCl_3$, TMS, δ (ppm)): 3.51 (3H, m), 6.34 (1H, s), 7.21–7.54 (4H, m), 7.81 (1H, s).

Production Example 2

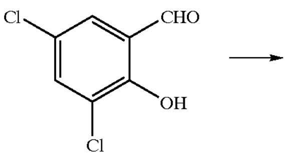

[2a]

-continued

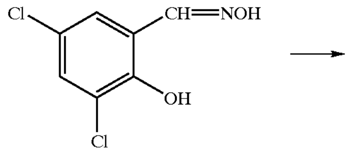

[2b]

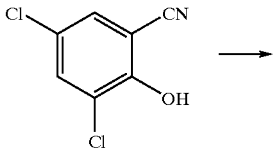

[2c]

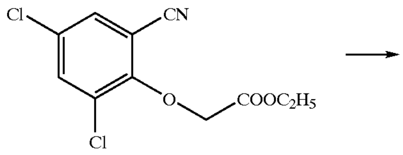

[2d]

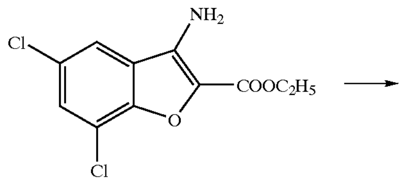

[2e]

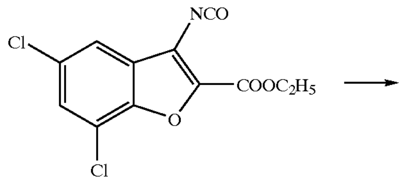

[2f]

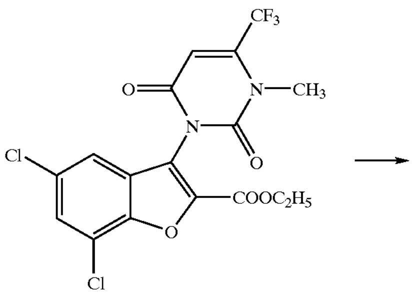

[2g]

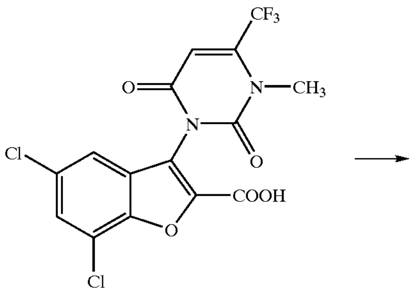

[2h]

-continued

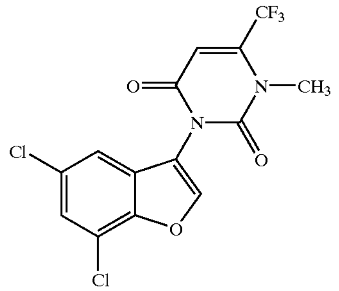

[2i]

To 200 ml of ethanol were added 25 g of compound 2a and 10.9 g of hydroxylamine hydrochloride, and the mixture was stirred at room temperature overnight. The reaction mixture was then poured into water, and the deposited crystals were collected by filtration and dried to give 26.06 g of compound 2b.

To a solution of 26.0 g of compound 2b in 100 ml of chloroform was added 22.4 g of 1,1'-carbonyldiimidazole under ice cooling, and the mixture was stirred at room temperature for 30 minutes, then heated and stirred at the reflux temperature of chloroform for 1 hour. The reaction mixture was then concentrated, and diluted hydrochloric acid was added to the residue, which was extracted with ethyl acetate. The organic layer was dried over anhydrous magnesium sulfate and then concentrated to give 15.88 g of compound 2c.

$^1$H-NMR (250 MHz, $CDCl_3$, TMS, δ (ppm)): 7.46 (1H, d, J=2.45 Hz), 7.57 (1H, d, J=2.45 Hz).

To a suspension of 16.5 g of potassium carbonate in 80 ml of acetone was added 15 g of compound 2c and then added 14.6 g of ethyl bromoacetate, and the mixture was heated and stirred at the reflux temperature of acetone for 4 hours. The reaction mixture was then cooled to room temperature and filtered to remove insoluble matter, and the filtrate was then concentrated to give compound 2d as a crude product.

To a solution of this crude product of compound 2d in 150 ml of N,N-dimethylformamide was added 50.0 g of potassium carbonate, and the mixture was heated and stirred at a temperature of 90° C. to 100° C. for 30 minutes. The reaction mixture was then cooled to room temperature and poured into water, and the deposited crystals were collected by filtration. The crystals were washed with water and dried to give 21.49 g of compound 2e.

$^1$H-NMR (300 MHz, $CDCl_3$, TMS, δ (ppm)): 1.44 (3H, t, J=7.07 Hz), 4.45 (2H, q, J=7.07 Hz), 4.82–5.13 (2H, br), 7.44–7.45 (2H, m).

To 60 ml of toluene were added 4.0 g of compound 2e, 2.8 g of trichloromethyl chloroformate, and 1 g of activated carbon (powder), and the. mixture was heated and stirred at the reflux temperature of toluene for 1 hour. The reaction mixture was then filtered, and the filtrate was concentrated to give 13.0 g of compound 2f as a crude product.

In a suspension of 0.64 g of sodium hydride in 20 ml of N,N-dimethylformamide was added 3.0 g of ethyl 4,4,4-trifluoro-3-aminichrotonate below 10° C., and the mixture was stirred for 30 minutes. 1b the reaction mixture was added dropwise at −30° C. a solution of 13.0 g of this crude product of compound 2f in 30 ml of tetrahydrofuran. After completion of the dropwise addition, the reaction mixture was warmed to room temperature and stirred at room temperature for 2 hours. To the reaction mixture was then added 3.0 g of methyl iodide, and the mixture was stirred at room temperature for 2 hours. The reaction mixture was then poured into water, which was extracted with ethyl acetate. The organic layer was washed with water and then with diluted hydrochloric acid, dried over anhydrous magnesium sulfate, then and concentrated. The residue was subjected to silica gel chromatography (eluent, hexane:ethyl acetate=4:1) to give 4.51 g of compound 2g.

$^1$H-NMR (300 MHz, $CDCl_3$, TMS, δ (ppm)): 1.33 (3H, t, J=7.06 Hz), 3.59 (3H, m), 4.39 (2H, q, J=6.93 Hz), 6.39 (1H, s), 7.36 (1H, d, J=2.65 Hz), 7.51 (1H, d, J=2.65 Hz).

First, 4.5 g of compound 2g was added to 20 ml of 85% sulfuric acid, and the mixture was heated to 100° C., at which temperature the mixture was kept and stirred for 30 minutes. The reaction mixture was then poured into water, and the deposited crystals were collected by filtration and dried to give 3.57 g of compound 2h.

$^1$H-NMR (250 MHz, $CDCl_3$, TMS, δ (ppm)): 3.59–3.60 (3H, m), 6.40 (1H, s), 7.38 (1H, d, J=1.77 Hz), 7.54 (1H, d, J=1.77 Hz).

To 10 ml of quinoline were added 3.0 g of compound 2h and 0.07 g of copper powder, and the mixture was heated to 120° C. to 150° C., at which temperature the mixture was kept and stirred for 30 minutes. The reaction mixture was then poured into water, which was extracted with ethyl acetate. The organic layer was washed with water and then with diluted hydrochloric acid, dried over anhydrous magnesium sulfate, and then concentrated. The crystals obtained were washed with t-butyl methyl ether to give 1.62 g of compound 2i (the present compound 1-2).

$^1$H-NMR (250 MHz, $CDCl_3$, TMS, δ (ppm)): 3.59–3.60 (3H, m), 6.40 (1H, s), 7.24 (1H, d, J=1.89), 7.37 (1H, d, J=1.89), 7.93 (1H, s).

Production Example 3

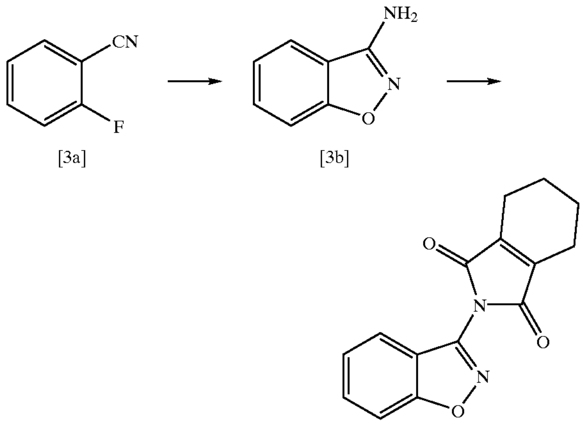

[3a]

[3b]

[3c]

To a solution of 9.77 g of acetohydroxamic acid in 150 ml of N,N-dimethylformamide was added 14.6 g of potassium t-butoxide at room temperature, and the mixture was. stirred at room temperature for 30 minutes. To the reaction mixture was added 10.5 g of compound 3a at room temperature, and the mixture was left undisturbed at room temperature for 3 days. The reaction mixture was then poured into water, which was extracted with ethyl acetate. The organic layer was washed with water and then with diluted hydrochloric acid, dried over anhydrous magnesium sulfate, and then concentrated. The crystals obtained were washed with n-hexane to give 6.95 g of compound 3b.

To 2 ml of propionic acid were added 500 mg of compound 3b and 567 mg of 3,4,5,6-tetrahydrophthalic anhydride, and the mixture was heated and stirred at the reflux temperature of propionic acid for 24 hours. The reaction mixture was subjected to silica gel column chromatography (eluent, hexane:ethyl acetate=5:1) to give 200 mg of compound 3c (the present compound 2-4).

$^{1}$H-NMR (250 MHz, $CDCl_3$, TMS, δ (ppm)): 1.84–1.89 (4H, m), 2.48–2.52 (4H, m), 7.31–7.40 (1H, m), 7.55–7.75 (3H, m).

Production Example 4

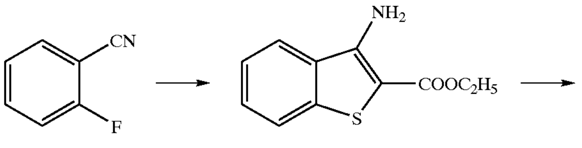

[4a] [4b]

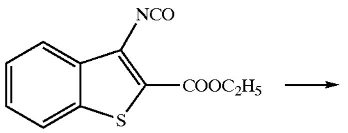

[4c]

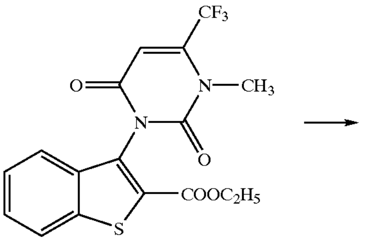

[4d]

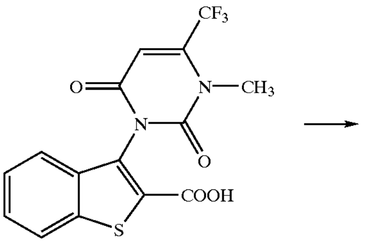

[4e]

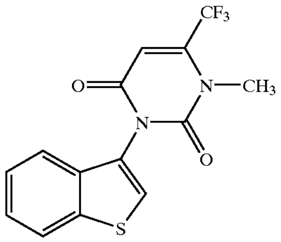

[4f]

To a solution of 10.4 g of ethyl thioglycolate in 20 ml of N,N-dimethylformamide were added 12.4 g of potassium carbonate and 20 ml of N,N-dimethylformamide, and the mixture was warmed to 40° C. To the reaction mixture was added 10.0 g of compound 4a, and the mixture was warmed to 85° C., at which temperature the mixture was kept and stirred for 2 hours. The reaction mixture was left undisturbed at room temperature overnight. To the reaction mixture were then added 33.7 g of potassium carbonate and 30 ml of N,N-dimethylformamide, and the mixture was heated and stirred at 100° C. to 110° C. for 4 hours. The reaction solution was then poured into water, which was extracted with ethyl acetate. The organic layer was washed with water and then with diluted hydrochloric acid, dried over anhydrous magnesium sulfate, and then concentrated The residue was subjected to silica gel column chromatography (eluent, hexane:ethyl acetate=4:1) to give 14.44 g of compound 4b.

$^{1}$H-NMR (250 MHz, $CDCl_3$, TMS, δ (ppm)): 1.39 (3H, t, J=7.09 Hz), 4.36 (2H, q, J=7.11 Hz), 5.90 (2H, bs), 7.34–7.74 (4H, m).

To a solution of 4.0 g of compound 4b in 50 ml of toluene was added 3.58 g of trichloromethyl chloroformate, and the mixture was heated and stirred at the reflux temperature of toluene for 1 hour. The reaction mixture was concentrated to give compound 4c as a crude product.

To a suspension of 0.87 g of sodium hydride in 15 ml of N,N-dimethylformamide was added 4.0 g of ethyl 4,4,4-trifluoro-3-aminochrotonate below 10° C., and the mixture was stirred for 30 minutes. To the reaction was then added dropwise at −30° C. a solution of this crude product of compound 4c in the whole amount dissolved in 50 ml of tetrahydrofuran. After completion of the dropwise addition, the mixture was warmed to room temperature and left undisturbed overnight. To the reaction mixture was then added 3.85 g of methyl iodide, and the mixture was stirred at room temperature for 3 hours. The reaction mixture was then poured into water, which was extracted with ethyl acetate. The organic layer was washed with water and then with diluted hydrochloric acid, dried over anhydrous magnesium sulfate, and then concentrated. The residue was subjected to silica gel column chromatography (eluent, hexane:ethyl acetate=4:1) to give 2.36 g of compound 4b as crystals.

m.p.: 112.6° C.

To 15 ml of 85% sulfuric acid was added 2.3 g of compound 4d, and the mixture was warmed to 110° C., at which temperature the mixture was kept and stirred for 15 minutes. The reaction mixture was then poured into water, and the precipitated crystals were collected by filtration and dried to give 1.61 g of compound 4e.

$^{1}$H-NMR (250 MHz, $CDCl_3$, TMS, δ (ppm)): 3.58 (3H, m), 6.42 (1H, s), 7.41–7.91 (4H, m).

To 12 ml of quinoline were added 1.5 g of compound 4e and 0.06 g of copper powder, and the mixture was warmed to 120° C. to 140° C., at which temperature the mixture was kept and stirred for 30 minutes. The reaction mixture was then poured into water, which was extracted with ethyl acetate. The organic layer was washed with water and then with diluted hydrochloric acid, dried over anhydrous magnesium sulfate, and then concentrated. The residue was subjected to silica gel chromatography (eluent, hexane:ethyl acetate=4:1) to give 1.07 g of compound 4f (the present compound 1-3).

m.p.: 156.8° C.

Production Example 5

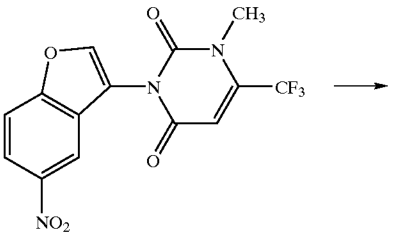

[5a]

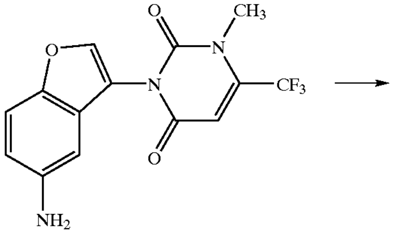

[5b]

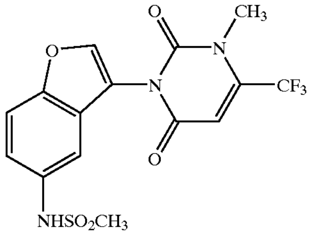

[5c]

According to the process as described above in Production Example 2, compound 5a (the present compound 1-6) was produced from 2-hydroxy-5-nitrobenzaldehyde.

m.p.: 231.9° C. (decomposition).

To a mixed solvent of 40 ml of acetic acid and 20 ml of water was added 4.5 g of iron powder, to which suspension 4.5 g of compound 5a was added, and the mixture was heated and stirred at the reflux temperature of the solvent for 20 minutes. The reaction mixture was then poured into water, which was extracted with ethyl acetate. The organic layer was washed with water and then with saturated aqueous sodium bicarbonate solution, dried over anhydrous magnesium sulfate, and then concentrated to give 2.64 g of compound 5b (the present compound 1-7).

$^1$H-NMR (300 MHz, $CDCl_3$, TMS, δ (ppm)): 3.25–3.82 (2H, br), 3.58 (3H, m), 6.39 (1H, s), 6.55 (1H, d, J=2.30 Hz), 6.71 (1H, dd, J=8.76 Hz, 2.30 Hz), 7.32 (1H, d, J=8.76 Hz), 7.73 (1H, s).

To a solution of 0.8 g of compound 5b dissolved in 6 ml of pyridine was added 0.3 g of methanesulfonyl chloride at room temperature, and the mixture was stirred for 2 hours. The reaction mixture was poured into water, which was extracted with ethyl acetate. The organic layer was washed with water, with aqueous hydrochloric acid solution, and then with water, dried over anhydrous magnesium sulfate, and then concentrated. The deposited crystals were washed with t-butyl methyl ether to give 0.55 g of compound 5c (the present compound 1-10).

m.p.: 105.3° C.

Production Example 6

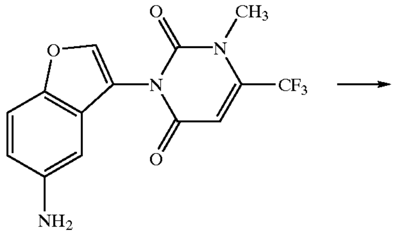

[5b]

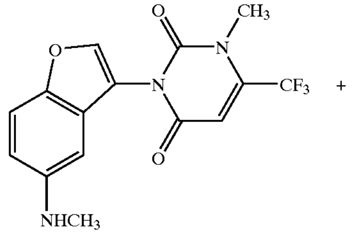

[6a]

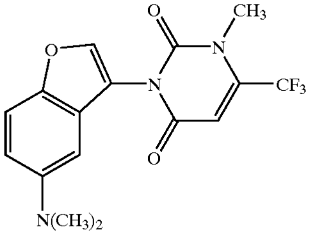

[6b]

To 6 ml of methyl iodide was added 0.6 g of compound 5b, and the mixture was heated and stirred at the reflux temperature of methyl iodide for 4 hours. The reaction mixture was concentrated, and the residue was subjected to silica gel chromatography (eluent, hexane:ethyl acetate=2:1) to give 0.14 g of compound 6a (the present compound 1-8) and 0.065 g of compound 6b (the present compound 1-9).

Compound 6a.

$^1$H-NMR (250 MHz, $CDCl_3$, TMS, δ (ppm)): 2.82 (3H, s), 3.57–3.58 (3H, m), 6.37–6.67 (3H, m), 7.33 (1H, d, J=8.85 Hz), 7.71 (1H, s).

Compound 6b.

m.p.: 166.1° C. (decomposition).

Production Example 7

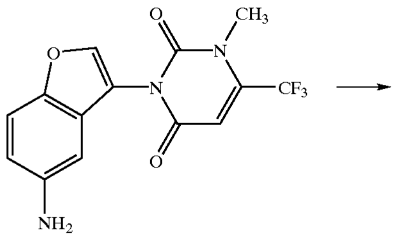

[5b]

-continued

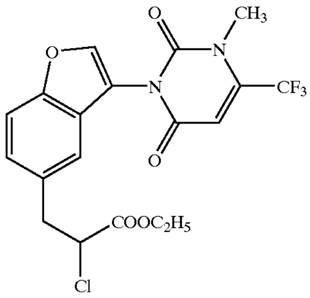

[7a]

To 10 ml of acetonitrile were added 0.53 g of copper (II) chloride and 0.57 g of isobutyl nitrite, to which 3 ml of ethyl acrylate was added under ice cooling, and the mixture was stirred for 10 minutes. A solution of 1.0 g of compound 5b dissolved in 5 ml of acetonitrile was then added to the reaction mixture under ice cooling. The mixture obtained was stirred for 2 hours. The reaction mixture was then poured into water, which was extracted with ethyl acetate. The organic layer was washed with diluted hydrochloric acid, dried over anhydrous magnesium sulfate, and then concentrated The residue was subjected to silica gel chromatography (eluent, hexane:ethyl acetate=3:1) to give 0.64 g of compound 7a (the present compound 1-407).

$^1$H-NMR (250 MHz, $CDCl_3$, TMS, δ (ppm)): 1.18 (3H, t, J.=7.12 Hz), 3.18–3.48 (2H, m), 3.56–3.57 (3H, m), 4.10–4.20 (2H, m), 4.41 (1H, t, J=7.43 Hz), 6.39 (1H, s), 7.19–7.49 (3H, m), 7.82 (1H, s).

Production Example 8

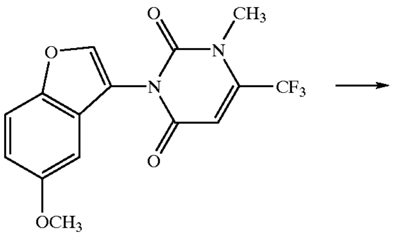

[8a]

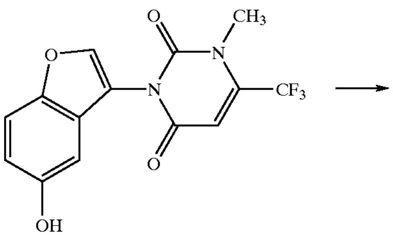

[8b]

-continued

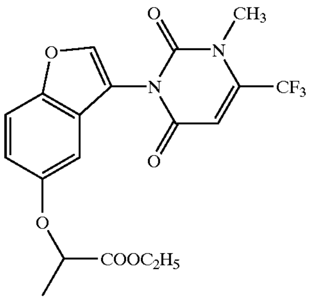

[8c]

According to the process as described above in Production Example 2, compound 8a (the present compound 1-5) was produced from 2-hydroxy-5-methoxybenzaldehyde.

m.p.: 135.0° C.

To a solution of 0.64 g of compound 8a dissolved in 4 ml of chloroform was added 0.5 g of iodotrimethylsilane, and the mixture was kept and stirred at 40° C. to 50° C. for 10.5 hours. The mixture was then left undisturbed at room temperature for a half day, to which 0.5 g of iodotrimethylsilane was further added, and the mixture was further kept and stirred at 40° C. to 50° C. for 10.5 hours. The reaction mixture was then poured into ice water, which was extracted with ethyl acetate. The organic layer was dried over anhydrous magnesium sulfate and then concentrated. The residue was subjected to silica gel chromatography (eluent, hexane:ethyl acetate=2:1) to give 0.37 g of compound 8b (the present compound 1-78).

$^1$H-NMR (250 MHz, $CDCl_3$, TMS, δ (ppm)): 3.58–3.59 (3H, m), 5.09 (1H, bs) 6.39 (1H, s), 6.68 (1H, d, J=2.32 Hz), 6.82 (1H, dd, J=8.83 Hz, 2.32 Hz), 7.37 (1H, d, J=8.85 Hz), 7.79 (1H, s).

To a suspension of 0.05 g of sodium hydride in 1 ml of N,N-dimethylformamide was added a solution of 0.35 g of compound 8b in 2 ml of N,N-dimethylformamide under ice cooling, and the mixture was stirred for 5 minutes. Then, 0.23 g of ethyl bromoacetate was added under ice cooling, and the mixture was stirred for 0.5 hour. The reaction mixture was poured into water, which was extracted with ethyl acetate. The organic layer was washed with diluted hydrochloric acid, dried over anhydrous magnesium sulfate, and then concentrated. The residue was subjected to silica gel chromatography (eluent, hexane:ethyl acetate=2:1) to give 0.34 g of compound 8c (the present compound 1-127).

$^1$H-NMR (250 MHz, $CDCl_3$, TMS, δ (ppm)): 1.21 (3H, t, J=7.06 Hz), 1.60 (3H, d, J=6.82 Hz), 3.58–3.59 (3H, m), 4.10–4.23 (2H, m), 4.73 (1H, q, J=6.82 Hz), 6.38 (1H, s), 6.74 (1H, d, J=2.52 Hz), 6.97 (1H, dd, J=9.21 Hz, 2.80 Hz), 7.43 (1H, d, J=9.29 Hz), 7.80 (1H, s).

Production Example 9

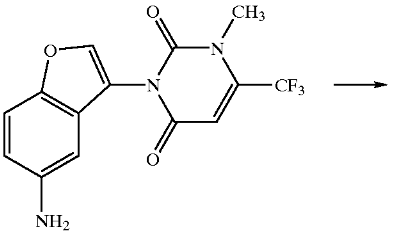

[5b]

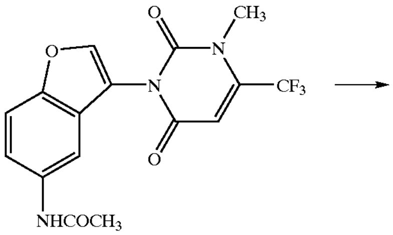

[9a]

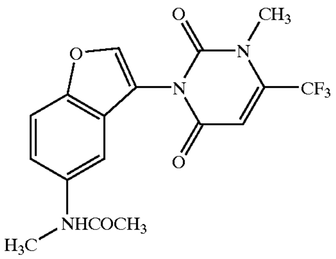

[9b]

In a solution of 1.0 g of compound 5b dissolved in 10 ml of acetic acid was added 0.045 g of acetic anhydride, and the mixture was stirred at room temperature for 3 hours. A mixed solution of hexane:ethyl acetate=1:1 was then added, and the deposited crystals were collected by filtration and dried to give 1.16 g of compound 9a (the present compound 1-24).

$^1$H-NMR (300 MHz, $CDCl_3$, TMS, δ (ppm)): 2.10 (3H, s), 3.59 (3H, s), 6.39 (1H, s), 7.12 (1H, dd, J=8.80 Hz, 2.10 Hz), 7.29 (1H, bs), 7.44 (1H, d, J=8.82 Hz), 7.77 (1H, d, J=1.88 Hz), 7.81 (1H, s).

In a solution of 1.0 g of compound 9a dissolved in 10 ml of dimethylformamide was added 0.11 g of sodium hydride at room temperature, and the mixture was stirred for 10 minutes. Then, 0.43 g of methyl iodide was added at room temperature, and the mixture was left undisturbed for 3 days. The reaction mixture was then poured into water, which was extracted with t-butyl methyl ether. The organic layer was washed with water and then with diluted hydrochloric acid, and dried over anhydrous magnesium sulfate, and then concentrated. The crystals obtained were washed with t-butyl methyl ether to give 0.36 g of compound 9b (the present compound 1-28).

m.p.: 207.2° C.

Production Example 10

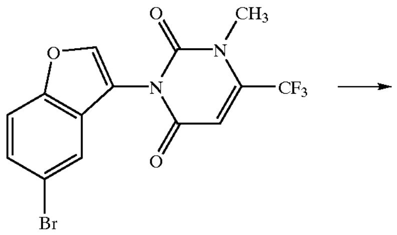

[10a]

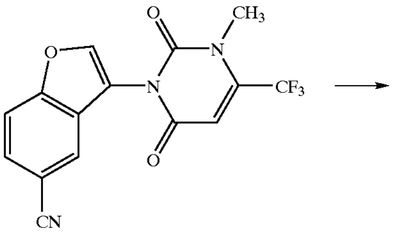

[10b]

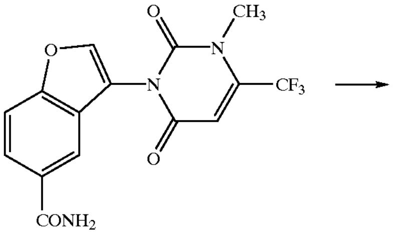

[10c]

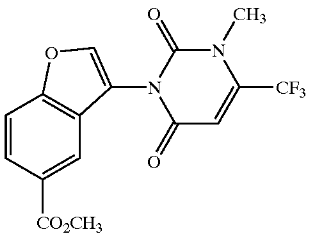

[10d]

According to the process as described above in Production Example 2, compound 10a (the present compound 1-75) was produced from 2-hydroxy-5-bromobenzaldehyde.

m.p.: 130.0° C.

To a solution of 1.85 g of compound 10a in 10 ml of N-methylpyrrolidone was added 0.67 g of copper (I) cyanide, and the mixture was heated and stirred at 170° C. to 180° C. for 6 hours. After cooling to room temperature, the reaction mixture was poured into water, which was extracted with t-butyl methyl ether. The organic layer was washed with cold ammonia water, with water, and then with diluted hydrochloric acid, dried over anhydrous magnesium sulfate, and then concentrated. The crystals obtained were washed with t-butyl methyl ether to give 0.85 g of compound 10b (the present compound 1-283).

m.p.: 174.3° C. (decomposition).

After 0.65 g of compound 10b was dissolved in 85% sulfuric acid, the solution was kept and stirred at 50° C. to 60° C. for 0.5 hour. The reaction mixture was then poured into water, which was extracted with ethyl acetate. The organic layer was washed with water, dried over anhydrous magnesium sulfate, and then concentrated. The crystals obtained were washed with t-butyl methyl ether to give 0.45 g of compound 10c (the present compound 1-293).

$^1$H-NMR (300 MHz, $CDCl_3$+DMSO, TMS, δ (ppm)): 3.60 (3H, s), 6.40 (1H, s), 7.58 (1H, d, J=8.76 Hz), 7.84–7.95 (3H, m).

First, 0.3 g of compound 10c was added to 10 ml of a solution of boron trifluoride methanol complex in methanol, and the mixture was heated and stirred at the reflux temperature for 7 hours. The reaction mixture was then poured into water, which was extracted with ethyl acetate. The organic layer was washed with water, dried over anhydrous magnesium sulfate, and then concentrated. The residue was subjected to silica gel chromatography (eluent, hexane:ethyl acetate=2:1) to give 0.22 g of compound 10d (the present compound 1-303).

$^1$H-NMR (300 MHz, $CDCl_3$, TMS, δ (ppm)): 3.59 (3H, m), 3.92 (3H, s), 6.40 (1H, s), 7.58 (1H, d, J=9.06 Hz), 7.89 (1H, s), 8.06–8.09 (2H, m).

Production Example 11

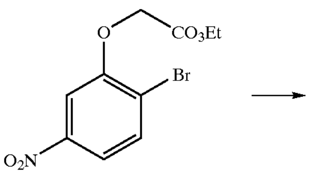

[11a]

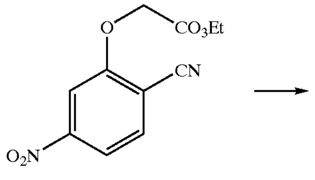

[11b]

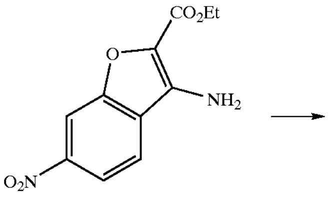

[11c]

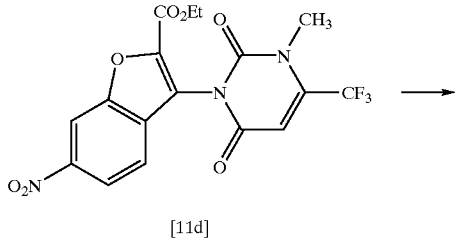

[11d]

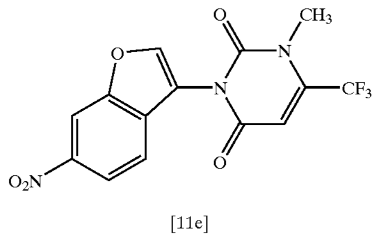

[11e]

To a solution of 10.45 g of compound 11a, which had been produced according to the process as described in the JP-A 58-79960 publication, in 30 ml of N-methylpyrrolidone was added 4.56 g of copper (I) cyanide, and the mixture was kept and stirred at 110° C. to 120° C. for 6 hours. After cooling to room temperature, the reaction mixture was poured into water, which was extracted with t-butyl methyl ether. The organic layer was washed with cold ammonia water, with water, and then with diluted hydrochloric acid, dried over anhydrous magnesium sulfate, and then concentrated. The crystals obtained were washed with t-butyl methyl ether to give 5.14 g of compound [11b].

$^1$H-NMR (300 MHz, $CDCl_3$, TMS, δ (ppm)): 1.32 (3H, t, J=7.17 Hz), 4.31 (2H, q, J=7.22 Hz), 4.89 (2H, s), 7.70 (1H, d, J=1.82 Hz), 7.80 (1H, d, J=8.57 Hz), 7.93–7.95 (1H, m).

To a solution of 5.1 g of compound 11b in 50 ml of N,N-dimethylformamide was added 3.3 g of potassium carbonate, and the mixture was kept and stirred at 100° C. for 30 minutes. The reaction mixture was then cooled to room temperature and poured into water. The deposited crystals were collected by filtration. The crystals were washed with water and dried to give 4.0 g of compound 11c.

$^1$H-NMR (300 MHz, $CDCl_3$, TMS, δ (ppm)): 1.46 (3H, t, J=7.24 Hz), 4.47 (2H, q, J=7.08 Hz), 5.30 (2H, bs), 7.69 (1H, d, J=8.67 Hz), 8.16 (1H, dd, J=8.76 Hz, 1.77 Hz), 8.34 (1H, d, J=1.87 Hz).

To a solution of 3.8 g of compound 11c in 50 ml of toluene was added 3.3 g of trichloromethyl chloroformate, and the mixture was heated and stirred at the reflux temperature of toluene for 1 hour. The reaction mixture was then concentrated to give a crude product of isocyanate.

To a suspension of 0.67 g of sodium hydride in 5 ml of N,N-dimethylformamide was added a solution of 3.1 g of ethyl 4,4,4-trifluoro-3-amino-crotonate in 5 ml of N,N-dimethylformamide below 10° C., and the mixture was stirred for 30 minutes. To the reaction mixture was then added dropwise a solution of the crude product of isocyanate obtained from compound 11c in 100 ml of tetrahydrofuran at −30° C. After completion of the dropwise addition, the mixture was warmed to room temperature and then stirred for 1 hour. To the reaction mixture was then added 4.3 g of methyl iodide, and the mixture was left undisturbed at room temperature overnight. The reaction mixture was then poured into water, which was extracted with ethyl acetate. The organic layer was washed with water and then with diluted hydrochloric acid, dried over anhydrous magnesium sulfate, and then concentrated. The residue was subjected to silica gel column chromatography (eluent, hexane:ethyl acetate=2:1) to give 3.80 g of compound 11d as crystals.

$^1$H-NMR (300 MHz, $CDCl_3$, TMS, δ (ppm)): 1.37 (3H, t, J=7.30 Hz), 3.36 (3H, m), 4.42 (2H, q, J=6.14 Hz), 6.14 (1H, s), 7.61 (1H, d, J=8.78 Hz), 8.26 (1H, dd, J=8.67 Hz, 2.12 Hz), 8.55 (1H, d, J=1.79 Hz).

First, 3.5 g of compound 11d was added to 20 ml of 85% sulfuric acid, and the mixture was kept and stirred at a temperature of 110° C. to 120° C. for 20 minutes. The reaction mixture was then poured into water, and the deposited crystals were collected by filtration and dried. The whole amount of the crystals obtained and 0.23 g of copper powder were added to 15 ml of quinoline, and the mixture was warmed to 120° C. to 130° C., at which temperature the mixture was kept and stirred for 1 hour. The reaction mixture was then poured into water, which was extracted with ethyl acetate. The organic layer was washed with water and then with diluted hydrochloric acid, dried over anhydrous magnesium sulfate, and then concentrated. The residue was subjected to silica gel chromatography (eluent, hexane:ethyl acetate=2.5:1) to give 1.05 g of compound 11e (the present compound 1-282).

$^1$H-NMR (300 MHz, $CDCl_3$, TMS, δ (ppm)): 3.59–3.61 (3H, m), 6.42 (1H, s), 7.47 (1H, d, J=8.71 Hz), 8.11 (1H, s), 8.21 (1H, dd, J=8.79 Hz, 2.06 Hz), 8.48 (1H, d, J=1.85 Hz).

Production Example 12

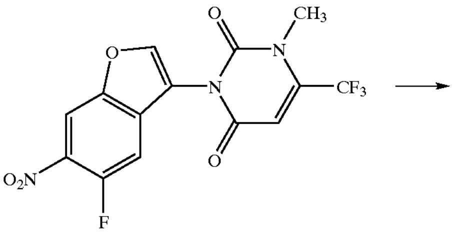

[12a]

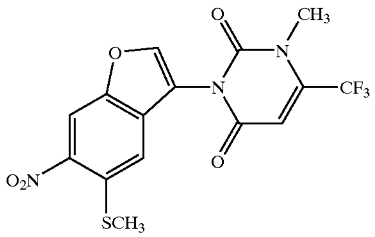

[12b]

According to the process as described in the JP-A 58-79960 publication, 2-bromo-4-fluoro-5-nitrophenol was obtained from 4-fluorophenol and then used as the starting material to produce compound 12a (the present compound 1-431) according to the process as described above in Production Example 11.

$^1$H-NMR (300 MHz, $CDCl_3$, TMS, δ (ppm)): 3.61–3.62 (3H, m), 6.42 (1H, s), 7.24 (1H, d, J=10.4 Hz), 8.13 (1H, s), 8.33 (1H, d, J=5.79 Hz).

To a solution of 0.6 g of compound 12a in 9 ml of N,N-dimethylformamide was added 0.12 g of sodium methylsulfide below 0° C., and the mixture was stirred for 2 hours. The reaction mixture was then poured into water, which was extracted with ethyl acetate. The organic layer was washed with water and then with diluted hydrochloric acid, dried over anhydrous magnesium sulfate, dried, and then concentrated. The crystals obtained were washed with t-butyl methyl ether to give 0.24 g of compound 12b (the present compound 1-201).

$^1$H-NMR (300 MHz, $CDCl_3$, TMS, δ (ppm)): 2.50 (s, 3H), 3.62 (3H, m), 6.43 (1H, s), 7.19 (1H, s), 8.07 (1H, s), 8.49 (1H, d, J=5.79 Hz).

Production Example 13

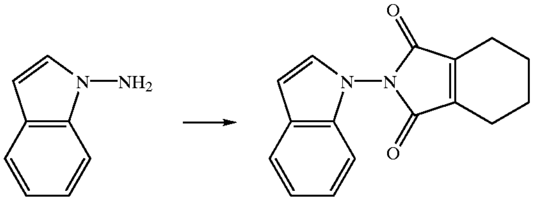

[13a] [13b]

First, 1.0 g of compound 13a and 1.15 g of 3,4,5,6-tetrahydrophthalic anhydride were added to 15 ml of acetic acid, and the mixture was heated and stirred at the reflux temperature for 1 hour. The reaction mixture was concentrated under reduced pressure, and the residue was washed with hexane:isopropanol=1:1 (v/v) to give 1.48 g of compound 13b (the present compound 2-2001).

$^1$H-NMR (250 MHz, $CDCl_3$, TMS, δ (ppm)): 1.75–1.95 (4H, m), 2.35–2.55 (4H, m), 6.64 (1H, m), 7.01–7.15 (4H, m), 7.63 (1H, d, J=7.0 Hz).

Production Example 14

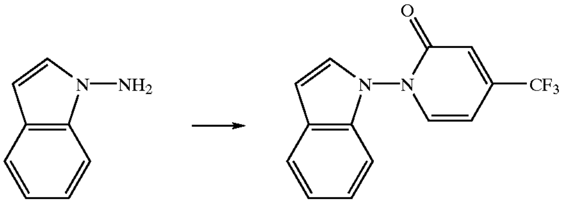

[13a] [14a]

First, 0.2 g of compound 13a and 0.4 g of ethyl 3-{[1-(dimethylamino)-methylidene]amino}-4,4,4-trifluoro-2-butenoate were added to 5 ml of acetic acid, and the mixture was stirred at room temperature for 2 hours. The reaction mixture was then poured into water, which was extracted with ethyl acetate. The organic, layer was washed with aqueous sodium hydrogencarbonate solution and then with saturated aqueous sodium chloride solution, dried over anhydrous magnesium sulfate, and then concentrated. The residue was subjected to silica gel chromatography to give 0.05 g of compound 14a (the present compound 3-2001).

$^1$H-NMR (300 MHz, $CDCl_3$, TMS, δ (ppm)): 6.74 (1H, d, J=3.5 Hz), 7.00–7.06 (2H, m), 7.10 (1H, d, J=3.5 Hz), 7.21–7.32 (2H, m), 7.68 (1H, dd, J=1.8 Hz, 6.7 Hz), 8.40 (1H, s).

Production Example 15

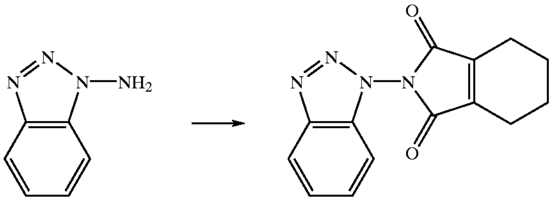

[15a] [15b]

To a solution of 1.5 g of compound 15a in 15 ml of acetic acid was added 1.9 g of 3,4,5,6-tetrahydrophthalic anhydride, and the mixture was heated at reflux for 6 hours. After cooling to room temperature, the reaction mixture was poured into ice water, which was extracted with ethyl acetate. The organic layer was washed with aqueous sodium hydrogencarbonate solution and then with saturated aqueous sodium chloride solution, dried over anhydrous magnesium sulfate, and then concentrated. The residue was subjected to silica gel column chromatography to give 3.0 g of compound 15b (the present compound 2-2004).

m.p.: 184.5° C.

Production Example 16

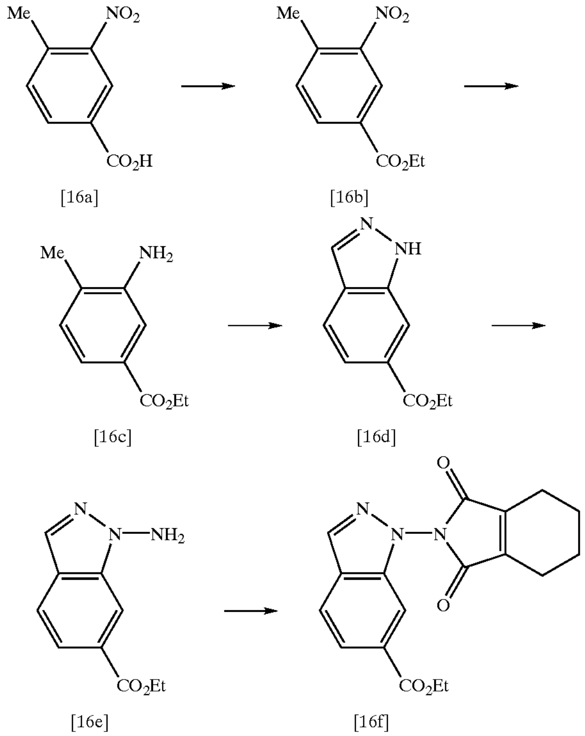

[16a] [16b] [16c] [16d] [16e] [16f]

First, 25 g of compound 16a was added to 40 ml of thionyl chloride, and the mixture was heated and stirred at the reflux temperature for 4 hours. The reaction mixture was concentrated under reduced pressure, to which residue was added 100 ml of ethanol. To the reaction mixture was then added dropwise 14 ml of pyridine under ice cooling, and the mixture was stirred at room temperature for 2 days and then left undisturbed for a half day. The reaction mixture was then concentrated, to which diluted hydrochloric acid was added, and the mixture was extracted with ethyl acetate. The organic, layer was washed with aqueous sodium hydrogencarbonate solution and then with saturated sodium chloride solution, dried over anhydrous magnesium sulfate, and then concentrated to give 27 g of compound 16b as a crude product.

$^1$H-NMR (300 MHz, $CDCl_3$, TMS, δ (ppm)): 1.42 (3H, t, J=7.2 Hz), 2.66 (3H, s), 4.42 (2H, q, J=7.2 Hz), 7.43 (1H, d,.J=8.0 Hz), 8.15 (1H, dd, J=1.7 Hz, 8.0 Hz), 8.60 (1H, d, J=1.7 Hz).

First, 5.4 g of iron powder was added to a mixed solvent of 20 ml of acetic acid and 150 ml of water, and the mixture was heated to 70° C., to which a solution of 5.0 g of compound 16b in 20 ml of ethyl acetate was added dropwise. After completion of the dropwise addition, the mixture was left cooling to room temperature and stirred for 2 hours. Water was poured into the reaction mixture, which was extracted with ethyl acetate. The organic layer was washed with aqueous sodium hydrogencarbonate solution, dried over anhydrous magnesium sulfate, and then concentrated to give 3.8 g of compound 16c as a crude product.

m.p.: 112.6° C.

To a solution of 1.0 g of compound 16c in 50 ml of acetic acid was added dropwise a solution of 0.42 g of sodium nitrite in 5 ml of water at 10° C. After completion of the dropwise addition, the mixture was left undisturbed at room temperature for a half day. Water was poured into the reaction mixture, which was extracted with ethyl acetate. The organic layer was washed with aqueous sodium hydrogencarbonate solution and then with saturated aqueous sodium chloride solution, dried over anhydrous magnesium sulfate, and then concentrated. The residue was subjected to silica gel chromatography to give 0.5 g of compound 16d.

$^1$H-NMR (250 MHz, $CDCl_3$, TMS, δ (ppm)): 1.44 (3H, t, J=7.1 Hz), 4.44 (2H, q, J=7.1 Hz), 7.78–7.89 (2H1, m), 8.16 (1H, d, J=1.1 Hz), 8.29 (1H, q, J=1.1 Hz).

To a solution of 1.0 g of compound 16d in 10 ml of N,N-dimethylformamide was added 0.2 g of sodium hydride at room temperature. After the gas evolution from the reaction mixture ceased, 1.0 g of o-(2,4-dinitrophenyl) hydroxylamine was added, and the mixture was stirred. After left undisturbed for 2 days, water was poured into the reaction mixture, which was extracted with ethyl acetate. The organic layer was washed with saturated aqueous sodium chloride solution, dried over anhydrous magnesium sulfate, and then concentrated. The residue was subjected to silica gel chromatography to give 0.36 g of compound 16e.

$^1$H-NMR (300 MHz, $CDCl_3$, TMS, δ (ppm)): 1.42 (3H, t, J=7.2 Hz), 4.41 (2H, q, J=7.2 Hz), 5.45 (2H, bs), 7.61–7.78 (2H, m), 7.86 (1H, s), 8.28 (1H, d, J=0.8 Hz).

First, 0.15 g of compound 16e and 0.12 g of 3,4,5,6-tetrahydrophthalic anhydride were dissolved in 10 ml of acetic acid, and the solution was heated and stirred at the reflux temperature for 1 hour. After the reaction mixture was left cooling to room temperature, water was poured into the reaction mixture, which was extracted with ethyl acetate. The organic layer was washed with aqueous sodium hydrogencarbonate solution and then with saturated sodium chloride solution, dried over anhydrous magnesium sulfate, and then concentrated. The residue was subjected to silica gel chromatography (eluent, hexane:ethyl acetate=3:1) to give 0.09 g of compound 16f (the present compound 2-2011).

$^1$H-NMR (300 MHz, $CDCl_3$, TMS, δ (ppm)): 1.42 (3H, t, J=7.2 Hz), 1.89 (4H, m), 2.50 (4H, m), 4.42 (2H, q, J=7.2 Hz), 7.79–7.84 (1H, m), 7.91–7.96 (1H, m), 8.03 (1H, m), 8.19 (1H, d, J=1.1 Hz).

Production Example 17

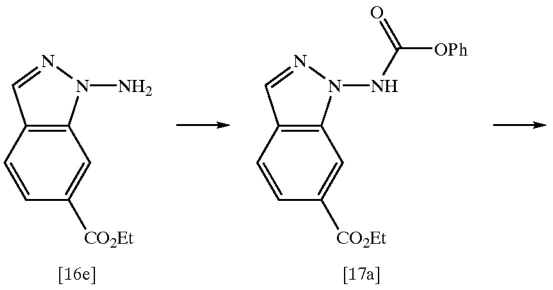

[16e] [17a]

-continued

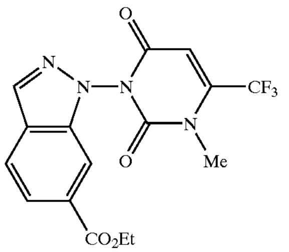

[17b]

First, 300 mg of compound 16e and 230 mg of phenyl chloroformate were dissolved in 10 ml of tetrahydrofuran, to which 120 mg of pyridine was added at room temperature. After stirring at room temperature for 1 hour, diluted hydrochloric acid was poured into the reaction mixture, which was extracted with ethyl acetate. The organic layer was dried over anhydrous magnesium sulfate and then concentrated. The residue was subjected to silica gel chromatography (eluent, hexane:ethyl acetate=2:1) to give 500 mg of compound 17a.

$^1$H-NMR (300 MHz, $CDCl_3$, TMS, δ (ppm)): 1.45 (3H, t, J=7.1 Hz), 4.45 (2H, q, J=7.1 Hz), 7.15–7.42 (5H, m), 7.76–7.80 (1H, m), 7.89–7.94 (1H, m), 8.09 (1H, s), 8.27 (1H, s).

To a mixture of 280 mg of ethyl 4,4,4-trifluoro-3-aminochrotonate and 5 ml of N,N-dimethylformamide was added 60 mg of sodium hydride at room temperature, and the mixture was stirred for 10 minutes. To the reaction solution was added dropwise a solution of 500 mg of compound 17a in 6 ml of N,N-dimethylformamide. The mixture was stirred at 80° C. for 2 hours and then left cooling to room temperature, to which 500 mg of iodomethane was added. After stirring at room temperature for 4 hours, diluted hydrochloric acid was poured into the reaction mixture, which was extracted with ethyl acetate. The organic layer was dried over anhydrous magnesium sulfate and then concentrated. The residue was subjected to silica gel chromatography (eluent, hexane:ethyl acetate=5:2) to give 100 mg of compound 17b (the present compound 1-2068).

$^1$H-NMR (300 MHz, $CDCl_3$, TMS, δ (ppm)): 1.41 (3H, t, J=7.1 Hz), 3.59 (3H, m), 4.41 (2H, q, J=7.1 Hz), 6.44 (1H, s), 7.84 (1H, d, J=9.1 Hz), 7.93–7.97 (2H, m), 8.24 (1H, d, J=0.8 Hz).

Production Example 18

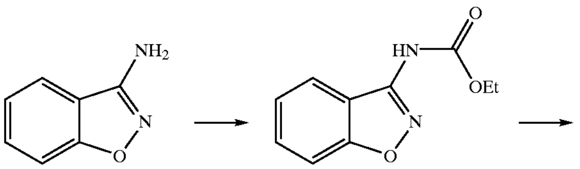

[3b] [18a]

-continued

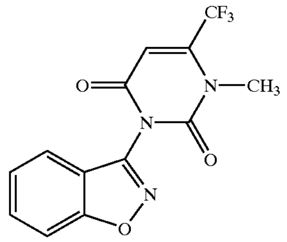

[18b]

To a solution of 2.0 g of compound 3b and 1.2 g of pyridine in 10 ml of tetrahydrofuran was added dropwise a solution of 1.6 g of $ClCO_2Et$ in 3ml of tetrahydrofuran at 0° C. to 10° C. After stirring at room temperature for 1 hour, diluted hydrochloric acid was added to the reaction mixture, which was extracted with ethyl acetate. The organic layer was concentrated, and the residue was subjected to silica gel column chromatography (eluent, hexane:ethyl acetate=3:1) to give 2.7 g of compound 18a.

$^1$H-NMR (300 MHz, $CDCl_3$, TMS, δ (ppm)): 1.37 (3H, t, J=7.2 Hz), 4.33 (2H, q, J=7.2 Hz), 7.26–7.34 (2H, m), 7.48–7.58 (2H, m), 8.17 (1H, d, J=4.1 Hz).

To 15 ml of N,N-dimethylformamide was added 0.5 g of sodium hydride, to which 2.4 g of $H_2N(CF_3)C{=}CHCO_2Et$ was added dropwise under ice cooling. After stirring at room temperature for 30 minutes, a solution of compound 18a dissolved in 5 ml of N,N-dimethylformamide was added dropwise thereto. After heating at 100° C. for 4 hours and at 120° C. for 2 hours, the reaction mixture was cooled to room temperature. Then, 2.0 g of iodomethane was added, and the mixture was left standing overnight, to which diluted hydrochloric acid was added. The mixture was extracted with ethyl acetate. The organic layer was dried over magnesium sulfate and then concentrated. The residue was subjected to silica gel column chromatography (eluent, hexane:ethyl acetate=3:1) to give 2.2 g of compound 18b (the present compound 1-875).

m.p.: 159.1° C.

Production Example 19

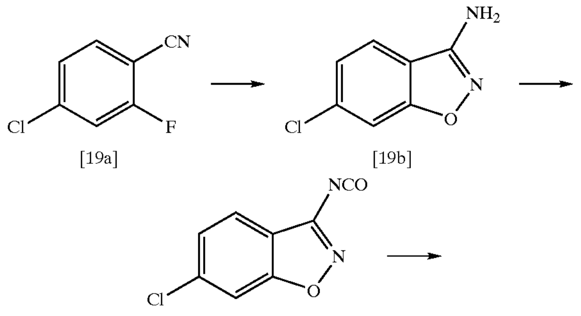

[19a] [19b]

[19c]

-continued

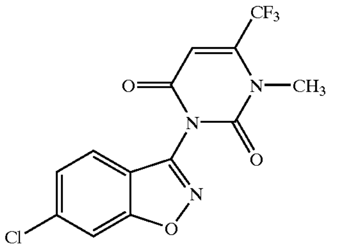

[19d]

First, 1.3 g of potassium tert-butoxide and 0.9 g of acetohydroxamic acid were added to 25 ml of N,N-dimethylformamide, and the mixture was stirred at room temperature for 30 minutes. A solution of 1.5 g of compound 19a dissolved in 5 ml of N,N-dimethylformamide was added dropwise thereto, and the mixture was then left standing at room temperature overnight. To the reaction mixture was added aqueous sodium chloride solution, which was extracted with ethyl acetate. The organic layer was dried with magnesium sulfate and then concentrated. The residue was subjected to silica gel column chromatography (eluent, hexane:ethyl acetate=2:1) to give 0.8 g of compound 19b.

$^1$H-NMR (250 MHz, $CDCl_3$, TMS, δ (ppm)): 4.38–4.64 (1H, br), 7.20–7.27 (2H, m), 7.43–7.47 (2H, m).

To 50 ml of toluene were added 2.1 g of compound 19b (produced in the same manner as described above) and 2.5 g of trichloromethyl chloroformate, and the mixture was heated at reflux for 2 hours. The reaction mixture was concentrated to give 2.5 g of compound 19c as a crude product.

To a suspension of 0.6 g of sodium hydride in 30 ml of N,N-dimethylformamide was added 2.7 g of ethyl 4,4,4-trifluoro-3-aminochrotonate at room temperature, and the mixture was stirred for 30 minutes. To the reaction mixture was then added dropwise a solution of the whole amount of the crude product of compound 19c dissolved in 50 ml of tetrahydrofuran at 0° C. After completion of the dropwise addition, the mixture was warmed to room temperature and stirred for 3 hours, to which 2.0 g of methyl iodide was added, and the mixture was left standing overnight. The reaction mixture was then poured into diluted hydrochloric acid, which was extracted with ethyl acetate. The organic layer was dried over magnesium sulfate and then concentrated. The residue was subjected to silica gel column chromatography (eluent, hexane:ethyl acetate=3:1) to give 80 mg of compound 19d (the present compound 1-877).

$^1$H-NMR (250 MHz, $CDCl_3$, TMS,. δ (ppm)): 3.57 (3H, q, J=1.2 Hz), 6.41 (1H, s), 7.36 (1H, dd, J=1.6 Hz, 8.5 Hz), 7.45 (1H, d, J=8.5 Hz), 7.71 (1H, d, J=1.6 Hz).

Production Example 20

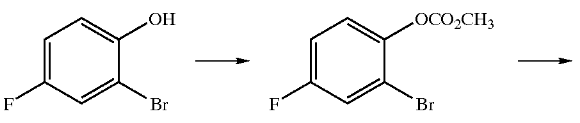

[20a] [20b]

-continued

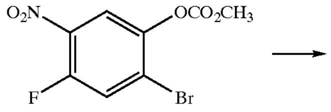

[20c]

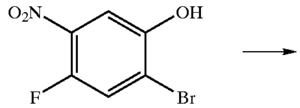

[20d]

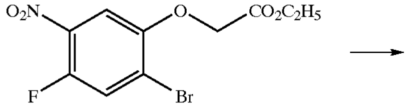

[20e]

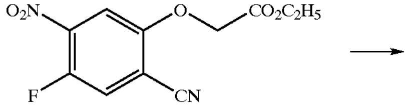

[20f]

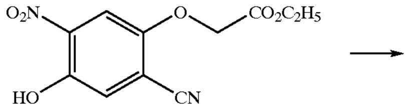

[20g]

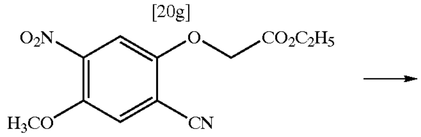

[20h]

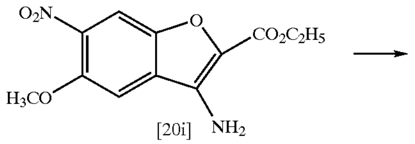

[20i]

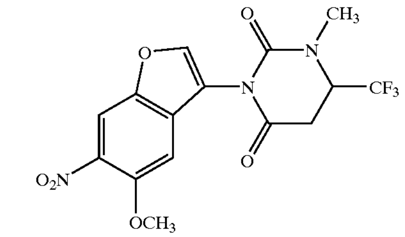

[20j]

To a mixed solution of 190.0 g of compound 20a, 122.9 g of methyl chloroformate, and 150 ml of water was added dropwise aqueous sodium hydroxide solution (50 g of NaOH and 100 ml of $H_2O$) below 10° C. After completion of the dropwise addition, the mixture was stirred for 2 hours. The crystals obtained were then collected by filtration, washed with a solution (isopropyl alcohol:water=1:1), and dried to give 160.5 g of compound 20b.

Then, 160.0 g of compound 20b was dissolved in 250 ml of concentrated sulfuric acid, to which a mixed acid (42.5 g of fuming nitric acid and 30 ml of concentrated sulfuric acid) was added dropwise below 5° C. After completion of the dropwise addition, the mixture was stirred for 2 hours. The reaction mixture was poured into ice water, and the deposited crystals were collected by filtration, washed with water, and dried to give 186.5 g of compound 20c.

$^1$H-NMR (300 MHz, $CDCl_3$, TMS, δ (ppm)): 3.98 (3H, s), 7.63 (1H, d, J=9.60 Hz), 8.03 (1H, d, J=6.83 Hz).

To 300 ml of water and 300 ml of ethanol was suspended 186.0 g of compound 20c, to which aqueous sodium hydroxide solution (60 g of NaOH and 120 ml of $H_2O$) was added dropwise at room temperature. After completion of the dropwise addition, the mixture was stirred for 1 hour and then concentrated to remove the ethanol. The residue obtained was made acidic by the addition of concentrated hydrochloric acid under ice cooling, which was extracted with ethyl acetate. The organic layer was dried over magnesium sulfate and then concentrated to give 141.1 g of compound 20d.

According to the process as described in Production Example 2, compound 20e was produced from compound 20d.

$^1$H-NMR (250 MHz, $CDCl_3$, TMS, δ (ppm)): 1.32 (3H, t, J=7.11 Hz), 4.30 (211, q, J=7.14 Hz), 4.77 (2H, s), 7.51 (1H, d, J=6.28 Hz), 7.58 (1H, d, J=9.81 Hz).

According to the process as described in Production Example 11, compound 20f was produced from compound 20e.

$^1$H-NMR (250 MHz, $CDCl_3$, TMS, δ (ppm)): 1.33 (3H, t, J=7.12 Hz), 4.30 (2H, q, J=7.12 Hz), 4.86 (2H, s), 7.52 (1H, d, J=5.66 Hz), 7.59 (1H, d, J=9.39 Hz).

First, 30 g of compound 20f was dissolved in 30 ml of N,N-dimethylformamide, to which 18.4 g of sodium acetate and 3 ml of water were added, and the mixture was kept and stirred at a temperature of 80° C. to 90° C. for 9 hours. After cooling to room temperature, diluted hydrochloric acid was poured into the reaction mixture, which was extracted with ethyl acetate. The organic layer was dried over magnesium sulfate and then concentrated. The residue was subjected to silica gel column chromatography (eluent, hexane:ethyl acetate=3:1) to give 13.6 g of compound 20 g.

$^1$H-NMR (300 MHz, $CDCl_3$, TMS, δ (ppm): 1.32 (3H, t, J=7.08 Hz), 4.29 (2H, q, J=7.08 Hz), 4.79 (2H, s), 7.48 (1H, s), 7.56 (1H, s).

First, 13 g of compound 20 g was dissolved in 40 ml of N,N-dimethylformamide, to which 7.3 g of potassium carbonate was added at room temperature. Then, 6.2 g of dimethylsulfuric acid was added at 30° C. to 40° C. thereto, and the mixture was stirred for 30 minutes. The reaction mixture was then poured into water, which was extracted with ethyl acetate. The organic layer was washed with diluted hydrochloric acid, dried over magnesium sulfate, and then concentrated. The crystals obtained were washed with a solution (t-butyl methyl ether:hexane=1:2) to give 10.7 g of compound 20h.

$^1$H-NMR (250 MHz, $CDCl_3$, TMS, δ (ppm)): 1.31 (3H, t, J=7.16 Hz), 4.00 (3H, s), 4.29 (2H, q, J=7.16 Hz), 4.78 (2H, s), 7.32 (1H, s), 7.34 (1H, s).

According to the process as described in Production Example 11, compound 20i was produced from compound 20h.

According to the process as described in Production Example 11, compound 20j (the present compound 1-86) was produced from compound 20i.

$^1$H-NMR (300 MHz, $CDCl_3$, TMS, δ (ppm)): 3.61 (3H, m), 3.95 (3H, s), 6.42 (1H, s), 6.89 (1H, s), 8.00 (1H, s), 8.09 (1H, s).

Examples of the present compounds are shown below together with their compound numbers.

Compounds of the general formula:

TABLE 1

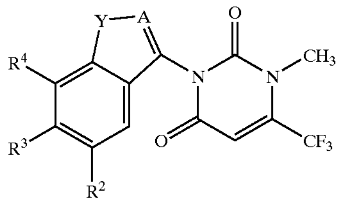

| Compound | $R^2$ | $R^3$ | $R^4$ | A | Y |
|---|---|---|---|---|---|
| 1-1 | H | H | H | CH | O |
| 1-2 | Cl | H | Cl | CH | O |
| 1-3 | H | H | H | CH | S |
| 1-4 | Cl | H | H | CH | O |
| 1-5 | $OCH_3$ | H | H | CH | O |
| 1-6 | $NO_2$ | H | H | CH | O |
| 1-7 | $NH_2$ | H | H | CH | O |
| 1-8 | $NHCH_3$ | H | H | CH | O |
| 1-9 | $N(CH_3)_2$ | H | H | CH | O |
| 1-10 | $NHSO_2CH_3$ | H | H | CH | O |
| 1-11 | $NHCH(CH_3)CO_2Et$ | H | H | CH | O |
| 1-12 | $NHCH(CH_3)CO_2Et$ | H | Cl | CH | O |
| 1-13 | $N(CH_3)CH(CH_3)CO_2Et$ | H | Cl | CH | O |
| 1-14 | $N(CH_3)SO_2CH_3$ | H | Cl | CH | O |
| 1-15 | $NHSO_2CH_3$ | H | Cl | CH | O |
| 1-16 | $NHCH(CH_3)CO_2Et$ | Cl | H | CH | O |
| 1-17 | $N(CH_3)CH(CH_3)CO_2Et$ | Cl | H | CH | O |

TABLE 2

| Compound | $R^2$ | $R^3$ | $R^4$ | A | Y |
|---|---|---|---|---|---|
| 1-18 | $N(CH_3SO_2CH_3$ | Cl | H | CH | O |
| 1-19 | $NHSO_2CH_3$ | Cl | H | CH | O |
| 1-20 | $NO_2$ | H | Cl | CH | O |
| 1-21 | $NH_2$ | H | Cl | CH | O |
| 1-22 | $NO_2$ | Cl | H | CH | O |
| 1-23 | $NH_2$ | Cl | H | CH | O |
| 1-24 | $NHCOCH_3$ | H | H | CH | O |
| 1-25 | $NHCOCF_3$ | H | H | CH | O |
| 1-26 | $NHSO_2Et$ | H | H | CH | O |
| 1-27 | $NHSO_2CH_2Cl$ | H | H | CH | O |
| 1-28 | $N(CH_3)COCH_3$ | H | H | CH | O |
| 1-29 | $N(CH_3)COCF_3$ | H | H | CH | O |
| 1-30 | $N(CH_3)SO_2Et$ | H | H | CH | O |
| 1-31 | $CO_2C(CH_3)_2CO_2Et$ | H | H | CH | O |
| 1-32 | $N(CH_3)SO_2CH_2Cl$ | H | H | CH | O |
| 1-33 | $NHCOCH_3$ | H | Cl | CH | O |
| 1-34 | $NHCOCF_3$ | H | Cl | CH | O |
| 1-35 | $NHSO_2Et$ | H | Cl | CH | O |
| 1-36 | $NHSO_2CH_2Cl$ | H | Cl | CH | O |
| 1-37 | $N(CH_3)COCH_3$ | Cl | H | CH | O |
| 1-38 | $N(CH_3)COCF_3$ | Cl | H | CH | O |
| 1-39 | $N(CH_3)SO_2Et$ | Cl | H | CH | O |
| 1-40 | $N(CH_3)SO_2CH_2Cl$ | Cl | H | CH | O |
| 1-42 | $NHCH_2CO_2Me$ | H | H | CH | O |
| 1-43 | $NHCH_2CO_2Et$ | H | H | CH | O |

TABLE 3

| Compound | $R^2$ | $R^3$ | $R^4$ | A | Y |
|---|---|---|---|---|---|
| 1-44 | $NHCH(CH_3)COOH$ | H | H | CH | O |
| 1-45 | $NHCH(CH_3)CONH_2$ | H | H | CH | O |
| 1-46 | $NHCH(CH_3)CONHCH_3$ | H | H | CH | O |
| 1-47 | $NHCH_2CO_2Me$ | H | Cl | CH | O |
| 1-48 | $NHCH_2CO_2Et$ | H | Cl | CH | O |
| 1-49 | $NHCH(CH_3)COOH$ | H | Cl | CH | O |
| 1-50 | $NHCH(CH_3)CONH_2$ | H | Cl | CH | O |
| 1-51 | $NHCH(CH_3)CONHCH_3$ | H | Cl | CH | O |

TABLE 3-continued

| Compound | $R^2$ | $R^3$ | $R^4$ | A | Y |
|---|---|---|---|---|---|
| 1-52 | $NHCH_2CO_2Me$ | Cl | H | CH | O |
| 1-53 | $NHCH_2CO_2Et$ | Cl | H | CH | O |
| 1-54 | $NHCH(CH_3)COOH$ | Cl | H | CH | O |
| 1-55 | $NHCH(CH_3)CONH_2$ | Cl | H | CH | O |
| 1-56 | $NHCH(CH_3)CONHCH_3$ | Cl | H | CH | O |
| 1-57 | $NHCH_2CH_2CH_3$ | H | H | CH | O |
| 1-58 | $NHCH_2CH{=}CH_2$ | H | H | CH | O |
| 1-59 | $NHCH_2C{\equiv}CH$ | H | H | CH | O |
| 1-60 | $N(CH_3)CH_2CH_2CH_3$ | H | H | CH | O |
| 1-61 | $N(CH_3)CH_2CH{=}CH_2$ | H | H | CH | O |
| 1-62 | $N(CH_3)CH_2C{\equiv}CH$ | H | H | CH | O |
| 1-63 | $NHCH_2CH_2CH_3$ | H | Cl | CH | O |
| 1-64 | $NHCH_2CH{=}CH_2$ | H | Cl | CH | O |
| 1-65 | $NHCH_2C{\equiv}CH$ | H | Cl | CH | O |
| 1-66 | $N(CH_3)CH_2CH_2CH_3$ | H | Cl | CH | O |
| 1-67 | $N(CH_3)CH_2CH{=}CH_2$ | H | Cl | CH | O |
| 1-68 | $N(CH_3)CH_2C{\equiv}CH$ | H | Cl | CH | O |

TABLE 4

| Compound | $R^2$ | $R^3$ | $R^4$ | A | Y |
|---|---|---|---|---|---|
| 1-69 | $NHCH_2CH_2CH_3$ | Cl | H | CH | O |
| 1-70 | $NHCH_2CH{=}CH_2$ | Cl | H | CH | O |
| 1-71 | $NHCH_2C{\equiv}CH$ | Cl | H | CH | O |
| 1-72 | $N(CH_3)CH_2CH_2CH_3$ | Cl | H | CH | O |
| 1-73 | $N(CH_3)CH_2CH{=}CH_2$ | Cl | H | CH | O |
| 1-74 | $N(CH_3)CH_2C{\equiv}CH$ | Cl | H | CH | O |
| 1-75 | Br | H | H | CH | O |
| 1-76 | Br | H | Cl | CH | O |
| 1-77 | Br | Cl | H | CH | O |
| 1-78 | OH | H | H | CH | O |
| 1-79 | OH | H | Cl | CH | O |
| 1-80 | OH | Cl | H | CH | O |
| 1-81 | OH | H | $NO_2$ | CH | O |
| 1-82 | OH | $NO_2$ | H | CH | O |
| 1-83 | $OCH_3$ | H | Cl | CH | O |
| 1-84 | $OCH_3$ | Cl | H | CH | O |
| 1-85 | $OCH_3$ | H | $NO_2$ | CH | O |
| 1-86 | $OCH_3$ | $NO_2$ | H | CH | O |
| 1-87 | $OCH(CH_3)CH_3$ | H | H | CH | O |
| 1-88 | $OCH(CH_3)CH_3$ | H | Cl | CH | O |
| 1-89 | $OCH(CH_3)CH_3$ | Cl | H | CH | O |
| 1-90 | $OCH(CH_3)CH_3$ | H | $NO_2$ | CH | O |
| 1-91 | $OCH(CH_3)CH_3$ | $NO_2$ | H | CH | O |
| 1-92 | $OCH_2CH{=}CH_2$ | H | H | CH | O |
| 1-93 | $OCH_2CH{=}CH_2$ | H | Cl | CH | O |

TABLE 5

| Compound | $R^2$ | $R^3$ | $R^4$ | A | Y |
|---|---|---|---|---|---|
| 1-94 | $OCH_2CH{=}CH_2$ | Cl | H | CH | O |
| 1-95 | $OCH_2CH{=}CH_2$ | H | $NO_2$ | CH | O |
| 1-96 | $OCH_2CH{=}CH_2$ | $NO_2$ | H | CH | O |
| 1-97 | $OCH(CH_3)CH{=}CH_2$ | H | H | CH | O |
| 1-98 | $OCH(CH_3)CH{=}CH_2$ | H | Cl | CH | O |
| 1-99 | $OCH(CH_3)CH{=}CH_2$ | Cl | H | CH | O |
| 1-100 | $OCH(CH_3)CH{=}CH_2$ | H | $NO_2$ | CH | O |
| 1-101 | $OCH(CH_3)CH{=}CH_2$ | $NO_2$ | H | CH | O |
| 1-102 | $OCH_2C(Cl){=}CH_2$ | H | H | CH | O |
| 1-103 | $OCH_2C(Cl){=}CH_2$ | H | Cl | CH | O |
| 1-104 | $OCH_2C(Cl){=}CH_2$ | Cl | H | CH | O |
| 1-105 | $OCH_2C(Cl){=}CH_2$ | H | $NO_2$ | CH | O |
| 1-106 | $OCH_2C(Cl){=}CH_2$ | $NO_2$ | H | CH | O |
| 1-107 | $OCH_2C{\equiv}CH$ | H | H | CH | O |
| 1-108 | $OCH_2C{\equiv}CH$ | H | Cl | CH | O |
| 1-109 | $OCH_2C{\equiv}CH$ | Cl | H | CH | O |
| 1-110 | $OCH_2C{\equiv}CH$ | H | $NO_2$ | CH | O |

TABLE 5-continued

| Compound | $R^2$ | $R^3$ | $R^4$ | A | Y |
|---|---|---|---|---|---|
| 1-111 | $OCH_2C{\equiv}CH$ | $NO_2$ | H | CH | O |
| 1-112 | $OCH(CH_3)C{\equiv}CH$ | H | H | CH | O |
| 1-113 | $OCH(CH_3)C{\equiv}CH$ | H | Cl | CH | O |
| 1-114 | $OCH(CH_3)C{\equiv}CH$ | Cl | H | CH | O |
| 1-115 | $OCH(CH_3)C{\equiv}CH$ | H | $NO_2$ | CH | O |
| 1-116 | $OCH(CH_3)C{\equiv}CH$ | $NO_2$ | H | CH | O |
| 1-117 | $OCH(CH_3)COOH$ | H | H | CH | O |
| 1-118 | $OCH(CH_3)COOH$ | H | Cl | CH | O |

TABLE 6

| Compound | $R^2$ | $R^3$ | $R^4$ | A | Y |
|---|---|---|---|---|---|
| 1-119 | $OCH(CH_3)COOH$ | Cl | H | CH | O |
| 1-120 | $OCH(CH_3)COOH$ | H | $NO_2$ | CH | O |
| 1-121 | $OCH(CH_3)COOH$ | $NO_2$ | H | CH | O |
| 1-122 | $OCH(CH_3)COOMe$ | H | H | CH | O |
| 1-123 | $OCH(CH_3)COOMe$ | H | Cl | CH | O |
| 1-124 | $OCH(CH_3)COOMe$ | Cl | H | CH | O |
| 1-125 | $OCH(CH_3)COOMe$ | H | $NO_2$ | CH | O |
| 1-126 | $OCH(CH_3)COOMe$ | $NO_2$ | H | CH | O |
| 1-127 | $OCH(CH_3)COOEt$ | H | H | CH | O |
| 1-128 | $OCH(CH_3)COOEt$ | H | Cl | CH | O |
| 1-129 | $OCH(CH_3)COOEt$ | Cl | H | CH | O |
| 1-130 | $OCH(CH_3)COOEt$ | H | $NO_2$ | CH | O |
| 1-131 | $OCH(CH_3)COOEt$ | $NO_2$ | H | CH | O |
| 1-132 | $OCH(CH_3)COOPr$ | H | H | CH | O |
| 1-133 | $OCH(CH_3)COOPr$ | H | Cl | CH | O |
| 1-134 | $OCH(CH_3)COOPr$ | Cl | H | CH | O |
| 1-135 | $OCH(CH_3)COOPr$ | H | $NO_2$ | CH | O |
| 1-136 | $OCH(CH_3)COOPr$ | $NO_2$ | H | CH | O |
| 1-137 | $OCH(CH_3)COO$-i-Pr | H | H | CH | O |
| 1-138 | $OCH(CH_3)COO$-i-Pr | H | Cl | CH | O |
| 1-139 | $OCH(CH_3)COO$-i-Pr | Cl | H | CH | O |
| 1-140 | $OCH(CH_3)COO$-i-Pr | H | $NO_2$ | CH | O |
| 1-141 | $OCH(CH_3)COO$-i-Pr | $NO_2$ | H | CH | O |
| 1-142 | $OCH(CH_3)COOBu$ | H | H | CH | O |
| 1-143 | $OCH(CH_3)COOBu$ | H | Cl | CH | O |

TABLE 7

| Compound | $R^2$ | $R^3$ | $R^4$ | A | Y |
|---|---|---|---|---|---|
| 1-144 | $OCH(CH_3)COOBu$ | Cl | H | CH | O |
| 1-145 | $OCH(CH_3)COOBu$ | H | $NO_2$ | CH | O |
| 1-146 | $OCH(CH_3)COOBu$ | $NO_2$ | H | CH | O |
| 1-147 | $OCH(CH_3)COOPen$ | H | H | CH | O |
| 1-148 | $OCH(CH_3)COOPen$ | H | Cl | CH | O |
| 1-149 | $OCH(CH_3)COOPen$ | Cl | H | CH | O |
| 1-150 | $OCH(CH_3)COOPen$ | H | $NO_2$ | CH | O |
| 1-151 | $OCH(CH_3)COOPen$ | $NO_2$ | H | CH | O |
| 1-152 | $OCH(CH_3)COO$-c-Pen | H | H | CH | O |
| 1-153 | $OCH(CH_3)COO$-c-Pen | H | Cl | CH | O |
| 1-154 | $OCH(CH_3)COO$-c-Pen | Cl | H | CH | O |
| 1-155 | $OCH(CH_3)COO$-c-Pen | H | $NO_2$ | CH | O |
| 1-156 | $OCH(CH_3)COO$-c-Pen | $NO_2$ | H | CH | O |
| 1-157 | $OCH(CH_3)COOHex$ | H | H | CH | O |
| 1-158 | $OCH(CH_3)COOHex$ | H | Cl | CH | O |
| 1-159 | $OCH(CH_3)COOHex$ | Cl | H | CH | O |
| 1-160 | $OCH(CH_3)COOHex$ | H | $NO_2$ | CH | O |
| 1-161 | $OCH(CH_3)COOHex$ | $NO_2$ | H | CH | O |
| 1-162 | $OCH(CH_3)COO$-c-Hex | H | H | CH | O |
| 1-163 | $OCH(CH_3)COO$-c-Hex | H | Cl | CH | O |
| 1-164 | $OCH(CH_3)COO$-c-Hex | Cl | H | CH | O |
| 1-165 | $OCH(CH_3)COO$-c-Hex | H | $NO_2$ | CH | O |
| 1-166 | $OCH(CH_3)COO$-c-Hex | $NO_2$ | H | CH | O |
| 1-167 | $OCH(CH_3)CO_2CH_2CO_2H$ | H | H | CH | O |
| 1-168 | $OCH(CH_3)CO_2CH_2CO_2H$ | H | Cl | CH | O |

TABLE 8

| Compound | R² | R³ | R⁴ | A | Y |
|---|---|---|---|---|---|
| 1-169 | OCH(CH₃)CO₂CH₂CO₂H | Cl | H | CH | O |
| 1-170 | OCH(CH₃)CO₂CH₂CO₂H | H | NO₂ | CH | O |
| 1-171 | OCH(CH₃)CO₂CH₂CO₂H | NO₂ | H | CH | O |
| 1-172 | OCH(CH₃)CO₂CH₂CO₂Me | H | H | CH | O |
| 1-173 | OCH(CH₃)CO₂CH₂CO₂Me | H | Cl | CH | O |
| 1-174 | OCH(CH₃)CO₂CH₂CO₂Me | Cl | H | CH | O |
| 1-175 | OCH(CH₃)CO₂CH₂CO₂Me | H | NO₂ | CH | O |
| 1-176 | OCH(CH₃)CO₂CH₂CO₂Me | NO₂ | H | CH | O |
| 1-177 | OCH(CH₃)CO₂CH₂CO₂Et | H | H | CH | O |
| 1-178 | OCH(CH₃)CO₂CH₂CO₂Et | H | Cl | CH | O |
| 1-179 | OCH(CH₃)CO₂CH₂CO₂Et | Cl | H | CH | O |
| 1-180 | OCH(CH₃)CO₂CH₂CO₂Et | H | NO₂ | CH | O |
| 1-181 | OCH(CH₃)CO₂CH₂CO₂Et | NO₂ | H | CH | O |
| 1-182 | OCH(CH₃)CO₂CH(CH₃)CO₂H | H | H | CH | O |
| 1-183 | OCH(CH₃)CO₂CH(CH₃)CO₂H | H | Cl | CH | O |
| 1-184 | OCH(CH₃)CO₂CH(CH₃)CO₂H | Cl | H | CH | O |
| 1-185 | OCH(CH₃)CO₂CH(CH₃)CO₂H | H | NO₂ | CH | O |
| 1-186 | OCH(CH₃)CO₂CH(CH₃)CO₂H | NO₂ | H | CH | O |
| 1-187 | OCH(CH₃)CO₂CH(CH₃)CO₂Me | H | H | CH | O |
| 1-188 | OCH(CH₃)CO₂CH(CH₃)CO₂Me | H | Cl | CH | O |
| 1-189 | OCH(CH₃)CO₂CH(CH₃)CO₂Me | Cl | H | CH | O |
| 1-190 | OCH(CH₃)CO₂CH(CH₃)CO₂Me | H | NO₂ | CH | O |
| 1-191 | OCH(CH₃)CO₂CH(CH₃)CO₂Me | NO₂ | H | CH | O |
| 1-192 | OCH(CH₃)CO₂CH(CH₃)CO₂Et | H | H | CH | O |
| 1-193 | OCH(CH₃)CO₂CH(CH₃)CO₂Et | H | Cl | CH | O |

TABLE 9

| Compound | R² | R³ | R⁴ | A | Y |
|---|---|---|---|---|---|
| 1-194 | OCH(CH₃)CO₂CH(CH₃)CO₂Et | Cl | H | CH | O |
| 1-195 | OCH(CH₃)CO₂CH(CH₃)CO₂Et | H | NO₂ | CH | O |
| 1-196 | OCH(CH₃)CO₂CH(CH₃)CO₂Et | NO₂ | H | CH | O |
| 1-197 | SCH₃ | H | H | CH | O |
| 1-198 | SCH₃ | H | Cl | CH | O |
| 1-199 | SCH₃ | Cl | H | CH | O |
| 1-200 | SCH₃ | H | NO₂ | CH | O |
| 1-201 | SCH₃ | NO₂ | H | CH | O |
| 1-202 | SCH(CH₃)CH₃ | H | H | CH | O |
| 1-203 | SCH(CH₃)CH₃ | H | Cl | CH | O |
| 1-204 | SCH(CH₃)CH₃ | Cl | H | CH | O |
| 1-205 | SCH(CH₃)CH₃ | H | NO₂ | CH | O |
| 1-206 | SCH(CH₃)CH₃ | NO₂ | H | CH | O |
| 1-207 | SCHCH=CH₂ | H | H | CH | O |
| 1-208 | SCHCH=CH₂ | H | Cl | CH | O |
| 1-209 | SCHCH=CH₂ | Cl | H | CH | O |
| 1-210 | SCHCH=CH₂ | H | NO₂ | CH | O |
| 1-211 | SCHCH=CH₂ | NO₂ | H | CH | O |
| 1-212 | SCHC≡CH | H | H | CH | O |
| 1-213 | SCHC≡CH | H | Cl | CH | O |
| 1-214 | SCHC≡CH | Cl | H | CH | O |
| 1-215 | SCHC≡CH | H | NO₂ | CH | O |
| 1-216 | SCHC≡CH | NO₂ | H | CH | O |
| 1-217 | SCH₂COOH | H | H | CH | O |
| 1-218 | SCH₂COOH | H | Cl | CH | O |

TABLE 10

| Compound | R² | R³ | R⁴ | A | Y |
|---|---|---|---|---|---|
| 1-219 | SCH₂COOH | Cl | H | CH | O |
| 1-220 | SCH₂COOH | H | NO₂ | CH | O |
| 1-221 | SCH₂COOH | NO₂ | H | CH | O |
| 1-222 | SCH₂COOMe | H | H | CH | O |
| 1-223 | SCH₂COOMe | H | Cl | CH | O |
| 1-224 | SCH₂COOMe | Cl | H | CH | O |
| 1-225 | SCH₂COOMe | H | NO₂ | CH | O |
| 1-226 | SCH₂COOMe | NO₂ | H | CH | O |
| 1-227 | SCH₂COOEt | H | H | CH | O |
| 1-228 | SCH₂COOEt | H | Cl | CH | O |

TABLE 10-continued

| Compound | R² | R³ | R⁴ | A | Y |
|---|---|---|---|---|---|
| 1-229 | SCH₂COOEt | Cl | H | CH | O |
| 1-230 | SCH₂COOEt | H | NO₂ | CH | O |
| 1-231 | SCH₂COOEt | NO₂ | H | CH | O |
| 1-232 | SCH(CH₃)COOH | H | H | CH | O |
| 1-233 | SCH(CH₃)COOH | H | Cl | CH | O |
| 1-234 | SCH(CH₃)COOH | Cl | H | CH | O |
| 1-235 | SCH(CH₃)COOH | H | NO₂ | CH | O |
| 1-236 | SCH(CH₃)COOH | NO₂ | H | CH | O |
| 1-237 | SCH(CH₃)COOMe | H | H | CH | O |
| 1-238 | SCH(CH₃)COOMe | H | Cl | CH | O |
| 1-239 | SCH(CH₃)COOMe | Cl | H | CH | O |
| 1-240 | SCH(CH₃)COOMe | H | NO₂ | CH | O |
| 1-241 | SCH(CH₃)COOMe | NO₂ | H | CH | O |
| 1-242 | SCH(CH₃)COOEt | H | H | CH | O |
| 1-243 | SCH(CH₃)COOEt | H | Cl | CH | O |

TABLE 11

| Compound | R² | R³ | R⁴ | A | Y |
|---|---|---|---|---|---|
| 1-244 | SCH(CH₃)COOEt | Cl | H | CH | O |
| 1-245 | SCH(CH₃)COOEt | H | NO₂ | CH | O |
| 1-246 | SCH(CH₃)COOEt | NO₂ | H | CH | O |
| 1-247 | SCH(CH₃)COO-i-Pr | H | H | CH | O |
| 1-248 | SCH(CH₃)COO-i-Pr | H | Cl | CH | O |
| 1-249 | SCH(CH₃)COO-i-Pr | Cl | H | CH | O |
| 1-250 | SCH(CH₃)COO-i-Pr | H | NO₂ | CH | O |
| 1-251 | SCH(CH₃)COO-i-Pr | NO₂ | H | CH | O |
| 1-252 | SCH(CH₃)CO₂CH₂CO₂H | H | H | CH | O |
| 1-253 | SCH(CH₃)CO₂CH₂CO₂H | H | Cl | CH | O |
| 1-254 | SCH(CH₃)CO₂CH₂CO₂H | Cl | H | CH | O |
| 1-255 | SCH(CH₃)CO₂CH₂CO₂H | H | NO₂ | CH | O |
| 1-256 | SCH(CH₃)CO₂CH₂CO₂H | NO₂ | H | CH | O |
| 1-257 | SCH(CH₃)CO₂CH₂CO₂Me | H | H | CH | O |
| 1-258 | SCH(CH₃)CO₂CH₂CO₂Me | H | Cl | CH | O |
| 1-259 | SCH(CH₃)CO₂CH₂CO₂Me | Cl | H | CH | O |
| 1-260 | SCH(CH₃)CO₂CH₂CO₂Me | H | NO₂ | CH | O |
| 1-261 | SCH(CH₃)CO₂CH₂CO₂Me | NO₂ | H | CH | O |
| 1-262 | SCH(CH₃)CO₂CH₂CO₂Et | H | H | CH | O |
| 1-263 | SCH(CH₃)CO₂CH₂CO₂Et | H | Cl | CH | O |
| 1-264 | SCH(CH₃)CO₂CH₂CO₂Et | Cl | H | CH | O |
| 1-265 | SCH(CH₃)CO₂CH₂CO₂Et | H | NO₂ | CH | O |
| 1-266 | SCH(CH₃)CO₂CH₂CO₂Et | NO₂ | H | CH | O |
| 1-267 | SCH(CH₃)CO₂CH(CH₃)CO₂H | H | H | CH | O |
| 1-268 | SCH(CH₃)CO₂CH(CH₃)CO₂H | H | Cl | CH | O |

TABLE 12

| Compound | R² | R³ | R⁴ | A | Y |
|---|---|---|---|---|---|
| 1-269 | SCH(CH₃)CO₂CH(CH₃)CO₂H | Cl | H | CH | O |
| 1-270 | SCH(CH₃)CO₂CH(CH₃)CO₂H | H | NO₂ | CH | O |
| 1-271 | SCH(CH₃)CO₂CH(CH₃)CO₂H | NO₂ | H | CH | O |
| 1-272 | SCH(CH₃)CO₂CH(CH₃)CO₂Me | H | H | CH | O |
| 1-273 | SCH(CH₃)CO₂CH(CH₃)CO₂Me | H | Cl | CH | O |
| 1-274 | SCH(CH₃)CO₂CH(CH₃)CO₂Me | Cl | H | CH | O |
| 1-275 | SCH(CH₃)CO₂CH(CH₃)CO₂Me | H | NO₂ | CH | O |
| 1-276 | SCH(CH₃)CO₂CH(CH₃)CO₂Me | NO₂ | H | CH | O |
| 1-277 | SCH(CH₃)CO₂CH(CH₃)CO₂Et | H | H | CH | O |
| 1-278 | SCH(CH₃)CO₂CH(CH₃)CO₂Et | H | Cl | CH | O |
| 1-279 | SCH(CH₃)CO₂CH(CH₃)CO₂Et | Cl | H | CH | O |
| 1-280 | SCH(CH₃)CO₂CH(CH₃)CO₂Et | H | NO₂ | CH | O |
| 1-281 | SCH(CH₃)CO₂CH(CH₃)CO₂Et | NO₂ | H | CH | O |
| 1-282 | H | NO₂ | H | CH | O |
| 1-283 | C≡N | H | H | CH | O |
| 1-284 | C≡N | H | Cl | CH | O |
| 1-285 | C≡N | Cl | H | CH | O |
| 1-286 | C≡N | H | NO₂ | CH | O |
| 1-287 | C≡N | NO₂ | H | CH | O |
| 1-288 | C(=O)H | H | H | CH | O |

TABLE 12-continued

| Compound | $R^2$ | $R^3$ | $R^4$ | A | Y |
|---|---|---|---|---|---|
| 1-289 | C(=O)H | H | Cl | CH | O |
| 1-290 | C(=O)H | Cl | H | CH | O |
| 1-291 | C(=O)H | H | $NO_2$ | CH | O |
| 1-292 | C(=O)H | $NO_2$ | H | CH | O |
| 1-293 | C(=O)$NH_2$ | H | H | CH | O |

TABLE 13

| Compound | $R^2$ | $R^3$ | $R^4$ | A | Y |
|---|---|---|---|---|---|
| 1-294 | C(=O)$NH_2$ | H | Cl | CH | O |
| 1-295 | C(=O)$NH_2$ | Cl | H | CH | O |
| 1-296 | C(=O)$NH_2$ | H | $NO_2$ | CH | O |
| 1-297 | C(=O)$NH_2$ | $NO_2$ | H | CH | O |
| 1-298 | $CO_2H$ | H | H | CH | O |
| 1-299 | $CO_2H$ | H | Cl | CH | O |
| 1-300 | $CO_2H$ | Cl | H | CH | O |
| 1-301 | $CO_2H$ | H | $NO_2$ | CH | O |
| 1-302 | $CO_2H$ | $NO_2$ | H | CH | O |
| 1-303 | $CO_2Me$ | H | H | CH | O |
| 1-304 | $CO_2Me$ | H | Cl | CH | O |
| 1-305 | $CO_2Me$ | Cl | H | CH | O |
| 1-306 | $CO_2Me$ | H | $NO_2$ | CH | O |
| 1-307 | $CO_2Me$ | $NO_2$ | H | CH | O |
| i-308 | $CO_2Et$ | H | H | CH | O |
| 1-309 | $CO_2Et$ | H | Cl | CH | O |
| 1-310 | $CO_2Et$ | Cl | H | CH | O |
| 1-311 | $CO_2Et$ | H | $NO_2$ | CH | O |
| 1-312 | $CO_2Et$ | $NO_2$ | H | CH | O |
| 1-313 | $CO_2CH_2CO_2H$ | H | H | CH | O |
| 1-314 | $CO_2CH_2CO_2H$ | H | Cl | CH | O |
| 1-315 | $CO_2CH_2CO_2H$ | Cl | H | CH | O |
| 1-316 | $CO_2CH_2CO_2H$ | H | $NO_2$ | CH | O |
| 1-317 | $CO_2CH_2CO_2H$ | $NO_2$ | H | CH | O |
| 1-318 | $CO_2CH_2CO_2Me$ | H | H | CH | O |

TABLE 14

| Compound | $R^2$ | $R^3$ | $R^4$ | A | Y |
|---|---|---|---|---|---|
| 1-319 | $CO_2CH_2CO_2Me$ | H | Cl | CH | O |
| 1-320 | $CO_2CH_2CO_2Me$ | Cl | H | CH | O |
| 1-321 | $CO_2CH_2CO_2Me$ | H | $NO_2$ | CH | O |
| 1-322 | $CO_2CH_2CO_2Me$ | $NO_2$ | H | CH | O |
| 1-323 | $CO_2CH_2CO_2Et$ | H | H | CH | O |
| 1-324 | $CO_2CH_2CO_2Et$ | H | Cl | CH | O |
| 1-325 | $CO_2CH_2CO_2Et$ | Cl | H | CH | O |
| 1-326 | $CO_2CH_2CO_2Et$ | H | $NO_2$ | CH | O |
| 1-327 | $CO_2CH_2CO_2Et$ | $NO_2$ | H | CH | O |
| 1-328 | $CO_2CH(CH_3)CO_2H$ | H | H | CH | O |
| 1-329 | $CO_2CH(CH_3)CO_2H$ | H | Cl | CH | O |
| 1-330 | $CO_2CH(CH_3)CO_2H$ | Cl | H | CH | O |
| 1-331 | $CO_2CH(CH_3)CO_2H$ | H | $NO_2$ | CH | O |
| 1-332 | $CO_2CH(CH_3)CO_2H$ | $NO_2$ | H | CH | O |
| 1-333 | $CO_2CH(CH_3)CO_2Me$ | H | H | CH | O |
| 1-334 | $CO_2CH(CH_3)CO_2Me$ | H | Cl | CH | O |
| 1-335 | $CO_2CH(CH_3)CO_2Me$ | Cl | H | CH | O |
| 1-336 | $CO_2CH(CH_3)CO_2Me$ | H | $NO_2$ | CH | O |
| 1-337 | $CO_2CH(CH_3)CO_2Me$ | $NO_2$ | H | CH | O |
| 1-338 | $CO_2CH(CH_3)CO_2Et$ | H | H | CH | O |
| 1-339 | $CO_2CH(CH_3)CO_2Et$ | H | Cl | CH | O |
| 1-340 | $CO_2CH(CH_3)CO_2Et$ | Cl | H | CH | O |
| 1-341 | $CO_2CH(CH_3)CO_2Et$ | H | $NO_2$ | CH | O |
| 1-342 | $CO_2CH(CH_3)CO_2Et$ | $NO_2$ | H | CH | O |
| 1-343 | $CO_2C(CH_3)_2CO_2H$ | H | H | CH | O |

TABLE 15

| Compound | $R^2$ | $R^3$ | $R^4$ | A | Y |
|---|---|---|---|---|---|
| 1-344 | $CO_2C(CH_3)_2CO_2H$ | H | Cl | CH | O |
| 1-345 | $CO_2C(CH_3)_2CO_2H$ | Cl | H | CH | O |
| 1-346 | $CO_2C(CH_3)_2CO_2H$ | H | $NO_2$ | CH | O |
| 1-347 | $CO_2C(CH_3)_2CO_2H$ | $NO_2$ | H | CH | O |
| 1-348 | $CO_2C(CH_3)_2CO_2Me$ | H | H | CH | O |
| 1-349 | $CO_2C(CH_3)_2CO_2Me$ | H | Cl | CH | O |
| 1-350 | $CO_2C(CH_3)_2CO_2Me$ | Cl | H | CH | O |
| 1-351 | $CO_2C(CH_3)_2CO_2Me$ | H | $NO_2$ | CH | O |
| 1-352 | $CO_2C(CH_3)_2CO_2Me$ | $NO_2$ | H | CH | O |
| 1-353 | $CO_2C(CH_3)_2CO_2Et$ | H | Cl | CH | O |
| 1-354 | $CO_2C(CH_3)_2CO_2Et$ | Cl | H | CH | O |
| 1-355 | $CO_2C(CH_3)_2CO_2Et$ | H | $NO_2$ | CH | O |
| 1-356 | $CO_2C(CH_3)_2CO_2Et$ | $NO_2$ | H | CH | O |
| 1-357 | $CH_3$ | H | H | CH | O |
| 1-358 | $CH_3$ | H | Cl | CH | O |
| 1-359 | $CH_3$ | GI | H | CH | O |
| 1-360 | $CH_3$ | H | $NO_2$ | CH | O |
| 1-361 | $CH_3$ | $NO_2$ | H | CH | O |
| 1-362 | $CF_3$ | H | H | CH | O |
| 1-363 | $CF_3$ | H | Cl | CH | O |
| 1-364 | $CF_3$ | Cl | H | CH | O |
| 1-365 | $CF_3$ | H | $NO_2$ | CH | O |
| 1-366 | $CF_3$ | $NO_2$ | H | CH | O |
| 1-367 | CH=CH$CO_2H$ | H | H | CH | O |

TABLE 16

| Compound | $R^2$ | $R^3$ | $R^4$ | A | Y |
|---|---|---|---|---|---|
| 1-368 | CH=CH$CO_2H$ | H | Cl | CH | O |
| 1-369 | CH=CH$CO_2H$ | Cl | H | CH | O |
| 1-370 | CH=CH$CO_2H$ | H | $NO_2$ | CH | O |
| 1-371 | CH=CH$CO_2H$ | $NO_2$ | H | CH | O |
| 1-372 | CH=CH$CO_2Me$ | H | H | CH | O |
| 1-373 | CH=CH$CO_2Me$ | H | Cl | CH | O |
| 1-374 | CH=CH$CO_2Me$ | Cl | H | CH | O |
| 1-375 | CH=CH$CO_2Me$ | H | $NO_2$ | CH | O |
| 1-376 | CH=CH$CO_2Me$ | $NO_2$ | H | CH | O |
| 1-377 | CH=CH$CO_2Et$ | H | H | CH | O |
| 1-378 | CH=CH$CO_2Et$ | H | Cl | CH | O |
| 1-379 | CH=CH$CO_2Et$ | Cl | H | CH | O |
| 1-380 | CH=CH$CO_2Et$ | H | $NO_2$ | CH | O |
| 1-381 | CH=CH$CO_2Et$ | $NO_2$ | H | CH | O |
| 1-382 | $CH_2CH_2CO_2H$ | H | H | CH | O |
| 1-383 | $CH_2CH_2CO_2H$ | H | Cl | CH | O |
| 1-384 | $CH_2CH_2CO_2H$ | Cl | H | CH | O |
| 1-385 | $CH_2CH_2CO_2H$ | H | $NO_2$ | CH | O |
| 1-386 | $CH_2CH_2CO_2H$ | $NO_2$ | H | CH | O |
| 1-387 | $CH_2CH_2CO_2Me$ | H | H | CH | O |
| 1-388 | $CH_2CH_2CO_2Me$ | H | Cl | CH | O |
| 1-389 | $CH_2CH_2CO_2Me$ | Cl | H | CH | O |
| 1-390 | $CH_2CH_2CO_2Me$ | H | $NO_2$ | CH | O |
| 1-391 | $CH_2CH_2CO_2Me$ | $NO_2$ | H | CH | O |
| 1-392 | $CH_2CH_2CO_2Et$ | H | H | CH | O |

TABLE 17

| Compound | $R^2$ | $R^3$ | $R^4$ | A | Y |
|---|---|---|---|---|---|
| 1-393 | $CH_2CH_2CO_2Et$ | H | Cl | CH | O |
| 1-394 | $CH_2CH_2CO_2Et$ | Cl | H | CH | O |
| 1-395 | $CH_2CH_2CO_2Et$ | H | $NO_2$ | CH | O |
| 1-396 | $CH_2CH_2CO_2Et$ | $NO_2$ | H | CH | O |
| 1-397 | $CH_2CH(Cl)CO_2H$ | H | H | CH | O |
| 1-398 | $CH_2CH(Cl)CO_2H$ | H | Cl | CH | O |
| 1-399 | $CH_2CH(Cl)CO_2H$ | Cl | H | CH | O |
| 1-400 | $CH_2CH(Cl)CO_2H$ | H | $NO_2$ | CH | O |
| 1-401 | $CH_2CH(Cl)CO_2H$ | $NO_2$ | H | CH | O |
| 1-402 | $CH_2CH(Cl)CO_2Me$ | H | H | CH | O |
| 1-403 | $CH_2CH(Cl)CO_2Me$ | H | Cl | CH | O |
| 1-404 | $CH_2CH(Cl)CO_2Me$ | Cl | H | CH | O |
| 1-405 | $CH_2CH(Cl)CO_2Me$ | H | $NO_2$ | CH | O |

TABLE 17-continued

| Compound | $R^2$ | $R^3$ | $R^4$ | A | Y |
|---|---|---|---|---|---|
| 1-406 | $CH_2CH(Cl)CO_2Me$ | $NO_2$ | H | CH | O |
| 1-407 | $CH_2CH(Cl)CO_2Et$ | H | H | CH | O |
| 1-408 | $CH_2CH(Cl)CO_2Et$ | H | Cl | CH | O |
| 1-409 | $CH_2CH(Cl)CO_2Et$ | Cl | H | CH | O |
| 1-410 | $CH_2CH(Cl)CO_2Et$ | H | $NO_2$ | CH | O |
| 1-411 | $CH_2CH(Cl)CO_2Et$ | $NO_2$ | H | CH | O |
| 1-412 | $C(=O)CH_3$ | H | H | CH | O |
| 1-413 | $C(=O)CH_3$ | H | Cl | CH | O |
| 1-414 | $C(=O)CH_3$ | Cl | H | CH | O |
| 1-415 | $C(=O)CH_3$ | H | $NO_2$ | CH | O |
| l-416 | $C(=O)CH_3$ | $NO_2$ | H | CH | O |
| 1-417 | $C(CH_3)=NOH$ | H | H | CH | O |

TABLE 18

| Compound | $R^2$ | $R^3$ | $R^4$ | A | Y |
|---|---|---|---|---|---|
| 1-418 | $C(CH_3)=NOH$ | H | Cl | CH | O |
| 1-419 | $C(CH_3)=NOH$ | Cl | H | CH | O |
| 1-420 | $C(CH_3)=NOH$ | H | $NO_2$ | CH | O |
| 1-421 | $C(CH_3)=NOH$ | $NO_2$ | H | CH | O |
| 1-422 | $C(CH_3)=NOMe$ | H | H | CH | O |
| 1-423 | $C(CH_3)=NOMe$ | H | Cl | CH | O |
| 1-424 | $C(CH_3)=NOMe$ | Cl | H | CH | O |
| 1-425 | $C(CH_3)=NOMe$ | H | $NO_2$ | CH | O |
| 1-426 | $C(CH_3)=NOMe$ | $NO_2$ | H | CH | O |
| 1-427 | F | H | H | CH | O |
| 1-428 | F | H | Cl | CH | O |
| 1-429 | F | Cl | H | CH | O |
| 1-430 | F | H | $NO_2$ | CH | O |
| 1-431 | F | $NO_2$ | H | CH | O |
| 1-432 | Cl | H | Cl | CH | S |
| 1-433 | Cl | H | H | CH | S |
| 1-434 | $OCH_3$ | H | H | CH | S |
| 1-435 | $NO_2$ | H | H | CH | S |
| 1-436 | $NH_2$ | H | H | CH | S |
| 1-437 | $NHCH_3$ | H | H | CH | S |
| 1-438 | $N(CH_3)_2$ | H | H | CH | S |
| 1-439 | $NHSO_2CH_3$ | H | H | CH | S |
| 1-440 | $NHCH(CH_3)CO_2Et$ | H | H | CH | S |
| 1-441 | $NHCH(CH_3)CO_2Et$ | H | Cl | CH | S |
| 1-442 | $N(CH_3)CH(CH_3)CO_2Et$ | H | Cl | CH | S |

TABLE 19

| Compound | $R^2$ | $R^3$ | $R^4$ | A | Y |
|---|---|---|---|---|---|
| 1-443 | $N(CH_3)SO_2CH_3$ | H | Cl | CH | S |
| 1-444 | $NHSO_2CH_3$ | H | Cl | CH | S |
| 1-445 | $NHCH(CH_3)CO_2Et$ | Cl | H | CH | S |
| 1-446 | $N(CH_3)CH(CH_3)CO_2Et$ | Cl | H | CH | S |
| 1-447 | $N(CH_3)SO_2CH_3$ | Cl | H | CH | S |
| 1-448 | $NHSO_2CH_3$ | Cl | H | CH | S |
| 1-449 | $NO_2$ | H | Cl | CH | S |
| 1-450 | $NH_2$ | H | Cl | CH | S |
| 1-451 | $NO_2$ | Cl | H | CH | S |
| 1-452 | $NH_2$ | Cl | H | CH | S |
| 1-453 | $NHCOCH_3$ | H | H | CH | S |
| 1-454 | $NHCOCF_3$ | H | H | CH | S |
| 1-455 | $NHSO_2Et$ | H | H | CH | S |
| 1-456 | $NHSO_2CH_2Cl$ | H | H | CH | S |
| 1-457 | $N(CH_3)COCH_3$ | H | H | CH | S |
| 1-458 | $N(CH_3)COCF_3$ | H | H | CH | S |
| 1-459 | $N(CH_3)SO_2Et$ | H | H | CH | S |
| 1-460 | $N(CH)SO_2CH_2Cl$ | H | H | CH | S |
| 1-461 | $NHCOCH_3$ | H | Cl | CH | S |
| 1-462 | $NHCOCF_3$ | H | Cl | CH | S |
| 1-463 | $NHSO_2Et$ | H | Cl | CH | S |
| 1-464 | $NHSO_2CH_2Cl$ | H | Cl | CH | S |
| 1-465 | $N(CH_3)COCH_3$ | Cl | H | CH | S |

TABLE 19-continued

| Compound | $R^2$ | $R^3$ | $R^4$ | A | Y |
|---|---|---|---|---|---|
| 1-466 | $N(CH_3)COCF_3$ | Cl | H | CH | S |
| 1-467 | $N(CH_3)SO_2Et$ | Cl | H | CH | S |

TABLE 20

| Compound | $R^2$ | $R^3$ | $R^4$ | A | Y |
|---|---|---|---|---|---|
| 1-468 | $N(CH_3)SO_2CH_2Cl$ | Cl | H | CH | S |
| 1-469 | $NHCH_2CO_2Me$ | H | H | CH | S |
| 1-470 | $NHCH_2CO_2Et$ | H | H | CH | S |
| 1-471 | $NHCH(CH_3)COOH$ | H | H | CH | S |
| 1-472 | $NHCH(CH_3)CONH_2$ | H | H | CH | S |
| 1-473 | $NHCH(CH_3)CONHCH_3$ | H | H | CH | S |
| 1-474 | $NHCH_2CO_2Me$ | H | Cl | CH | S |
| 1-475 | $NHCH_2CO_2Et$ | H | Cl | CH | S |
| 1-476 | $NHCH(CH_3)COOH$ | H | Cl | CH | S |
| 1-477 | $NHCH(CH_3)CONH_2$ | H | Cl | CH | S |
| 1-478 | $NHCH(CH_3)CONHCH_3$ | H | Cl | CH | S |
| 1-479 | $NHCH_2CO_2Me$ | Cl | H | GH | S |
| 1-480 | $NHCH_2CO_2Et$ | Cl | H | CH | S |
| 1-481 | $NHCH(CH_3)COOH$ | Cl | H | CH | S |
| 1-482 | $NHCH(CH_3)CONH_2$ | Cl | H | CH | S |
| 1-483 | $NHCH(CH_3)CONHCH_3$ | Cl | H | CH | S |
| 1-484 | $NHCH_2CH_2CH_3$ | H | H | CH | S |
| 1-485 | $NHCH_2CH=CH_2$ | H | H | CH | S |
| 1-486 | $NHCH_2C\equiv CH$ | H | H | CH | S |
| 1-487 | $N(CH_3)CH_2CH_2CH_3$ | H | H | CH | S |
| 1-488 | $N(CH_3)CH_2CH=CH_2$ | H | H | CH | S |
| 1-489 | $N(CH_3)CH_2C\equiv CH$ | H | H | CH | S |
| 1-490 | $NHCH_2CH_2CH_3$ | H | Cl | CH | S |
| 1-491 | $NHCH_2CH=CH_2$ | H | Cl | CH | S |
| 1-492 | $NHCH_2C\equiv CH$ | H | Cl | CH | S |

TABLE 21

| Compound | $R^2$ | $R^3$ | $R^4$ | A | Y |
|---|---|---|---|---|---|
| 1-493 | $N(CH_3)CH_2CH_2CH_3$ | H | Cl | CH | S |
| 1-494 | $N(CH_3)CH_2CH=CH_2$ | H | Cl | CH | S |
| 1-495 | $N(CH_3)CH_2C\equiv CH$ | H | Cl | CH | S |
| 1-496 | $NHCH_2CH_2CH_3$ | Cl | H | CH | S |
| 1-497 | $NHCH_2CH=CH_2$ | Cl | H | CH | S |
| 1-498 | $NHCH_2C\equiv CH$ | Cl | H | CH | S |
| 1-499 | $N(CH_3)CH_2CH_2CH_3$ | Cl | H | CH | S |
| 1-500 | $N(CH_3)CH_2CH=CH_2$ | Cl | H | CH | S |
| 1-501 | $N(CH_3)CH_2C\equiv CH$ | Cl | H | CH | S |
| 1-502 | Br | H | H | CH | S |
| 1-503 | Br | H | Cl | CH | S |
| 1-504 | Br | Cl | H | CH | S |
| 1-505 | OH | H | H | CH | S |
| 1-506 | OH | H | Cl | CH | S |
| 1-507 | OH | Cl | H | CH | S |
| 1-508 | OH | H | $NO_2$ | CH | S |
| 1-509 | OH | $NO_2$ | H | CH | S |
| 1-510 | $OCH_3$ | H | Cl | CH | S |
| 1-511 | $OCH_3$ | Cl | H | CH | S |
| 1-512 | $OCH_3$ | H | $NO_2$ | CH | S |
| 1-513 | $OCH_3$ | $NO_2$ | H | CH | S |
| 1-514 | $OCH(CH_3)CH_3$ | H | H | CH | S |
| 1-515 | $OCH(CH_3)CH_3$ | H | Cl | CH | S |
| 1-516 | $OCH(CH_3)CH_3$ | Cl | H | CH | S |
| 1-517 | $OCH(CH_3)CH_3$ | H | $NO_2$ | CH | S |

TABLE 22

| Compound | $R^2$ | $R^3$ | $R^4$ | A | Y |
|---|---|---|---|---|---|
| 1-518 | $OCH(CH_3)CH_3$ | $NO_2$ | H | CH | S |
| 1-519 | $OCH_2CH=CH_2$ | H | H | CH | S |
| 1-520 | $OCH_2CH=CH_2$ | H | Cl | CH | S |
| 1-521 | $OCH_2CH=CH_2$ | Cl | H | CH | S |

TABLE 22-continued

| Compound | $R^2$ | $R^3$ | $R^4$ | A | Y |
|---|---|---|---|---|---|
| 1-522 | $OCH_2CH{=}CH_2$ | H | $NO_2$ | CH | S |
| 1-523 | $OCH_2CH{=}CH_2$ | $NO_2$ | H | CH | S |
| 1-524 | $OCH(CH_3)CH{=}CH_2$ | H | H | CH | S |
| 1-525 | $OCH(CH_3)CH{=}CH_2$ | H | Cl | CH | S |
| 1-526 | $OCH(CH_3)CH{=}CH_2$ | Cl | H | CH | S |
| 1-527 | $OCH(CH_3)CH{=}CH_2$ | H | $NO_2$ | CH | S |
| 1-528 | $OCH(CH_3)CH{=}CH_2$ | $NO_2$ | H | CH | S |
| 1-529 | $OCH_2C(Cl){=}CH_2$ | H | H | CH | S |
| 1-530 | $OCH_2C(Cl){=}CH_2$ | H | Cl | CH | S |
| 1-531 | $OCH_2C(Cl){=}CH_2$ | Cl | H | CH | S |
| 1-532 | $OCH_2C(Cl){=}CH_2$ | H | $NO_2$ | CH | S |
| 1-533 | $OCH_2C(Cl){=}CH_2$ | $NO_2$ | H | CH | S |
| 1-534 | $OCH_2C{\equiv}CH$ | H | H | CH | S |
| 1-535 | $OCH_2C{\equiv}CH$ | H | Cl | CH | S |
| 1-536 | $OCH_2C{\equiv}CH$ | Cl | H | CH | S |
| 1-537 | $OCH_2C{\equiv}CH$ | H | $NO_2$ | CH | S |
| 1-538 | $OCH_2C{\equiv}CH$ | $NO_2$ | H | CH | S |
| 1-539 | $OCH(CH_3)C{\equiv}CH$ | H | H | CH | S |
| 1-540 | $OCH(CH_3)C{\equiv}CH$ | H | Cl | CH | S |
| 1-541 | $OCH(CH_3)C{\equiv}CH$ | Cl | H | CH | S |
| 1-542 | $OCH(CH_3)C{\equiv}CH$ | H | $NO_2$ | CH | S |

TABLE 23

| Compound | $R^2$ | $R^3$ | $R^4$ | A | Y |
|---|---|---|---|---|---|
| 1-543 | $OCH(CH_3)C{\equiv}CH$ | $NO_2$ | H | CH | S |
| 1-544 | $OCH(CH_3)COOH$ | H | H | CH | S |
| 1-545 | $OCH(CH_3)COOH$ | H | Cl | CH | S |
| 1-546 | $OCH(CH_3)COOH$ | Cl | H | CH | S |
| 1-547 | $OCH(CH_3)COOH$ | H | $NO_2$ | CH | S |
| 1-548 | $OCH(CH_3)COOH$ | $NO_2$ | H | CH | S |
| 1-549 | $OCH(CH_3)COOMe$ | H | H | CH | S |
| 1-550 | $OCH(CH_3)COOMe$ | H | Cl | CH | S |
| 1-551 | $OCH(CH_3)COOMe$ | Cl | H | CH | S |
| 1-552 | $OCH(CH_3)COOMe$ | H | $NO_2$ | CH | S |
| 1-553 | $OCH(CH_3)COOMe$ | $NO_2$ | H | CH | S |
| 1-554 | $OCH(CH_3)COOEt$ | H | H | CH | S |
| 1-555 | $OCH(CH_3)COOEt$ | H | Cl | CH | S |
| 1-556 | $OCH(CH_3)COOEt$ | Cl | H | CH | S |
| 1-557 | $OCH(CH_3)COOEt$ | H | $NO_2$ | CH | S |
| 1-558 | $OCH(CH_3)COOEt$ | $NO_2$ | H | CH | S |
| 1-559 | $OCH(CH_3)COOPr$ | H | H | CH | S |
| 1-560 | $OCH(CH_3)COOPr$ | H | Cl | CH | S |
| 1-561 | $OCH(CH_3)COOPr$ | Cl | H | CH | S |
| 1-562 | $OCH(CH_3)COOPr$ | H | $NO_2$ | CH | S |
| 1-563 | $OCH(CH_3)COOPr$ | $NO_2$ | H | CH | S |
| 1-564 | $OCH(CH_3)COO$-i-Pr | H | H | CH | S |
| 1-565 | $OCH(CH_3)COO$-i-Pr | H | Cl | CH | S |
| 1-566 | $OCH(CH_3)COO$-i-Pr | Cl | H | CH | S |
| 1-567 | $OCH(CH_3)COO$-i-Pr | H | $NO_2$ | CH | S |

TABLE 24

| Compound | $R^2$ | $R^3$ | $R^4$ | A | Y |
|---|---|---|---|---|---|
| 1-568 | $OCH(CH_3)COO$-i-Pr | $NO_2$ | H | CH | S |
| 1-569 | $OCH(CH_3)COOBu$ | H | H | CH | S |
| 1-570 | $OCH(CH_3)COOBu$ | H | Cl | CH | S |
| 1-571 | $OCH(CH_3)COOBu$ | Cl | H | CH | S |
| 1-572 | $OCH(CH_3)COOBu$ | H | $NO_2$ | CH | S |
| 1-573 | $OCH(CH_3)COOBu$ | $NO_2$ | H | CH | S |
| 1-574 | $OCH(CH_3)COOPen$ | H | H | CH | S |
| 1-575 | $OCH(CH_3)COOPen$ | H | Cl | CH | S |
| 1-576 | $OCH(CH_3)COOPen$ | Cl | H | CH | S |
| 1-577 | $DCH(CH_3)COOPen$ | H | $NO_2$ | CH | S |
| 1-578 | $OCH(CH_3)COOPen$ | $NO_2$ | H | CH | S |
| 1-579 | $OCH(CH_3)COO$-c-Pen | H | H | CH | S |
| 1-580 | $OCH(CH_3)COO$-c-Pen | H | Cl | CH | S |
| 1-581 | $OCH(CH_3)COO$-c-Pen | Cl | H | CH | S |
| 1-582 | $OCH(CH_3)COO$-c-Pen | H | $NO_2$ | CH | S |
| 1-583 | $OCH(CH_3)COO$-c-Pen | $NO_2$ | H | CH | S |

TABLE 24-continued

| Compound | $R^2$ | $R^3$ | $R^4$ | A | Y |
|---|---|---|---|---|---|
| 1-584 | $OCH(CH_3)COOHex$ | H | H | CH | S |
| 1-585 | $OCH(CH_3)COOHex$ | H | Cl | CH | S |
| 1-586 | $OCH(CH_3)COOHex$ | Cl | H | CH | S |
| 1-587 | $OCH(CH_3)COOHex$ | H | $NO_2$ | CH | S |
| 1-588 | $OCH(CH_3)COOHex$ | $NO_2$ | H | CH | S |
| 1-589 | $OCH(CH_3)COO$-c-Hex | H | H | CH | S |
| 1-590 | $OCH(CH_3)COO$-c-Hex | H | Cl | CH | S |
| 1-591 | $OCH(CH_3)COO$-c-Hex | Cl | H | CH | S |
| 1-592 | $OCH(CH_3)COO$-c-Hex | H | $NO_2$ | CH | S |

TABLE 25

| Compound | $R^2$ | $R^3$ | $R^4$ | A | Y |
|---|---|---|---|---|---|
| 1-593 | $OCH(CH_3)COO$-c-Hex | $NO_2$ | H | CH | S |
| 1-594 | $OCH(CH_3)CO_2CH_2CO_2H$ | H | H | CH | S |
| 1-595 | $OCH(CH_3)CO_2CH_2CO_2H$ | H | Cl | CH | S |
| 1-596 | $OCH(CH_3)CO_2CH_2CO_2H$ | Cl | H | CH | S |
| 1-597 | $OCH(CH_3)CO_2CH_2CO_2H$ | H | $NO_2$ | CH | S |
| 1-598 | $OCH(CH_3)CO_2CH_2CO_2H$ | $NO_2$ | H | CH | S |
| 1-599 | $OCH(CH_3)CO_2CH_2CO_2Me$ | H | H | CH | S |
| 1-600 | $OCH(CH_3)CO_2CH_2CO_2Me$ | H | Cl | CH | S |
| 1-601 | $OCH(CH_3)CO_2CH_2CO_2Me$ | Cl | H | CH | S |
| 1-602 | $OCH(CH_3)CO_2CH_2CO_2Me$ | H | $NO_2$ | CH | S |
| 1-603 | $OCH(CH_3)CO_2CH_2CO_2Me$ | $NO_2$ | H | CH | S |
| 1-604 | $OCH(CH_3)CO_2CH_2CO_2Et$ | H | H | CH | S |
| 1-605 | $OCH(CH_3)CO_2CH_2CO_2Et$ | H | Cl | CH | S |
| 1-606 | $OCH(CH_3)CO_2CH_2CO_2Et$ | Cl | H | CH | S |
| 1-607 | $OCH(CH_3)CO_2CH_2CO_2Et$ | H | $NO_2$ | CH | S |
| 1-608 | $OCH(CH_3)CO_2CH_2CO_2Et$ | $NO_2$ | H | CH | S |
| 1-609 | $OCH(CH_3)CO_2CH(CH_3)CO_2H$ | H | H | CH | S |
| 1-610 | $OCH(CH_3)CO_2CH(CH_3)CO_2H$ | H | Cl | CH | S |
| 1-611 | $OCH(CH_3)CO_2CH(CH_3)CO_2H$ | Cl | H | CH | S |
| 1-612 | $OCH(CH_3)CO_2CH(CH_3)CO_2H$ | H | $NO_2$ | CH | S |
| 1-613 | $OCH(CH_3)CO_2CH(CH_3)CO_2H$ | $NO_2$ | H | CH | S |
| 1-614 | $OCH(CH_3)CO_2CH(CH_3)CO_2Me$ | H | H | CH | S |
| 1-615 | $OCH(CH_3)CO_2CH(CH_3)CO_2Me$ | H | Cl | CH | S |
| 1-616 | $OCH(CH_3)CO_2CH(CH_3)CO_2Me$ | Cl | H | CH | S |
| 1-617 | $OCH(CH_3)CO_2CH(CH_3)CO_2Me$ | H | $NO_2$ | CH | S |

TABLE 26

| Compound | $R^2$ | $R^3$ | $R^4$ | A | Y |
|---|---|---|---|---|---|
| 1-618 | $OCH(CH_3)CO_2CH(CH_3)CO_2Me$ | $NO_2$ | H | CH | S |
| 1-619 | $OCH(CH_3)CO_2CH(CH_3)CO_2Et$ | H | H | CH | S |
| 1-620 | $OCH(CH_3)CO_2CH(CH_3)CO_2Et$ | H | Cl | CH | S |
| 1-621 | $OCH(CH_3)CO_2CH(CH_3)CO_2Et$ | Cl | H | CH | S |
| 1-622 | $OCH(CH_3)CO_2CH(CH_3)CO_2Et$ | H | $NO_2$ | CH | S |
| 1-623 | $OCH(CH_3)CO_2CH(CH_3)CO_2Et$ | $NO_2$ | H | CH | S |
| 1-624 | $SCH_3$ | H | H | CH | S |
| 1-625 | $SCH_3$ | H | Cl | CH | S |
| 1-626 | $SCH_3$ | Cl | H | CH | S |
| 1-627 | $SCH_3$ | H | $NO_2$ | CH | S |
| 1-628 | $SCH_3$ | $NO_2$ | H | CH | S |
| 1-629 | $SCH(CH_3)CH_3$ | H | H | CH | S |
| 1-630 | $SCH(CH_3)CH_3$ | H | Cl | CH | S |
| 1-631 | $SCH(CH_3)CH_3$ | Cl | H | CH | S |
| 1-632 | $SCH(CH_3)CH_3$ | H | $NO_2$ | CH | S |
| 1-633 | $SCH(CH_3)CH_3$ | $NO_2$ | H | CH | S |
| 1-634 | $SCHCH{=}CH_2$ | H | H | CH | S |
| 1-635 | $SCHCH{=}CH_2$ | H | Cl | CH | S |
| 1-636 | $SCHCH{=}CH_2$ | Cl | H | CH | S |
| 1-637 | $SCHCH{=}CH_2$ | H | $NO_2$ | CH | S |
| 1-638 | $SCHCH{=}CH_2$ | $NO_2$ | H | CH | S |
| 1-639 | $SCHC{\equiv}CH$ | H | H | CH | S |
| 1-640 | $SCHC{\equiv}CH$ | H | Cl | CH | S |
| 1-641 | $SCHC{\equiv}CH$ | Cl | H | CH | S |
| 1-642 | $SCHC{\equiv}CH$ | H | $NO_2$ | CH | S |

TABLE 27

| Compound | $R^2$ | $R^3$ | $R^4$ | A | Y |
|---|---|---|---|---|---|
| 1-643 | SCHC≡CH | $NO_2$ | H | CH | S |
| 1-644 | $SCH_2COOH$ | H | H | CH | S |
| 1-645 | $SCH_2COOH$ | H | Cl | CH | S |
| 1-646 | $SCH_2COOH$ | Cl | H | CH | S |
| 1-647 | $SCH_2COOH$ | H | $NO_2$ | CH | S |
| 1-648 | $SCH_2COOH$ | $NO_2$ | H | CH | S |
| 1-649 | $SCH_2COOMe$ | H | H | CH | S |
| 1-650 | $SCH_2COOMe$ | H | Cl | CH | S |
| 1-651 | $SCH_2COOMe$ | Cl | H | CH | S |
| 1-652 | $SCH_2COOMe$ | H | $NO_2$ | CH | S |
| 1-653 | $SCH_2COOMe$ | $NO_2$ | H | CH | S |
| 1-654 | $SCH_2COOEt$ | H | H | CH | S |
| 1-655 | $SCH_2COOEt$ | H | Cl | CH | S |
| 1-656 | $SCH_2COOEt$ | Cl | H | CH | S |
| 1-657 | $SCH_2COOEt$ | H | $NO_2$ | CH | S |
| 1-658 | $SCH_2COOEt$ | $NO_2$ | H | CH | S |
| 1-659 | $SCH(CH_3)COOH$ | H | H | CH | S |
| 1-660 | $SCH(CH_3)COOH$ | H | Cl | CH | S |
| 1-661 | $SCH(CH_3)COOH$ | Cl | H | CH | S |
| 1-662 | $SCH(CH_3)COOH$ | H | $NO_2$ | CH | S |
| 1-663 | $SCH(CH_3)COOH$ | $NO_2$ | H | CH | S |
| 1-664 | $SCH(CH_3)COOMe$ | H | H | CH | S |
| 1-665 | $SCH(CH_3)COOMe$ | H | Cl | CH | S |
| 1-666 | $SCH(CH_3)COOMe$ | Cl | H | CH | S |
| 1-667 | $SCH(CH_3)COOMe$ | H | $NO_2$ | CH | S |

TABLE 28

| Compound | $R^2$ | $R^3$ | $R^4$ | A | Y |
|---|---|---|---|---|---|
| 1-668 | $SCH(CH_3)COOMe$ | $NO_2$ | H | CH | S |
| 1-669 | $SCH(CH_3)COOEt$ | H | H | CH | S |
| 1-670 | $SCH(CH_3)COOEt$ | H | Cl | CH | S |
| 1-671 | $SCH(CH_3)COOEt$ | Cl | H | CH | S |
| 1-672 | $SCH(CH_3)COOEt$ | H | $NO_2$ | CH | S |
| 1-673 | $SCH(CH_3)COOEt$ | $NO_2$ | H | CH | S |
| 1-674 | $SCH(CH_3)COO$-i-Pr | H | H | CH | S |
| 1-675 | $SCH(CH_3)COO$-i-Pr | H | Cl | CH | S |
| 1-676 | $SCH(CH_3)COO$-i-Pr | Cl | H | CH | S |
| 1-677 | $SCH(CH_3)COO$-i-Pr | H | $NO_2$ | CH | S |
| 1-678 | $SCH(CH_3)COO$-i-Pr | $NO_2$ | H | CH | S |
| 1-679 | $SCH(CH_3)CO_2CH_2CO_2H$ | H | H | CH | S |
| 1-680 | $SCH(CH_3)CO_2CH_2CO_2H$ | H | Cl | CH | S |
| 1-681 | $SCH(CH_3)CO_2CH_2CO_2H$ | Cl | H | CH | S |
| 1-682 | $SCH(CH_3)CO_2CH_2CO_2H$ | H | $NO_2$ | CH | S |
| 1-683 | $SCH(CH_3)CO_2CH_2CO_2H$ | $NO_2$ | H | CH | S |
| 1-684 | $SCH(CH_3)CO_2CH_2CO_2Me$ | H | H | CH | S |
| 1-685 | $SCH(CH_3)CO_2CH_2CO_2Me$ | H | Cl | CH | S |
| 1-686 | $SCH(CH_3)CO_2CH_2CO_2Me$ | Cl | H | CH | S |
| 1-687 | $SCH(CH_3)CO_2CH_2CO_2Me$ | H | $NO_2$ | CH | S |
| 1-688 | $SCH(CH_3)CO_2CH_2CO_2Me$ | $NO_2$ | H | CH | S |
| 1-689 | $SCH(CH_3)CO_2CH_2CO_2Et$ | H | H | CH | S |
| 1-690 | $SCH(CH_3)CO_2CH_2CO_2Et$ | H | Cl | CH | S |
| 1-691 | $SCH(CH_3)CO_2CH_2CO_2Et$ | Cl | H | OH | S |
| 1-692 | $SCH(CH_3)CO_2CH_2CO_2Et$ | H | $NO_2$ | CH | S |

TABLE 29

| Compound | $R^2$ | $R^3$ | $R^4$ | A | Y |
|---|---|---|---|---|---|
| 1-693 | $SCH(CH_3)CO_2CH_2CO_2Et$ | $NO_2$ | H | CH | S |
| 1-694 | $SCH(CH_3)CO_2CH(CH_3)CO_2H$ | H | H | CH | S |
| 1-695 | $SCH(CH_3)CO_2CH(CH_3)CO_2H$ | H | Cl | CH | S |
| 1-696 | $SCH(CH_3)CO_2CH(CH_3)CO_2H$ | Cl | H | CH | S |
| 1-697 | $SCH(CH_3)CO_2CH(CH_3)CO_2H$ | H | $NO_2$ | CH | S |
| 1-698 | $SCH(CH_3)CO_2CH(CH_3)CO_2H$ | $NO_2$ | H | CH | S |
| 1-699 | $SCH(CH_3)CO_2CH(CH_3)CO_2Me$ | H | H | CH | S |
| 1-700 | $SCH(CH_3)CO_2CH(CH_3)CO_2Me$ | H | Cl | CH | S |
| 1-701 | $SCH(CH_3)CO_2CH(CH_3)CO_2Me$ | Cl | H | CH | S |
| 1-702 | $SCH(CH_3)CO_2CH(CH_3)CO_2Me$ | H | $NO_2$ | CH | S |
| 1-703 | $SCH(CH_3)CO_2CH(CH_3)CO_2Me$ | $NO_2$ | H | CH | S |

TABLE 29-continued

| Compound | $R^2$ | $R^3$ | $R^4$ | A | Y |
|---|---|---|---|---|---|
| 1-704 | $SCH(CH_3)CO_2CH(CH_3)CO_2Et$ | H | H | CH | S |
| 1-705 | $SCH(CH_3)CO_2CH(CH_3)CO_2Et$ | H | Cl | CH | S |
| 1-706 | $SCH(CH_3)CO_2CH(CH_3)CO_2Et$ | Cl | H | CH | S |
| 1-707 | $SCH(CH_3)CO_2CH(CH_3)CO_2Et$ | H | $NO_2$ | CH | S |
| 1-708 | $SCH(CH_3)CO_2CH(CH_3)CO_2Et$ | $NO_2$ | H | CH | S |
| 1-709 | H | $NO_2$ | H | CH | S |
| 1-710 | C≡N | H | H | CH | S |
| 1-711 | C≡N | H | Cl | CH | S |
| 1-712 | C≡N | Cl | H | CH | S |
| 1-713 | C≡N | H | $NO_2$ | CH | S |
| 1-714 | C≡N | $NO_2$ | H | CH | S |
| 1-715 | C(=O)H | H | H | CH | S |
| 1-716 | C(=O)H | H | Cl | CH | S |
| 1-717 | C(=O)H | Cl | H | CH | S |

TABLE 30

| Compound | $R^2$ | $R^3$ | $R^4$ | A | Y |
|---|---|---|---|---|---|
| 1-718 | C(=O)H | H | $NO_2$ | CH | S |
| 1-719 | C(=O)H | $NO_2$ | H | CH | S |
| 1-720 | $C(=O)NH_2$ | H | H | CH | S |
| 1-721 | $C(=O)NH_2$ | H | Cl | CH | S |
| 1-722 | $C(=O)NH_2$ | Cl | H | CH | S |
| 1-723 | $C(=O)NH_2$ | H | $NO_2$ | CH | S |
| 1-724 | $C(=O)NH_2$ | $NO_2$ | H | CH | S |
| 1-725 | $CO_2H$ | H | H | CH | S |
| 1-726 | $CO_2H$ | H | Cl | CH | S |
| 1-727 | $CO_2H$ | Cl | H | CH | S |
| 1-728 | $CO_2H$ | H | $NO_2$ | CH | S |
| 1-729 | $CO_2H$ | $NO_2$ | H | CH | S |
| 1-730 | $CO_2Me$ | H | H | CH | S |
| 1-731 | $CO_2Me$ | H | Cl | CH | S |
| 1-732 | $CO_2Me$ | Cl | H | CH | S |
| 1-733 | $CO_2Me$ | H | $NO_2$ | CH | S |
| 1-734 | $CO_2Me$ | $NO_2$ | H | CH | S |
| 1-735 | $CO_2Et$ | H | H | CH | S |
| 1-736 | $CO_2Et$ | H | Cl | CH | S |
| 1-737 | $CO_2Et$ | Cl | H | CH | S |
| 1-738 | $CO_2Et$ | H | $NO_2$ | CH | S |
| 1-739 | $CO_2Et$ | $NO_2$ | H | CH | S |
| 1-740 | $CO_2CH_2CO_2H$ | H | H | CH | S |
| 1-741 | $CO_2CH_2CO_2H$ | H | Cl | CH | S |
| 1-742 | $CO_2CH_2CO_2H$ | Cl | H | CH | S |

TABLE 31

| Compound | $R^2$ | $R^3$ | $R^4$ | A | Y |
|---|---|---|---|---|---|
| 1-743 | $CO_2CH_2CO_2H$ | H | $NO_2$ | CH | S |
| 1-744 | $CO_2CH_2CO_2H$ | $NO_2$ | H | CH | S |
| 1-745 | $CO_2CH_2CO_2Me$ | H | H | CH | S |
| 1-746 | $CO_2CH_2CO_2Me$ | H | Cl | CH | S |
| 1-747 | $CO_2CH_2CO_2Me$ | Cl | H | CH | S |
| 1-748 | $CO_2CH_2CO_2Me$ | H | $NO_2$ | CH | S |
| 1-749 | $CO_2CH_2CO_2Me$ | $NO_2$ | H | CH | S |
| 1-750 | $CO_2CH_2CO_2Et$ | H | H | CH | S |
| 1-751 | $CO_2CH_2CO_2Et$ | H | Cl | CH | S |
| 1-752 | $CO_2CH_2CO_2Et$ | Cl | H | CH | S |
| 1-753 | $CO_2CH_2CO_2Et$ | H | $NO_2$ | CH | S |
| 1-754 | $CO_2CH_2CO_2Et$ | $NO_2$ | H | CH | S |
| 1-755 | $CO_2CH(CH_3)CO_2H$ | H | H | CH | S |
| 1-756 | $CO_2CH(CH_3)CO_2H$ | H | Cl | CH | S |
| 1-757 | $CO_2CH(CH_3)CO_2H$ | Cl | H | CH | S |
| 1-758 | $CO_2CH(CH_3)CO_2H$ | H | $NO_2$ | CH | S |
| 1-759 | $CO_2CH(CH_3)CO_2H$ | $NO_2$ | H | CH | S |
| 1-760 | $CO_2CH(CH_3)CO_2Me$ | H | H | CH | S |
| 1-761 | $CO_2CH(CH_3)CO_2Me$ | H | Cl | CH | S |
| 1-762 | $CO_2CH(CH_3)CO_2Me$ | Cl | H | CH | S |
| 1-763 | $CO_2CH(CH_3)CO_2Me$ | H | $NO_2$ | CH | S |
| 1-764 | $CO_2CH(CH_3)CO_2Me$ | $NO_2$ | H | CH | S |

TABLE 31-continued

| Compound | $R^2$ | $R^3$ | $R^4$ | A | Y |
|---|---|---|---|---|---|
| 1-765 | $CO_2CH(CH_3)CO_2Et$ | H | H | CH | S |
| 1-766 | $CO_2CH(CH_3)CO_2Et$ | H | Cl | CH | S |
| 1-767 | $CO_2CH(CH_3)CO_2Et$ | Cl | H | CH | S |

TABLE 32

| Compound | $R^2$ | $R^3$ | $R^4$ | A | Y |
|---|---|---|---|---|---|
| 1-768 | $CO_2CH(CH_3)CO_2Et$ | H | $NO_2$ | CH | S |
| 1-769 | $CO_2CH(CH_3)CO_2Et$ | $NO_2$ | H | CH | S |
| 1-770 | $CO_2C(CH_3)_2CO_2H$ | H | H | CH | S |
| 1-771 | $CO_2C(CH_3)_2CO_2H$ | H | Cl | CH | S |
| 1-772 | $CO_2C(CH_3)_2CO_2H$ | Cl | H | CH | S |
| 1-773 | $CO_2C(CH_3)_2CO_2H$ | H | $NO_2$ | CH | S |
| 1-774 | $CO_2C(CH_3)_2CO_2H$ | $NO_2$ | H | CH | S |
| 1-775 | $CO_2C(CH_3)_2CO_2Me$ | H | H | CH | S |
| 1-776 | $CO_2C(CH_3)_2CO_2Me$ | H | Cl | CH | S |
| 1-777 | $CO_2C(CH_3)_2CO_2Me$ | Cl | H | CH | S |
| 1-778 | $CO_2C(CH_3)_2CO_2Me$ | H | $NO_2$ | CH | S |
| 1-779 | $CO_2C(CH_3)_2CO_2Me$ | $NO_2$ | H | CH | S |
| 1-780 | $CO_2C(CH_3)_2CO_2Et$ | H | H | CH | S |
| 1-781 | $CO_2C(CH_3)_2CO_2Et$ | H | Cl | CH | S |
| 1-782 | $CO_2C(CH_3)_2CO_2Et$ | Cl | H | CH | S |
| 1-783 | $CO_2C(CH_3)_2CO_2Et$ | H | $NO_2$ | CH | S |
| 1-784 | $CO_2C(CH_3)_2CO_2Et$ | $NO_2$ | H | CH | S |
| 1-785 | $CH_3$ | H | H | CH | S |
| 1-786 | $CH_3$ | H | Cl | CH | S |
| 1-787 | $CH_3$ | Cl | H | CH | S |
| 1-788 | $CH_3$ | H | $NO_2$ | CH | S |
| 1-789 | $CH_3$ | $NO_2$ | H | CH | S |
| 1-790 | $CF_3$ | H | H | CH | S |
| 1-791 | $CF_3$ | H | Cl | CH | S |
| 1-792 | $CF_3$ | Cl | H | CH | S |

TABLE 33

| Compound | $R^2$ | $R^3$ | $R^4$ | A | Y |
|---|---|---|---|---|---|
| 1-793 | $CF_3$ | H | $NO_2$ | CH | S |
| 1-794 | $CF_3$ | $NO_2$ | H | CH | S |
| 1-795 | $CH{=}CHCO_2H$ | H | H | CH | S |
| 1-796 | $CH{=}CHCO_2H$ | H | Cl | CH | S |
| 1-797 | $CH{=}CHCO_2H$ | Cl | H | CH | S |
| 1-798 | $CH{=}CHCO_2H$ | H | $NO_2$ | CH | S |
| 1-799 | $CH{=}CHCO_2H$ | $NO_2$ | H | CH | S |
| 1-800 | $CH{=}CHCO_2Me$ | H | H | CH | S |
| 1-801 | $CH{=}CHCO_2Me$ | H | Cl | CH | S |
| 1-802 | $CH{=}CHCO_2Me$ | Cl | H | CH | S |
| 1-803 | $CH{=}CHCO_2Me$ | H | $NO_2$ | CH | S |
| 1-804 | $CH{=}CHCO_2Me$ | $NO_2$ | H | CH | S |
| 1-805 | $CH{=}CHCO_2Et$ | H | H | CH | S |
| 1-806 | $CH{=}CHCO_2Et$ | H | Cl | CH | S |
| 1-807 | $CH{=}CHCO_2Et$ | Cl | H | CH | S |
| 1-808 | $CH{=}CHCO_2Et$ | H | $NO_2$ | CH | S |
| 1-809 | $CH{=}CHCO_2Et$ | $NO_2$ | H | CH | S |
| 1-810 | $CH_2CH_2CO_2H$ | H | H | CH | S |
| 1-811 | $CH_2CH_2CO_2H$ | H | Cl | CH | S |
| 1-812 | $CH_2CH_2CO_2H$ | Cl | H | CH | S |
| 1-813 | $CH_2CH_2CO_2H$ | H | $NO_2$ | CH | S |
| 1-814 | $CH_2CH_2CO_2H$ | $NO_2$ | H | CH | S |
| 1-815 | $CH_2CH_2CO_2Me$ | H | H | CH | S |
| 1-816 | $CH_2CH_2CO_2Me$ | H | Cl | CH | S |
| 1-817 | $CH_2CH_2CO_2Me$ | Cl | H | CH | S |

TABLE 34

| Compound | $R^2$ | $R^3$ | $R^4$ | A | Y |
|---|---|---|---|---|---|
| 1-818 | $CH_2CH_2CO_2Me$ | H | $NO_2$ | CH | S |
| 1-819 | $CH_2CH_2CO_2Me$ | $NO_2$ | H | CH | S |
| 1-820 | $CH_2CH_2CO_2Et$ | H | H | CH | S |
| 1-821 | $CH_2CH_2CO_2Et$ | H | Cl | CH | S |
| 1-822 | $CH_2CH_2CO_2Et$ | Cl | H | CH | S |
| 1-823 | $CH_2CH_2CO_2Et$ | H | $NO_2$ | CH | S |
| 1-824 | $CH_2CH_2CO_2Et$ | $NO_2$ | H | CH | S |
| 1-825 | $CH_2CH(Cl)CO_2H$ | H | H | CH | S |
| 1-826 | $CH_2CH(Cl)CO_2H$ | H | Cl | CH | S |
| 1-827 | $CH_2CH(Cl)CO_2H$ | Cl | H | CH | S |
| 1-828 | $CH_2CH(Cl)CO_2H$ | H | $NO_2$ | CH | S |
| 1-829 | $CH_2CH(Cl)CO_2H$ | $NO_2$ | H | CH | S |
| 1-830 | $CH_2CH(Cl)CO_2Me$ | H | H | CH | S |
| 1-831 | $CH_2CH(Cl)CO_2Me$ | H | Cl | CH | S |
| 1-832 | $CH_2CH(Cl)CO_2Me$ | Cl | H | CH | S |
| 1-833 | $CH_2CH(Cl)CO_2Me$ | H | $NO_2$ | CH | S |
| 1-834 | $CH_2CH(Cl)CO_2Me$ | $NO_2$ | H | CH | S |
| 1-835 | $CH_2CH(Cl)CO_2Et$ | H | H | CH | S |
| 1-836 | $CH_2CH(Cl)CO_2Et$ | H | Cl | CH | S |
| 1-837 | $CH_2CH(Cl)CO_2Et$ | Cl | H | CH | S |
| 1-838 | $CH_2CH(Cl)CO_2Et$ | H | $NO_2$ | CH | S |
| 1-839 | $CH_2CH(Cl)CO_2Et$ | $NO_2$ | H | CH | S |
| 1-840 | $C({=}O)CH_3$ | H | H | CH | S |
| 1-841 | $C({=}O)CH_3$ | H | Cl | CH | S |
| 1-842 | $C({=}O)CH_3$ | Cl | H | CH | S |

TABLE 35

| Compound | $R^2$ | $R^3$ | $R^4$ | A | Y |
|---|---|---|---|---|---|
| 1-843 | $C({=}O)CH_3$ | H | $NO_2$ | CH | S |
| 1-844 | $C({=}O)CH_3$ | $NO_2$ | H | CH | S |
| 1-845 | $C(CH_3){=}NOH$ | H | H | CH | S |
| 1-846 | $C(CH_3){=}NOH$ | H | Cl | CH | S |
| 1-847 | $C(CH_3){=}NOH$ | Cl | H | CH | S |
| 1-848 | $C(CH_3){=}NOH$ | H | $NO_2$ | CH | S |
| 1-849 | $C(CH_3){=}NOH$ | $NO_2$ | H | CH | S |
| 1-850 | $C(CH_3){=}NOMe$ | H | H | CH | S |
| 1-851 | $C(CH_3){=}NOMe$ | H | Cl | CH | S |
| 1-852 | $C(CH_3){=}NOMe$ | Cl | H | CH | S |
| 1-853 | $C(CH_3){=}NOMe$ | H | $NO_2$ | CH | S |
| 1-854 | $C(CH_3){=}NOMe$ | $NO_2$ | H | CH | S |
| 1-855 | F | H | H | CH | S |
| 1-856 | F | H | Cl | CH | S |
| 1-857 | F | Cl | H | CH | S |
| 1-858 | F | H | $NO_2$ | CH | S |
| 1-859 | F | $NO_2$ | H | CH | S |
| 1-860 | H | H | Cl | CH | O |
| 1-861 | H | Cl | H | CH | O |
| 1-862 | H | Cl | Cl | CH | O |
| 1-863 | H | H | Cl | CH | S |
| 1-864 | H | Cl | H | CH | S |
| 1-865 | H | Cl | Cl | CH | S |
| 1-866 | $CH{=}NOH$ | H | Cl | CH | O |
| 1-867 | $CH{=}NOH$ | Cl | H | CH | O |

TABLE 36

| Compound | $R^2$ | $R^3$ | $R^4$ | A | Y |
|---|---|---|---|---|---|
| 1-868 | $CH{=}NOH$ | H | $NO_2$ | CH | O |
| 1-869 | $CH{=}NOH$ | $NO_2$ | H | CH | O |
| 1-870 | $CH{=}NOCH_3$ | H | H | CH | O |
| 1-871 | $CH{=}NOCH_3$ | H | Cl | CH | O |
| 1-872 | $CH{=}NOCH_3$ | Cl | H | CH | O |
| 1-873 | $CH{=}NOCH_3$ | H | $NO_2$ | CH | O |
| 1-874 | $CH{=}NOCH_3$ | $NO_2$ | H | CH | O |
| 1-875 | H | H | H | N | O |
| 1-876 | H | H | Cl | N | O |
| 1-877 | H | Cl | H | N | O |
| 1-878 | H | H | $NO_2$ | N | O |
| 1-879 | H | $NO_2$ | H | N | O |
| 1-880 | OH | H | H | N | O |
| 1-881 | OH | H | Cl | N | O |

TABLE 36-continued

| Compound | $R^2$ | $R^3$ | $R^4$ | A | Y |
|---|---|---|---|---|---|
| 1-882 | OH | Cl | H | N | O |
| 1-883 | OH | H | $NO_2$ | N | O |
| 1-884 | OH | $NO_2$ | H | N | O |
| 1-885 | $OCH_3$ | H | H | N | O |
| 1-886 | $OCH_3$ | H | Cl | N | O |
| 1-887 | $OCH_3$ | Cl | H | N | O |
| 1-888 | $OCH_3$ | H | $NO_2$ | N | O |
| 1-889 | $OCH_3$ | $NO_2$ | H | N | O |
| 1-890 | $OCH(CH_3)CH_3$ | H | H | N | O |
| 1-891 | $OCH(CH_3)CH_3$ | H | Cl | N | O |
| 1-892 | $OCH(CH_3)CH_3$ | Cl | H | N | O |

TABLE 37

| Compound | $R^2$ | $R^3$ | $R^4$ | A | Y |
|---|---|---|---|---|---|
| 1-893 | $OCH(CH_3)CH_3$ | H | $NO_2$ | N | O |
| 1-894 | $OCH(CH_3)CH_3$ | $NO_2$ | H | N | O |
| 1-895 | $OCH_2C{\equiv}CH$ | H | H | N | O |
| 1-896 | $OCH_2C{\equiv}CH$ | H | Cl | N | O |
| 1-897 | $OCH_2C{\equiv}CH$ | Cl | H | N | O |
| 1-898 | $OCH_2C{\equiv}CH$ | H | $NO_2$ | N | O |
| 1-899 | $OCH_2C{\equiv}CH$ | $NO_2$ | H | N | O |
| 1-900 | $OCH(CH_3)C{\equiv}CH$ | H | H | N | O |
| 1-901 | $OCH(CH_3)C{\equiv}CH$ | H | Cl | N | O |
| 1-902 | $OCH(CH_3)C{\equiv}CH$ | Cl | H | N | O |
| 1-903 | $OCH(CH_3)C{\equiv}CH$ | H | $NO_2$ | N | O |
| 1-904 | $OCH(CH_3)C{\equiv}CH$ | $NO_2$ | H | N | O |
| 1-905 | $OCH_2CH{=}CH_2$ | H | H | N | O |
| 1-906 | $OCH_2CH{=}CH_2$ | H | Cl | N | O |
| 1-907 | $OCH_2CH{=}CH_2$ | Cl | H | N | O |
| 1-908 | $OCH_2CH{=}CH_2$ | H | $NO_2$ | N | O |
| 1-909 | $OCH_2CH{=}CH_2$ | $NO_2$ | H | N | O |
| 1-910 | $OCH_2CO_2H$ | H | H | N | O |
| 1-911 | $OCH_2CO_2H$ | H | Cl | N | O |
| 1-912 | $OCH_2CO_2H$ | Cl | H | N | O |
| 1-913 | $OCH_2CO_2H$ | H | $NO_2$ | N | O |
| 1-914 | $OCH_2CO_2H$ | $NO_2$ | H | N | O |
| 1-915 | $OCH_2CO_2Et$ | H | H | N | O |
| 1-916 | $OCH_2CO_2Et$ | H | Cl | N | O |
| 1-917 | $OCH_2CO_2Et$ | Cl | H | N | O |

TABLE 38

| Compound | $R^2$ | $R^3$ | $R^4$ | A | Y |
|---|---|---|---|---|---|
| 1-918 | $OCH_2CO_2Et$ | H | $NO_2$ | N | O |
| 1-919 | $OCH_2CO_2Et$ | $NO_2$ | H | N | O |
| 1-920 | $OCH(CH_3)CO_2H$ | H | H | N | O |
| 1-921 | $OCH(CH_3)CO_2H$ | H | Cl | N | O |
| 1-922 | $OCH(CH_3)CO_2H$ | Cl | H | N | O |
| 1-923 | $OCH(CH_3)CO_2H$ | H | $NO_2$ | N | O |
| 1-924 | $OCH(CH_3)CO_2H$ | $NO_2$ | H | N | O |
| 1-925 | $OCH(CH_3)CO_2Me$ | H | H | N | O |
| 1-926 | $OCH(CH_3)CO_2Me$ | H | Cl | N | O |
| 1-927 | $OCH(CH_3)CO_2Me$ | Cl | H | N | O |
| 1-928 | $OCH(CH_3)CO_2Me$ | H | $NO_2$ | N | O |
| 1-929 | $OCH(CH_3)CO_2Me$ | $NO_2$ | H | N | O |
| 1-930 | $OCH(CH_3)CO_2Et$ | H | H | N | O |
| 1-931 | $OCH(CH_3)CO_2Et$ | H | Cl | N | O |
| 1-932 | $OCH(CH_3)CO_2Et$ | Cl | H | N | O |
| 1-933 | $OCH(CH_3)CO_2Et$ | H | $NO_2$ | N | O |
| 1-934 | $OCH(CH_3)CO_2Et$ | $NO_2$ | H | N | O |
| 1-935 | $CO_2H$ | H | H | N | O |
| 1-936 | $CO_2H$ | H | Cl | N | O |
| 1-937 | $CO_2H$ | Cl | H | N | O |
| 1-938 | $CO_2H$ | H | $NO_2$ | N | O |
| 1-939 | $CO_2H$ | $NO_2$ | H | N | O |
| 1-940 | $CO_2Me$ | H | H | N | O |
| 1-941 | $CO_2Me$ | H | Cl | N | O |
| 1-942 | $CO_2Me$ | Cl | H | N | O |

TABLE 39

| Compound | $R^2$ | $R^3$ | $R^4$ | A | Y |
|---|---|---|---|---|---|
| 1-943 | $CO_2Me$ | H | $NO_2$ | N | O |
| 1-944 | $CO_2Me$ | $NO_2$ | H | N | O |
| 1-945 | $CO_2Et$ | H | H | N | O |
| 1-946 | $CO_2Et$ | H | Cl | N | O |
| 1-947 | $CO_2Et$ | Cl | H | N | O |
| 1-948 | $CO_2Et$ | H | $NO_2$ | N | O |
| 1-949 | $CO_2Et$ | $NO_2$ | H | N | O |
| 1-950 | $CO_2CH(CH_3)CO_2Et$ | H | H | N | O |
| 1-951 | $CO_2CH(CH_3)CO_2Et$ | H | Cl | N | O |
| 1-952 | $CO_2CH(CH_3)CO_2Et$ | Cl | H | N | O |
| 1-953 | $CO_2CH(CH_3)CO_2Et$ | H | $NO_2$ | N | O |
| 1-954 | $CO_2CH(CH_3)CO_2Et$ | $NO_2$ | H | N | O |
| 1-955 | $CO_2C(CH_3)_2CO_2Et$ | H | H | N | O |
| 1-956 | $CO_2C(CH_3)_2CO_2Et$ | H | Cl | N | O |
| 1-957 | $CO_2C(CH_3)_2CO_2Et$ | Cl | H | N | O |
| 1-958 | $CO_2C(CH_3)_2CO_2Et$ | H | $NO_2$ | N | O |
| 1-959 | $CO_2C(CH_3)_2CO_2Et$ | $NO_2$ | H | N | O |
| 1-960 | C(=O)H | H | H | N | O |
| 1-961 | C(=O)H | H | Cl | N | O |
| 1-962 | C(=O)H | Cl | H | N | O |
| 1-963 | C(=O)H | H | $NO_2$ | N | O |
| 1-964 | C(=O)H | $NO_2$ | H | N | O |
| 1-965 | $CH{=}CHCO_2Et$ | H | H | N | O |
| 1-966 | $CH{=}CHCO_2Et$ | H | Cl | N | O |
| 1-967 | $CH{=}CHCO_2Et$ | Cl | H | N | O |

TABLE 40

| Compound | $R^2$ | $R^3$ | $R^4$ | A | Y |
|---|---|---|---|---|---|
| 1-968 | $CH{=}CHCO_2Et$ | H | $NO_2$ | N | O |
| 1-969 | $CH{=}CHCO_2Et$ | $NO_2$ | H | N | O |
| 1-970 | CH=NOH | H | H | N | O |
| 1-971 | CH=NOH | H | Cl | N | O |
| 1-972 | CH=NOH | Cl | H | N | O |
| 1-973 | CH=NOH | H | $NO_2$ | N | O |
| 1-974 | CH=NOH | $NO_2$ | H | N | O |
| 1-975 | $CH{=}NOCH_3$ | H | H | N | O |
| 1-976 | $CH{=}NOCH_3$ | H | Cl | N | O |
| 1-977 | $CH{=}NOCH_3$ | Cl | H | N | O |
| 1-978 | $CH{=}NOCH_3$ | H | $NO_2$ | N | O |
| 1-979 | $CH{=}NOCH_3$ | $NO_2$ | H | N | O |
| 1-980 | $CH_2CH_2CO_2Et$ | H | H | N | O |
| 1-981 | $CH_2CH_2CO_2Et$ | H | Cl | N | O |
| 1-982 | $CH_2CH_2CO_2Et$ | Cl | H | N | O |
| 1-983 | $CH_2CH_2CO_2Et$ | H | $NO_2$ | N | O |
| 1-984 | $CH_2CH_2CO_2Et$ | $NO_2$ | H | N | O |
| 1-985 | $CH_2CH(Cl)CO_2Et$ | H | H | N | O |
| 1-986 | $CH_2CH(Cl)CO_2Et$ | H | Cl | N | O |
| 1-987 | $CH_2CH(Cl)CO_2Et$ | Cl | H | N | O |
| 1-988 | $CH_2CH(Cl)CO_2Et$ | H | $NO_2$ | N | O |
| 1-989 | $CH_2CH(Cl)CO_2Et$ | $NO_2$ | H | N | O |
| 1-990 | H | Cl | Cl | N | O |
| 1-991 | $CF_3$ | H | Cl | N | O |
| 1-992 | $CF_3$ | Cl | H | N | O |

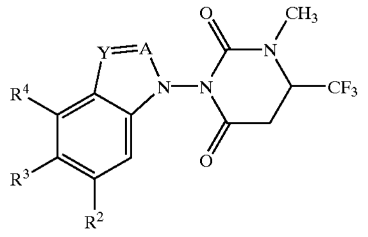

TABLE 41

| Compound | $R^2$ | $R^3$ | $R^4$ | A | Y |
|---|---|---|---|---|---|
| 1-2001 | H | H | H | CH | CH |
| 1-2002 | Cl | H | H | CH | CH |

TABLE 41-continued

| Compound | $R^2$ | $R^3$ | $R^4$ | A | Y |
|---|---|---|---|---|---|
| 1-2003 | H | Cl | H | CH | CH |
| 1-2004 | H | H | Cl | CH | CH |
| 1-2005 | $NO_2$ | H | H | CH | CH |
| 1-2006 | H | $NO_2$ | H | CH | CH |
| 1-2007 | H | H | $NO_2$ | CH | CH |
| 1-2008 | OH | H | H | CH | CH |
| 1-2009 | $OCH_3$ | H | H | CH | CH |
| 1-2010 | $OCH_2CO_2CH_3$ | H | H | CH | CH |
| 1-2011 | $OCH_2CO_2C_2H_5$ | H | H | CH | CH |
| 1-2012 | $OCH(CH_3)CO_2CH_3$ | H | H | CH | CH |
| 1-2013 | $OCH(CH_3)CO_2C_2H_5$ | H | H | CH | CH |
| 1-2014 | $OC(CH_3)_2CO_2CH_3$ | H | H | CH | CH |
| 1-2015 | $OC(CH_3)_2CO_2C_2H_5$ | H | H | CH | CH |
| 1-2016 | $CO_2H$ | H | H | CH | CH |
| 1-2017 | $CO_2CH_3$ | H | H | CH | CH |
| 1-2018 | $CO_2C_2H_5$ | H | H | CH | CH |
| 1-2019 | $CO_2CH_2CO_2C_2H_5$ | H | H | CH | CH |
| 1-2020 | $CO_2CH(CH_3)CO_2C_2H_5$ | H | H | CH | CH |
| 1-2021 | $CO_2C(CH_3)_2CO_2C_2H_5$ | H | H | CH | CH |
| 1-2022 | OH | Cl | H | CH | CH |
| 1-2023 | $OCH_3$ | Cl | H | CH | CH |
| 1-2024 | $OCH_2CO_2CH_3$ | Cl | H | CH | CH |
| 1-2025 | $OCH_2CO_2C_2H_5$ | Cl | H | CH | CH |

TABLE 42

| Compound | $R^2$ | $R^3$ | $R^4$ | A | Y |
|---|---|---|---|---|---|
| 1-2026 | $OCH(CH_3)CO_2CH_3$ | Cl | H | CH | CH |
| 1-2027 | $OCH(CH_3)CO_2C_2H_5$ | Cl | H | CH | CH |
| 1-2028 | $OC(CH_3)_2CO_2CH_3$ | Cl | H | CH | CH |
| 1-2029 | $OC(CH_3)_2CO_2C_2H_5$ | Cl | H | CH | CH |
| 1-2030 | $CO_2H$ | Cl | H | CH | CH |
| 1-2031 | $CO_2CH_3$ | Cl | H | CH | CH |
| 1-2032 | $CO_2C_2H_5$ | Cl | H | CH | CH |
| 1-2033 | $CO_2CH_2CO_2C_2H_5$ | Cl | H | CH | CH |
| 1-2034 | $CO_2CH(CH_3)CO_2C_2H_5$ | Cl | H | CH | CH |
| 1-2035 | $CO_2C(CH_3)_2CO_2C_2H_5$ | Cl | H | CH | CH |
| 1-2036 | OH | $NO_2$ | H | CH | CH |
| 1-2037 | $OCH_3$ | $NO_2$ | H | CH | CH |
| 1-2038 | $OCH_2CO_2CH_3$ | $NO_2$ | H | CH | CH |
| 1-2039 | $OCH_2CO_2C_2H_5$ | $NO_2$ | H | CH | CH |
| 1-2040 | $OCH(CH_3)CO_2CH_3$ | $NO_2$ | H | CH | CH |
| 1-2041 | $OCH(CH_3)CO_2C_2H_5$ | $NO_2$ | H | CH | CH |
| 1-2042 | $OC(CH_3)_2CO_2CH_3$ | $NO_2$ | H | CH | CH |
| 1-2043 | $OC(CH_3)_2CO_2C_2H_5$ | $NO_2$ | H | CH | CH |
| 1-2044 | $CO_2H$ | $NO_2$ | H | CH | CH |
| 1-2045 | $CO_2CH_3$ | $NO_2$ | H | CH | CH |
| 1-2046 | $CO_2C_2H_5$ | $NO_2$ | H | CH | CH |
| 1-2047 | $CO_2CH_2CO_2C_2H_5$ | $NO_2$ | H | CH | CH |
| 1-2048 | $CO_2CH(CH_3)CO_2C_2H_5$ | $NO_2$ | H | CH | CH |
| 1-2049 | $CO_2C(CH_3)_2CO_2C_2H_5$ | $NO_2$ | H | CH | CH |
| 1-2050 | Cl | H | Cl | CH | CH |

TABLE 43

| Compound | $R^2$ | $R^3$ | $R^4$ | A | Y |
|---|---|---|---|---|---|
| 1-2051 | H | H | H | N | CH |
| 1-2052 | Cl | H | H | N | CH |
| 1-2053 | H | Cl | H | N | CH |
| 1-2054 | H | H | Cl | N | CH |
| 1-2055 | $NO_2$ | H | H | N | CH |
| 1-2056 | H | $NO_2$ | H | N | CH |
| 1-2057 | H | H | $NO_2$ | N | CH |
| 1-2058 | OH | H | H | N | CH |
| 1-2059 | $OCH_3$ | H | H | N | CH |
| 1-2060 | $OCH_2CO_2CH_3$ | H | H | N | CH |
| 1-2061 | $OCH_2CO_2C_2H_5$ | H | H | N | CH |
| 1-2062 | $OCH(CH_3)CO_2CH_3$ | H | H | N | CH |
| 1-2063 | $OCH(CH_3)_2CO_2C_2H_5$ | H | H | N | CH |
| 1-2064 | $OC(CH_3)_2CO_2CH_3$ | H | H | N | CH |

TABLE 43-continued

| Compound | $R^2$ | $R^3$ | $R^4$ | A | Y |
|---|---|---|---|---|---|
| 1-2065 | $OC(CH_3)_2CO_2C_2H_5$ | H | H | N | CH |
| 1-2066 | $CO_2H$ | H | H | N | CH |
| 1-2067 | $CO_2CH_3$ | H | H | N | CH |
| 1-2068 | $CO_2C_2H_5$ | H | H | N | CH |
| 1-2069 | $CO_2CH_2CO_2C_2H_5$ | H | H | N | CH |
| 1-2070 | $CO_2CH(CH_3)CO_2C_2H_5$ | H | H | N | CH |
| 1-2071 | $CO_2C(CH_3)_2CO_2C_2H_5$ | H | H | N | CH |
| 1-2072 | OH | Cl | H | N | CH |
| 1-2073 | $OCH_3$ | Cl | H | N | CH |
| 1-2074 | $OCH_2CO_2CH_3$ | Cl | H | N | CH |
| 1-2075 | $OCH_2CO_2C_2H_5$ | Cl | H | N | CH |

TABLE 44

| Compound | $R^2$ | $R^3$ | $R^4$ | A | Y |
|---|---|---|---|---|---|
| 1-2076 | $OCH(CH_3)CO_2CH_3$ | Cl | H | N | CH |
| 1-2077 | $OCH(CH_3)CO_2C_2H_5$ | Cl | H | N | CH |
| 1-2078 | $OC(CH_3)_2CO_2CH_3$ | Cl | H | N | CH |
| 1-2079 | $OC(CH_3)_2CO_2C_2H_5$ | Cl | H | N | CH |
| 1-2080 | $CO_2H$ | Cl | H | N | CH |
| 1-2081 | $CO_2CH_3$ | Cl | H | N | CH |
| 1-2082 | $CO_2C_2H_5$ | Cl | H | N | CH |
| 1-2083 | $CO_2CH_2CO_2C_2H_5$ | Cl | H | N | CH |
| 1-2084 | $CO_2CH(CH_3)CO_2C_2H_5$ | Cl | H | N | CH |
| 1-2085 | $CO_2C(CH_3)_2CO_2C_2H_5$ | Cl | H | N | CH |
| 1-2086 | OH | $NO_2$ | H | N | CH |
| 1-2087 | $OCH_3$ | $NO_2$ | H | N | CH |
| 1-2088 | $OCH_2CO_2CH_3$ | $NO_2$ | H | N | CH |
| 1-2089 | $OCH_2CO_2C_2H_5$ | $NO_2$ | H | N | CH |
| 1-2090 | $OCH(CH_3)CO_2CH_3$ | $NO_2$ | H | N | CH |
| 1-2091 | $OCH(CH_3)CO_2C_2H_5$ | $NO_2$ | H | N | CH |
| 1-2092 | $OC(CH_3)_2CO_2CH_3$ | $NO_2$ | H | N | CH |
| 1-2093 | $OC(CH_3)_2CO_2C_2H_5$ | $NO_2$ | H | N | CH |
| 1-2094 | $CO_2H$ | $NO_2$ | H | N | CH |
| 1-2095 | $CO_2CH_3$ | $NO_2$ | H | N | CH |
| 1-2096 | $CO_2C_2H_5$ | $NO_2$ | H | N | CH |
| 1-2097 | $CO_2CH_2CO_2C_2H_5$ | $NO_2$ | H | N | CH |
| 1-2098 | $CO_2CH(CH_3)CO_2C_2H_5$ | $NO_2$ | H | N | CH |
| 1-2099 | $CO_2C(CH_3)_2CO_2C_2H_5$ | $NO_2$ | H | N | CH |
| 1-2100 | Cl | H | Cl | N | CH |

TABLE 45

| Compound | $R^2$ | $R^3$ | $R^4$ | A | Y |
|---|---|---|---|---|---|
| 1-2101 | H | H | H | CH | N |
| 1-2102 | Cl | H | H | CH | N |
| 1-2103 | H | Cl | H | CH | N |
| 1-2104 | H | H | Cl | CH | N |
| 1-2105 | $NO_2$ | H | H | CH | N |
| 1-2106 | H | $NO_2$ | H | CH | N |
| 1-2107 | H | H | $NO_2$ | CH | N |
| 1-2108 | OH | H | H | CH | N |
| 1-2109 | $OCH_3$ | H | H | CH | N |
| 1-2110 | $OCH_2CO_2CH_3$ | H | H | CH | N |
| 1-2111 | $OCH_2CO_2C_2H_5$ | H | H | CH | N |
| 1-2112 | $OCH(CH_3)CO_2CH_3$ | H | H | CH | N |
| 1-2113 | $OCH(CH_3)CO_2C_2H_5$ | H | H | CH | N |
| 1-2114 | $OC(CH_3)_2CO_2CH_3$ | H | H | CH | N |
| 1-2115 | $OC(CH_3)_2CO_2C_2H_5$ | H | H | CH | N |
| 1-2116 | $CO_2H$ | H | H | CH | N |
| 1-2117 | $CO_2CH_3$ | H | H | CH | N |
| 1-2118 | $CO_2C_2H_5$ | H | H | CH | N |
| 1-2119 | $CO_2CH_2CO_2C_2H_5$ | H | H | CH | N |
| 1-2120 | $CO_2CH(CH_3)CO_2C_2H_5$ | H | H | CH | N |
| 1-2121 | $CO_2C(CH_3)_2CO_2C_2H_5$ | H | H | CH | N |
| 1-2122 | OH | Cl | H | CH | N |
| 1-2123 | $OCH_3$ | Cl | H | CH | N |
| 1-2124 | $OCH_2CO_2CH_3$ | Cl | H | CH | N |
| 1-2125 | $OCH_2CO_2C_2H_5$ | Cl | H | CH | N |

TABLE 46

| Compound | $R^2$ | $R^3$ | $R^4$ | A | Y |
|---|---|---|---|---|---|
| 1-2126 | $OCH(CH_3)CO_2CH_3$ | Cl | H | CH | N |
| 1-2127 | $OCH(CH_3)CO_2C_2H_5$ | Cl | H | CH | N |
| 1-2128 | $OC(CH_3)_2CO_2CH_3$ | Cl | H | CH | N |
| 1-2129 | $OC(CH_3)_2CO_2C_2H_5$ | Cl | H | CH | N |
| 1-2130 | $CO_2H$ | Cl | H | CH | N |
| 1-2131 | $CO_2CH_3$ | Cl | H | CH | N |
| 1-2132 | $CO_2C_2H_5$ | Cl | H | CH | N |
| 1-2133 | $CO_2CH_2CO_2C_2H_5$ | Cl | H | CH | N |
| 1-2134 | $CO_2CH(CH_3)CO_2C_2H_5$ | Cl | H | CH | N |
| 1-2135 | $CO_2C(CH_3)_2CO_2C_2H_5$ | Cl | H | CH | N |
| 1-2136 | OH | $NO_2$ | H | CH | N |
| 1-2137 | $OCH_3$ | $NO_2$ | H | CH | N |
| 1-2138 | $OCH_2CO_2CH_3$ | $NO_2$ | H | CH | N |
| 1-2139 | $OCH_2CO_2C_2H_5$ | $NO_2$ | H | CH | N |
| 1-2140 | $OCH(CH_3)CO_2CH_3$ | $NO_2$ | H | CH | N |
| 1-2141 | $OCH(CH_3)CO_2C_2H_5$ | $NO_2$ | H | CH | N |
| 1-2142 | $OC(CH_3)_2CO_2CH_3$ | $NO_2$ | H | CH | N |
| 1-2143 | $OC(CH_3)_2CO_2C_2H_5$ | $NO_2$ | H | CH | N |
| 1-2144 | $CO_2H$ | $NO_2$ | H | CH | N |
| 1-2145 | $CO_2CH_3$ | $NO_2$ | H | CH | N |
| 1-2146 | $CO_2C_2H_5$ | $NO_2$ | H | CH | N |
| 1-2147 | $CO_2CH_2CO_2C_2H_5$ | $NO_2$ | H | CH | N |
| 1-2148 | $CO_2CH(CH_3)CO_2C_2H_5$ | $NO_2$ | H | CH | N |
| 1-2149 | $CO_2C(CH_3)_2CO_2C_2H_5$ | $NO_2$ | H | CH | N |
| 1-2150 | Cl | H | Cl | CH | N |

TABLE 47

| Compound | $R^2$ | $R^3$ | $R^4$ | A | Y |
|---|---|---|---|---|---|
| 1-2151 | H | H | H | N | N |
| 1-2152 | Cl | H | H | N | N |
| 1-2153 | H | Cl | H | N | N |
| 1-2154 | H | H | Cl | N | N |
| 1-2155 | $NO_2$ | H | H | N | N |
| 1-2156 | H | $NO_2$ | H | N | N |
| 1-2157 | H | H | $NO_2$ | N | N |
| 1-2158 | OH | H | H | N | N |
| 1-2159 | $OCH_3$ | H | H | N | N |
| 1-2160 | $OCH_2CO_2CH_3$ | H | H | N | N |
| 1-2161 | $OCH_2CO_2C_2H_5$ | H | H | N | N |
| 1-2162 | $OCH(CH_3)CO_2CH_3$ | H | H | N | N |
| 1-2163 | $OCH(CH_3)CO_2C_2H_5$ | H | H | N | N |
| 1-2164 | $OC(CH_3)_2CO_2CH_3$ | H | H | N | N |
| 1-2165 | $OC(CH_3)_2CO_2C_2H_5$ | H | H | N | N |
| 1-2166 | $CO_2H$ | H | H | N | N |
| 1-2167 | $CO_2CH_3$ | H | H | N | N |
| 1-2168 | $CO_2C_2H_5$ | H | H | N | N |
| 1-2169 | $CO_2CH_2CO_2C_2H_5$ | H | H | N | N |
| 1-2170 | $CO_2CH(CH_3)CO_2C_2H_5$ | H | H | N | N |
| 1-2171 | $CO_2C(CH_3)_2CO_2C_2H_5$ | H | H | N | N |
| 1-2172 | OH | Cl | H | N | N |
| 1-2173 | $OCH_3$ | Cl | H | N | N |
| 1-2174 | $OCH_2CO_2CH_3$ | Cl | H | N | N |
| 1-2175 | $OCH_2CO_2C_2H_5$ | Cl | H | N | N |

TABLE 48

| Compound | $R^2$ | $R^3$ | $R^4$ | A | Y |
|---|---|---|---|---|---|
| 1-2176 | $OCH(CH_3)CO_2CH_3$ | Cl | H | N | N |
| 1-2177 | $OCH(CH_3)CO_2C_2H_5$ | Cl | H | N | N |
| 1-2178 | $OC(CH_3)_2CO_2CH_3$ | Cl | H | N | N |
| 1-2179 | $OC(CH_3)_2CO_2C_2H_5$ | Cl | H | N | N |
| 1-2180 | $CO_2H$ | Cl | H | N | N |
| 1-2181 | $CO_2CH_3$ | Cl | H | N | N |
| 1-2182 | $CO_2C_2H_5$ | Cl | H | N | N |
| 1-2183 | $CO_2CH_2CO_2C_2H_5$ | Cl | H | N | N |
| 1-2184 | $CO_2CH(CH_3)CO_2C_2H_5$ | Cl | H | N | N |
| 1-2185 | $CO_2C(CH_3)_2CO_2C_2H_5$ | Cl | H | N | N |
| 1-2186 | OH | $NO_2$ | H | N | N |
| 1-2187 | $OCH_3$ | $NO_2$ | H | N | N |

TABLE 48-continued

| Compound | $R^2$ | $R^3$ | $R^4$ | A | Y |
|---|---|---|---|---|---|
| 1-2188 | $OCH_2CO_2CH_3$ | $NO_2$ | H | N | N |
| 1-2189 | $OCH_2CO_2C_2H_5$ | $NO_2$ | H | N | N |
| 1-2190 | $OCH(CH_3)CO_2CH_3$ | $NO_2$ | H | N | N |
| 1-2191 | $OCH(CH_3)CO_2C_2H_5$ | $NO_2$ | H | N | N |
| 1-2192 | $OC(CH_3)_2CO_2CH_3$ | $NO_2$ | H | N | N |
| 1-2193 | $OC(CH_3)_2CO_2C_2H_5$ | $NO_2$ | H | N | N |
| 1-2194 | $CO_2H$ | $NO_2$ | H | N | N |
| 1-2195 | $CO_2CH_3$ | $NO_2$ | H | N | N |
| 1-2196 | $CO_2C_2H_5$ | $NO_2$ | H | N | N |
| 1-2197 | $CO_2CH_2CO_2C_2H_5$ | $NO_2$ | H | N | N |
| 1-2198 | $CO_2CH(CH_3)CO_2C_2H_5$ | $NO_2$ | H | N | N |
| 1-2199 | $CO_2C(CH_3)_2CO_2C_2H_5$ | $NO_2$ | H | N | N |
| 1-2200 | Cl | H | Cl | N | N |

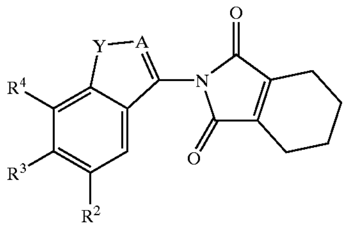

TABLE 49

| Compound | $R^2$ | $R^3$ | $R^4$ | A | Y |
|---|---|---|---|---|---|
| 2-1 | H | H | H | CH | O |
| 2-2 | Cl | H | Cl | CH | O |
| 2-3 | H | H | H | CH | S |
| 2-4 | H | H | H | N | O |
| 2-5 | Cl | H | Cl | N | O |
| 2-6 | H | H | H | N | S |
| 2-7 | $OCH_3$ | H | H | CH | O |
| 2-8 | $OCH_3$ | H | H | N | O |
| 2-9 | $NHCH_3$ | H | H | CH | O |
| 2-10 | $NHCH_3$ | H | H | N | O |
| 2-11 | $OCH_2CH{=}CH_2$ | H | H | CH | O |
| 2-12 | $OCH_2CH{=}CH_2$ | H | H | N | O |
| 2-13 | $CO_2CH_2CO_2Et$ | H | H | CH | O |
| 2-14 | $CO_2CH_2CO_2Et$ | H | H | N | O |
| 2-15 | $OCH_2CO_2C_2H_5$ | H | H | CH | O |
| 2-16 | $OCH_2CO_2C_2H_5$ | H | H | N | O |
| 2-17 | $OCH(CH_3)CH{=}CH_2$ | H | H | CH | O |
| 2-18 | $OCH(CH_3)CH{=}CH_2$ | H | H | N | O |
| 2-19 | $CO_2CH(CH_3)CO_2Et$ | H | H | CH | O |
| 2-20 | $CO_2CH(CH_3)CO_2Et$ | H | H | N | O |
| 2-21 | $OCH(CH_3)CO_2C_2H_5$ | H | H | CH | O |
| 2-22 | $OCH(CH_3)CO_2C_2H_5$ | H | H | N | O |
| 2-23 | $OCH(CH_3)C{\equiv}CH$ | H | H | CH | O |
| 2-24 | $OCH(CH_3)C{\equiv}CH$ | H | H | N | O |
| 2-25 | $OCH_2C{\equiv}CH$ | H | H | CH | O |

TABLE 50

| Compound | $R^2$ | $R^3$ | $R^4$ | A | Y |
|---|---|---|---|---|---|
| 2-26 | $OCH_2C{\equiv}CH$ | H | H | N | O |
| 2-27 | $OCH_3$ | $NO_2$ | H | CH | O |
| 2-28 | $OCH_3$ | $NO_2$ | H | N | O |
| 2-29 | $OCH_3$ | H | Cl | CH | O |
| 2-30 | $OCH_3$ | H | Cl | N | O |
| 2-31 | $CH_2CO_2CH_3$ | H | H | CH | O |
| 2-32 | $CH_2CO_2CH_3$ | H | H | N | O |
| 2-33 | $CH_2CO_2CH_3$ | $NO_2$ | H | CH | O |
| 2-34 | $CH_2CO_2CH_3$ | $NO_2$ | H | N | O |
| 2-35 | $CH_2CO_2CH_3$ | H | Cl | CH | O |

TABLE 50-continued

| Compound | $R^2$ | $R^3$ | $R^4$ | A | Y |
|---|---|---|---|---|---|
| 2-36 | $CH_2CO_2CH_3$ | H | Cl | N | O |
| 2-37 | $OCH(CH_3)CO_2C_2H_5$ | $NO_2$ | H | CH | O |
| 2-38 | $OCH(CH_3)CO_2C_2H_5$ | $NO_2$ | H | N | O |
| 2-39 | $OCH(CH_3)CO_2C_2H_5$ | H | Cl | CH | O |
| 2-40 | $OCH(CH_3)CO_2C_2H_5$ | H | Cl | N | O |
| 2-41 | $OCH_2C\equiv CH$ | $NO_2$ | H | CH | O |
| 2-42 | $OCH_2C\equiv CH$ | $NO_2$ | H | N | O |
| 2-43 | $OCH_2C\equiv CH$ | H | Cl | CH | O |
| 2-44 | $OCH_2C\equiv CH$ | H | Cl | N | O |
| 2-45 | $OCH(CH_3)C\equiv CH$ | $NO_2$ | H | N | O |
| 2-46 | $OCH(CH_3)C\equiv CH$ | $NO_2$ | H | CH | O |
| 2-47 | $OCH(CH_3)C\equiv CH$ | H | Cl | N | O |
| 2-48 | $OCH(CH_3)C\equiv CH$ | H | Cl | CH | O |
| 2-49 | $SCH(CH_3)CO_2C_2H_5$ | $NO_2$ | H | CH | O |
| 2-50 | $SCH(CH_3)CO_2C_2H_5$ | $NO_2$ | H | N | O |

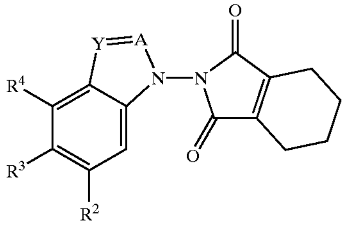

TABLE 51

| Compound | $R^2$ | $R^3$ | $R^4$ | A | Y |
|---|---|---|---|---|---|
| 2-2001 | H | H | H | CH | CH |
| 2-2002 | H | H | H | CH | N |
| 2-2003 | H | H | H | N | CH |
| 2-2004 | H | H | H | N | N |
| 2-2005 | $OCH_3$ | H | H | CH | CH |
| 2-2006 | $OCH_3$ | H | H | CH | N |
| 2-2007 | $OCH_3$ | H | H | N | CH |
| 2-2008 | $OCH_3$ | H | H | N | N |
| 2-2009 | $CO_2Et$ | H | H | CH | CH |
| 2-2010 | $CO_2Et$ | H | H | CH | N |
| 2-2011 | $CO_2Et$ | H | H | N | CH |
| 2-2012 | $CO_2Et$ | H | H | N | N |
| 2-2013 | $OCH_2CO_2C_2H_5$ | H | H | CH | CH |
| 2-2014 | $OCH_2CO_2C_2H_5$ | H | H | CH | N |
| 2-2015 | $OCH_2CO_2C_2H_5$ | H | H | N | CH |
| 2-2016 | $OCH_2CO_2C_2H_5$ | H | H | N | N |
| 2-2017 | $OCH(CH_3)CO_2C_2H_5$ | H | H | CH | CH |
| 2-2018 | $OCH(CH_3)CO_2C_2H_5$ | H | H | CH | N |
| 2-2019 | $OCH(CH_3)CO_2C_2H_5$ | H | H | N | CH |
| 2-2020 | $OCH(CH_3)CO_2C_2H_5$ | H | H | N | N |
| 2-2021 | $OCH_2C\equiv CH$ | H | H | CH | CH |
| 2-2022 | $OCH_2C\equiv CH$ | H | H | CH | N |
| 2-2023 | $OCH_2C\equiv CH$ | H | H | N | CH |
| 2-2024 | $OCH_2C\equiv CH$ | H | H | N | N |
| 2-2025 | $OCH(CH_3)C\equiv CH$ | H | H | N | N |

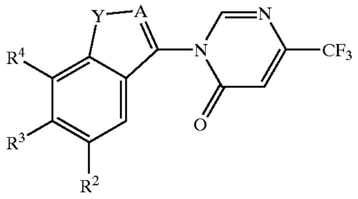

TABLE 52

| Compound | $R^2$ | $R^3$ | $R^4$ | A | Y |
|---|---|---|---|---|---|
| 3-1 | H | H | H | CH | O |
| 3-2 | Cl | H | Cl | CH | O |

TABLE 52-continued

| Compound | $R^2$ | $R^3$ | $R^4$ | A | Y |
|---|---|---|---|---|---|
| 3-3 | H | H | H | CH | S |
| 3-4 | H | H | H | N | O |
| 3-5 | Cl | H | Cl | N | O |
| 3-6 | H | H | H | N | S |
| 3-7 | $OCH_3$ | H | H | CH | O |
| 3-8 | $OCH_3$ | H | H | N | O |
| 3-9 | $NHCH_3$ | H | H | CH | O |
| 3-10 | $NHCH_3$ | H | H | N | O |
| 3-11 | $OCH_2CH{=}CH_2$ | H | H | CH | O |
| 3-12 | $OCH_2CH{=}CH_2$ | H | H | N | O |
| 3-13 | $CO_2CH_2CO_2Et$ | H | H | CH | O |
| 3-14 | $CO_2CH_2CO_2Et$ | H | H | N | O |
| 3-15 | $OCH_2CO_2C_2H_5$ | H | H | CH | O |
| 3-16 | $OCH_2CO_2C_2H_5$ | H | H | N | O |
| 3-17 | $OCH(CH_3)CH{=}CH_2$ | H | H | CH | O |
| 3-18 | $OCH(CH_3)CH{=}CH_2$ | H | H | N | O |
| 3-19 | $CO_2CH(CH_3)CO_2Et$ | H | H | CH | O |
| 3-20 | $CO_2CH(CH_3)CO_2Et$ | H | H | N | O |
| 3-21 | $OCH(CH_3)CO_2C_2H_5$ | H | H | CH | O |
| 3-22 | $OCH(CH_3)CO_2C_2H_5$ | H | H | N | O |
| 3-23 | $OCH(CH_3)C\equiv CH$ | H | H | CH | O |
| 3-24 | $OCH(CH_3)C\equiv CH$ | H | H | N | O |
| 3-25 | $OCH_2C\equiv CH$ | H | H | CH | O |

TABLE 53

| Compound | $R^2$ | $R^3$ | $R^4$ | A | Y |
|---|---|---|---|---|---|
| 3-26 | $OCH_2C\equiv CH$ | H | H | N | O |
| 3-27 | $OCH_3$ | $NO_2$ | H | CH | O |
| 3-28 | $OCH_3$ | $NO_2$ | H | N | O |
| 3-29 | $OCH_3$ | H | Cl | CH | O |
| 3-30 | $OCH_3$ | H | Cl | N | O |
| 3-31 | $CH_2CO_2CH_3$ | H | H | CH | O |
| 3-32 | $CH_2CO_2CH_3$ | H | H | N | O |
| 3-33 | $CH_2CO_2CH_3$ | $NO_2$ | H | CH | O |
| 3-34 | $CH_2CO_2CH_3$ | $NO_2$ | H | N | O |
| 3-35 | $CH_2CO_2CH_3$ | H | Cl | CH | O |
| 3-36 | $CH_2CO_2CH_3$ | H | Cl | N | O |
| 3-37 | $OCH(CH_3)CO_2C_2H_5$ | $NO_2$ | H | CH | O |
| 3-38 | $OCH(CH_3)CO_2C_2H_5$ | $NO_2$ | H | N | O |
| 3-39 | $OCH(CH_3)CO_2C_2H_5$ | H | Cl | CH | O |
| 3-40 | $OCH(CH_3)CO_2C_2H_5$ | H | Cl | N | O |
| 3-41 | $OCH_2C\equiv CH$ | $NO_2$ | H | CH | O |
| 3-42 | $OCH_2C\equiv CH$ | $NO_2$ | H | N | O |
| 3-43 | $OCH_2C\equiv CH$ | H | Cl | CH | O |
| 3-44 | $OCH_2C\equiv CH$ | H | Cl | N | O |
| 3-45 | $OCH(CH_3)C\equiv CH$ | $NO_2$ | H | N | O |
| 3-46 | $OCH(CH_3)C\equiv CH$ | $NO_2$ | H | CH | O |
| 3-47 | $OCH(CH_3)C\equiv CH$ | H | Cl | N | O |
| 3-48 | $OCH(CH_3)C\equiv CH$ | H | Cl | CH | O |
| 3-49 | $SCH(CH_3)CO_2C_2H_5$ | $NO_2$ | H | CH | O |
| 3-50 | $SCH(CH_3)CO_2C_2H_5$ | $NO_2$ | H | N | O |

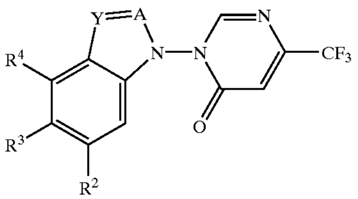

TABLE 54

| Compound | $R^2$ | $R^3$ | $R^4$ | A | Y |
|---|---|---|---|---|---|
| 3-2001 | H | H | H | CH | CH |
| 3-2002 | H | H | H | CH | N |

TABLE 54-continued

| Compound | $R^2$ | $R^3$ | $R^4$ | A | Y |
|---|---|---|---|---|---|
| 3-2003 | H | H | H | N | CH |
| 3-2004 | H | H | H | N | N |
| 3-2005 | $OCH_3$ | H | H | CH | CH |
| 3-2006 | $OCH_3$ | H | H | CH | N |
| 3-2007 | $OCH_3$ | H | H | N | CH |
| 3-2008 | $OCH_3$ | H | H | N | N |
| 3-2009 | $CO_2Et$ | H | H | CH | CH |
| 3-2010 | $CO_2Et$ | H | H | CH | N |
| 3-2011 | $CO_2Et$ | H | H | N | CH |
| 3-2012 | $CO_2Et$ | H | H | N | N |
| 3-2013 | $OCH_2CO_2C_2H_5$ | H | H | CH | CH |
| 3-2014 | $OCH_2CO_2C_2H_5$ | H | H | CH | N |
| 3-2015 | $OCH_2CO_2C_2H_5$ | H | H | N | CH |
| 3-2016 | $OCH_2CO_2C_2H_5$ | H | H | N | N |
| 3-2017 | $OCH(CH_3)CO_2C_2H_5$ | H | H | CH | CH |
| 3-2018 | $OCH(CH_3)CO_2C_2H_5$ | H | H | CH | N |
| 3-2019 | $OCH(CH_3)CO_2C_2H_5$ | H | H | N | CH |
| 3-2020 | $OCH(CH_3)CO_2C_2H_5$ | H | H | N | N |
| 3-2021 | $OCH_2C{\equiv}CH$ | H | H | CH | CH |
| 3-2022 | $OCH_2C{\equiv}CH$ | H | H | CH | N |
| 3-2023 | $OCH_2C{\equiv}CH$ | H | H | N | CH |
| 3-2024 | $OCH_2C{\equiv}CH$ | H | H | N | N |
| 3-2025 | $OCH(CH_3)C{\equiv}CH$ | H | H | N | N |

For some of the present compounds, melting points or $^1$H-NMR data as their physical properties are shown below.

The Present Compound 1-4 m.p.: 132.1° C.

The Present Compound 1-11

$^1$H-NMR (250 MHz, $CDCl_3$, TMS, δ (ppm)): 1.20 (3H, t, J=7.14 Hz), 1.44 (3H, d, J=6.92 Hz), 3.56 (3H, m), 4.06–4.20 (4H, m), 6.38 (1H, s), 6.42 (1H, d, J=2.33 Hz), 6.67 (1H, dd, J=8.87 Hz, 2.33 Hz), 7.32 (1H, d, J=8.87 Hz), 7.72 (1H, s).

The Present Compound 1-76

$^1$H-NMR (300 MHz, $CDCl_3$, TMS, δ (ppm)): 3.60 (3H, s), 6.40 (1H, s), 7.39 (1H, d, J=1.52 Hz), 7.51 (1H, d, J=1.52 Hz), 7.91 (1H, s).

The Present Compound 1-77

$^1$H-NMR (300 MHz, $CDCl_3$, TMS, δ (ppm)): 3.59 (3H, s), 6.40 (1H, s), 7.61 (1H, s), 7.69 (1H, s), 7.84 (1H, s).

The Present Compound 1-80

$^1$H-NMR (250 MHz, $CDCl_3$, TMS, δ (ppm)): 3.58–3.60 (3H, m), 5.47 (1H, s), 6.40 (1H, s), 6.92 (1H, s), 7.56 (1H, s), 7.80 (1H, s).

The Present Compound 1-82

$^1$H-NMR (300 MHz, $CDCl_3$, TMS, δ (ppm)): 3.60–3.61 (3H, m), 6.41 (1H, s), 7.02 (1H, s), 8.05 (1H, s), 8.35 (1H, s), 10.46 (1H, s).

The Present Compound 1-83

$^1$H-NMR (300 MHz, $CDCl_3$, TMS, δ (ppm)): 3.59 (3H, s), 3.80 (3H, s), 6.39 (1H, s), 6.64 (1H, d, J=2.19 Hz), 7.00 (1H, d, J=2.19 Hz), 7.85 (1H, s).

The Present Compound 1-84

$^1$H-NMR (250 MHz, $CDCl_3$, TMS, δ (ppm)): 3.60–3.61 (3H, m), 3.91 (3H, s), 6.41 (1H, s), 6.75 (1H, s), 7.61 (1H, s), 7.80 (1H, s).

The Present Compound 1-86

$^1$H-NMR (300 MHz, $CDCl_3$, TMS, δ (ppm)): 3.61 (3H, m), 3.95 (3H, s), 6.42 (1H, s), 6.89 (1H, s), 8.00 (1H, s), 8.09 (1H, s).

The Present Compound 1-128

$^1$H-NMR (250 MHz, $CDCl_3$, TMS, δ (ppm)): 1.22 (3H, t, J=7.08 Hz), 1.60 (3H, d, J=6.76 Hz), 3.58 (3H, m), 4.15–4.24 (2H, m), 4.71 (1H, q, J=6.78 Hz), 6.39 (1H, s), 6.66 (1H, d, J=2.33 Hz), 7.03 (1H, d, J=2.33 Hz), 7.86 (1H, s).

The Present Compound 1-129

$^1$H-NMR (300 MHz, $CDCl_3$, TMS, δ (ppm)): 1.20 (3H, t, J=7.17 Hz), 1.66 (3H, d, J=6.76 Hz), 3.57 (3H, s), 4.18 (2H, q, J=7.10 Hz), 4.72 (1H, q, J=6.85 Hz), 6.38 (1H, s), 6.83 (1H, s), 7.60 (1H, s), 7.80 (1H, s).

The Present Compound 1-131

$^1$H-NMR (300 MHz, $CDCl_3$, TMS, δ (ppm)): 1.20 (3H, t, J=7.20 Hz), 1.67 (3H, d, J=6.90 Hz), 3.60 (3H, m), 4.18 (2H, q, J=7.09 Hz), 4.80 (1H, q, J=6.80 Hz), 6.40 (1H, s), 6.92 (1H, s), 8.02 (1H, s), 8.09 (1H, s).

The Present Compound 1-246

$^1$H-NMR (250 MHz, $CDCl_3$, TMS, δ (ppm)): 1.13 (3H, t, J=7.07 Hz), 1.55 (3H, d, J=7.25 Hz), 3.61–3.62 (3H, m), 3.96 (1H, q, J=7.14 Hz), 4.08–4.15 (2H, m), 6.42 (1H, s), 8.10 (1H, s), 8.28 (1H, s).

The Present Compound 1-285

$^1$H-NMR (300 MHz, $CDCl_3$, TMS, δ (ppm)): 3.61 (3H, m), 6.42 (1H, s), 7.72 (1H, s), 7.73 (1H, s), 7.98 (1H, s).

The Present Compound 1-289

$^1$H-NMR (300 MHz, $CDCl_3$, TMS, δ (ppm)): 3.61–3.62 (3H, m), 6.43 (1H, s), 7.81 (1H, d, J=1.26 Hz), 7.93 (1H, d, J=1.44 Hz), 8.02 (1H, s), 10.00 (1H, s).

The Present Compound 1-304

$^1$H-NMR (300 MHz, $CDCl_3$, TMS, δ (ppm)): 3.60 (3H, s), 3.94 (3H, s), 6.41 (1H, s), 7.97 (1H, s), 7.98 (1H, d, J=1.35 Hz), 8.09 (1H,d, J=1.35 Hz).

The Present Compound 1-305

$^1$H-NMR (300 MHz, $CDCl_3$, TMS, δ (ppm)): 3.59 (3H, m), 3.93 (3H, s), 6.40 (1H, s), 7.67 (1H, s), 7.87 (1H, s), 7.89 (1H, s).

The Present Compound 1-358

$^1$H-NMR (300 MHz, $CDCl_3$, TMS, δ (ppm)): 2.40 (3H, s), 3.59 (3H, m), 6.40 (1H, s), 7.01 (1H, s), 7.19 (1H, s), 7.85 (1H, s).

The Present Compound 1-361

$^1$H-NMR (300 MHz, $CDCl_3$, TMS, δ (ppm)): 2.67 (3H, s), 3.61 (3H, m), 6.42 (1H, s), 7.27 (1H, s), 8.03 (1H, s), 8.27 (1H, s).

The Present Compound 1-378 m.p.: 208.2° C.

The Present Compound 1-861 m.p.: 135.9° C.

The Present Compound 1-864 m.p.: 183.8° C.

The Present Compound 1-871 m.p.: 193.2° C.

The Present Compound 1-882

$^1$H-NMR (300 MHz, $CDCl_3$, TMS, δ (ppm)): 3.59–3.61 (3H, m), 6.42 (1H, s), 6.98 (1H, s), 7.85 (1H, s).

The Present Compound 1-887

$^1$H-NMR (300 MHz, $CDCl_3$, TMS, δ (ppm)): 3.61 (3H, s), 3.96 (1H, s), 6.44 (1H, s), 6.91 (1H, s), 7.94 (1H, s).

The Present Compound 1-892

$^1$H-NMR (300 MHz, $CDCl_3$, TMS, δ (ppm)): 1.41 (6H, d, J=6.3 Hz), 3.60 (3H, d, J=1.1 Hz), 4.56–4.68 (1H, m), 6.43 (1H, s), 6.91 (1H, s), 7.91 (1H, s).

The Present Compound 1-932

$^1$H-NMR (300 MHz, $CDCl_3$, TMS, δ (ppm)): 1.19 (3H, t, J=7.1 Hz), 1.73 (3H, d, J=7.0), 3.59–3.61 (3H, m), 4.14–4.23 (2H, m), 4.81 (1H, q, J=7.1 Hz), 6.42 (1H, s), 6.87 (1H, s), 7.96 (1H, s).

The following are Formulation Examples in which the present compounds are indicated by their compound numbers in Tables 1 to 54 and parts are by weight.

Formulation Example 1

Fifty parts of each of the present compounds 1-1 to 1-992, 1-2001 to 1-2200, 2-1 to 2-50, 2-2001 to 2-2025, 3-1 to 3-50 and 3-2001 to 3-2025, 3 parts of calcium lignin sulfonate, 2 parts of sodium lauryl sulfate, and 45 parts of synthetic hydrated silicon oxide are well pulverized and mixed to give a wettable powder for each compound.

Formulation Example 2

Ten parts of each of the present compounds 1-1 to 1-992, 1-2001 to 1-2200, 2-1 to 2-50, 2-2001 to 2025, 3-1 to 3-50 and 3-2001 to 3-2025, 14 parts of polyoxyethylene styryl phenyl ether, 6 parts of calcium dodecylbenzenesulfonate, 35 parts of xylene, and 35 parts of cyclohexanone are well mixed to an emulsifiable concentrate for each compound.

Formulation Example 3

Two parts of each of the present compounds 1-1 to 1-992, 1-2001 to 1-2200, 2-1 to 2-50, 2-2001 to 2025, 3-1 to 3-50 and 3-2001 to 3-2025, 2 parts of synthetic hydrated silicon oxide, 2 parts of calcium lignin sulfonate, 30 parts of bentonite, and 64 parts of kaolin clay are well pulverized and mixed, and the mixture is well kneaded with water, followed by granulation and drying, to give a granule for each compound.

Formulation Example 4

Twenty-five parts of each of the present compounds 1-1 to 1-992, 1-2001 to 1-2200, 2-1 to 2-50, 2-2001 to 2025, 3-1 to 3-50 and 3-2001 to 3-2025, 50 parts of 10% aqueous polyvinyl alcohol solution, and 25 parts of water are mixed and pulverized until the mean particle size reaches 5 μm or smaller to give a flowable for each compound.

Formulation Example 5

Five parts of each of the present compounds 1-1 to 1-992, 1-2001 to 1-2200, 2-1 to 2-50, 2-2001 to 2-2025, 3-1 to 3-50 and 3-2001 to 3-2025 is added to 40 parts of 10% aqueous polyvinyl alcohol solution, and the mixture is emulsified by dispersion with a homogenizer until the mean particle size reaches 10 μm or smaller, followed by addition of 55 parts of water, to give a concentrated emulsion for each compound The following are Test Examples for demonstrating that the present compounds are useful as active ingredients of herbicides. In Test Examples, the present compounds are designated by their compound numbers in Tables 1 to 54.

Test Example 1

Cylindrical plastic pots of 10 cm in diameter and 10 cm in depth were filled with soil, seeded with velvetleaf (Abutilon theophrasti), and kept in a greenhouse for 14 days. After that, according to Formulation Example 2, compound 1-1, 1-2, 1-3, 1-4, 1-5, 1-8, 1-9, 1-10, 1-11, 1-24, 1-28, 1-75, 1-82, 1-84, 1-86, 1-127, 1-129, 1-131, 1-201, 1-246, 1-282, 1-283, 1-289, 1-293, 1-303, 1-358, 1-361, 1-378, 1-407, 1-431, 1-861, 1-871, 1-877, 1-892, 1-2068, 2-4 or 2-2011 was formulated into an emulsifiable concentrate, which was diluted in a prescribed amount with water containing a spreading agent and then uniformly sprayed over the foliage of the plants with a sprayer at a ratio of 1000 liters per hectare. The pots were further kept in the greenhouse for 8 days and examined for herbicidal activity. As a result, it was found that compounds 1-1, 1-2, 1-3, 1-4, 1-5, 1-8, 1-9, 1-10, 1-11, 1-24, 1-28, 1-75, 1-82, 1-84, 1-86, 1-127, 1-129, 1-131, 1-201, 1-246, 1-282, 1-283, 1-289, 1-293, 1-303, 1-358, 1-361, 1-378, 1-407, 1-431, 1-861, 1-871, 1-877, 1-892, 1-2068, 2-4 and 2-2011 completely inhibited the growth of velvetleaf at a dosage of 2000 g/ha.

Test Example 2

Cylindrical plastic pots of 10 cm in diameter and 10 cm in depth were filled with soil, seeded with velvetleaf (*Abutilon theophrasti*), and kept in a greenhouse for 14 days. After that, according to Formulation Example 2, compound 2-2001 or 3-2001 was formulated into an emulsifiable concentrate, which was diluted in a prescribed amount with water containing a spreading agent and then uniformly sprayed over the foliage of the plants with a sprayer at a ratio of 1000 liters per hectare. The pots were further kept in the greenhouse for 5 days and examined for herbicidal activity. As a result, it was found that compounds .2-2001 and 3-2001 completely killed velvetleaf at a dosage of 8000 g/ha.

Test Example 3

Cylindrical plastic pots of 10 cm in diameter and 10 cm in depth were filled with soil and seeded with velvetleaf (*Abutilon theophrasti*). According to Formulation Example 2, compound 1-1, 1-2, 1-3, 1-4, 1-5, 1-8, 1-9, 1-10, 1-11, 1-24, 1-28, 1-75, 1-82, 1-84, 1-86, 1-127, 1-129, 1-131, 1-201, 1-246, 1-282, 1-283, 1-289, 1-293, 1-303, 1-358, 1-361, 1-378, 1-407, 1-431, 1-861, 1-877 or 1-892 was formulated into an emulsifiable concentrate, which was diluted in a prescribed amount with water and then uniformly sprayed over the surface of the soil in the pots with a sprayer at a ratio of 1000 liters per hectare. The pots were kept in a greenhouse for 9 days and examined for herbicidal activity. As a result, it was found that compounds 1-1, 1-2, 1-3, 1-4, 1-5, 1-8, 1-9, 1-10, 1-11, 1-24, 1-28, 1-75, 1-82, 1-84, 1-86, 1-127, 1-129, 1-131, 1-201, 1-246, 1-282, 1-283, 1-289, 1-293, 1-303, 1-358, 1-361, 1-378, 1-407, 1-431, 1-861, 1-877 and 1-892 completely inhibited the germination of velvetleaf at a dosage of 2000 g/ha.

Test Example 4

Cylindrical plastic pots of 9 cm in diameter and 11 cm of depth were filled with soil, seeded with barnyardgrass (*Echinochloa oryzicola*), flooded into a paddy field, and kept in a greenhouse for 12 days. According to Formulation Example 2, compound 1-1, 1-2, 1-3, 1-4, 1-5, 1-8, 1-9, 1-10, 1-11, 1-75, 1-82, 1-84, 1-86, 1-127, 1-129, 1-131, 1-201, 1-246, 1-282, 1-283, 1-289, 1-293, 1-303, 1-358, 1-361, 1-378, 1-407, 1-431, 1-861, 1-864, 1-877 or 1-892 was formulated into an emulsifiable concentrate, which was diluted in a prescribed amount with water and then applied on the water surface in the pots at a ratio of 50 liters per are. The pots were further kept in the greenhouse for 9 days and examined for herbicidal activity. As a result, it was found that compounds 1-1, 1-2, 1-3, 1-4, 1-5, 1-8, 1-9, 1-10, 1-11, 1-75, 1-82, 1-84, 1-86, 1-127, 1-129, 1-131, 1-201, 1-246, 1-282, 1-283, 1-289, 1-293, 1-303, 1-358, 1-361, 1-378, 1-407, 1-431, 1-861, 1-864, 1-877 and 1-892 completely inhibited the growth of barnyardgrass at a dosage of 1000 g/ha.

Industrial applicability

The condensed heterocyclic compounds of the present invention are useful as active ingredients of herbicides because of their excellent herbicidal activity.

What is claimed is:

1. A condensed heterocyclic compound of general formula I

[I]

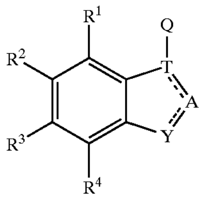

wherein T is carbon and the bond between T and A is a double bond, the bond between A and Y is a single bond, and Y is oxygen;

A is C—$R^{141}$ wherein $R^{141}$ is hydrogen;

$R^1$ is hydrogen, halogen, $C_1$–$C_3$ alkyl, $C_1$–$C_3$ haloalkyl, hydroxymethyl, nitro, or cyano;

$R^2$ is hydrogen, halogen, $C_1$–$C_{11}$, alkyl $C_1$–$C_{11}$ haloalkyl, hydroxymethyl, nitro, cyano, —N($R^9$)$R^{19}$, —$OR^{11}$, —$SR^{12}$, —$SO_2R^{13}$, —COX, —$COOR^{14}$, —CON($R^{15}$)$R^{16}$, —$COOR^{17}$, —C($R^{26}$)=$NOR^{19}$, —C($R^{27}$)=C($R^{21}$)$R^{22}$, or —OH($R^{23}$)—CH($R^{24}$)$R^{25}$;

$R^3$ is hydrogen, halogen, $C_1$–$C_{11}$ alkyl, $C_1$–$C_{11}$ haloalkyl, hydroxymethyl, nitro, cyano, —N($R^{59}$)$R^{60}$, —$OR^{61}$, —$SR^{62}$, —$SO_2R^{63}$, —COX, —$COOR^{64}$, —CON($R^{65}$)$R^{66}$, —$COR^{67}$, —C($R^{76}$)=$CR^{69}$, —C($R^{77}$)=C($R^{71}$)$R^{72}$, or —CH($R^{73}$)—CH($R^{74}$)$R^{75}$;

$R^4$ is hydrogen, halogen, $C_1$–$C_3$, alkyl, $C_1$–$C_3$ haloalkyl, hydroxymethyl, nitro, or cyano;

wherein X is chlorine or bromine;

$R^9$ and $R^{59}$ are independently hydrogen, $C_1$–$C_5$ alkyl, ($C_1$–$C_5$ alkyl)carbonyl, or ($C_1$–$C_5$ alkoxy) carbonyl;

$R^{10}$, $R^{11}$, and $R^{12}$ are independently hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl, $C_3$–$C_{10}$ cycloalkyl $C_1$–$C_3$ alkyl, $C_3$–$C_{10}$ alkenyl, $C_3$–$C_{10}$ haloalkenyl, $C_3$–$C_{10}$ alkynyl, $C_3$–$C_{10}$ haloalkynyl, cyano $C_1$–$C_6$ alkyl, ($C_1$–$C_5$ alkyl) carbonyl, ($C_1$–$C_5$ haloalkyl)carbonyl, ($C_3$–$C_{10}$ cycloalkyl)carbonyl, ($C_1$–$C_5$ alkyl)carbonyl $C_1$–$C_5$ alkyl, ($C_1$–$C_5$ haloalkyl)carbonyl $C_1$–$C_5$ alkyl, hydroxy $C_1$–$C_5$ alkyl, $C_1$–$C_5$ alkoxy $C_1$–$C_5$ alkyl, $C_1$–$C_5$ alkylthio $C_1$–$C_5$ alkyl, ($C_1$–$C_5$ alkoxy)carbonyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, —C($R^{43}$)($R^{44}$)—C(=O)ON($R^{45}$)$R^{46}$, —C($R^{47}$) ($R^{48}$)—CON($R^{49}$)$R^{50}$, —$CH_2$—C($R^{56}$)=N—$OR^{55}$, —CHMe—C($R^{58}$)=$NOR^{57}$, ($C_3$–$C_{10}$ alkenoxy)carbonyl $C_1$–$C_5$ alkyl, ($C_3$–$C_{10}$ alkynoxy)carbonyl $C_1$–$C_5$ alkyl, phenoxycarbonyl, benzyloxycarbonyl, carboxy ($C_1$–$C_5$ alkoxy)carbonyl $C_1$–$C_5$ alkyl, ($C_1$–$C_{10}$ alkoxy) carbonyl ($C_1$–$C_5$ alkoxy)carbonyl $C_1$–$C_5$ alkyl, ($C_1$–$C_{10}$ haloalkoxy)carbonyl ($C_1$–$C_5$ alkoxy)carbonyl $C_1$–$C_5$ alkyl, ($C_3$–$C_{10}$ cycloalkoxy)carbonyl ($C_1$–$C_5$ alkoxy)carbonyl $C_1$–$C_5$ alkyl, ($C_3$–$C_{10}$ alkenoxy) carbonyl($C_1$–$C_5$ alkoxy)carbonyl $C_1$–$C_5$ alkyl, ($C_3$–$C_{10}$ alkynoxy)carbonyl($C_1$–$C_5$ alkoxy)carbonyl $C_1$–$C_5$ alkyl, carboxy($C_1$–$C_5$ alkyl)carbonyl, ($C_1$–$C_{10}$ alkoxy) carbonyl($C_1$–$C_5$ alkyl)carbonyl, ($C_1$–$C_{10}$ haloalkoxy) carbonyl ($C_1$–$C_5$ alkyl)carbonyl, $C_1$–$C_5$ alkylsulfonyl, $C_1$–$C_5$ haloalkylsulfonyl, —$SO_2N$($R^{51}$)$R^{52}$, —CON($R^{53}$)$R^{54}$, optionally substituted benzyl, or optionally substituted phenyl;

$R^{60}$, $R^{61}$, and $R^{62}$ are independently hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl, $C_3$–$C_{10}$ cycloalkyl $C_1$–$C_3$ alkyl, $C_3$–$C_{10}$ alkenyl, $C_3$–$C_{10}$ haloalkenyl, $C_3$–$C_{10}$ alkynyl, $C_3$–$C_{10}$ haloalkynyl, cyano $C_1$–$C_6$ alkyl, ($C_1$–$C_5$ alkyl) carbonyl, ($C_1$–$C_5$ haloalkyl)carbonyl, ($C_3$–$C_{10}$ cycloalkyl)carbonyl, ($C_1$–$C_5$ alkyl)carbonyl $C_1$–$C_5$ alkyl, ($C_1$–$C_5$ haloalkyl)carbonyl $C_1$–$C_5$ alkyl, hydroxy $C_1$–$C_5$ alkyl, $C_1$–$C_5$ alkoxy $C_1$–$C_5$ alkyl, $C_1$–$C_5$ alkylthio $C_1$–$C_5$ alkyl, $C_1$–$C_6$ alkoxy)carbonyl, carboxy $C_1$–$C_5$ alkyl, ($C_1$–$C_{10}$ alkoxy)carbonyl $C_1$–$C_5$ alkyl, ($C_1$–$C_{10}$ haloalkoxy carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, —C($R^{163}$)($R^{164}$)—C(=O)ON($R^{165}$)$R^{166}$, —C($R^{167}$)($R^{168}$)—CON($R^{169}$)$R^{170}$, —$CH_2$—C(=$NOR^{175}$)$R^{176}$, —CHMe—C(=$NOR^{177}$)$R^{178}$, ($C_3$–$C_{10}$ alkenoxy) carbonyl $C_1$–$C_5$ alkyl, ($C_3$–$C_{10}$ alkynoxy)carbonyl $C_1$–$C_5$ alkyl, phenoxycarbonyl, benzyloxycarbonyl, carboxy($C_1$–$C_5$ alkoxy)carbonyl $C_1$–$C_5$ alkyl, ($C_1$–$C_{10}$ alkoxy)carbonyl ($C_1$–$C_5$ alkoxy)carbonyl $C_1$–$C_5$ alkyl, ($C_1$–$C_{10}$ haloalkoxy)carbonyl ($C_1$–$C_5$ alkoxy)carbonyl $C_1$–$C_5$ alkyl, ($C_3$–$C_{10}$ cycloalkoxy)carbonyl ($C_1$–$C_5$ alkoxy)carbonyl $C_1$–$C_5$ alkyl, ($C_3$–$C_{10}$ alkenoxy) carbonyl($C_1$–$C_5$ alkoxy)carbonyl $C_1$–$C_5$ alkyl, ($C_3$–$C_{10}$ alkynoxy)carbonyl ($C_1$–$C_5$ alkoxy)carbonyl $C_1$–$C_5$ alkyl, carboxy($C_1$–$C_5$ alkyl)carbonyl, ($C_1$–$C_{10}$ alkoxy) carbonyl($C_1$–$C_5$ alkyl)carbonyl, ($C_1$–$C_{10}$ haloalkoxy) carbonyl($C_1$–$C_5$ alkyl)carbonyl, $C_1$–$C_5$ alkylsulfonyl, $C_1$–$C_5$ haloalkylsulfonyl, —$SO_2N$($R^{171}$)$R^{172}$, —CON($R^{173}$)$R^{174}$, optionally substituted benzyl, or optionally substituted phenyl;

wherein $R^{43}$, $R^{44}$, $R^{163}$, and $R^{164}$ are independently hydrogen, halogen, $C_1$–$C_5$ alkyl, or $C_1$–$C_5$ haloalkyl;

$R^{45}$, $R^{46}$, $R^{165}$, and $R^{166}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{45}$ and $R^{46}$ may be combined at their ends to form, together with the adjacent nitrogen atom, a 3- to 7-membered saturated rind, or $R^{165}$ and $R^{166}$ may be combined at their ends to form together with the adjacent nitrogen atom, a 3- to 7-membered saturated ring;

$R^{47}$, $R^{48}$, $R^{167}$, and $R^{168}$ are independently hydrogen, halogen, $C_1$–$C_5$ alkyl, or $C_1$–$C_5$ haloalkyl;

$R^{49}$, $R^{50}$, $R^{169}$, and $R^{170}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{49}$ and $R^{50}$ may be combined at their ends to form, together with the adjacent nitrogen atom, a 3- to 7-membered saturated ring containing zero to one oxygen atom or NH group in the ring, or $R^{169}$ and $R^{170}$ may be combined at their ends to form, together with the adjacent nitrogen atom, a 3- to 7-membered saturated ring containing zero to one oxygen atom or NH group in the ring;

$P^{51}$, $R^{52}$, $R^{171}$ and $R^{172}$ are independently hydrogen, $C_1$–$C_5$ alkyl $C_1$–$C_5$ haloalkyl, $C_3$–$C_8$ cycloalkyl, $C_3$–$C_6$ alkenyl; or $C_3$–$C_6$ alkynyl; or $R^{51}$ and $R^{52}$ may be combined at their ends to form, together with the adjacent nitrogen atom, a 3- to 7-membered saturated ring containing zero to one oxygen atom or NH group in the ring, or $R^{171}$ and $^{172}$ may be combined at their ends to form, together with the adjacent nitrogen atom, a 3- to 7-membered saturated ring containing zero to one oxygen atom or NH group in the ring;

$R^{53}$, $R^{54}$, $R^{173}$, and $R^{174}$ are independently hydrogen, $C_1$–$C_5$ alkyl, $C_1$–$C_5$ haloalkyl, $C_3$–$C_8$ cycloalkyl, $C_3$–$C_6$ alkynyl, or $C_3$–$C_6$ alkynyl; or $R^{53}$ and $R^{54}$ may be combined at their ends to form, together with the adjacent nitrogen atom, a 3- to 7-membered saturated ring containing zero to one oxygen atom or NH group in the ring, or $R^{173}$ and $R^{174}$ may be combined at their ends to form, together with the adjacent nitrogen atom, a 3- to 7-membered saturated ring containing zero to one oxygen atom or NH group in the ring;

$R^{55}$, $R^{57}$, $R^{175}$, and $R^{177}$ are independently hydrogen or $C_1$–$C_3$ alkyl;

$R^{56}$, $R^{58}$, $R^{176}$, and $R^{178}$ are independently hydrogen, $C_1$–$C_5$ alkyl, ($C_1$–$C_5$ alkoxy)carbonyl, ($C_1$–$C_5$ haloalkoxy)carbonyl, ($C_3$–$C_5$ cycloalkoxy)carbonyl, ($C_3$–$C_5$ alkenoxy)carbonyl, or ($C_3$–$C_5$ alkynoxy) carbonyl;

$R^{13}$ is hydroxy, chlorine, $C_1$–$C_{10}$ alkyl, $C_1$–$C_{10}$ haloalkyl, carboxy $C_1$–$C_5$ alkyl, ($C_1$–$C_{10}$ alkoxy)carbonyl, $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, —N($R^{79}$)$R^{80}$, or —O$R^{81}$;

$R^{63}$ hydroxy, chlorine, $C_1$–$C_{10}$ alkyl, $C_1$–$C_{10}$ haloalkyl, carboxy $C_1$–$C_5$ alkyl, ($C_1$–$C_{10}$ alkoxy)carbonyl, $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, —N($R^{179}$) $R^{180}$, or —O$R^{181}$;

wherein $R^{79}$ and $R^{179}$ are independently hydrogen, $C_1$–$C_5$ alkyl, $C_1$–$C_5$ haloalkyl, $C_3$–$C_8$ cycloalkyl, $C_3$–$C_6$ alkenyl, $C_3$–$C_6$ alkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl, $C_1$–$C_5$ alkyl, or ($C_3$–$C_{10}$ halocycloalkoxy)carbonyl $C_1$–$C_5$ alkyl; $R^{80}$ and $R^{180}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{79}$ and $R^{80}$ may be combined at their ends to form, together with the adjacent nitrogen atom, a 3- or 7-membered saturated ring containing zero to one oxygen atom or NH group in the ring; or $R^{179}$ and $R^{180}$ may be combined at their ends to form, together with the adjacent nitrogen atom, a 3- or 7-membered saturated ring containing zero to one oxygen atom or NH group in the ring; and $R^{81}$ and $R^{181}$ are independently $C_1$–$C_5$ alkyl, $C_1$–$C_5$ haloalkyl, $C_3$–$C_8$ cycloalkyl, $C_3$–$C_6$ alkenyl, $C_3$–$C_6$ alkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl;

$R^{14}$ is hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl, $C_3$–$C_{10}$ cycloalkyl $C_1$–$C_3$ alkyl, $C_3$–$C_{10}$ alkenyl, $C_3$–$C_{10}$ haloalkenyl, $C_3$–$C_{10}$ alkynyl, $C_3$–$C_{10}$ haloalkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, ($C_3$–$C_{10}$ alkenoxy) carbonyl $C_1$–$C_5$ alkyl, ($C_3$–$C_{10}$ alkynoxy) carbonyl $C_1$–$C_5$ alkyl, —N($R^{82}$)$R^{83}$, optionally substituted benzyl, or optionally substituted phenyl;

$R^{64}$ is hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl, $C_3$–$C_{10}$ cycloalkyl $C_1$–$C_3$ alkyl, $C_3$–$C_{10}$ alkenyl, $C_3$–$C_{10}$ haloalkenyl, $C_3$–$C_{10}$ alkynyl, $C_3$–$C_{10}$ haloalkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, ($C_3$–$C_{10}$ halocycloalkoxy)carbonyl $C_1$–$C_5$ alkyl, ($C_3$–$C_{10}$ alkenoxy)carbonyl $C_1$–$C_5$ alkyl, ($C_3$–$C_{10}$ alkynoxy) carbonyl $C_1$–$C_5$ alkyl, —N($R^{182}$)$R^{183}$, optionally substituted benzyl, or optionally substituted phenyl;

wherein $R^{82}$ and $R^{182}$ are independently hydrogen, $C_1$–$C_5$ alkyl, $C_1$–$C_5$ haloalkyl, $C_3$–$C_8$ cycloalkyl, $C_3$–$C_6$ alkenyl, $C_3$–$C_6$ alkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy) carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl; $R^{83}$ sand $R^{183}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{82}$ and $R^{83}$ may be combined at their ends to form, together with the adjacent nitrogen atom, a 3- to 7-membered saturated ring containing zero to one oxygen atom or NH group in the ring; or $R^{182}$ and $R^{183}$ may be combined at their ends to form, together with the adjacent nitrogen atom, a 3- to 7-membered saturated ring containing zero to one oxygen atom or NH group in the ring;

$R^{15}$ and $R^{65}$ are independently hydrogen, $C_1$–$C_{10}$ alkyl, $C_1$–$C_{10}$ haloalkyl, $C_3$–$C_{10}$ cycloalkyl, $C_3$–$C_{10}$ cycloalkyl $C_1$–$C_3$ alkyl, $C_3$–$C_{10}$ alkenyl, $C_3$–$C_{10}$ alkynyl, cyano $C_1$–$C_6$ alkyl, carboxy $C_1$–$C_5$ alkyl, ($C_1$–$C_{10}$ alkoxy)carbonyl $C_1$–$C_5$ alkyl, optionally substituted benzyl, or optionally substituted phenyl; $R^{16}$ and $R^{56}$ are independently hydrogen, $C_1$–$C_{10}$ alkyl, or $C_1$–$C_{10}$ haloalkyl; or $R^{15}$ and $R^{16}$ may be combined at their ends to form, together with the adjacent nitrogen atom, a 3- to 7-membered saturated ring containing zero to one oxygen atom or NH group in the ring; or $R^{65}$ and $R^{66}$ may be, combined at their ends to form, together with the adjacent nitrogen atom, a 3- to 7-membered saturated ring containing zero to one oxygen atom or NH group in the ring;

$R^{17}$, $R^{26}$, $R^{27}$, $R^{67}$, $R^{76}$, and $R^{77}$ are independently hydrogen, cyano, $C_1$–$C_{10}$ alkyl, $C_1$–$C_{10}$ haloalkyl, $C_3$–$C_{10}$ cycloalkyl, $C_3$–$C_{10}$ cycloalkyl $C_1$–$C_3$ alkyl, ($C_1$–$C_6$ alkoxy)carbonyl, or ($C_1$–$C_6$ alkoxy) carbonylmethyl;

$R^{19}$ and $R^{69}$ are independently hydrogen, $C_1$–$C_{10}$ alkyl, $C_1$–$C_{10}$ haloalkyl, $C_3$–$C_{10}$ cycloalkyl, $C_3$–$C_{10}$ halocycloalkyl, $C_3$–$C_{10}$ cycloalkyl $C_1$–$C_3$ alkyl, $C_3$–$C_{10}$ alkenyl, $C_3$–$C_{10}$ haloalkenyl, $C_3$–$C_{10}$ alkynyl, $C_3$–$C_{10}$ haloalkynyl, cyano $C_1$–$C_6$ alkyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl;

$R^{21}$ and $R^{71}$ are independently hydrogen, halogen, $C_1$–$C_3$ alkyl, or $C_1$–$C_3$ haloalkyl;

$R^{22}$ and $R^{25}$ are independently carboxy, ($C_1$–$C_{10}$ alkoxy) carbonyl, ($C_1$–$C_{10}$ haloalkoxy)carbonyl, ($C_3$–$C_{10}$ cyrloalkoxy)carbonyl ($C_3$–$C_{10}$ halocycloalkoxy) carbonyl, carboxy($C_1$–$C_5$ alkoxy)carbonyl, ($C_1$–$C_{10}$ alkoxy)carbonyl ($C_1$–$C_5$ alkoxy)carbonyl, ($C_1$–$C_{10}$ haloalkoxy)carbonyl ($C_1$–$C_5$ alkoxy)carbonyl, ($C_3$–$C_{10}$ cycloalkoxy)carbonyl ($C_1$–$C_5$ alkoxy)carbonyl, ($C_3$–$C_{10}$ alkenoxy)carbonyl ($C_1$–$C_5$ alkoxy)carbonyl, ($C_3$–$C_{10}$ alkynoxy)carbonyl ($C_1$–$C_5$ alkoxy)carbonyl, —CON($R^{84}$)$R^{85}$, or —C(═O)ON($R^{86}$)$R^{87}$;

$R^{72}$ and $R^{75}$ are independently carboxy, ($C_1$–$C_{10}$ alkoxy) carbonyl, ($C_1$–$C_{10}$ haloalkoxy)carbonyl, ($C_3$–$C_{10}$ cycloalkoxy)carbonyl, ($C_3$–$C_{10}$ halocycloalkoxy) carbonyl, carboxy($C_1$–$C_5$ alkoxy)carbonyl, ($C_1$–$C_{10}$ alkoxy)carbonyl ($C_1$–$C_5$ alkoxy) carbonyl, ($C_1$–$C_{10}$ haloalkoxy)carbonyl ($C_1$–$C_5$ alkoxy)carbonyl, ($C_3$–$C_{10}$ cycloalkoxy)carbonyl ($C_1$–$C_5$ alkoxy)carbonyl, ($C_3$–$C_{10}$ alkenoxy)carbonyl ($C_1$–$C_5$ alkoxy)carbonyl, ($C_3$–$C_{10}$ alkynoxy)carbonyl ($C_1$–$C_5$ alkoxy carbonyl, —CON($R^{184}$)$R^{185}$, or —C(=O)ON($R^{186}$)$R^{187}$;

wherein $R^{84}$ and $R^{184}$ are independently hydrogen, $C_1$–$C_5$ alkyl, $C_1$–$C_5$ haloalkyl, $C_3$–$C_8$ cycloalkyl, $C_3$–$C_6$ alkenyl, ($C_3$–$C_6$ alkynyl, carboxy $C_1$–$C_5$ alkyl, ($C_1$–$C_{10}$ alkoxy)carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl; $R^{85}$ and $R^{185}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{84}$ and $R^{85}$ may be combined at their ends to form, together with the adjacent nitrogen atom, a 3- to 7-membered saturated ring containing zero to one oxygen atom or NH group in the ring; or $R^{184}$ and $R^{185}$ may be combined at their ends to form, together with the adjacent nitrogen atom, a 3- to 7-membered saturated ring containing zero to one oxygen atom or NH group in the ring;

$R^{86}$ and $R^{186}$ are independently hydrogen, $C_1$–$C_5$ alkyl, $C_1$–$C_5$ haloalkyl, $C_3$–$C_8$ cycloalkyl, $C_3$–$C_6$ alkenyl, $C_3$–$C_6$ alkynyl, carboxy $C_1$–$C_5$ alkyl, ($C_1$–$C_{10}$ alkoxy) carbonyl $C_1$–$C_5$ alkyl, ($C_1$–$C_{10}$ haloalkoxy)carbonyl $C_1$–$C_5$ alkyl, ($C_3$–$C_{10}$ cycloalkoxy)carbonyl $C_1$–$C_5$ alkyl, or ($C_3$–$C_{10}$ halocycloalkoxy)carbonyl $C_1$–$C_5$ alkyl; $R^{87}$ and $R^{187}$ are independently hydrogen, $C_1$–$C_5$ alkyl, $C_1$–$C_5$ haloalkyl, $C_3$–$C_8$ cycloalkyl, $C_3$–$C_6$ alkenyl, or $C_3$–$C_6$ alkynyl; or $R^{86}$ and $R^{87}$ may be combined at their ends to form, together with the adjacent nitrogen atom, a 3- to 7-membered saturated ring; or $R^{186}$ and $R^{187}$ may be combined at their ends to form, together with the adjacent nitrogen atom, a 3- to 7-membered saturated ring;

$R^{23}$, $R^{24}$, $R^{73}$, and $R^{74}$ are independently hydrogen, halogen, $C_1$–$C_3$ alkyl, or $C_1$–$C_3$ haloalkyl; and Q is any one group of Q14, Q15, or Q17 of the general formula:

Q14

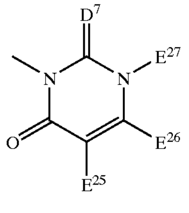

Q15

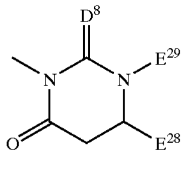

-continued

Q17

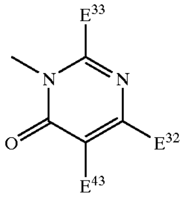

wherein:

in Q14, $E^{25}$ is hydrogen, $C_1$–$C_3$ alkyl, or halogen; $E^{26}$ is $C_1$–$C_3$ alkyl optionally substituted with halogen; $E^{27}$ is hydrogen, amino, $C_1$–$C_6$ alkyl, $C_3$–$C_6$ alkenyl, $C_3$–$C_6$ alkynyl, or optionally substituted benzyl; and $D^7$ is oxygen or sulfur;

in Q15, $E^{28}$ is $C_1$–$C_3$ alkyl optionally substituted with halogen; $E^{29}$ is hydrogen, amino, $C_1$–$C_6$ alkyl, $C_3$–$C_6$ alkenyl, $C_3$–$C_6$ alkynyl, or optionally substituted benzyl; and Do is oxygen or sulfur; and in Q17, $E^{32}$ is $C_1$–$C_3$ alkyl optionally substituted with halogen; $E^{33}$ is hydrogen, halogen, amino, $C_1$–$C_3$ alkyl optionally substituted with halogen, $C_1$–$C_3$ alkoxy optionally substituted with halogen, or $C_1$–$C_3$ alkylthio optionally substituted with halogen; and $E^{43}$ is hydrogen or $C_1$–$C_3$ alkyl optionally substituted with halogen.

2. The condensed heterocyclic compound according to claim 1, wherein Q is Q14.

3. The condensed heterocyclic compound according to claim 1, wherein Q is Q15.

4. The condensed heterocyclic compound according to claim 1, wherein Q is Q1, of which $E^1$ and $E^2$ are combined at their ends to form $C_2$–$C_6$ alkylene (which alkylene may optionally be substituted with methyl or halogen) or $C_2$–$C_5$ alkenylene (which alkenylene may optionally be substituted with methyl or halogen); or Q is Q2, of which $E^3$ and $E^4$ are combined at their ends to form $C_2$–$C_5$ alkylene (which alkylene may optionally be substituted with methyl or halogen) or $C_2$–$C_5$ alkenylene (which alkenylene may optionally be substituted with methyl or halogen), and $D^1$ and $Z^1$ are as defined above; or Q is Q4, of which $E^6$ is $C_1$–$C_6$ alkyl optionally substituted with halogen and $E^7$ is $C_1$–$C_6$ alkyl optionally substituted with halogen; or Q is Q4, of which $E^6$ and $E^7$ are combined at their ends to form $C_2$–$C_5$ alkylene (which alkylene may optionally be substituted with methyl or halogen) or $C_2$–$C_5$ alkenylene (which alkenylene may optionally be substituted with methyl or halogen); or Q is Q6, of which $E^{44}$ is chlorine or bromine, $E^{10}$ is $C_1$–$C_6$ alkyl optionally substituted with halogen, and $E^{11}$ is $C_1$–$C_6$ alkyl optionally substituted with halogen; or Q is Q6, of which $E^{44}$ is chlorine or bromine, and $E^{10}$ and $E^{11}$ are combined at their ends to form $C_2$–$C_5$ alkylene (which alkylene may optionally be substituted with methyl or halogen) or $C_2$–$C_5$ alkenylene (which alkylene may optionally be substituted with methyl or halogen).

5. The condensed heterocyclic compound according to claim 1, wherein Q is Q1, of which $E^1$ and $E^2$ are combined at their ends to form tetramethylene (which tetramethylene may optionally be substituted with methyl or halogen); or Q is Q2, of which $E^3$ and $E^4$ are combined at their ends to form tetramethylene (which tetramethylene may optionally be substituted with methyl or halogen), $D^1$ is oxygen, and $Z^1$ is nitrogen; or Q is Q4, of which $E^6$ is methyl substituted with fluorine, or ethyl substituted with fluorine, and $E^7$ is methyl or ethyl; or Q is Q4, of which $E^6$ and $E^7$ are combined at their ends to form tetramethylene (which tetramethylene may optionally be substituted with methyl or halogen); or Q is Q6, of which $E^{44}$ is chlorine or bromine, $E^{10}$ is methyl substituted with fluorine, or ethyl substituted with fluorine, and $E^{11}$ is methyl or ethyl; or Q is Q6, of which $E^{10}$ and $E^{11}$ are combined at their ends to form tetramethylene (which tetramethylene may optionally be substituted with methyl or halogen).

6. The condensed heterocyclic compound according to claim 1, wherein Q is Q17.

7. The condensed heterocyclic compound according to claim 1, wherein Q is Q14, of which $E^{25}$ is hydrogen, $E^{26}$ is $C_1$–$C_3$ alkyl optionally substituted with halogen, $E^{27}$ is $C_1$–$C_3$ alkyl, and $D^7$ is oxygen.

8. The condensed heterocyclic compound according to claim 1, wherein Q is Q14, of which $E^{25}$ is hydrogen, $E^{26}$ is methyl substituted with fluorine, or ethyl substituted with fluorine, $E^{27}$ is methyl or ethyl, and $D^7$ is oxygen.

9. The condensed heterocyclic compound according to any one of claims 1, 2, 3, 4, 5, 6, 7, or 8 wherein A s nitrogen, CH, $CCH_3$, CCl, or CBr.

10. The condensed heterocyclic compound according to claim 1, wherein $R^1$ is hydrogen or halogen.

11. The condensed heterocyclic compound according to claim 1, wherein T is nitrogen.

12. The condensed heterocyclic compound according to claim 1, wherein $R^2$ is hydrogen, halogen, $C_1$–$C_{11}$ alkyl, nitro, cyano, —$N(R^9)R^{10}$, —$OR^{11}$, —$SR^{12}$, $COOR^{14}$, —$CON(R^{15})R^{16}$, —$COR^{17}$, —$C(R^{26})$=$NOR^{19}$, —$C(R^{27})$=$C(R^{21})R^{22}$, or —$CH(R^{23})$—$CH(R^{24})R^{25}$.

13. The condensed heterocyclic compound according to claim 1, wherein $R^3$ is hydrogen, halogen, or nitro.

14. The condensed heterocyclic compound according to claim 1, wherein $R^4$ is hydrogen or halogen.

15. The condensed heterocyclic compound according to claim 1, wherein T is carbon, A is CH, Y is oxygen, $R^1$ is hydrogen, Q is Q14, $E^{25}$ is hydrogen, $E^{26}$ is trifluoromethyl, and $E^{27}$ is methyl.

16. A herbicidal composition comprising a condensed heterocyclic compound according to claim 1, and an inert carrier or diluent.

17. A method for controlling weeds, which comprises applying an effective amount of a condensed heterocyclic compound according to claim 1, to weeds or to a place where weeds are growing or will grow.

* * * * *

UNITED STATES PATENT AND TRADEMARK OFFICE

CERTIFICATE OF CORRECTION

PATENT NO. : 6,586,368 B1

DATED : July 1, 2003
INVENTOR(S) : Minoru Takano, Shinichi Kawamura and Takashi Komori It is certified that error appears in the above-identified patent and that said Letters Patent is hereby corrected as shown below:

Title page, Item [54] and Column 1, lines 1-2,
Title, should read as follows: -- CONDENSED HETEROCYCLIC COMPOUNDS AND HERBICIDES CONTAINING THEM --

Title page,
Item [56], References Cited, insert:
-- U.S. PATENT DOCUMENTS
5,661,108 8/1997 Crawford --

Column 180, line 32 through Column 182, line 3,
Please cancel claims 4, 5, 9 and 11.

Signed and Sealed this

Sixth Day of July, 2004

JON W. DUDAS
*Acting Director of the United States Patent and Trademark Office*